(12) United States Patent
Ding et al.

(10) Patent No.: US 7,666,864 B2
(45) Date of Patent: Feb. 23, 2010

(54) BICYCLIC NITROIMIDAZOLE-SUBSTITUTED PHENYL OXAZOLIDINONES

(75) Inventors: Charles Z. Ding, Foster City, CA (US);
Genliang Lu, Winchester, MA (US);
Keith Combrink, Arlington, TX (US);
Dianjun D. Chen, Houston, TX (US);
Minsoo Song, Dobbs Ferry, NY (US);
Jiancheng Wang, Revere, MA (US);
Zhenkun Ma, Westfield, NJ (US); Brian Desmond Palmer, Waitakere (NZ);
Adrian Blaser, Waitakere (NZ);
Andrew M. Thompson, Auckland (NZ);
Iveta Kmentova, Jahodna (SK); Hamish Scott Sutherland, Auckland (NZ);
William Alexander Denny, Auckland (NZ)

(73) Assignee: Global Alliance for TB Drug Development, New York, NY (US)

( * ) Notice: Subject to any disclaimer, the term of this patent is extended or adjusted under 35 U.S.C. 154(b) by 0 days.

(21) Appl. No.: 12/411,220

(22) Filed: Mar. 25, 2009

(65) Prior Publication Data

US 2009/0281088 A1 Nov. 12, 2009

Related U.S. Application Data

(60) Provisional application No. 61/070,855, filed on Mar. 26, 2008.

(51) Int. Cl.
*C07D 498/04* (2006.01)
*A61K 31/424* (2006.01)
*A61K 31/5365* (2006.01)
*A61K 31/553* (2006.01)

(52) U.S. Cl. ............... 514/230.5; 544/91; 540/552; 548/218; 514/211.1; 514/375

(58) Field of Classification Search ............ 544/91; 540/552; 548/218; 514/211.1, 230.5, 375
See application file for complete search history.

(56) References Cited

U.S. PATENT DOCUMENTS

| 4,801,600 | A | 1/1989 | Wang et al. |
|---|---|---|---|
| 4,921,869 | A | 5/1990 | Wang et al. |
| 5,547,950 | A | 8/1996 | Hutchinson et al. |
| 5,736,545 | A | 4/1998 | Gadwood et al. |
| 5,880,118 | A | 3/1999 | Barbachyn et al. |
| 5,981,528 | A | 11/1999 | Gravestock |
| 6,087,358 | A | 7/2000 | Baker et al. |
| 6,968,962 | B2 | 11/2005 | Toma |
| 7,129,259 | B2 | 10/2006 | Chen et al. |
| 7,262,212 | B2 | 8/2007 | Tsubouchi et al. |
| 2007/0155714 | A1 | 7/2007 | Hubschwerlen et al. |
| 2008/0119478 | A1 | 5/2008 | Tsubouchi et al. |

FOREIGN PATENT DOCUMENTS

| EP | 0 316 594 B1 | 5/1989 |
|---|---|---|
| EP | 0 352 781 A3 | 1/1990 |
| WO | WO 2004/078753 A1 | 9/2004 |
| WO | WO 2005/054234 A2 | 6/2005 |
| WO | WO 2006/022794 A1 | 3/2006 |
| WO | WO 2006/038100 A1 | 4/2006 |
| WO | WO 2006/043121 A1 | 4/2006 |

OTHER PUBLICATIONS

Najarajan, K, et al., Nitroimidazoles XXI**2, 3-Dihydro-6-Nitroimidazo u2, 1-b 3/4 Oxazoles with Antitubercular Activity, European Journal of Medicinal Chemistry, Editions Scientifique Elsevier, Paris, FR, vol. 24, Jan. 1, 1989, pp. 631-633.
International Search Report; European Patent Office, Jul. 17, 2009.

*Primary Examiner*—Kahsay T Habte
(74) *Attorney, Agent, or Firm*—Jackson Walker L.L.P.

(57) ABSTRACT

The current invention provides a series of bicyclic nitroimidazole-substituted phenyl oxazolidinones in which a bicyclic nitroimidazole pharmacophore is covalently bonded to a phenyl oxazolidinone, their pharmaceutical compositions, and the method of use of the compositions for prevention and treatment of bacterial infections. The bicyclic nitroimidazole-substituted phenyl oxazolidinones possess surprising antibacterial activity against wild-type and resistant strains of pathogens, and are therefore useful for the prevention, control and treatment of a number of human and veterinary bacterial infections caused by these pathogens, such as *Mycobacterium tuberculosis*.

15 Claims, 22 Drawing Sheets

BICYCLIC NITROIMIDAZOLE-SUBSTITUTED PHENYL OXAZOLIDINONES

This application claims priority to U.S. Provisional Patent Application Ser. No. 61/070,855, entitled "Bicyclic Nitroimidazole-Substituted Phenyl Oxazolidinones," filed on Mar. 26, 2008, the entire content of which is hereby incorporated by reference.

BACKGROUND

The present invention relates bicyclic nitroimidazole-substituted phenyl oxazolidinones wherein a bicyclic nitroimidazole pharmacophore is chemically linked with a phenyl oxazolidinone pharmacophore via a covalent bond.

The disturbing increase in bacterial resistance to existing antibacterial agents is a major clinical challenge. Accordingly, there is a need in the art for compounds, compositions, and methods of treating warm-blooded animals that suffer from a bacterial infection and are resistant to conventional antibacterial treatments. The rise of multidrug-resistant tuberculosis ("MDRTB") is a profound public threat. Tuberculosis ("TB") is highly contagious. The caustic pathogenic *Mycobacterium tuberculosis* bacteria are easily passed from person to person in airborne droplets formed when a person with active TB sneezes or coughs. MDRTB is extraordinarily difficult to treat, and a majority of patients do not respond to conventional therapy. Total treatment costs for an individual with MDRTB can be as much as 10 times the cost of traditional treatment, and the cost of the treatment drugs alone can be as much as 21 times as great. The preferred treatment for classical TB consists of isoniazid, rifampin, pyrazinamide and ethambutol, four drugs combination in the first two month of intense treatment phase, followed by four month of second phase of treatment with rifampin and isoniazid two drug cocktail. MDRTB patients require specialized treatment with additional medications, which may include streptomycin and ciprofloxacin for almost two years.

Bicyclic nitroimidazoles are known antibacterials, and they are potent agents against *Mycobacterium tuberculosis* bacteria. A series of nitroimidazo[2,1-b]oxazole derivates are reported to exhibit antimicrobial properties, including antitubercular activity (Nagarajan, K. 1989). The compound of formula (a) in which R is ethyl, (i.e. 2-ethyl-5-nitro-2,3-dihydro[2,1-b]imidazo-oxazole, also known as CGI 17341) has been shown to exhibit activity against *Mycobacterium tuberculosis* (Ashtekar, D. 1993). More recently, 2,3-dihydro-6-nitroimidazo[2,1-b]oxazoles (WO 2005/042542 A1 and Sasaki, H. 2006) described by formula (b) were disclosed as agents for the treatment of tuberculosis, wherein $R_1$ represents H, alkyls etc.; $R_2$ is alkoxy, aryloxy etc. Another class of bicyclic nitroimidazoles is nitro-[2,1-b]imidazopyran compounds, which are reported to exhibit antimicrobial properties, including antitubercular activity (U.S. Pat. No. 6,087,358), as shown by formula (c), wherein $R_1$ and $R_2$ are various alkyloxy or aryloxy substituents; X is O, S, $NR_2$ etc.; Y, Z are $CH_2$, $CHR_2$ and heteroatoms etc.

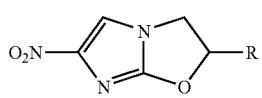

(a)

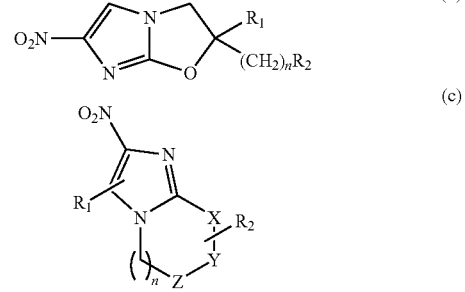

Oxazolidinones are a new class of synthetic antimicrobial agents which kill gram positive pathogens by inhibiting a very early stage of protein synthesis. Oxazolidinones inhibit the formation of ribosomal initiation complex involving 30S and 50S ribosomes leading to prevention of initiation complex formation. Due to their novel mechanism of action, these compounds are active against pathogens resistant to other clinically prescribed antibiotics. WO2006043121 discloses heteroaryl-substituted piperazinyl phenyl oxazolidinones; U.S. Pat. No. 5,736,545 describes azolyl piperazinyl phenyl oxazolidinones; U.S. Pat. No. 5,880,118 discloses substituted oxazine and thiazine oxazolidinone antimicrobials. U.S. Pat. No. 6,968,962 discloses phenyloxazolidinones having a C—C bond to 4-8 membered heterocyclic rings. U.S. Pat. No. 5,981,528 discloses antibiotic oxazolidinone derivatives.

Other earlier publications in the area of oxazolidinones are U.S. Pat. Nos. 4,801,600, 4,921,869, EPA 0352781 (Jan. 31, 1989) and EPA 0316594 (May 24, 1989).

Although oxazolidinones and bicyclic nitroimidazoles are known, there are no references that disclose covalently bonding a phenyl oxazolidinone to a bicyclic nitroimidazole pharmacophore and using the resulting bicyclic nitroimidazole-substituted phenyl oxazolidinones as anti-bacterial agents against aerobic and anaerobic Gram-positive and Gram-negative bacteria, especially mycobacteria and clostridia.

SUMMARY

The present invention pertains to bicyclic nitroimidazole-substituted phenyl oxazolidinones that show surprisingly synergistic effects against *Mycobacterium tuberculosis* under anaerobic growth conditions.

The inventive hybrid compounds are dual-functional antimicrobials acting as both an oxazolidinone and a nitroimidazole without in vivo biotransformations. The present invention also relates to a method of preparing pharmacologically active bicyclic nitroimidazole-substituted phenyl oxazolidinones and various intermediates used in the method. The inventive bicyclic nitroimidazole-substituted phenyl oxazolidinones are useful as antimicrobial agents effective against a number of human and veterinary aerobic and anaerobic Gram positive, Gram negative pathogens, including the Staphylococci, for example *S. aureus*; Enterococci, for example *E. faecalis*; Streptococci, for example *S. pneumoniae*; *Haemophilus*, for example *H. influenza*; *Moraxella*, for example *M. catarrhalis*; and *Escherichia* for example *E. coli*; Mycobacteria, for example *M. tuberculosis*; *Helicobacter*, for example *H. pylori*; *Clostridium*, for example *C. difficile*; *Bacteroides* for example, *B. fragilis*, *B. vulgates*; intercellular microbes, for example *Chlamydia* and *Rickettsiae*; and *Mycoplasma*, for example *M. pneumoniae*, and others. The inventive bicyclic nitroimidazole-substituted phenyl oxazolidinones show surprising activity against anaerobes, and therefore may be used as agents effective in the treatment of pathogenic infections, such as infections of mycobacteria, *Clostridium, Cryptosporidium* or *Helicobacter*. The present invention also relates to pharmaceutical compositions containing the bicyclic nitroimidazole-substituted phenyl oxazolidinones, as well as to methods of treating and preventing bacterial infections using such compositions.

In its principle embodiment, the current invention provides a series of bicyclic nitroimidazole-substituted phenyl oxazolidinones represented by general formula I:

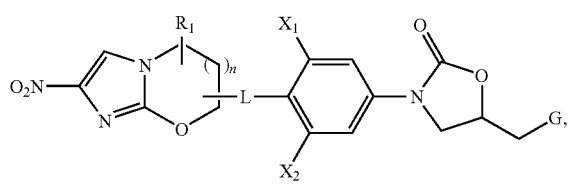

or a pharmaceutically acceptable salt thereof;

wherein $R_1$ is hydrogen, $(C_1-C_6)$alkyl, aryl, heteroaryl, or heterocycloalkyl; n is 0, 1, or 2; $X_1$ and $X_2$ are independently H, $CF_3$, Cl, $OCF_3$ or F; G is —OH, -substituted or unsubstituted triazole, heteroaryl or —$NHCOR_2$; $R_2$ is $(C_1-C_6)$alkyl, cycloalkyl, aryl, or heteroaryl; L is a bond, or a linker group selected from one or a combinations of two to five of the following groups:

1) $(C_1-C_6)$alkylene,
2) $(C_3-C_8)$cycloalkylene,
3) arylene,
4) heteroarylene,
5) heterocycloalkylene containing one to three heteroatoms,
6) —C(=O)—,
7) —O—,
8) —S(O)$_n$—, wherein n is number 0, 1, or 2,
9) —N($R_3$)—,
10) C($R_4$)=C($R_5$)—, wherein the carbon or nitrogen atoms of the linker group is optionally substituted by one to three substituents; $R_3$, $R_4$ and $R_5$ are hydrogen, $(C_1-C_6)$alkyl, aryl, heteroaryl, or heterocycloalkyl; $R_4$ and $R_5$ can join together to form a bond.

Another aspect of the present invention is to provide a pharmaceutical composition containing a compound of formula (I) and a pharmaceutically acceptable carrier, diluent, or excipient.

One other aspect of the present invention is to provide a method of treating microbial infections in a mammal comprising administering to the mammal the pharmaceutical composition containing pharmaceutically effective amount of a compound of formula (I).

DETAILED DESCRIPTION OF PREFERRED EMBODIMENTS

Figure 1:
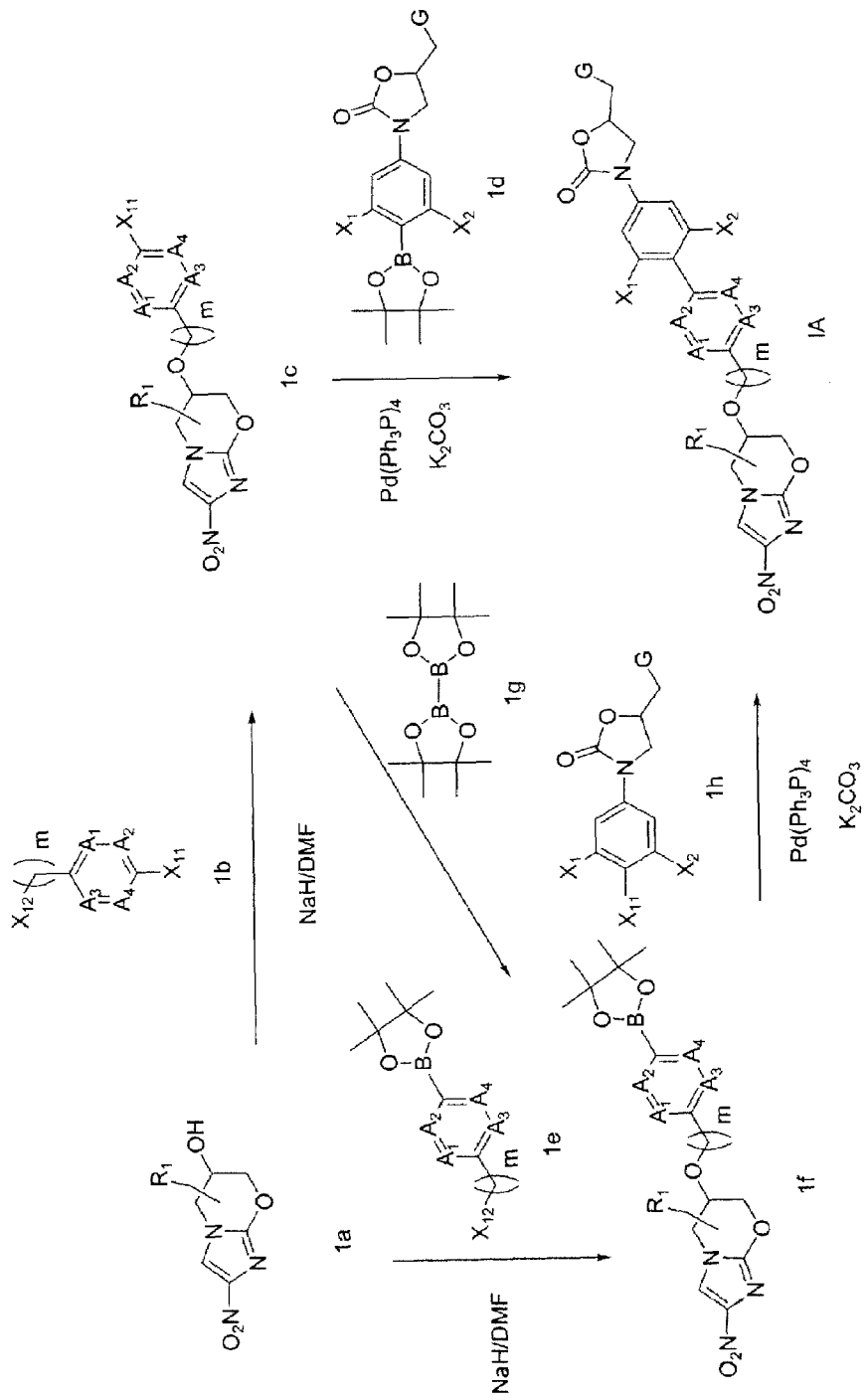
FIG. 1 shows a general method of synthesizing bicyclic nitroimidazole-substituted phenyl oxazolidinones of formula (I) having either 1, 3 or 1,4-substituted arylene or heteroarylene in the linkage group "L".
Figure 2:
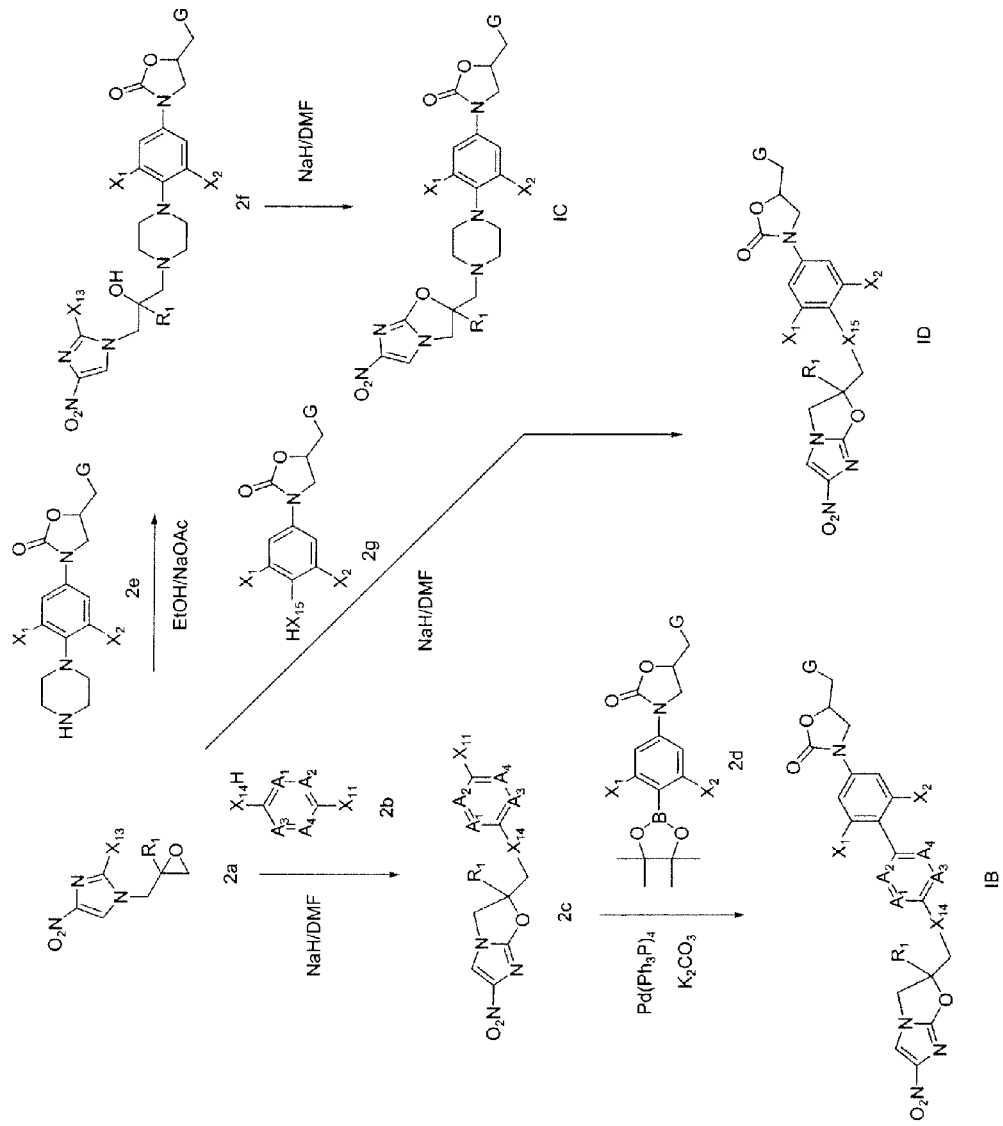
FIG. 2 shows another general method of synthesizing bicyclic nitroimidazole-substituted phenyl oxazolidinones of formula (I) having various linker groups "L" and having a bicyclic nitroimidazooxazole pharmacophore.

As used herein, the terms and phrases have the meanings and definitions known in the art. Some of the more commonly used phrases are described in more detail below.

The carbon atom content of various hydrocarbon-containing moieties is indicated by a prefix designating the minimum and maximum number of carbon atoms in the moiety, i.e., the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "alkyl," as used herein, refers to a monovalent radical of saturated, straight or branched chain hydrocarbon group. Examples of alkyl groups include methyl, ethyl, propyl, iso-propyl, n-butyl, iso-butyl, tert-butyl, neo-pentyl, and n-hexyl. The alkyl groups of this invention are optionally substituted. The preferred alkyl group of this invention has one to six carbons.

The term "alkenyl," as used herein, refers to a monovalent radical of unsaturated, straight or branched chain hydrocarbon group with at least one C=C double bond. Examples of alkenyl group include allyl or propenyl, butenyl, isobutenyl, pentenyl and the likes. The alkenyl groups of this invention are optionally substituted.

The term "alkynyl," as used herein, refers to a monovalent radical of unsaturated, straight or branched chain hydrocarbon group with at least one C≡C triple bond. Examples of alkynyl group include propargyl, butynyl, isobutynyl, pentynyl and the likes. The alkynyl groups of this invention are optionally substituted.

The term "alkylene," "alkenylene" or "alkynylene" as used herein, refers to bivalent radicals of alkyl, alkenyl, or alkynyl group as defined above. Examples of alkylene groups include methylene, ethylene, propylene, iso-propylene, n-butylene, isobutylene, n-hexylene and the like. Examples of alkenylene groups include ethenylene, propenylene and the like. Examples of alkynylene groups include ethynylene, propynylene and the like. The "alkylene," "alkenylene" or "alkynylene" groups of this invention are optionally substituted.

The term "alkylamino," as used herein, refers to an amino group (—$NH_2$), wherein one hydrogen atom is replaced by an alkyl group. Examples of alkylamino include methylamino, ethylamino, propylamino, and isopropylamino.

The term "alkylthio," as used herein, refers to an alkyl group, as defined herein, attached to a sulfur atom. Examples of alkylthio include methylthio, ethylthio, propylthio, and isopropylthio.

The term "alkoxy," as used herein, refers to an alkyl group, as previously defined, attached to an oxygen atom. Examples of alkoxy include methoxy, ethoxy, propoxy, iso-propoxy, n-butoxy, tert-butoxy, neo-pentoxy and n-hexyloxy. The alkoxy groups of this invention are optionally substituted.

The term "aryl" as used herein refers to a monovalent radical of carbocyclic aromatic group including phenyl, naphthyl, and anthracenyl. The aryl groups of this invention are optionally substituted.

The term "arylene" as used herein refers to bivalent radical of aryl group as defined above, which are optionally substituted, such as phenylene.

The term "cycloalkyl," as used herein, refers to a monovalent radical of saturated carbocyclic group having three to eight carbons such as cyclopropyl, cyclobutyl, cyclopentyl, cyclohexyl, cycloheptyl and cyclooctyl. The cycloalkyl groups of this invention are optionally substituted.

The term "cycloalkylene," as used herein, refers to bivalent radical of saturated carbocyclic groups having three to eight carbons. The cycloalkylene groups of this invention are optionally substituted.

The term "halogen," or "halide" as used herein, refers to fluorine, chlorine, bromine and iodine atoms and the term "halo" refers to —F, —Cl, —Br, and —I as substituent.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole. The heteroaryl groups of this invention are optionally substituted.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene groups are optionally substituted.

The term "heteroatom," as used herein, refers to an oxygen, nitrogen or sulfur atom.

The term "heterocycloalkyl" as used herein, refers to a non-aromatic five-, six- or seven-membered ring or a bi- or tricyclic group having one or more heteroatoms independently selected from oxygen, sulfur and nitrogen wherein each 5-membered ring has zero to one double bonds and each six-membered ring has zero to 2 double bonds. The nitrogen and sulfur heteroatoms are optionally be oxidized, the nitrogen heteroatom can optionally be quaternized, and any of the above heterocyclic rings can be fused to an aryl or heteroaryl ring. Representative heterocycloalkyls include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofuranyl. The heterocycloalkyl groups of this invention are optionally substituted with one, two, or three substituents independently selected from —F, —Cl, —OH, —$NO_2$, —CN, —C(O)-alkyl, —C(O)-aryl, —C(O)-heteroaryl, —$CO_2$-alkyl, —$CO_2$-aryl, —$CO_2$-heteroaryl, —C(O)$NH_2$, —C(O)NH-alkyl, —C(O)NH-aryl, —C(O)NH-heteroaryl, —OC(O)-alkyl, —OC(O)-aryl, —OC(O)-heteroaryl, —OC(O)$NH_2$, —OC(O)NH-alkyl, —OC(O)NH-aryl, —OCONH-heteroaryl, —NHC(O)-alkyl, —NHC(O)-aryl, —NHC(O)-heteroaryl, —$NHCO_2$-alkyl, —$NHCO_2$-aryl, —$NHCO_2$-heteroaryl, —NHC(O)$NH_2$, —NHC(O)NH-alkyl, —NHC(O)NH-aryl, —NHC(O)NH-heteroaryl, —$SO_2$-alkyl, —$SO_2$-aryl, —$SO_2$-heteroaryl, —$SO_2NH_2$, —$SO_2$NH-alkyl, —$SO_2$NH-aryl, —$SO_2$NH-heteroaryl, -alkyl, -cycloalkyl, -cycloheteroalkyl, —$CF_3$, —$CH_2$OH, $CH_2NH_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "heterocycloalkylene" as used herein, refers to a bivalent heterocycloalkyl group as defined above. The heterocycloalkylene groups of this invention can be optionally substituted.

The term "hydroxyl" as used herein, refers to —OH.

The term "optional", "optionally" or "optionally substituted" means that the subsequently described event or circumstance may, but need not, occur, and that the description includes instances where the event or circumstance occurs and instances in which it does not. For example, "aryl group optionally substituted with one to three substituents" means that the substituents may but need not be present, and the description includes situations where the aryl group is mono-, di-, or tri-substituted with substituents and situations where the aryl group is not substituted with the substituent group.

The term "substituent," as used herein, refers to —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted," as used herein, refers to having one or more substituents covalently attached.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof.

A "pharmaceutically acceptable carrier, diluent, or excipient" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes: preventing the disease, i.e. causing the clinical symptoms of the disease not to develop in a mammal that may be exposed to or predisposed to the disease but does not yet experience or display symptoms of the disease, inhibiting the disease, i.e., arresting or reducing the development of the disease or its clinical symptoms, or relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Leaving group" has the meaning conventionally associated with it in synthetic organic chemistry i.e., an atom or group capable of being displaced by a nucleophile and includes halogen, alkylsulfonyloxy, ester, or amino such as chloro, bromo, iodo, mesyloxy, tosyloxy, trifluorosulfonyloxy, methoxy, N,O-dimethylhydroxyl-amino, and the like.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

In its principle embodiment, the current invention provides a series of nitroimidazole-substituted phenyl oxazolidinones represented by general formula I:

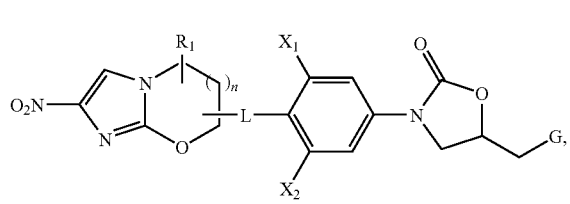

I or a pharmaceutically acceptable salt thereof, wherein R$_1$ is hydrogen, (C$_1$-C$_6$)alkyl, aryl, heteroaryl, or heterocycloalkyl; n is 0, 1, or 2; X$_1$ and X$_2$ are independently H, CF$_3$, Cl, OCF$_3$ or F; G is —OH, -substituted or unsubstituted triazole, heteroaryl or —NHCOR$_2$; R$_2$ is (C$_1$-C$_6$)alkyl, cycloalkyl, aryl, or heteroaryl; L is a bond, or a linker group selected from one or a combinations of two to five of the following groups:
1) (C$_1$-C$_6$)alkylene,
2) (C$_3$-C$_8$)cycloalkylene,
3) arylene,
4) heteroarylene,
5) heterocycloalkylene containing one to three heteroatoms,
6) —C(=O)—,
7) —O—,
8) —S(O)$_n$—, wherein n is number 0, 1, or 2,
9) —N(R$_3$)—,
10) (R$_4$)=C(R$_5$)—, wherein the carbon or nitrogen atoms of the linker group is optionally substituted by one to three substituents; R$_3$, R$_4$ and R$_5$ are hydrogen, (C$_1$-C$_6$)alkyl, aryl, heteroaryl, or heterocycloalkyl; R$_4$ and R$_5$ can join together to form a bond.

Preferred compounds of the invention of formula (I) are those wherein L is a bond or a group selected from one or a combination of two to three structural elements of:

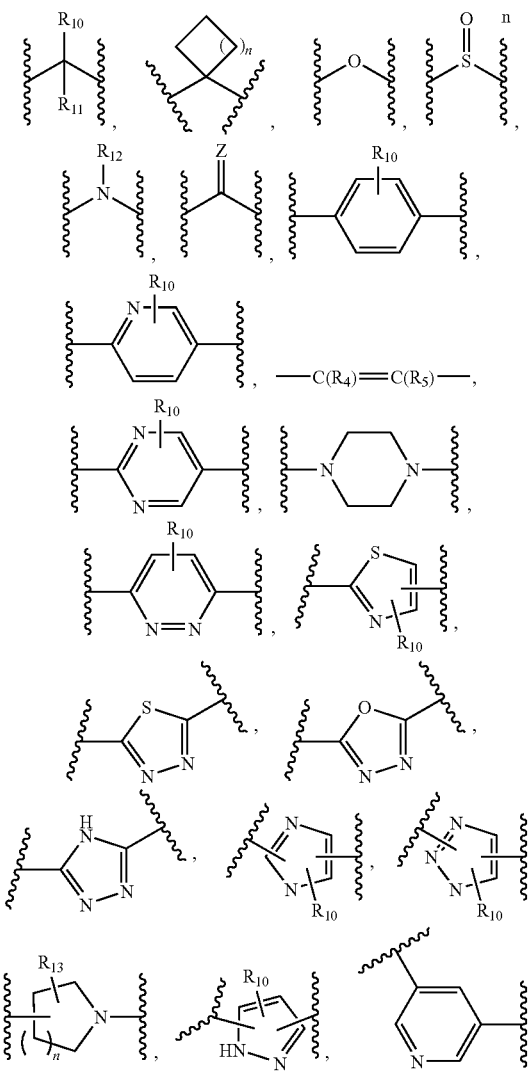

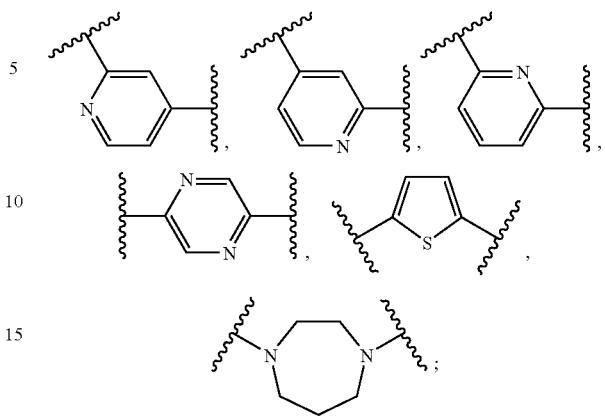

wherein R$_{10}$, R$_{11}$, R$_{12}$ and R$_{13}$ are independently H, hydroxyl, amino, alkyl, alkylamino, alkoxy, aryl, heteroaryl that are optionally substituted; R$_{13}$ in conjunction with nitroimidazole ring can form a spiro cyclic structure, such as,

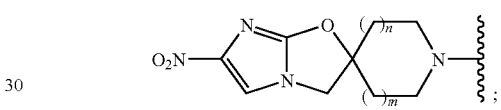

m and n are independently a number 0, 1 or 2; Z is O, S, CR$_{14}$R$_{15}$, wherein R$_{14}$ and R$_{15}$ are independently H, alkyl, aryl or heteroaryl group; and G is hydroxyl, —NHCOCH$_3$, triazole.

More preferred compounds of the present invention are those represented by general formula II:

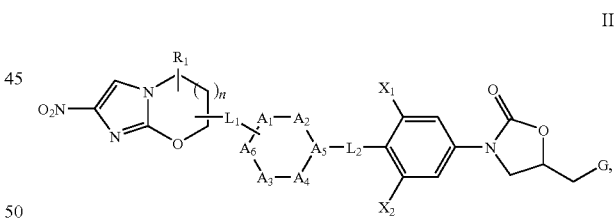

or a pharmaceutically acceptable salt thereof, wherein A$_1$ through A$_6$ are independently selected from a bond, heteroatom or carbon optionally substituted with or without a substituent; L$_1$ and L$_2$ are independently selected from a bond,

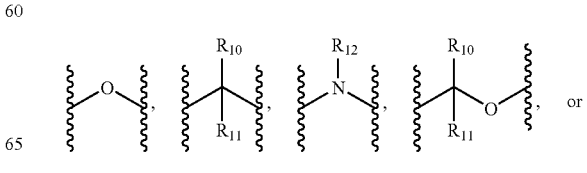

-continued

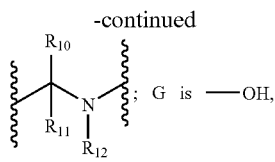; G is —OH,

-substituted or unsubstituted triazole, or —NHCOCH$_3$; with the proviso that A$_1$ through A$_6$ are not more than two (2) consecutive heteroatoms.

The most preferred group of compounds are: (S,S)—N-{3-[3-Fluoro-4-(4-{2-[4-(2-nitro-6,7-dihydro-5H-imidazo[2,1-b][1,3]oxazin-6-yloxymethyl)-phenoxy]-acetyl}-piperazin-1-yl)-phenyl]-2-oxo-oxazolidin-5-ylmethyl}-acetamide; (S,S)—N-(3-{3-Fluoro-4-[4-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide; (S,S)—N-(3-{3-Fluoro-4-[3-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide; (S,S)—N-(3-{3-Fluoro-4-[5-(2-nitro-6,7-dihydro-5H-imidazo[2,1-b][1,3]oxazin-6-yloxymethyl)-pyridin-2-yloxy]-phenyl}-2-oxo-oxazolidin-5-ylmethyl)-acetamide; (S,S)—N-(3-{3-Fluoro-4-[4-(2-nitro-6,7-dihydro-5H-imidazo[2,1-b][1,3]oxazin-6-yloxymethyl)-phenoxy]-phenyl}-2-oxo-oxazolidin-5-ylmethyl)-acetamide; (S,S)—N-[3-(3-Fluoro-4-{1-[4-(2-nitro-6,7-dihydro-5H-imidazo[2,1-b][1,3]oxazin-6-yloxymethyl)-benzyl]-1H-[1,2,3]triazol-4-ylmethoxy}-phenyl)-2-oxo-oxazolidin-5-ylmethyl]-acetamide; (S,S)—N-(3-{3-Fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide; (S,S)—N-(3-{3-Fluoro-4-[2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide; (S,S)—N-(3-{3-Fluoro-4-[2-(2-nitro-6,7-dihydro-5H-imidazo[2,1-b][1,3]oxazin-6-yloxy)-pyridin-4-yl]-phenyl}-2-oxo-oxazolidin-5-ylmethyl)-acetamide; N-(3-{3-Fluoro-4-[5-(2-methyl-6-nitro-2,3-dihydro-imidazo[2,1-b]oxazol-2-ylmethoxy)-pyridin-3-yl]-phenyl}-2-oxo-oxazolidin-5-ylmethyl)-acetamide; (S,S)—N-(3-{3-Fluoro-4-[5-(2-nitro-6,7-dihydro-5H-imidazo[2,1-b][1,3]oxazin-6-yloxymethyl)-pyridin-2-yl]-phenyl}-2-oxo-oxazolidin-5-ylmethyl)-acetamide; (S,S)—N-(3-{3-Fluoro-4-[6-(2-nitro-6,7-dihydro-5H-imidazo[2,1-b][1,3]oxazin-6-yloxymethyl)-pyridin-3-yl]-phenyl}-2-oxo-oxazolidin-5-ylmethyl)-acetamide; (S,S)—N-(3-{3-Fluoro-4-[6-(2-nitro-6,7-dihydro-5H-imidazo[2,1-b][1,3]oxazin-6-yloxy)-pyridazin-3-yl]-phenyl}-2-oxo-oxazolidin-5-ylmethyl)-acetamide; (S,S)—N-(3-{3-Fluoro-4-[4-morpholin-4-yl-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide; (S,S)—N-(3-{3-Fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide; (S,S)—N-(3-{4-[4-Dimethylamino-2-(2-nitro-6,7-dihydro-5H-imidazo[2,1-b][1,3]oxazin-6-yloxy)-pyrimidin-5-yl]-3-fluoro-phenyl}-2-oxo-oxazolidin-5-ylmethyl)-acetamide; (S,S)-5-{4-[5-(Acetylamino-methyl)-2-oxo-oxazolidin-3-yl]-2-fluoro-phenyl}-2-(2-nitro-6,7-dihydro-5H-imidazo[2,1-b][1,3]oxazin-6-yloxy)-nicotinic acid methyl ester; (S,S)-5-{4-[5-(Acetylamino-methyl)-2-oxo-oxazolidin-3-yl]-2-fluoro-phenyl}-2-(2-nitro-6,7-dihydro-5H-imidazo[2,1-b][1,3]oxazin-6-yloxy)-nicotinic acid; (S,S)—N-(3-{3-Fluoro-4-[4-(2-nitro-6,7-dihydro-5H-imidazo[2,1-b][1,3]oxazin-6-yloxy)-pyrimidin-2-yl]-phenyl}-2-oxo-oxazolidin-5-ylmethyl)-acetamide; (S,S)—N-(3-{3-Fluoro-4-[2-(2-nitro-6,7-dihydro-5H-imidazo[2,1-b][1,3]oxazin-6-yloxy)-pyrimidin-4-yl]-phenyl}-2-oxo-oxazolidin-5-ylmethyl)-acetamide; (S,S)—N-(3-{3-Fluoro-4-[5-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide; (S,S)—N-(3-{3-Fluoro-4-[2-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide; N-(3-{3-Fluoro-4-[5-(2-methyl-6-nitro-2,3-dihydro-imidazo[2,1-b]oxazol-2-ylmethoxy)-pyridin-2-yl]-phenyl}-2-oxo-oxazolidin-5-ylmethyl)-acetamide; (S,S)—N-(3-{3-Fluoro-4-[4-(4-methoxy-benzyloxy)-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide; (S,S)—N-(3-{3-Fluoro-4-[2-(2-nitro-6,7-dihydro-5H-imidazo[2,1-b][1,3]oxazin-6-yloxy)-6-oxo-1,6-dihydro-pyrimidin-5-yl]-phenyl}-2-oxo-oxazolidin-5-ylmethyl)-acetamide; (S,S)—N-(3-{3-Fluoro-4-[2-(2-nitro-6,7-dihydro-5H-imidazo[2,1-b][1,3]oxazin-6-yloxy)-4-trifluoromethyl-pyrimidin-5-yl]-phenyl}-2-oxo-oxazolidin-5-ylmethyl)-acetamide; (S,S)—N-{3-[2,6-Difluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide; N-{3-[4-(6-Nitro-imidazo[2,1-b]-2(3H)-8-aza-spiro[4,5]dec-8-yl)-3-fluorophenyl]-2-oxo-oxazolidin-5(S)-ylmethyl}-acetamide; (S,R)-3-[2-Fluoro-4'-(2-nitro-6,7-dihydro-5H-imidazo[2,1-b][1,3]oxazin-6-yloxymethyl)-biphenyl-4-yl]-5-hydroxymethyl-oxazolidin-2-one; (S,R)-3-{3-Fluoro-4-[2-(2-nitro-6,7-dihydro-5H-imidazo[2,1-b][1,3]oxazin-6-yloxy)-pyrimidin-5-yl]-phenyl}-5-hydroxymethyl-oxazolidin-2-one; (S,R)-3-{3-Fluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one; (S,S)—N-{3-[2-Fluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide; (S,S)—N-[3-(3-Fluoro-4-{4-[2-(2-nitro-6,7-dihydro-5H-imidazo[2,1-b][1,3]oxazin-6-yloxy)-acetyl]-piperazin-1-yl}-phenyl)-2-oxo-oxazolidin-5-ylmethyl]-acetamide; N-(3-{3-Fluoro-4-[4-(2-methyl-6-nitro-2,3-dihydro-imidazo[2,1-b]oxazol-2-ylmethyl)-piperazin-1-yl]-phenyl}-2-oxo-oxazolidin-5-ylmethyl)-acetamide; (S,R)-3-[2-Fluoro-4'-(2-nitro-6,7-dihydro-5H-imidazo[2,1-b][1,3]oxazin-6-yloxymethyl)-biphen-4-yl]-5-[1,2,3]triazol-1-ylmethyl-oxazolidin-2-one; (S,R)-3-{3-Fluoro-4-[6-(2-nitro-6,7-dihydro-5H-imidazo[2,1-b][1,3]oxazin-6-yloxymethyl)-pyridin-3-yl]-phenyl}-5-[1,2,3]triazol-1-ylmethyl-oxazolidin-2-one; N-{3-[2-Fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide; N-{3-[2-Fluoro-3'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide; N-{3-[2'-Chloro-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide; N-{3-[3'-Chloro-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide; N-{3-[3'-Cyano-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide; N-(3-{2-Fluoro-4'-[(2-methyl-6-nitro-2,3-dihydro-imidazo[2,1-b]oxazol-2-ylmethyl)-amino]-biphenyl-4-yl}-2-oxo-oxazolidin-5-ylmethyl)-acetamide; (S,S)—N-(3-{3-Fluoro-4-[3-(2-nitro-6,7-dihydro-5H-imidazo[2,1-b][1,3]oxazin-6-yloxy)- propenyl]-phenyl}-2-oxo-oxazolidin-5-ylmethyl)-acetamide; (E)-N-(3-{3-Fluoro-4-[2-(2-nitro-6,7-dihydro-5H-imidazo[2,1-b][1,3]oxazin-6(S)-yloxy)-vinyl]-phenyl}-2-oxo-oxazolidin-5(S)-ylmethyl)-acetamide; N-(3-{3-Fluoro-4-[1-(2-nitro-6,7-dihydro-5H-imidazo[2,1-b][1,3]oxazin-6(S)-yloxymethyl)-vinyl]-phenyl}-2-oxo-oxazolidin-5(S)-ylmethyl)-acetamide; N-(3-{3-Fluoro-4-[2-(2-nitro-6,7-dihydro-5H-imidazo[2,1-b][1,3]oxazin-6-yloxy)-acetyl]-phenyl}-2-oxo-oxazolidin-5-ylmethyl)-acetamide; N-(3-{3-Fluoro-4-[1-hydroxy-1-hydroxymethyl-2-(2-nitro-6,7-dihydro-5H-imidazo[2,1-b][1,3]oxazin-6-yloxy)-ethyl]-phenyl}-2-oxo-oxazolidin-5-ylmethyl)-acetamide; (S,S)—N-(3-{3-Fluoro-4-[3-(2-nitro-6,7-dihydro-5H-imidazo[2,1-b][1,3]oxazin-6-yloxy)-prop-1-ynyl]-phenyl}-2-oxo-oxazolidin-5-ylmethyl)-acetamide; (S,S)—N-{3-[2,2'-Difluoro-5'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide; (S,S)—N-{3-[2-Fluoro-3'-(2-nitro-6,7-dihydro-5H-imidazo[2,1-b][1,3]oxazin-6-loxymethyl)-biphenyl-4-yl]-2-oxo-oxazolidin-5-ylmethyl}-acetamide; and N-{3-[3-Fluoro-4-(2-methyl-6-nitro-2,3-dihydro-imidazo[2,1-b]oxazol-2-ylmethoxy)-phenyl]-2-oxo-oxazolidin-5-ylmethyl}-acetamide, and their pharmaceutically acceptable salts thereof.

The bicyclic nitroimidazole-substituted phenyl oxazolidinones of the present invention can be prepared by following general synthetic schemes.

Scheme 1, shown in FIG. 1, illustrates a general method of synthesizing bicyclic nitroimidazole-substituted phenyl oxazolidinones (IA) of formula (I) having either 1,3 or 1,4-substituted arylene or heteroarylene in the linkage group "L". Bicyclic nitroimidazoles, such as nitroimidazooxine (1a), prepared similarly by following the synthesis disclosed in U.S. Pat. No. 6,087,358, undergoes substitution reaction with either 1, 3 or 1,4-substituted aryl or heteroaryl compound (1b), wherein $A_1$, $A_2$, $A_3$ and A4 are selected from a bond, N, O or carbon having optional substituent attached; $X_{11}$ is Cl, Br or I; $X_{12}$ is a leaving group; m is 0 or 1; in organic solvent, such as DMF, in the presence of a base, such as sodium hydride, at a temperature range of –80° C. to 80° C., to give ether compound (1c). The ether compound (1c) is coupled to phenyloxazolidinone boronic ester compound (1d) (prepared as described by U.S. Pat. No. 7,129,259 or WO 2004/078753), under the biaryl coupling (or Suzuki, or palladium catalysis) conditions, such as in organic or aqueous organic solvent, like THF or DMF and water, in the presence of a catalyst, such as palladium tetrakistriphenylphosphine (Pd $(Ph_3P)_4$), and a base, such as potassium carbonate, at a temperature from rt to 110° C. to produce bicyclic nitroimidazole-substituted phenyl oxazolidinone (IA) of this invention.

Alternative synthesis of bicyclic nitroimidazole-substituted phenyl oxazolidinone (IA) is through substitution reaction of the compound (1a) with either 1, 3 or 1,4-substituted aryl or heteroaryl boronic ester compound (1e) having a leaving group $X_{12}$ to give ether compound (1f). The reaction is carried out similarly to the transformation of compound (1a) to ether compound (1c). The boronic ester compound (1f) is optionally prepared from ether compound (1c) and diboronic ester (1g) under the similar palladium catalyzed (or Suzuki) coupling conditions as described above. The resulting compound (1f) is coupled to halo-substituted phenyl oxazolidinone (1h) (prepared as described by WO 2006/038100), under the similar Suzuki conditions to produce bicyclic nitroimidazole-substituted phenyl oxazolidinone (IA) of this invention.

Scheme 2 illustrates another general method of synthesizing bicyclic nitroimidazole-substituted phenyl oxazolidinones of formula (I) having various linker groups "L" and having a bicyclic nitroimidazooxazole pharmacophore. Bicyclic nitroimidazole-substituted phenyl oxazolidinones of formula (IB) having arylene or heteroarylene linker group are prepared from nitroimidazole epoxide (2a). The synthesis of nitroimidazole epoxide (2a) is disclosed (Sasaki, H. 2006). Epoxide ring opening, followed by ring closure are carried out by reaction with either 1, 3 or 1,4-substituted aryl or heteroaryl compound (2b) having a nucleophile $X_{14}$, wherein $X_{14}$ is O, NH or S, is carried out in the presence or absence of a base, such as sodium hydride, in organic solvent, such as DMF, ethanol, at a temperature range of –80° C. to 100° C., to produce bicyclic nitroimidazooxazole derivative compound (2c). In cases where $X_{14}$ is NH, the reaction is optionally carried out in the presence of a copper salt, such as cuprous bromide. Coupling the phenyl oxazolidinone boronic ester derivative (2d) under the Suzuki conditions as before generate compound (IB). Bicyclic nitroimidazole-substituted phenyl oxazolidinones of formula (IC) having a piperazine group in the linker "L" is prepared also from nitroimidazole epoxide (2a). The synthesis of phenyl oxazolidinone piperazine (2e) is known in the art (U.S. Pat. No. 5,547,950 or Brickner 1996). Epoxide opening with phenyl oxazolidinone piperazine is affected in such as, ethanol, in the presence or absence of a base, such as sodium acetate, at a temperature range from room temperature to 100° C. The resultant aminoalcohol (2f) is treated with a base, such as sodium hydride in organic solvent, such as DMF to generate compound (IC). Bicyclic nitroimidazole-substituted phenyl oxazolidinones of formula (ID) having an ether or sulfide linker group are prepared from nitroimidazole epoxide (2a) and phenyl oxazolidinone (2g) having a nucleophile $X_{15}$, wherein $X_{15}$ is O, NH, or S (prepared as described by US Pub. No. US2007/0155714). The preparation is carried out in solvent, such as DMF and in the presence or absence of a base, such as sodium hydride, or similarly as described (Sasaki, H. et al: Journal of Medicinal Chemistry (2006), 49(26), 7854-7860).

Figure 3:
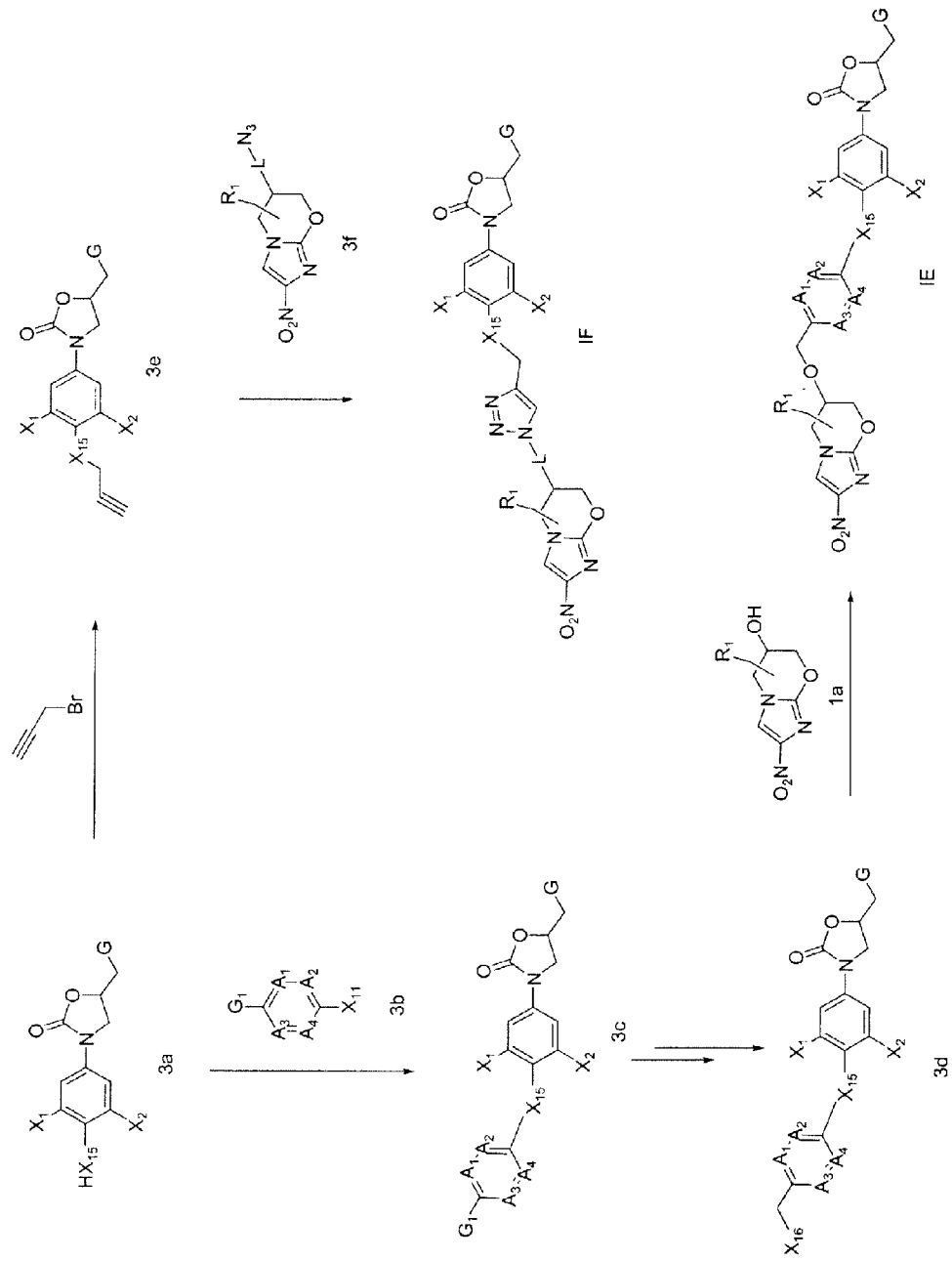
FIG. 3 shows another general method of synthesizing bicyclic nitroimidazole-substituted phenyl oxazolidinones of formula (I) having various arylene or heteroarylene group in linker "L" and having a bicyclic nitroimidazooxazole pharmacophore.

Scheme 3, shown in FIG. 3, illustrates yet another general method of synthesizing bicyclic nitroimidazole-substituted phenyl oxazolidinones of formula (I) having various arylene or heteroarylene group in linker "L" and having a bicyclic nitroimidazooxazole pharmacophore. Bicyclic nitroimidazole-substituted phenyl oxazolidinones of formula (IE) having arylene or heteroarylene linker group and a heteroatom $X_{15}$, as defined above, are prepared from heteroatom-substituted phenyl oxazolidinones (3a) (prepared similarly as described by US2007/0155714). Aryl substitution with the compound (3b), having a leaving group $X_{11}$ and an electron-withdrawing group $G_2$, such as a carboxaldehyde, or an ester, gives coupling product (3c). The reaction is carried out in a solvent, such as DMF or DMSO, in the presence of a base, such as potassium carbonate, or cesium carbonate, and in the presence or absence of a phase-transfer catalyst, such as tetrabutyl ammonium bromide at temperature range from room temperature to 200° C. The carboxaldehyde or ester group $G_2$ is transformed to an alcohol, utilizing a reducing agent, such as sodium borohydride, in a solvent, such as ethanol, followed by further transformation of the reduction product (3c) to compound (3d), having a leaving group $X_{16}$, such as a methanesulfonate, or a halide. Coupling of the compound (3d) with bicyclic nitroimidazole (1a) done as before produces bicyclic nitroimidazole-substituted phenyl oxazolidinones of formula (IE). The inventive bicyclic nitroimidazole-substituted phenyl oxazolidinone of formula (IF) is prepared by reaction of propargyl bromide with compound (3a). Displacement of bromide gives the compound (3e), which reacts with an azido-substituted bicyclic nitroimidazole (3f), in the presence of a copper catalyst, such as copper sulfate, to give bicyclic nitroimidazole-substituted phenyl oxazolidinone of formula (IF) having a triazole in the linker group "L".

Figure 4:
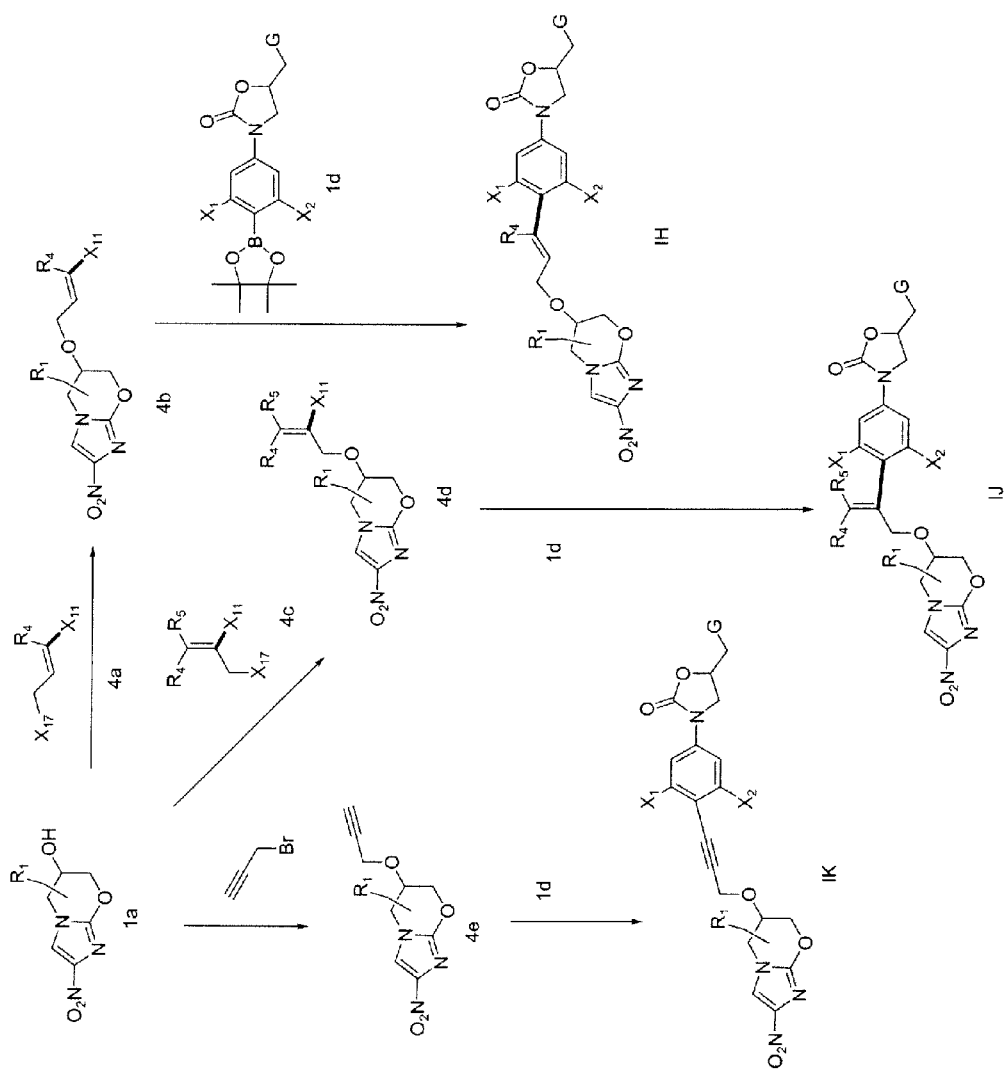
FIG. 4 shows another general method of synthesizing bicyclic nitroimidazole-substituted phenyl oxazolidinones of formula (I) having various alkylene, alkenylene or alkynylene group in the linker "L" and having a bicyclic nitroimidazooxazole pharmacophore.

Scheme 4, shown in FIG. 4, illustrates yet another general method of synthesizing bicyclic nitroimidazole-substituted phenyl oxazolidinones of formula (I) having various alkylene, alkenylene or alkynylene group in the linker "L" and having a bicyclic nitroimidazooxazole pharmacophore. Alkylation of the compound (1a) with an allyl halide or compounds with other leaving group $X_{17}$ (4a) to give the compound (4b), which is carried out in a solvent, such as DMF, and in the presence of a base, such as sodium hydride at temperature from rt to 80° C. The compound (4b) is coupled to phenyl oxazolidinone boronic ester (Id) under the similar palladium catalysis conditions as defined above (or Suzuki) to give bicyclic nitroimidazole-substituted phenyl oxazolidinones of formula (IH). Similar reaction sequences with different substituted allyl halide or the likes produce bicyclic nitroimidazole-substituted phenyl oxazolidinones of formula (IJ) and (IK) of the inventive compounds of the formula (I).

The above syntheses schemes are preferred schemes for the synthesis of bicyclic nitroimidazole-substituted phenyl oxazolidinones. It is apparent to one skilled in art that other sequence of the reactions, and alternative reagents can be used for the synthesis of the same. These alternatives are within the scope of this invention.

The preferred compounds of the present invention are optically pure diastereomer having the (S) or (R)-configuration in either the linker "L" or both phenyl oxazolidinone and nitroimidazole pharmacophore. It is known in the art that one diastereomers is superior to the other in activity. However, the racemic mixture also is useful, although a greater amount of the racemic material may be required to produce the same effect as the pure diastereomer.

If desired, the mixture of pure diastereomer is resolved by means known to those skilled in the art. Single pure material can be obtained by resolution of the diastereomeric mixture by HPLC. Alternatively, resolution of the racemic mixture can be accomplished by selective crystallization of a salt form using methods known to those skilled in the art.

A compound of formula (I), or a prodrug or a pharmaceutically acceptable salt or solvate thereof, can be administered as the neat compound or as a pharmaceutical composition containing the inventive compound.

The pharmaceutical compositions of the present invention can be prepared by admixing a compound of formula (I) with a solid or liquid pharmaceutically acceptable carrier, and, optionally, with pharmaceutically acceptable adjuvants and excipients employing standard and conventional techniques. Solid form compositions include powders, tablets, dispersible granules, capsules, cachets and suppositories. A solid carrier can be at least one substance, which also can function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, a low melting wax, cocoa butter, and the like. Liquid form compositions include solutions, suspensions, and emulsions. For example, compounds of the present invention can be dissolved in water, water-propylene glycol, or water-polyethylene glycol, optionally containing suitable conventional coloring agents, flavoring agents, stabilizers and thickening agents. The inventive bicyclic nitroimidazole-substituted phenyl oxazolidinones of formula (I) can be used alone, or in conjunction with other antibacterial agents and/or non-antibacterial agents, as known to those skilled in the art.

Humans and other mammals, for example, cattle, horses, sheep, hogs, dogs, and cats, can be treated with the present invention. The present invention can be administered in a manner and in dosage forms similar to those of the known anti-bacterial agents described above. In therapeutic use for treating, or combating, bacterial infections in humans and warm-blooded animals, the compounds of formula (I), or pharmaceutical compositions thereof, are administered by conventional techniques, such as orally in solid and liquid dosage forms and/or parenterally (IV, IM, SC), at a unit dosage form to obtain and maintain a concentration, that is, an amount, or blood-level of active component in the animal undergoing treatment which is antibacterially effective or appropriate.

Generally, the amount of compound (I) in a pharmaceutical composition is about 0.5% to about 90% by weight. An anti-bacterially effective dosage of compound (I) is about 0.1 to about 100 mg/kg of body weight/day, more preferably about 3 to about 50 mg/kg of body weight/day. The quantity of the bicyclic nitroimidazole-substituted phenyl oxazolidinones of formula (I) in the pharmaceutical composition, the exact unit dosage form thereof to be administered, the frequency of administration, and the route of administration will vary, and can be adjusted widely depending upon a number of factors known to those skilled in the art including the particular mode of administration, the particular compound being used, the potency of the particular compound, the desired concentration, the age, weight, sex, and general physical condition and requirements of the patient, the nature and severity of the bacterial infection being treated, and the like, as is well known to the physician treating infectious diseases. Also, it is to be understood that the initial dosage administered can be increased beyond the above upper level in order to rapidly achieve the desired blood-level or the initial dosage can be smaller than the optimum and the daily dosage can be progressively increased during the course of treatment depending on the particular situation. The usual pharmaceutical dosage forms appropriate for parenteral (mixture, suspension in oil) and oral (tablet, capsule, syrup, suspension, etc) administration are known to those skilled in the art.

Compounds of the present invention can be administered by any suitable route, for example by oral, topical, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or infused together with an IV fluid, like 5% dextrose or normal saline.

If the compounds or pharmaceutical compositions of the present invention are administered parenterally, i.e., by injection, for example, by intravenous injection or by other parenteral routes of administration, it generally is as a soluble salt (acid addition salt or base salt) of the compound according to formula (I) in a pharmaceutically acceptable amount dissolved in a pharmaceutically acceptable liquid carrier such as, for example, water-for-injection, and a buffer to provide a suitable buffered isotonic solution, for example, having a pH of about 3.5 to about 10.

Suitable-buffering agents include, for example, trisodium orthophosphate, sodium bicarbonate, sodium citrate, N-methylglucamine, L(+)-lysine, and L(+)-arginine. A compound of formula (I) generally is dissolved in the carrier in an amount sufficient to provide a pharmaceutically acceptable injectable concentration in the range of about 1 to about 400 mg/ml of solution. The resulting liquid pharmaceutical composition is administered so as to obtain the above-mentioned antibacterially effective amount of dosage.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention can be delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances, which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

For topical administration, the present compounds can be applied in neat form, e.g., when the compound is a liquid. However, it is desirable to administer the compounds to the skin as compositions in combination with a dermatologically acceptable carrier, which can be a solid, semi-solid, or a liquid. Useful solid carriers include, but are not limited to, finely divided solids such as talc, clay, microcrystalline cellulose, silica, alumina, and the like. Useful liquid carriers include, but are not limited to, water, alcohols, glycols, and water-alcohol/glycol blends in which the present compounds can be dissolved or dispersed at effective levels, optionally with the aid of a surfactant. Adjuvants, such as fragrances and additional antimicrobial agents, can be added to optimize the properties for a given use. The resultant liquid compositions can be applied topically by absorbent pads, used to impregnate bandages and other dressings, or sprayed onto the affected area using pump-type or aerosol sprayers.

For veterinary use, a compound of formula (I) or a nontoxic sale thereof, is administered as a suitably acceptable formulation in accordance with normal veterinary practice. The veterinarian can readily determine the dosing regimen and route of administration that is most appropriate for a particular animal.

GENERAL METHODS AND DEFINITIONS

All starting material used in these examples are either purchased from commercial sources or prepared according to published procedures. Reagents were purchased from commercial sources and used without further purification. All temperatures are in degrees Centigrade. When solvent pairs are used, the ratios of solvents used are volume/volume (v/v). When the solution of a solid in a solvent is used the ratio of the solid to the solvent is weight/volume (wt/v). Reactions with moisture-sensitive reagents were performed under a nitrogen atmosphere. Concentration of solution or removal of solvent was performed by reduced pressure (in vacuo) rotary evaporation. Flash chromatography is performed using silica gel 60 as normal phase adsorbent or C18 silica gel as reverse phase adsorbent. Thin layer chromatography ("TLC") is performed using pre-coated plates purchased from E. Merck and spots are visualized with long-wave ultraviolet light followed by an appropriate staining reagent. Preparative thin-layer chromatography (TLC) was performed using EM silica gel (SG) 60 $F_{254}$ plates (20×20 cm, thickness 2 mm), bands are visualized with long-wave ultraviolet light lamp. Nuclear magnetic resonance ("NMR") spectra are recorded on a Varian 400

MHz magnetic resonance spectrometer. ¹H NMR refers to proton nuclear magnetic resonance spectroscopy with chemical shifts reported in ppm downfield from tetramethylsilane or using the residual solvent signal (CHCl₃=δ7.27, CH₃OD=δ3.31) as internal standard. ¹H NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electrospray ionization mass spectra are recorded on a Finnegan LCQ advantage spectrometer and reported as M+H or M+Na, referring to protonated molecular ion or its sodium complex.

ABBREVIATIONS

Abbreviations as used herein have the meanings known by one skilled in the art. Specifically, Ac represents acetyl group, BOC represents t-butoxycarbonyl group, Bn represents benzyl group, Bu represents butyl group, Bz represents benzoyl group, Cbz represents benzyloxycarbonyl group, DCM represents dichloromethane, DMAP represents 4-N,N-dimethylaminopyridine, DMF represents N,N-dimethylformamide, DMSO represents dimethyl sulfoxide, Et represents ethyl group, EtOAc represents ethyl acetate, Me represents methyl group, Ph represents phenyl group, Pr represents propyl group, TEA represents triethylamine, TFA represents trifluoroacetic acid, THF represents tetrahydrofuran, and TMS is trimethylsilyl group. The following abbreviations are also used: millimole (mmol), milliliter (mL), milligram (mg), microliter (uL), microgram (ug).

EXAMPLES

The following examples describe how to prepare the various compounds and/or perform the various processes of the invention, and are to be construed as merely illustrative, and not limitations of the preceding disclosure in any way whatsoever. Those skilled in the art will recognize appropriate variations from the procedures both as to reagents and as to reaction conditions and techniques.

Example 1

(S,S)—N-{3-[3-Fluoro-4-(4-{2-[4-(2-nitro-6,7-dihydro-5H-imidazo[2,1-b][1,3]oxazin-6-yloxymethyl)-phenoxy]-acetyl}-piperazin-1-yl)-phenyl]-2-oxo-oxazolidin-5-ylmethyl}-acetamide Step 1. (4-Hydroxymethyl-phenoxy)-acetic acid tert-butyl ester. A suspension of 4-hydroxymethylphenol (3.70 g, 30 mmol), bromoacetic acid tert-butyl ester (6.0 mL, 40 mmol), K₂CO₃ (16.6 g, 120 mmol) in acetonitrile (100 mL) was stirred at 60° C. for 16 h under N₂. The reaction mixtures were filtered, and the solvents were removed under reduced pressure to provide the crude product that was purified by flash chromatography with EtOAc/hexane afforded the title product as oil (6.22 g, 87%). ¹H NMR (400 MHz, CDCl₃) δ 7.29 (d, J=8.0 Hz, 2H), 6.88 (d, J=8.4 Hz, 2H), 4.62 (d, J=5.6 Hz, 2H), 4.52 (s, 2H), 1.49 (s, 9H).

Step 2. (4-Chloromethyl-phenoxy)-acetic acid tert-butyl ester. To a stirred solution of (4-hydroxymethyl-phenoxy)-acetic acid tert-butyl ester (2.38 g, 10 mmol) in methylene chloride (50 mL) at 0° C. under N₂ was added triethylamine (3.5 mL, 25 mmol), followed by MsCl (1.20 mL, 15 mmol). The mixture was stirred at 0° C. for 1 h and at room temperature for 2 hours. The resultant mixture was diluted with methylene chloride and washed with water, 5% K₂CO₃ solution and saturated brine. The organic layer is dried over anhydrous Na₂SO₄, filtered and evaporated to give the title product as oil (2.40 g, 94%). ¹H NMR (400 MHz, CDCl₃) δ7.32 (d, J=8.4 Hz, 2H), 6.87 (d, J=8.4 Hz, 2H), 4.56 (s, 2H), 4.51 (s, 2H), 1.48 (s, 9H).

Step 3. (S)-[4-(2-Nitro-6,7-dihydro-5H-imidazo[2,1-b][1,3]oxazin-6-yloxylmethyl)-phenoxy]-acetic acid tert-butyl ester. To a stirred solution of 2-nitro-6,7-dihydro-5H-imidazo[2,1-b][1,3]oxazin-6(S)-ol (148 mg, 0.80 mmol) and (4-chloromethyl-phenoxy)-acetic acid tert-butyl ester (300 mg, 1.0 mmol) in anhydrous DMF (8.0 mL) at −60° C. under N₂ was added 60% NaH (50 mg, 1.3 mmol). The resultant mixture was allowed to slowly warm to room temperature and stirred at room temperature for 1.5 hours. The mixture was diluted with EtOAc, washed with water, dried over sodium sulfate, and concentrated in vacuo. The crude product was purified by preparative TLC plates (5% MeOH in dichloromethane) to give the title product (142 mg, 44%). ESI MS m/z 406 (M+H⁺), 428 (M+Na⁺); ¹H NMR (400 MHz, CDCl₃) δ 7.38 (s, 1H), 7.23 (d, J=8.4 Hz, 2H), 6.87 (d, J=8.4 Hz, 2H), 4.67-4.53 (m, 3H), 4.52 (s, 2H), 4.31 (d, J=11.6 Hz, 1H), 4.15-4.06 (m, 3H), 1.49 (s, 9H).

Step 4. (S)—N-{3-[3-Fluoro-4-(4-{2-[4-(2-nitro-6,7-dihydro-5H-imidazo[2,1-b][1,3]oxazin-6-yloxymethyl)-phenoxy]-acetyl}-piperazin-1-yl)-phenyl]-2-oxo-oxazolidin-5-ylmethyl}-acetamide. A solution of [4-(2-nitro-6,7-dihydro-

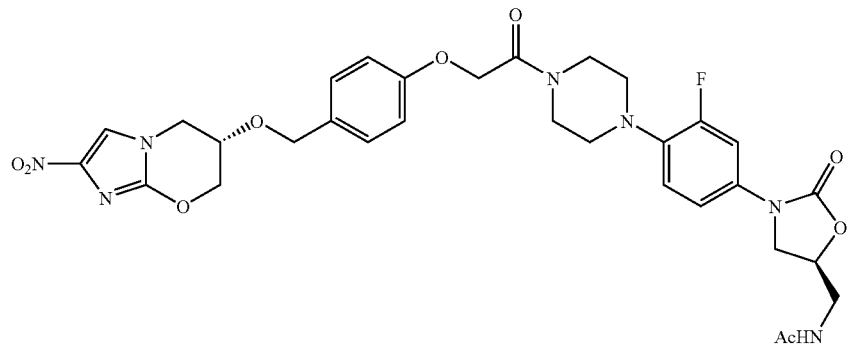

5H-imidazo[2,1-b][1,3]oxazin-6(S)-yloxylmethyl)-phenoxy]-acetic acid tert-butyl ester (100 mg, 0.25 mmol) in TFA/CH$_2$Cl$_2$ (2 mL) was stirred at room temperature for 2 h. The resultant mixture was concentrated in vacuo, and diluted with DCM, to the solution was added N-[3-(3-fluoro-4-piperazin-1-yl-phenyl)-2-oxo-oxazolidin-5-ylmethyl]-acetamide (50 mg, 0.15 mmol) (prepared by following the procedure disclosed by U.S. Pat. No. 5,547,950 or Brickner 1996), HOBt (21.6 mg, 0.16 mmol), EDCI (30.7 mg, 0.16 mmol) and DIPEA (0.20 ml). The mixture was stirred at room temperature for 24 hours diluted with DCM, washed with sat. NaHCO$_3$, 1 N HCl and sat. NaHCO$_3$, dried over sodium sulfate, and concentrated in vacuo. The crude product was purified by preparative TLC plates (5% MeOH in dichloromethane) to give the title product as a solid (6.0 mg, 4%). ESI MS m/z 668.4 (M+H$^+$).

Example 2
(S,S)—N-(3-{3-Fluoro-4-[4-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide mmol) in acetonitrile (5.0 mL) was stirred at 50° C. under nitrogen for 2 days. The reaction mixture was diluted with EtOAc, filtered and evaporated. The crude product was purified by preparative TLC plates (5% MeOH in dichloromethane) to give the title product as a solid (8.0 mg, 10%). ESI MS m/z 556.4 (M+H$^+$); $^1$H NMR (400 MHz, acetone) δ 7.67 (s, 1H), 7.51 (dd, J=14.0, 2.8 Hz, 1H), 7.36 (d, J=7.6 Hz, 2H), 7.28 (d, J=7.6 Hz, 2H), 7.08 (d, J=8.8 Hz, 1H), 7.04 (dd, J=9.2, 2.8 Hz, 1H), 5.53 (s, 2H), 5.09 (d, J=8.8 Hz, 1H), 4.70-4.63 (m, 3H), 4.45 (d, J=11.6 Hz, 1H), 4.33-4.27 (m, 2H), 4.03 (t, J=8.8 Hz, 1H), 3.71 (dd, J=9.2, 6.8 Hz, 1H), 2.76-2.73 (m, 3H), 1.95 (s, 3H).

Example 3

(S,S)—N-(3-{3-Fluoro-4-[3-(2-nitro-6,7-dihydro-5H-Imidazo[2,1-b][1,3]oxazin-6-yloxymethyl)-benzyloxy]-phenyl}-2-oxo-oxazolidin-5-ylmethyl)-acetamide:

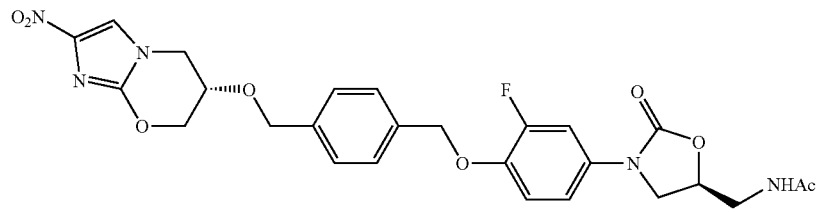

Step 1. 6(S)-(4-Chloromethyl-benzyloxy)-2-nitro-6,7-dihydro-5H-imidazo[2,1-b][1,3]oxazine. To a stirred solution of 2-nitro-6,7-dihydro-5H-imidazo[2,1-b][1,3]oxazin-6(S)-ol (0.1 g, 0.54 mmol) in anhydrous DMF (1 mL) was added NaH (60% dispersion in oil, 26.0 mg, 0.65 mmol) and stirred at 0° C. for 30 min. 1,4-Bis-chloromethyl-benzene (472 mg, 2.7 mmol) in anhydrous DMF (0.5 mL) was added to the reaction mixture and stirred at 0° C. for 30 min, and at room temperature for additional 3 hours. The reaction mixture was diluted with ethyl acetate and washed with water and saturated brine. The organic layer was dried over anhydrous Na$_2$SO$_4$, filtered and evaporated. The residue was washed with hexanes and gave the title compound as solid (65 mg, 37%). ESI MS m/z 324 (M+H$^+$); $^1$H NMR (400 MHz, CDCl$_3$) δ 7.39-7.24 (m, 5H), 4.72 (d, J=30.0 Hz, 1H), 4.59 (m, 2H), 4.32 (d, J=30.0 Hz, 1H), 4.16 (m, 1H), 1.60 (s, 4H).

Step 2. (S,S)—N-(3-{3-Fluoro-4-[4-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide. A suspension of 6(S)-(4-chloromethyl-benzyloxy)-2-nitro-6,7-dihydro-5H-imidazo[2,1-b][1,3]oxazine (48 mg, 0.15 mmol), N-[3-(3-fluoro-4-hydroxy-phenyl)-2-oxo-oxazolidin-5(S)-ylmethyl]-acetamide (40 mg, 0.15 mmol) (prepared as described by US2007/0155714), K$_2$CO$_3$ (207 mg, 1.5

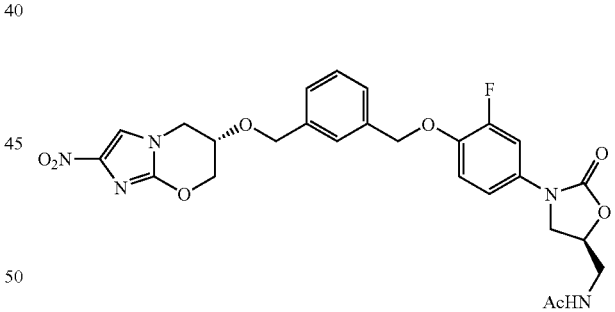

Step 1. 6(S)-(3-Chloromethyl-benzyloxy)-2-nitro-6,7-dihydro-5H-imidazo[2,1-b][1,3]oxazine. The title compound was prepared by following the same procedure as described in the preparation of Example 2, except 1,3-bis-(chloromethyl)-benzene was used in place of 1,4-bis-(chloromethyl)-benzene. ESI MS m/z 473 (M+H$^+$); $^1$H NMR (400 MHz, CDCl$_3$) δ7.38 (s, 1H), 7.32-7.19 (m, 4H), 4.71 (d, J=30 Hz, 1H), 4.60 (d, J=21 Hz, 2H), 4.33 (d, J=30.0 Hz, 1H), 4.15 (m, 3H), 3.45 (s, 2H), 3.41 (s, 4H), 2.37 (s, 4H), 1.44 (s, 9H).

Step 2. (S,S)—N-(3-{3-Fluoro-4-[3-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide. The title compound was prepared by following the same procedure as described for the preparation of Example 2, except starting material 6-(3-chloromethyl-benzyloxy)-2-nitro-6,7-dihydro-5H-imidazo[2,1-b][1,3]oxazine in place of 6-(4-chloromethyl-benzyloxy)-2-nitro-6,7-dihydro-5H-imidazo[2,1-b][1,3]oxazine was used. ESI MS m/z 556.4 (M+H).

Example 4

(S,S)—N-(3-{3-Fluoro-4-[5-(2-nitro-6,7-dihydro-5H-imidazo[2,1-b][1,3]oxazin-6-yloxymethyl)-pyridin-2-yloxy]-phenyl}-2-oxo-oxazolidin-5-ylmethyl)-acetamide:

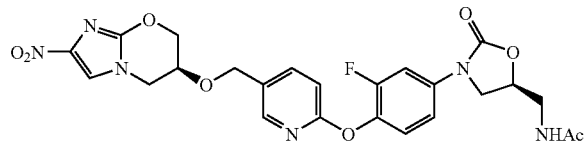

Step 1. N-{3-[3-Fluoro-4-(5-formyl-pyridin-2-yloxy)-phenyl]-2-oxo-oxazolidin-5(S)-ylmethyl}-acetamide. A suspension of 6-fluoro-pyridine-3-carbaldehyde (125 mg, 1.0 mmol), N-[3-(3-fluoro-4-hydroxy-phenyl)-2-oxo-oxazolidin-5(S)-ylmethyl]-acetamide (200 mg, 0.746 mmol), $K_2CO_3$ (552 mg, 4.0 mmol) in acetonitrile (20 mL) was stirred at 60° C. under nitrogen for 15 h. The reaction mixture was diluted with EtOAc, filtered and evaporated. The crude product was purified by flash chromatography (1:1 hexane/EtOAc followed by 1% MeOH in EtOAc) to give the title product as oil (235 mg, 84%). ESI MS m/z 374 (M+H$^+$); $^1$H NMR (400 MHz, CD$_3$OD) δ 9.97 (s, 1H), 8.60 (d, J=2.0 Hz, 1H), 8.29 (dd, J=8.4, 2.4 Hz, 1H), 7.70 (dd, J=12.0, 1.6 Hz, 1H), 7.33-7.20 (m, 3H), 4.80-4.78 (m, 1H), 4.19 (t, J=9.0 Hz, 1H), 3.85 (dd, J=9.6, 6.4 Hz, 1H), 3.58 (d, J=4.8 Hz, 2H), 1.97 (s, 3H).

Step 2. N-{3-[3-Fluoro-4-(5-hydroxymethyl-pyridin-2-yloxy)-phenyl]-2-oxo-oxazolidin-5(S)-ylmethyl}-acetamide. To a solution of N-{3-[3-fluoro-4-(5-formyl-pyridin-2-yloxy)-phenyl]-2-oxo-oxazolidin-5(S)-ylmethyl}-acetamide (230 mg, 0.62 mmol) in MeOH (25 mL) was added NaBH$_4$ (70 mg, 1.86 mmol) at room temperature. The mixture was stirred at room temperature for 24 h, quenched with 1 NHCl (2 ml), diluted with EtOAc, washed with H$_2$O. The organic layer was dried and concentrated in vacuo to give the title product as colorless oil (232 mg, 100%). ESI MS m/z (M+H$^+$) 376; $^1$H NMR (400 MHz, CD$_3$OD) δ 8.03 (d, J=2.4 Hz, 1H), 7.83 (dd, J=8.8, 2.4 Hz, 1H), 7.67 (dd, J=12.8, 2.4 Hz, 1H), 7.30 (dd, J=8.8, 2.4 Hz, 1H), 7.25 (d, J=8.4 Hz, 1H), 7.00 (d, J=8.4 Hz, 1H), 4.80-4.78 (m, 1H), 4.57 (s, 2H), 4.18 (t, J=9.2 Hz, 1H), 3.84 (dd, J=9.2, 6.8 Hz, 1H), 3.57 (d, J=4.8 Hz, 1H), 1.97 (s, 3H).

Step 3. Methanesulfonic acid 6-{4-[5(S)-(acetylaminomethyl)-2-oxo-oxazolidin-3-yl]-2-fluoro-phenoxy}-pyridin-3-ylmethyl ester. To a solution of N-{3-[3-fluoro-4-(5-hydroxymethyl-pyridin-2-yloxy)-phenyl]-2-oxo-oxazolidin-5(S)-ylmethyl}-acetamide (250 mg, 0.67 mmol) and triethylamine (0.35 mL) in dichloromethane (10 mL) was added methanesulfonyl chloride (0.10 mL, 1.34 mmol) at 0° C. under nitrogen. The mixture was stirred at 0° C. for 1 hour and at room temperature for 2 hours. The reaction mixture was poured into water, extracted with dichloromethane, dried over sodium sulfate, and concentrated in vacuo to give yellowish oil. This is directly used for next step.

Step 4. (S,S)—N-(3-{3-Fluoro-4-[5-(2-nitro-6,7-dihydro-5H-imidazo[2,1-b][1,3]oxazin-6-yloxymethyl)-pyridin-2-yloxy]-phenyl}-2-oxo-oxazolidin-5-ylmethyl)-acetamide.

To a solution of 2-nitro-6,7-dihydro-5H-imidazo[2,1-b][1,3]oxazin-6(S)-ol (111 mg, 0.60 mmol) and methanesulfonic acid 6-{4-[5(S)-(acetylamino-methyl)-2-oxo-oxazolidin-3-yl]-2-fluoro-phenoxy}-pyridin-3-ylmethyl ester from step 3 in DMF (10 mL) at −60° C. under nitrogen was added NaH (30 mg, 0.72 mmol, 60% purity). The mixture was slowly warmed to room temperature and stirred at room temperature for 4 h. The reaction mixture was poured into water, extracted with EtOAc, dried over sodium sulfate, and concentrated in vacuo to give crude product, which was purified by flash chromatography on silica eluting with 5% MeOH in dichloromethane to give the title product as a pale yellowish solid (92 mg, 25% over 2 steps). ESI MS m/z 543.4 (M+H$^+$); $^1$H NMR (400 MHz, CDCl$_3$) δ 8.00 (d, J=2.4 Hz, 1H), 7.67 (dd, J=8.4, 2.4 Hz, 1H), 7.61 (dd, J=12.4, 2.4 Hz, 1H), 7.39 (s, 1H), 7.20-7.17 (m, 2H), 6.99 (d, J=8.8 Hz, 1H), 6.08 (t, J=6.0 Hz, 1H), 5.28 (s, 2H), 4.79-4.76 (m, 1H), 4.64-4.53 (m, 3H), 4.32 (d, J=12.0 Hz, 1H), 4.19-4.10 (m, 2H), 4.04 (t, J=9.0 Hz, 1H), 3.79-3.64 (m, 2H), 2.03 (s, 3H).

Example 5

(S,S)—N-(3-{3-Fluoro-4-[4-(2-nitro-6,7-dihydro-5H-imidazo[2,1-b][1,3]oxazin-6-yloxymethyl)-phenoxy]-phenyl}-2-oxo-oxazolidin-5-ylmethyl)-acetamide

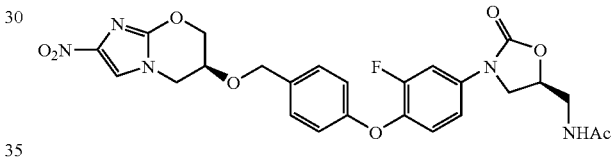

Step 1. N-{3-[3-Fluoro-4-(4-formyl-phenoxy)-phenyl]-2-oxo-oxazolidin-5(S)-ylmethyl}-acetamide. A suspension of 4-fluoro-benzaldehyde (276 mg, 2.22 mmol), N-[3-(3-fluoro-4-hydroxy-phenyl)-2-oxo-oxazolidin-5-ylmethyl]-acetamide (300 mg, 1.11 mmol), and K$_2$CO$_3$ (828 mg, 6.0 mmol) in DMF (15 mL) was stirred at 90° C. under nitrogen for 20 h. The reaction mixture was diluted with EtOAc, washed with water and concentrated in vacuo. The crude product was purified by flash chromatography (1:1 hexane/EtOAc followed by EtOAc) to give the title product as oil (325 mg, 79%). ESI MS m/z (M+H$^+$) 373; $^1$H NMR (400 MHz, CDCl$_3$) δ 9.91 (s, 1H), 7.84 (d, J=8.0 Hz, 2H), 7.64 (d, J=12.4 Hz, 1H), 7.26 (d, J=1.6 Hz, 1H), 7.18 (d, J=6.8 Hz, 1H), 7.00 (d, J=7.2 Hz, 2H), 6.25 (t, J=5.8 Hz, 1H), 4.83-4.80 (m, 1H), 4.08 (t, J=9.0 Hz, 1H), 3.82 (t, J=8.0 Hz, 1H), 3.75-3.62 (m, 2H), 2.04 (s, 3H).

Step 2. N-{3-[3-Fluoro-4-(4-hydroxymethyl-phenoxy)-phenyl]-2-oxo-oxazolidin-5(S)-ylmethyl}-acetamide. The title compound was prepared by following the same procedure as described in the preparation of Example 4, except N-{3-[3-fluoro-4-(4-formyl-phenoxy)-phenyl]-2-oxo-oxazolidin-5-ylmethyl}-acetamide was used in place of N-{3-[3-fluoro-4-(5-formyl-pyridin-2-yloxy)-phenyl]-2-oxo-oxazolidin-5-ylmethyl}-acetamide. ESI MS m/z 375 (M+H$^+$).

Step 3. N-{3-[4-(4-Chloromethyl-phenoxy)-3-fluoro-phenyl]-2-oxo-oxazolidin-5(S)-ylmethyl}-acetamide. To a solution of N-{3-[3-fluoro-4-(4-hydroxymethyl-phenoxy)-phenyl]-2-oxo-oxazolidin-5(S)-ylmethyl}-acetamide (250 mg, 0.67 mmol) and triethylamine (0.35 mL) in dichloromethane (10 mL) was added methanesulfonyl chloride (0.10 mL, 1.34 mmol) at 0° C. under nitrogen. The mixture was stirred at 0°

C. for 1 hour and at room temperature for 2 hours. The reaction mixture was poured into water, extracted with dichloromethane, dried over sodium sulfate, and concentrated in vacuo to give crude product which was purified by flash chromatography on silica eluting using EtOAc to give the title compound as oil (210 mg, 80%). ESI MS m/z 393 (M+H$^+$).

Step 4. N-(3-{3-Fluoro-4-[4-(2-nitro-6,7-dihydro-5H-imidazo[2,1-b][1,3]oxazin-6-yloxymethyl)-phenoxy]-phenyl}-2-oxo-oxazolidin-5-ylmethyl)-acetamide. The title compound was prepared by following the same procedure as described in the preparation of Example 4, except N-{3-[4-(4-chloromethyl-phenoxy)-3-fluoro-phenyl]-2-oxo-oxazolidin-5-ylmethyl}-acetamide was used in place of methanesulfonic acid 6-{4-[5-(acetylamino-methyl)-2-oxo-oxazolidin-3-yl]-2-fluoro-phenoxy}-pyridin-3-ylmethyl ester. ESI MS m/z 542.4 (M+H$^+$).

Example 6

(S,S)—N-[3-(3-Fluoro-4-{1-[4-(2-nitro-6,7-dihydro-5H-imidazo[2,1-b][1,3]oxazin-6-yloxymethyl)-benzyl]-1H-[1,2,3]triazol-4-ylmethoxy}-phenyl)-2-oxo-oxazolidin-5-ylmethyl]-acetamide

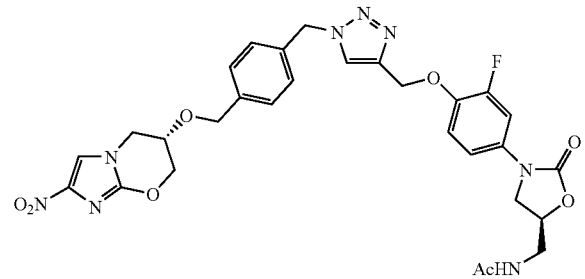

Step 1. N-[3-(3-Fluoro-4-prop-2-ynyloxy-phenyl)-2-oxo-oxazolidin-5(S)-ylmethyl]-acetamide. A suspension of propargyl bromide (97 mg, 0.82 mmol), N-[3-(3-fluoro-4-hydroxy-phenyl)-2-oxo-oxazolidin-5-ylmethyl]-acetamide (183 mg, 0.68 mmol), and K$_2$CO$_3$ (500 mg) in acetonitrile (15 mL) was stirred at 55° C. under nitrogen for 3 h. The reaction mixture was diluted with EtOAc, washed with water and evaporated to give the title product as oil (186 mg, 89%). This was directly used for next step. ESI MS m/z 307 (M+H$^+$).

Step 2. 6(S)-(4-Azidomethyl-benzyloxy)-2-nitro-6,7-dihydro-5H-imidazo[2,1-b][1,3]oxazine. A suspension of 6(S)-(4-chloromethyl-benzyloxy)-2-nitro-6,7-dihydro-5H-imidazo[2,1-b][1,3]oxazine (650 mg, 2.0 mmol) and NaN$_3$ (780 mg, 12 mmol) in acetonitrile (20 mL) was stirred at 75° C. for 24 h. The reaction mixture was filtered, and solvents were removed under reduced pressure to give the title product as a yellowish solid (0.65 g, 98%). ESI MS m/z 331 (M+H$^+$); $^1$H NMR (400 MHz, CDCl$_3$) δ 7.37 (s, 1H), 7.33-7.32 (m, 4H), 4.74 (d, J=12.0 Hz, 1H), 4.64-4.59 (m, 2H), 4.36-4.33 (m, 3H), 4.19-4.11 (m, 3H).

Step 3. (S,S)—N-[3-(3-Fluoro-4-{1-[4-(2-nitro-6,7-dihydro-5H-imidazo[2,1-b][1,3]oxazin-6-yloxymethyl)-benzyl]-1H-[1,2,3]triazol-4-ylmethoxy}-phenyl)-2-oxo-oxazolidin-5-ylmethyl]-acetamide. To a solution of N-[3-(3-fluoro-4-prop-2-ynyloxy-phenyl)-2-oxo-oxazolidin-5(S)-ylmethyl]-acetamide (76 mg, 0.25 mmol) and 6(S)-(4-azidomethyl-benzyloxy)-2-nitro-6,7-dihydro-5H-imidazo[2,1-b][1,3]oxazine (83 mg, 0.25 mmol) in THF (8.0 mL) under nitrogen was added Cu (16 mg, 0.25 mmol), CuSO$_4$ (0.10 mL, 0.25 N in water) and water (2.0 mL). The reaction mixtures were stirred at room temperature under nitrogen for 24 hours. The volatile solvent was removed under reduced pressure and the crude product was purified by preparative TLC (5% MeOH in dichloromethane) to afford the title product as yellow solid (90 mg, 57%). ESI MS m/z 627.5 (M+H$^+$).

Example 7

(S,S)—N-(3-{3-Fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide

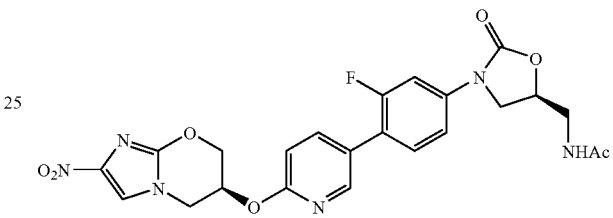

Step 1. 6(S)-(5-Bromo-pyridin-2-yloxy)-2-nitro-6,7-dihydro-5H-imidazo[2,1-b][1,3]oxazine. To a solution of 2-nitro-6,7-dihydro-5H-imidazo[2,1-b][1,3]oxazin-6(S)-ol (463 mg, 2.5 mmol) and 5-bromo-2-fluoro-pyridine (528 mg, 3.0 mmol) in DMF at −60° C. under nitrogen was added NaH (200 mg, 5.0 mmol). The mixture was slowly warmed to room temperature and stirred at room temperature for 2 h. The reaction mixture was diluted with EtOAc, washed with brine and concentrated in vacuo. The crude product was recrystallized from MeOH/H$_2$O to give the title compound as a yellow solid (0.603 g, 70%). ESI MS m/z 341, 343 (bromine pattern, M+H$^+$).

Step 2. (S,S)—N-(3-{3-Fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide. To a suspension of 6-(5-bromo-pyridin-2-yloxy)-2-nitro-6,7-dihydro-5H-imidazo[2,1-b][1,3]oxazine (150 mg, 0.44 mmol), N-{3-[3-fluoro-4-(4,4,5,5-tetramethyl-[1,3,2]dioxaborolan-2-yl)-phenyl]-2-oxo-oxazolidin-5-ylmethyl}-acetamide (166 mg, 0.44 mmol) (prepared as described by Chen, S. et al: U.S. Pat. No. 7,129,259 or Gravestock et. al. WO 2004/078753), Pd(Ph$_3$P)$_4$ (58 mg, 0.05 mmol) and K$_2$CO$_3$ (121 mg, 0.88 mmol) in DMF/H$_2$O (10/1.5.5 mL) was degassed. The mixture was heated to 80° C. for 2.5 h, diluted with EtOAc, washed with brine and concentrated in vacuo to give a crude product. The crude product was purified by flash chromatography (5% MeOH in EtOAc) to afford the title product (143 mg, 63%). ESI MS m/z 513.4 (M+H$^+$); $^1$H NMR (400 MHz, CDCl$_3$) δ 8.29 (s, 1H), 7.81 (d, J=8.4 Hz, 1H), 7.57 (d, J=12.8, 2.8 Hz, 1H), 7.45 (s, 1H), 7.39 (t, J=8.6 Hz, 1H), 7.30 (dd, J=8.8, 2.0 Hz, 1H), 6.86 (d, J=8.8 Hz, 1H), 5.99 (t, J=6.0 Hz, 1H), 5.79 (brs, 1H), 4.86-4.81 (m, 2H), 4.54 (d, J=10.8 Hz, 1H), 4.41 (d, J=2.4 Hz, 2H), 4.11-4.06 (m, 1H), 3.83 (dd, J=8.8, 6.8 Hz, 1H), 3.72-3.66 (m, 2H), 2.03 (s, 3H).

Example 8

(S,S)—N-(3-{3-Fluoro-4-[2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide

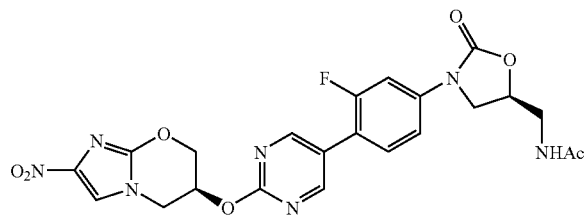

Step 1. 6(S)-(5-Bromo-pyrimidin-2-yloxy)-2-nitro-6,7-dihydro-5H-imidazo[2,1-b][1,3]oxazine. The title compound was prepared by following the same procedure as described for the preparation of Example 7, except 5-bromo-2-fluoro-pyrimidine was used in place of 5-bromo-2-fluoro-pyridine. ESI MS m/z 342, 344 (bromine, M+H$^+$); $^1$H NMR (400 MHz, CDCl$_3$) δ 8.59 (s, 2H), 7.44 (s, 1H), 5.60 (s, 1H), 4.85 (d, J=14.8 Hz, 1H), 4.55 (d, J=12.0 Hz, 1H), 4.48-4.38 (m, 2H).

Step 2. (S,S)—N-(3-{3-Fluoro-4-[2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide. The title compound was prepared by following the same procedure as described in the preparation of Example 7, except 6-(5-bromo-pyrimidin-2-yloxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 514.5 (M+H$^+$); $^1$H NMR (400 MHz, DMSO) δ 8.85 (s, 2H), 8.26 (t, J=5.8 Hz, 1H), 8.06 (s, 1H), 7.68 (d, J=8.8 Hz, 1H), 7.64 (dd, J=12.0, 2.0 Hz, 1H), 7.44 (dd, J=8.0, 2.4 Hz, 1H), 5.73 (s, 1H), 4.78-4.69 (m, 3H), 4.47 (s, 2H), 4.16 (t, J=9.2 Hz, 1H), 3.76 (dd, J=9.2, 6.4 Hz, 1H), 3.41 (t, J=5.2 Hz, 2H), 1.81 (s, 3H).

Example 9

(S,S)—N-(3-{3-Fluoro-4-[2-(2-nitro-6,7-dihydro-5H-imidazo[2,1-b][1,3]oxazin-6-yloxy)-pyridin-4-yl]-phenyl}-2-oxo-oxazolidin-5-ylmethyl)-acetamide

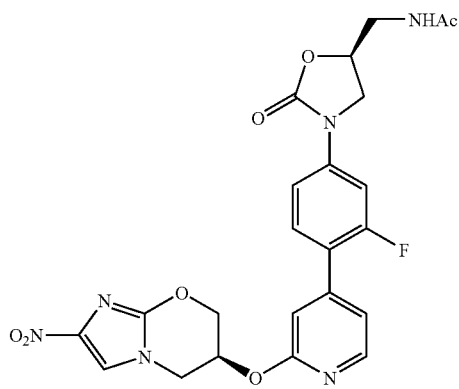

Step 1. 6(S)-(4-Bromo-pyridin-2-yloxy)-2-nitro-6,7-dihydro-5H-imidazo[2,1-b][1,3]oxazine. The title compound was prepared by following the same procedure as described in the preparation of Example 7, except 4-bromo-2-fluoro-pyridine was used in place of 5-bromo-2-fluoro-pyridine. ESI MS m/z 341, 343 (bromine isotope pattern: M+H); $^1$H NMR (400 MHz, CDCl$_3$) δ 7.96 (d, J=5.2 Hz, 1H), 7.43 (s, 1H), 7.14 (dd, J=5.2, 1.2 Hz, 1H), 7.00 (d, J=1.2 Hz, 1H), 5.72 (bs, 1H), 4.78 (dt, J=12.8, 2.6 Hz, 1H), 4.51 (d, J=12.0 Hz, 1H), 4.42-4.35 (m, 2H).

Step 2. N-(3-{3-Fluoro-4-[2-(2-nitro-6,7-dihydro-5H-imidazo[2,1-b][1,3]oxazin-6-yloxy)-pyridin-4-yl]-phenyl}-2-oxo-oxazolidin-5-ylmethyl)-acetamide. The title compound was prepared by following the same procedure as described in the preparation of Example 7, except 6-(4-bromo-pyridin-2-yloxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 513.3 (M+H$^+$); $^1$H NMR (400 MHz, CDCl$_3$) δ 8.17 (d, J=5.2 Hz, 1H), 7.57 (dd, J=13.2, 2.0 Hz, 1H), 7.46 (d, J=5.2 Hz, 1H), 7.43 (d, J=8.4 Hz, 1H), 7.29 (dd, J=9.2, 2.8 Hz, 1H), 7.17 (m, 1H), 6.94 (s, 1H), 6.07 (t, J=5.2 Hz, 1H), 5.78-5.79 (m, 1H), 4.85-4.82 (m, 2H), 4.55 (d, J=12.4 Hz, 1H), 4.40 (d, J=2.4 Hz, 2H), 3.82 (dd, J=8.8, 6.4 Hz, 1H), 3.72-3.63 (m, 2H), 2.03 (s, 3H).

Example 10

N-(3-{3-Fluoro-4-[5-(2-methyl-6-nitro-2,3-dihydro-imidazo[2,1-b]oxazol-2-ylmethoxy)-pyridin-3-yl]-phenyl}-2-oxo-oxazolidin-5-ylmethyl)-acetamide

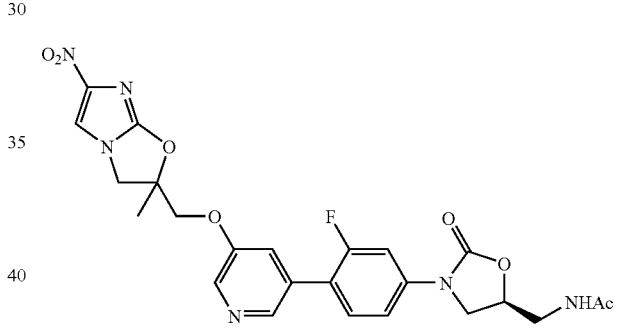

Step 1. 2-(5-Bromo-pyridin-3-yloxymethyl)-2-methyl-6-nitro-2,3-dihydro-imidazo[2,1-b]oxazole. To a solution of 5-bromo-pyridin-3-ol (0.87 g, 5.0 mmol) and 2-bromo-1-(2-methyl-oxiranylmethyl)-4-nitro-1H-imidazole (1.305 g, 5.0 mmol) in DMF (20 ml) was added sodium hydride (0.28 g, 7.0 mmol, 60% in mineral oil) at 0° C. The mixture was stirred at 0° C. for 10 min and at 50° C. for 2 h. The resultant mixture is cooled, diluted with water and extracted with ethyl acetate. The combined extracts were dried, concentrated and residue was purified by silica gel chromatography eluting with hexane/EtOAc to give the title product (260 mg, 15%) as yellow oil. ESI MS m/z 355, 357 (bromine isotope pattern, M+H$^+$); $^1$H NMR (400 MHz, CDCl$_3$) δ 8.19 (s, 1H), 8.00 (s, 1H), 7.57 (s, 1H), 7.36 (s, 1H), 4.47 (d, J=10.4 Hz, 1H), 4.30 (d, J=10.4, 1H), 4.14 (d, J=10.4 Hz, 1H), 4.07 (d, J=10.4 Hz, 1H), 1.80 (s, 3H).

Step 2. N-(3-{3-Fluoro-4-[5-(2-methyl-6-nitro-2,3-dihydro-imidazo[2,1-b]oxazol-2-ylmethoxy)-pyridin-3-yl]-phenyl}-2-oxo-oxazolidin-5-ylmethyl)-acetamide. The title compound (a mixture of two diastereomers) was prepared by following the same procedure as described in the preparation of Example 7, except 2-(5-bromo-pyridin-3-yloxymethyl)-2-methyl-6-nitro-2,3-dihydro-imidazo[2,1-b]oxazole was used in place of 6-(5-bromo-pyridin-2-yloxy)-2-nitro-6,7-dihydro-5H-imidazo[2,1-b][1,3]oxazine. ESI MS m/z 527.3 (M+H⁺); ¹H NMR (400 MHz, DMSO) δ 8.36 (s, 1H), 8.21 (d, J=2.8 Hz, 1H), 7.90 (s, 1H), 7.67 (dd, J=13.2, 2 Hz, 1H), 7.57 (t, J=8.8 Hz, 2H), 7.42 (dd, J=8.8, 2.4 Hz, 1H), 4.85-4.80 (m, 1H), 4.61-4.49 (m, 2H), 4.41 (d, J=10.8 Hz, 1H), 4.24-4.17 (m, 2H), 3.86 (dd, J=9.2, 6.4 Hz, 1H), 3.57 (dd, J=4.8 Hz, 1H), 1.96 (s, 3H), 1.78 (s, 3H).

Example 11

(S,S)—N-(3-{3-Fluoro-4-[5-(2-nitro-6,7-dihydro-5H-imidazo[2,1-b][1,3]oxazin-6-yloxymethyl)-pyridin-2-yl]-phenyl}-2-oxo-oxazolidin-5-ylmethyl)-acetamide

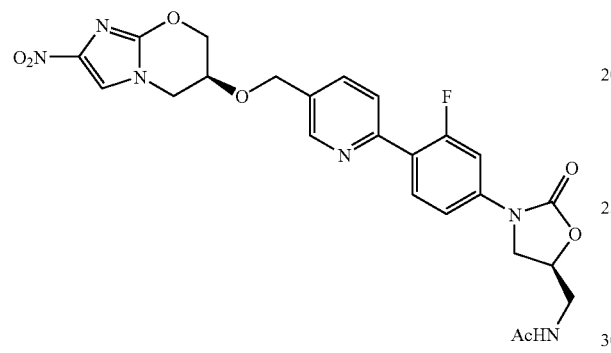

Step 1. (6-Bromo-pyridin-3-yl)-methanol. The title compound was prepared by following the same procedure as described in the preparation of Example 4 (step 2), except 6-bromo-pyridine-3-carbaldehyde was used in place of N-{3-[3-fluoro-4-(5-formyl-pyridin-2-yloxy)-phenyl]-2-oxo-oxazolidin-5-ylmethyl}-acetamide. ¹H NMR (400 MHz, CDCl₃) δ 8.32 (s, 1H), 7.58 (d, J=8.4 Hz, 1H), 7.46 (d, J=8.4 Hz, 1H), 4.70 (s, 2H), 2.32 (s, 1H).

Step 2. Methanesulfonic acid 6-bromo-pyridin-3-ylmethyl ester and 2-bromo-5-chloromethyl-pyridine. The title compounds were prepared by following the same procedure as described in the preparation of Example 4 (step 3), except (6-bromo-pyridin-3-yl)-methanol was used in place of N-{3-[3-fluoro-4-(5-hydroxymethyl-pyridin-2-yloxy)-phenyl]-2-oxo-oxazolidin-5-ylmethyl}-acetamide.

Step 3. 6(S)-(6-Bromo-pyridin-3-ylmethoxy)-2-nitro-6,7-dihydro-5H-imidazo[2,1-b][1,3]oxazine. The title compound was prepared by following the same procedure as described in the preparation of Example 7, except a mixture of methanesulfonic acid 6-bromo-pyridin-3-ylmethyl ester and 2-bromo-5-chloromethyl-pyridine produced as above were used in place of 5-bromo-2-fluoro-pyridine. ESI MS m/z 355, 357 (bromine isotope, M+H⁺); ¹H NMR (400 MHz, DMSO) δ 8.32 (d, J=2.8 Hz, 1H), 8.01 (s, 1H), 7.66 (dd, J=8.0, 2.0 Hz, 1H), 7.61 (d, J=7.6 Hz, 1H), 4.64-4.60 (m, 3H), 4.43 (d, J=11.6 Hz, 1H), 4.22-4.17 (m, 3H).

Step 4. (S,S)—N-(3-{3-Fluoro-4-[5-(2-nitro-6,7-dihydro-5H-imidazo[2,1-b][1,3]oxazin-6-yloxymethyl)-pyridin-2-yl]-phenyl}-2-oxo-oxazolidin-5-ylmethyl)-acetamide. The title compound was prepared by following the same procedure as described in the preparation of Example 7, except 6-(6-bromo-pyridin-3-ylmethoxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 527.5 (M+H⁺); ¹H NMR (400 MHz, DMSO) δ 8.62 (s, 1H), 8.25 (t, J=6.0 Hz, 1H), 8.03 (s, 1H), 7.98 (t, J=8.8 Hz, 1H), 7.81 (d, J=8.0, 1H), 7.75 (d, J=8.0 Hz, 1H), 7.59 (dd, J=14.0, 2.4 Hz, 1H), 7.43 (dd, J=8.8, 2.0 Hz, 1H), 4.75-4.67 (m, 3H), 4.46 (d, J=11.6 Hz, 1H), 4.25-4.23 (m, 2H), 4.15 (t, J=13.0 Hz, 1H), 3.77 (dd, J=9.2, 6.8 Hz, 1H), 3.40-3.20 (m, 4H), 2.05 (s, 1.35H), 1.81 (s, 1.65H).

Example 12

(S,S)—N-(3-{3-Fluoro-4-[6-(2-nitro-6,7-dihydro-5H-imidazo[2,1-b][1,3]oxazin-6-yloxymethyl)-pyridin-3-yl]-phenyl}-2-oxo-oxazolidin-5-ylmethyl)-acetamide

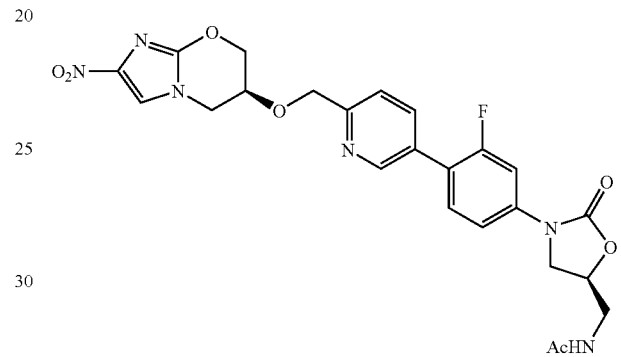

Step 1. Methanesulfonic acid 5-bromo-pyridin-2-ylmethyl ester. The title compound was prepared by following the same procedure as described in the preparation of Example 4 (step 3), except (5-Bromo-pyridin-2-yl)-methanol was used in place of N-{3-[3-fluoro-4-(5-hydroxymethyl-pyridin-2-yloxy)-phenyl]-2-oxo-oxazolidin-5-ylmethyl}-acetamide. ESI MS m/z 266 and 268 (bromine isotope pattern, M+H⁺).

Step 2. 6(S)-(5-Bromo-pyridin-2-ylmethoxy)-2-nitro-6,7-dihydro-5H-imidazo[2,1-b][1,3]oxazine. The title compound was prepared by following the same procedure as described in the preparation of Example 7, except methanesulfonic acid 5-bromo-pyridin-2-ylmethyl ester were used in place of 5-bromo-2-fluoro-pyridine. ESI MS m/z 355 and 357 (bromine isotope pattern, M+H⁺).

Step 3. (S,S)—N-(3-{3-Fluoro-4-[6-(2-nitro-6,7-dihydro-5H-imidazo[2,1-b][1,3]oxazin-6-yloxymethyl)-pyridin-3-yl]-phenyl}-2-oxo-oxazolidin-5-ylmethyl)-acetamide. The title compound was prepared by following the same procedure as described in the preparation of Example 7, except 6(S)-(5-bromo-pyridin-2-ylmethoxy)-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ¹H NMR (400 MHz, DMSO) δ 8.66 (s, 1H), 8.24 (t, J=5.2 Hz, 1H), 8.01 (s, 1H), 7.93 (d, J=8.8 Hz, 1H), 7.61 (dd, J=4.8, 2.8 Hz, 1H), 7.58 (d, J=9.2 Hz, 1H), 7.43 (d, J=8.0 Hz, 1H), 7.40 (dd, J=8.8, 2.4 Hz, 1H), 4.75-4.67 (m, 3H), 4.46 (d, J=11.2 Hz, 1H), 4.32-4.29 (m, 2H), 4.21 (dd, J=13.2, 3.6 Hz, 1H), 4.13 (t, J=9.0 Hz, 1H), 3.74 (dd, J=9.2, 6.4 Hz, 1H), 3.88 (t, J=6.0 Hz, 1H), 3.40-3.20 (m, 3H), 1.80 (s, 3H).

Example 13

(S,S)—N-(3-{3-Fluoro-4-[6-(2-nitro-6,7-dihydro-5H-imidazo[2,1-b][1,3]oxazin-6-yloxy)-pyridazin-3-yl]-phenyl}-2-oxo-oxazolidin-5-ylmethyl)-acetamide

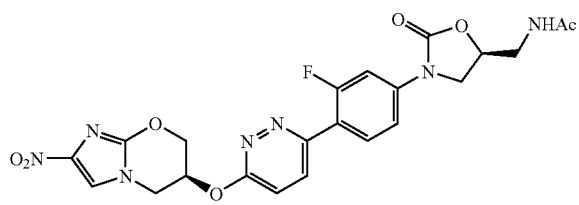

Step 1. 6(S)-(6-Chloro-pyridazin-3-yloxy)-2-nitro-6,7-dihydro-5H-imidazo[2,1-b][1,3]oxazine. The title compound was prepared by following the same procedure as described in the preparation of Example 7, except 3,6-dichloro-pyridazine was used in place of 5-bromo-2-fluoro-pyridine. ESI MS m/z 298 (M+H$^+$).

Step 2. (S,S)—N-(3-{3-Fluoro-4-[6-(2-nitro-6,7-dihydro-5H-imidazo[2,1-b][1,3]oxazin-6-yloxy)-pyridazin-3-yl]-phenyl}-2-oxo-oxazolidin-5-ylmethyl)-acetamide. The title compound was prepared by following the same procedure as described in the preparation of Example 7, except 6(S)-(6-chloro-pyridazin-3-yloxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 514.4 (M+H$^+$); $^1$H NMR (400 MHz, DMSO) δ 8.23 (bs, 1H), 8.05 (s, 1H), 7.97 (dd, J=8.8, 1.6 Hz, 1H), 7.93 (d, J=8.8 Hz, 1H), 7.63 (dd, J=14.0, 2.4 Hz, 1H), 7.48 (dd, J=8.8, 2.0 Hz, 1H), 7.38 (d, J=9.2 Hz, 1H), 5.99 (s, 1H), 4.82-4.72 (m, 3H), 4.51 (s, 1H), 4.17 (t, J=9.0 Hz, 1H), 3.78 (dd, J=9.2, 6.0 Hz, 1H), 3.41 (t, J=5.2 Hz, 2H), 3.30-3.20 (m, 1H), 1.81 (s, 3H).

Example 14

(S,S)—N-(3-{3-Fluoro-4-[4-morpholin-4-yl-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide

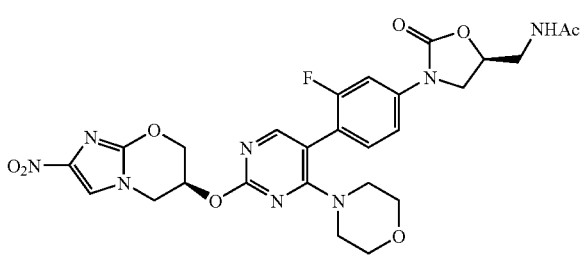

Step 1. 6(S)-(5-Bromo-4-morpholin-4-yl-pyrimidin-2-yloxy)-2-nitro-6,7-dihydro-5H-imidazo[2,1-b][1,3]oxazine. The title compound was prepared by following the same procedure as described in the preparation of Example 7, except 4-(6-bromo-2-chloro-pyrimidin-4-yl)-morpholine was used in place of 5-bromo-2-fluoro-pyridine. ESI MS m/z 427, 429 (bromine isotope, M+H$^+$); $^1$H NMR (400 MHz, CDCl$_3$) δ 8.19 (s, 1H), 7.43 (s, 1H), 5.54 (brs, 1H), 4.84-4.74 (m, 2H), 4.52-4.38 (m, 2H), 3.78-3.71 (m, 8H).

Step 2. (S,S)—N-(3-{3-Fluoro-4-[4-morpholin-4-yl-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide. The title compound was prepared by following the same procedure as described in the preparation of Example 7, except 6(S)-(5-bromo-4-morpholin-4-yl-pyrimidin-2-yloxy)-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ESI MS m/z 599.5 (M+H$^+$).

Example 15

(S,S)—N-(3-{3-Fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide

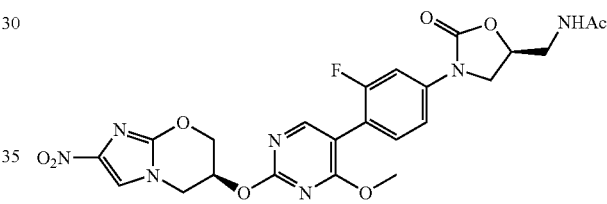

Step 1. 6(S)-(5-Bromo-4-methoxy-pyrimidin-2-yloxy)-2-nitro-6,7-dihydro-5H-imidazo[2,1-b][1,3]oxazine. The title compound was prepared by following the same procedure as described in the preparation of Example 7, except 5-bromo-2-chloro-4-methoxy-pyrimidine was used in place of 5-bromo-2-fluoro-pyridine. ESI MS m/z 372, 374 (M+H$^+$); $^1$H NMR (400 MHz, CDCl$_3$) δ 8.30 (s, 1H), 7.43 (s, 1H), 5.61 (brs, 1H), 4.84 (dt, J=12.4, 2.4 Hz, 1H), 4.53 (d, J=11.6 Hz, 1H), 4.20-4.04 (m, 2H), 4.03 (s, 3H).

Step 2. (S,S)—N-(3-{3-Fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide. The title compound was prepared by following the same procedure as described in the preparation of Example 7, except 6-(5-bromo-4-methoxy-pyrimidin-2-yloxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 544.4 (M+H$^+$); $^1$H NMR (400 MHz, DMSO) δ 8.34 (s, 1H), 8.22 (t, J=5.8 Hz, 1H), 8.05 (s, 1H), 7.55 (dd, J=12.8, 2.0 Hz, 1H), 7.42 (t, J=8.4 Hz, 1H), 7.36 (dd, J=8.8, 2.0 Hz, 1H), 4.79-4.68 (m, 2H), 4.46 (s, 1H), 4.13 (t, J=9.0 Hz, 1H), 3.87 (s, 2H), 3.74 (dd, J=9.2, 6.4 Hz, H), 3.40 (t, J=5.4 Hz, 2H), 3.30-3.20 (m, 1H), 1.81 (s, 3H).

Example 16

(S,S)—N-(3-{4-[4-Dimethylamino-2-(2-nitro-6,7-dihydro-5H-imidazo[2,1-b][1,3]oxazin-6-yloxy)-pyrimidin-5-yl]-3-fluoro-phenyl}-2-oxo-oxazolidin-5-ylmethyl)-acetamide

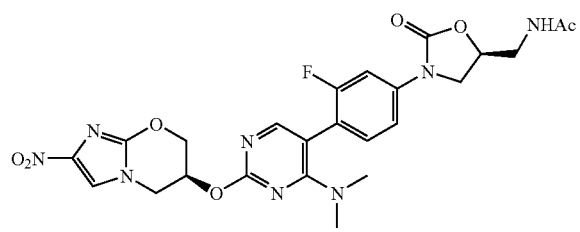

Step 1. [5-Bromo-2-(2-nitro-6,7-dihydro-5H-imidazo[2,1-b][1,3]oxazin-6(S)-yloxy)-pyrimidin-4-yl]-dimethylamine. The title compound was prepared by following the same procedure as described in the preparation of Example 7, except (5-bromo-2-chloro-pyrimidin-4-yl)-dimethyl-amine was used in place of 5-bromo-2-fluoro-pyridine. ESI MS m/z 385, 387 (M+H$^+$); $^1$H NMR (400 MHz, CDCl$_3$) δ 8.11 (s, 1H), 7.42 (s, 1H), 5.53-5.51 (m, 1H), 4.81 (dd, J=12.8, 3.6 Hz, 1H), 4.50 (dd, J=12.0, 2.0 Hz, 1H), 4.36 (d, J=3.2 Hz, 2H), 3.24 (s, 6H).

Step 2. (S,S)—N-(3-{3-Fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide. The title compound was prepared by following the same procedure as described in the preparation of Example 7, except [5-bromo-2-(2-nitro-6,7-dihydro-5H-imidazo[2,1-b][1,3]oxazin-6(S)-yloxy)-pyrimidin-4-yl]-dimethyl-amine was used in place of 6-(5-bromo-pyridin-2-yloxy)-2-nitro-6,7-dihydro-5H-imidazo[2,1-b][1,3]oxazine. ESI MS m/z 557.4 (M+H$^+$).

Example 17

(S,S)-5-{4-[5-(Acetylamino-methyl)-2-oxo-oxazolidin-3-yl]-2-fluoro-phenyl}-2-(2-nitro-6,7-dihydro-5H-imidazo[2,1-b][1,3]oxazin-6-yloxy)-nicotinic acid methyl ester

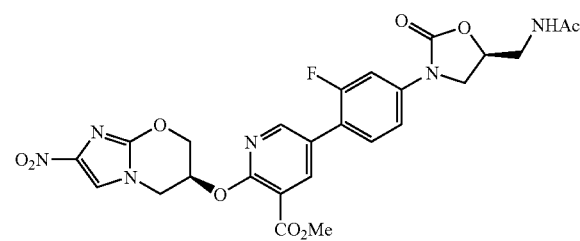

Step 1. 5-Bromo-2-(2-nitro-6,7-dihydro-5H-imidazo[2,1-b][1,3]oxazin-6(S)-yloxy)-nicotinic acid methyl ester. The title compound was prepared by following the same procedure as described in the preparation of Example 7, except 5-bromo-2-chloro-nicotinic acid methyl ester was used in place of 5-bromo-2-fluoro-pyridine. ESI MS m/z 399, 341 (bromine isotope, M+H$^+$); $^1$H NMR (400 MHz, DMSO) δ 8.55 (s, 1H), 8.28 (s, 1H), 8.01 (s, 1H), 5.77 (s, 1H), 4.66 (s, 2H), 4.42 (dd, J=13.6, 4.0 Hz, 1H), 4.32 (d, J=14.0 Hz, 1H), 3.60 (s, 3H).

Step 2. (S,S)—N-(3-{3-Fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide. The title compound was prepared by following the same procedure as described in the preparation of Example 7, except 5-bromo-2-(2-nitro-6,7-dihydro-5H-imidazo[2,1-b][1,3]oxazin-6(S)-yloxy)-nicotinic acid methyl ester was used in place of 6(S)-(5-bromo-pyridin-2-yloxy)-2-nitro-6,7-dihydro-5H-imidazo[2,1-b][1,3]oxazine. ESI MS m/z 571.5 (M+H$^+$).

Example 18

(S,S)-5-{4-[5-(Acetylamino-methyl)-2-oxo-oxazolidin-3-yl]-2-fluoro-phenyl}-2-(2-nitro-6,7-dihydro-5H-imidazo[2,1-b][1,3]oxazin-6-yloxy)-nicotinic acid

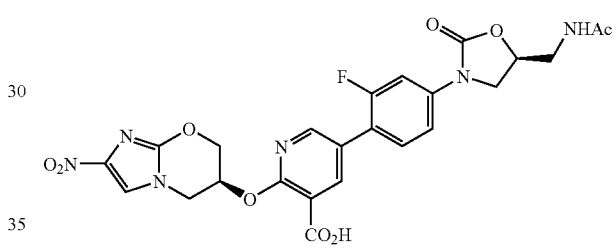

A solution of (S,S)—N-(3-{3-fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide (20 mg, 0.035 mmol) and LiOH (50 mg, 2.0 mmol) in MeOH (5.0 ml) and water (1.5 mL) was stirred at 40° C. for 2 h. The mixture was acidified by 1 N HCl, extracted with EtOAc, and concentrated in vacuo to give the title product (15.0 mg, 77%) as a yellow solid. ESI MS m/z 563.3 (M+Li$^+$).

Example 19

(S,S)—N-(3-{3-Fluoro-4-[4-(2-nitro-6,7-dihydro-5H-imidazo[2,1-b][1,3]oxazin-6-yloxy)-pyrimidin-2-yl]-phenyl}-2-oxo-oxazolidin-5-ylmethyl)-acetamide

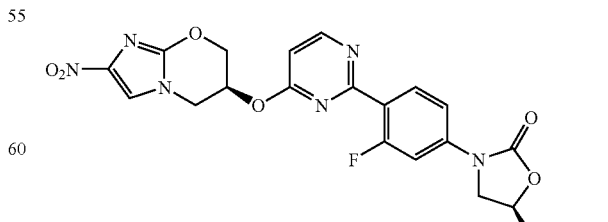

Step 1. 6(S)-(2-Chloro-pyrimidin-4-yloxy)-2-nitro-6,7-dihydro-5H-imidazo[2,1-b][1,3]oxazine and 6(S)-(4-chloropyrimidin-2-yloxy)-2-nitro-6,7-dihydro-5H-imidazo[2,1-b][1,3]oxazine. To a solution of 2-nitro-6,7-dihydro-5H-imidazo[2,1-b][1,3]oxazin-6(S)-ol (452 mg, 2.44 mmol) and 2,4-dichloro-pyrimidine (1.09 g, 7.32 mmol) in DMF at −60° C. under nitrogen was added NaH (200 mg, 5.0 mmol). The mixture was slowly warmed to 0° C. and stirred at 0° C. for 3 h. The reaction mixture was quenched with MeOH and EtOAc, washed with brine and concentrated in vacuo. The crude product was purified by flash chromatography eluting with hexane/EtOAc to give 6(S)-(2-chloro-pyrimidin-4-yloxy)-2-nitro-6,7-dihydro-5H-imidazo[2,1-b][1,3]oxazine (367 mg) as a white solid and 6(S)-(4-chloro-pyrimidin-2-yloxy)-2-nitro-6,7-dihydro-5H-imidazo[2,1-b][1,3]oxazine (120 mg) as a white solid. Both compounds gave ESI MS m/z 297 (M+H$^+$).

Step 2. (S,S)—N-(3-{3-Fluoro-4-[4-(2-nitro-6,7-dihydro-5H-imidazo[2,1-b][1,3]oxazin-6-yloxy)-pyrimidin-2-yl]-phenyl}-2-oxo-oxazolidin-5-ylmethyl)-acetamide. The title compound was prepared by following the same procedure as described in the preparation of Example 7, except 6(S)-(2-chloro-pyrimidin-4-yloxy)-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ESI MS m/z 514 (M+H$^+$); $^1$H NMR (400 MHz, DMSO) δ 8.65 (d, J=7.0 Hz, 1H), 8.23-8.18 (m, 2H), 8.03 (s, 1H), 7.58 (dd, J=14.4, 2.4 Hz, 1H), 7.44 (dd, J=9.2, 2.4 Hz, 1H), 6.93 (d, J=6.0 Hz, 1H), 5.89 (s, 1H), 4.78-4.70 (m, 3H), 4.49-4.44 (m, 2H), 4.17 (t, J=9.0 Hz, 1H), 3.78 (dd, J=8.8, 6.4 Hz, 1H), 3.41 (t, J=5.4 Hz, 2H), 1.81 (s, 3H).

Example 20

(S,S)—N-(3-{3-Fluoro-4-[2-(2-nitro-6,7-dihydro-5H-imidazo[2,1-b][1,3]oxazin-6-yloxy)-pyrimidin-4-yl]-phenyl}-2-oxo-oxazolidin-5-ylmethyl)-acetamide

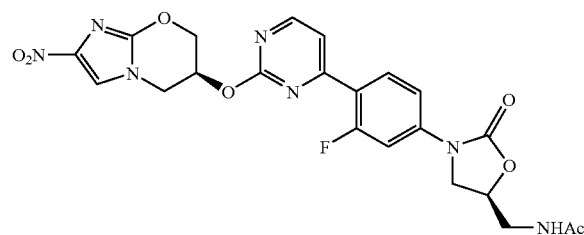

The title compound was prepared by following the same procedure as described in the preparation of Example 7, except 6(S)-(4-chloro-pyrimidin-2-yloxy)-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ESI MS m/z 514 (M+H$^+$); $^1$H NMR (400 MHz, DMSO) δ 8.68 (d, J=4.8 Hz, 1H), 8.22-8.15 (m, 2H), 8.03 (s, 1H), 7.60 (dd, J=14.4, 2.4 Hz, 1H), 7.56 (d, J=4.4 Hz, 1H), 7.46 (dd, J=8.8, 1.6 Hz, 1H), 5.77 (s, 1H), 4.78-4.68 (m, 3H), 4.46 (s, 2H), 4.15 (t, J=9.0 Hz, 1H), 3.78 (dd, J=8.8, 6.8 Hz, 1H), 3.40 (t, J=5.6 Hz, 2H), 1.81 (s, 3H).

Example 21

(S,S)—N-(3-{3-Fluoro-4-[5-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide

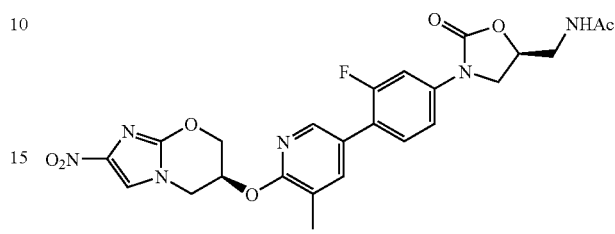

Step 1. 6(S)-(5-Bromo-3-methyl-pyridin-2-yloxy)-2-nitro-6,7-dihydro-5H-imidazo[2,1-b][1,3]oxazine. The title compound was prepared by following the same procedure as described in the preparation of Example 7, except 5-bromo-2-fluoro-3-methyl-pyridine was used in place of 5-bromo-2-fluoro-pyridine. ESI MS m/z 355, 357 (M+H$^+$); $^1$H NMR (400 MHz, CDCl$_3$) δ 8.01 (s, 1H), 7.57 (s, 1H), 7.43 (s, 1H), 5.68 (brs, 1H), 4.80-4.76 (m, 1H), 4.51 (d, J=12.0 Hz, 1H), 4.39-4.36 (m, 2H), 2.09 (s, 3H).

Step 2. N-(3-{3-Fluoro-4-[4-methoxy-2-(2-nitro-6,7-dihydro-5H-imidazo[2,1-b][1,3]oxazin-6(S)-yloxy)-pyrimidin-5-yl]-phenyl}-2-oxo-oxazolidin-5(S)-ylmethyl)-acetamide. The title compound was prepared by following the same procedure as described in the preparation of Example 7, except 6(S)-(5-bromo-3-methyl-pyridin-2-yloxy)-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ESI MS m/z 527.3 (M+H$^+$); $^1$H NMR (400 MHz, CDCl$_3$) δ 7.95 (s, 1H), 7.56 (s, 1H), 7.49 (dd, J=12.8, 2.0 Hz, 1H), 7.38 (s, 1H), 7.32 (t, J=8.4 Hz, 1H), 7.24-7.21 (m, 1H), 5.89 (t, J=6.0 Hz, 1H), 5.73 (s, 1H), 4.78-4.75 (m, 2H), 4.48 (d, J=12.8 Hz, 1H), 4.36 (d, J=2.4 Hz, 2H), 3.76 (dd, J=9.2, 6.8 Hz, 1H), 3.66-3.59 (m, 2H), 2.10 (s, 3H), 1.97 (s, 3H).

Example 22

(S,S)—N-(3-{3-Fluoro-4-[2-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide

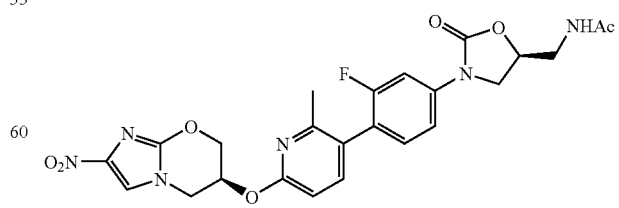

Step 1. 6(S)-(5-Bromo-6-methyl-pyridin-2-yloxy)-2-nitro-6,7-dihydro-5H-imidazo[2,1-b][1,3]oxazine. The title compound was prepared by following the same procedure as described in the preparation of Example 7, except 3-bromo-6-fluoro-2-methyl-pyridine was used in place of 5-bromo-2-fluoro-pyridine. ESI MS m/z 355, 357 (M+H⁺); ¹H NMR (400 MHz, DMSO) δ 7.69 (d, J=8.8 Hz, 1H), 7.42 (s, 1H), 6.50 (d, J=8.4 Hz, 1H), 5.72 (brs, 1H), 4.78 (dt, J=12.4, 2.6 Hz, 1H), 4.50 (d, J=12.4 Hz, 1H), 4.36 (d, J=3.2 Hz, 1H), 4.34 (t, J=2.2 Hz, 1H), 2.54 (s, 3H).

Step 2. N-(3-{3-Fluoro-4-[2-methyl-6-(2-nitro-6,7-dihydro-5H-imidazo[2,1-b][1,3]oxazin-6(S)-yloxy)-pyridin-3-yl]-phenyl}-2-oxo-oxazolidin-5(S)-ylmethyl)-acetamide. The title compound was prepared by following the same procedure as described in the preparation of Example 7, except 6-(5-bromo-6-methyl-pyridin-2-yloxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 527.3 (M+H⁺); ¹H NMR (400 MHz, DMSO) δ 8.23 (t, J=5.6 Hz, 1H), 8.06 (s, 1H), 7.60-7.55 (m, 2H), 7.40-7.35 (m, 2H), 6.77 (d, J=8.8 Hz, 1H), 5.76 (brs, 1H), 4.74-4.67 (m, 3H), 4.47 (dd, J=13.6, 2.8 Hz, 1H), 4.38 (d, J=13.6 Hz, 1H), 4.15 (t, J=9.2 Hz, 1H), 3.76 (dd, J=8.8, 6.4 Hz, 1H), 3.41 (t, J=6.2 Hz, 2H), 2.23 (s, 3H), 1.82 (s, 3H).

Example 23

N-(3-{3-Fluoro-4-[5-(2-methyl-6-nitro-2,3-dihydro-imidazo[2,1-b]oxazol-2-ylmethoxy)-pyridin-2-yl]-phenyl}-2-oxo-oxazolidin-5-ylmethyl)-acetamide

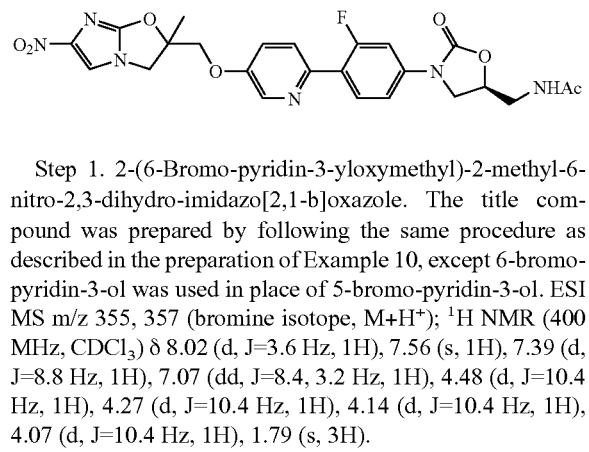

Step 1. 2-(6-Bromo-pyridin-3-yloxymethyl)-2-methyl-6-nitro-2,3-dihydro-imidazo[2,1-b]oxazole. The title compound was prepared by following the same procedure as described in the preparation of Example 10, except 6-bromo-pyridin-3-ol was used in place of 5-bromo-pyridin-3-ol. ESI MS m/z 355, 357 (bromine isotope, M+H⁺); ¹H NMR (400 MHz, CDCl₃) δ 8.02 (d, J=3.6 Hz, 1H), 7.56 (s, 1H), 7.39 (d, J=8.8 Hz, 1H), 7.07 (dd, J=8.4, 3.2 Hz, 1H), 4.48 (d, J=10.4 Hz, 1H), 4.27 (d, J=10.4 Hz, 1H), 4.14 (d, J=10.4 Hz, 1H), 4.07 (d, J=10.4 Hz, 1H), 1.79 (s, 3H).

Step 2. N-(3-{3-Fluoro-4-[5-(2-methyl-6-nitro-2,3-dihydro-imidazo[2,1-b]oxazol-2-ylmethoxy)-pyridin-2-yl]-phenyl}-2-oxo-oxazolidin-5-ylmethyl)-acetamide. The title compound (a mixture of two diasteroemers) was prepared by following the same procedure as described in the preparation of Example 7, except 2-(6-bromo-pyridin-3-yloxymethyl)-2-methyl-6-nitro-2,3-dihydro-imidazo[2,1-b]oxazole was used in place of 6(S)-(5-bromo-pyridin-2-yloxy)-2-nitro-6,7-dihydro-5H-imidazo[2,1-b][1,3]oxazine. ESI MS m/z 527.3 (M+H); ¹H NMR (400 MHz, DMSO) δ 8.34 (d, J=3.2 Hz, 1H), 8.23 (t, J=5.8 Hz, 1H), 8.15 (s, 1H), 7.93 (t, J=9.0 Hz, 1H), 7.71 (dd, J=8.8, 1.2 Hz, 1H), 7.57 (dd, J=14.4, 2.0 Hz, 1H), 7.47 (dd, J=8.8, 2.8 Hz, 1H), 7.40 (dd, J=8.8, 2.0 Hz, 1H), 4.76-4.71 (m, 1H), 4.43 (d, J=2.4 Hz, 1H), 4.39 (d, J=10.8 Hz, 1H), 4.19 (d, J=10.4 Hz, 1H), 4.14 (t, J=9.2 Hz, 1H), 3.76 (dd, J=9.2, 6.8 Hz, 1H), 3.40 (t, J=5.4 Hz, 2H), 1.81 (s, 3H), 1.69 (s, 3H).

Example 24

(S,S)—N-(3-{3-Fluoro-4-[4-(4-methoxy-benzyloxy)-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide

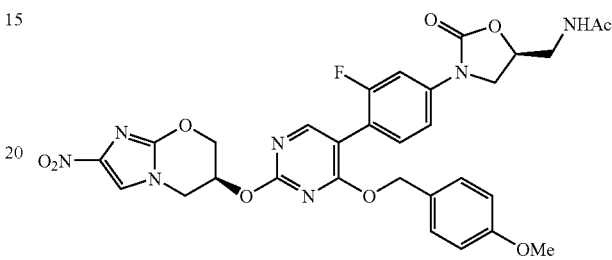

Step 1. 5-Bromo-2-chloro-4-(4-methoxy-benzyloxy)-pyrimidine. To a solution of (4-methoxy-phenyl)-methanol (1.38 g, 10 mmol) and 5-bromo-2,4-dichloro-pyrimidine (4.6 g, 20 mmol) in THF at −15° C. under nitrogen was added NaH (480 mg, 12 mmol). The mixture was stirred at 15° C. for 2 h. The reaction mixture was quenched with MeOH, diluted with EtOAc, washed with brine and concentrated in vacuo. The crude product was recrystallized from MeOH/H₂O to give the title compound (1.0 g) as a yellow solid.

Step 2. 6(S)-[5-Bromo-4-(4-methoxy-benzyloxy)-pyrimidin-2-yloxy]-2-nitro-6,7-dihydro-5H-imidazo[2,1-b][1,3]oxazine. The title compound was prepared by following the same procedure as described in the preparation of Example 7, except 5-bromo-2-chloro-4-(4-methoxy-benzyloxy)-pyrimidine was used in place of 5-bromo-2-fluoro-pyridine. ESI MS m/z 478, 480 (M+H⁺); ¹H NMR (400 MHz, CDCl₃) δ 8.31 (s, 1H), 7.43 (s, 1H), 7.36 (d, J=8.4 Hz, 2H), 6.91 (d, J=8.8 Hz, 2H), 5.56 (s, 1H), 5.39 (s, 2H), 4.82 (d, J=12.0 Hz, 1H), 4.51 (d, J=12.8 Hz, 1H), 4.37 (s, 2H), 3.82 (s, 3H).

Step 3. (S,S)—N-(3-{3-Fluoro-4-[4-(4-methoxy-benzyloxy)-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide. The title compound is prepared by following the same procedure as described in the preparation of Example 7, except 6(S)-[5-bromo-4-(4-methoxy-benzyloxy)-pyrimidin-2-yloxy]-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ESI MS m/z 650.8 (M+H⁺); ¹H NMR (400 MHz, CDCl₃) δ 8.20 (s, 1H), 7.54 (dd, J=12.4, 2.0 Hz, 1H), 7.44 (s, 1H), 7.34-7.21 (m, 4H), 6.86 (d, J=8.8 Hz, 1H), 6.00 (t, J=6.4 Hz, 1H), 5.66 (brs, 1H), 5.35 (s, 2H), 4.85 (dd, J=12.0, 2.8 Hz, 1H), 4.82-4.77 (m, 1H), 4.53 (d, J=11.2 Hz, 2H), 4.06 (t, J=9.0 Hz, 1H), 3.78 (s, 3H), 3.74-3.61 (m, 3H), 2.02 (s, 3H).

Example 25

(S,S)—N-(3-{3-Fluoro-4-[2-(2-nitro-6,7-dihydro-5H-imidazo[2,1-b][1,3]oxazin-6-yloxy)-6-oxo-1,6-dihydro-pyrimidin-5-yl]-phenyl}-2-oxo-oxazolidin-5-ylmethyl)-acetamide

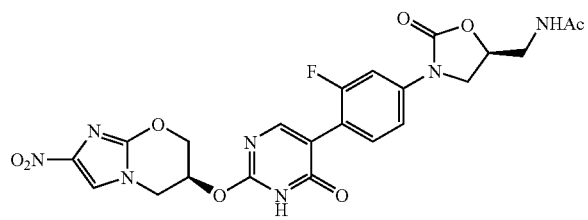

To a solution of (S,S)—N-(3-{3-Fluoro-4-[4-(4-methoxy-benzyloxy)-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide (60 mg, 0.092 mmol) in TFA/methylene chloride (3.0 mL, 1/1) was stirred at rt for 1 h. Solvents were evaporated and triturated with ether to give the title product (43 mg, 88%) as a pale yellow solid. ESI MS m/z 530.4 (M+H+).

Example 26

(S,S)—N-(3-{3-Fluoro-4-[2-(2-nitro-6,7-dihydro-5H-imidazo[2,1-b][1,3]oxazin-6-yloxy)-4-trifluoromethyl-pyrimidin-5-yl]-phenyl}-2-oxo-oxazolidin-5-ylmethyl)-acetamide:

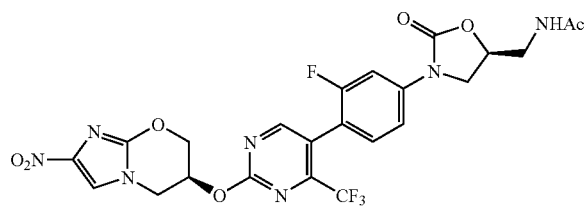

Step 1. 6-(5-Bromo-4-trifluoromethyl-pyrimidin-2-yloxy)-2-nitro-6,7-dihydro-5H-imidazo[2,1-b][1,3]oxazine. The title compound was prepared by following the same procedure as described in the preparation of Example 7, except 5-bromo-2-chloro-4-trifluoromethyl-pyrimidine (prepared as described by Ondi 2004) was used in place of 5-bromo-2-fluoro-pyridine. ESI MS m/z 410, 412 (bromine isotope, M+H+); 1H NMR (400 MHz, CDCl3) δ 8.87 (s, 1H), 7.46 (s, 1H), 5.66 (s, 1H), 4.88 (d, J=14.8 Hz, 1H), 4.57 (d, J=12.8 Hz, 1H), 4.50-4.40 (m, 2H).

Step 2. (S,S)—N-(3-{3-Fluoro-4-[2-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide. The title compound was prepared by following the same procedure as described in the preparation of Example 7, except 6(S)-(5-bromo-4-trifluoromethyl-pyrimidin-2-yloxy)-2-nitro-6,7-dihydro-5H-imidazo[2,1-b][1,3]oxazine was used in place of 6(S)-(5-bromo-pyridin-2-yloxy)-2-nitro-6,7-dihydro-5H-imidazo[2,1-b][1,3]oxazine. ESI MS m/z 582.5 (M+H+); 1H NMR (400 MHz, CDCl3) δ 8.65 (s, 1H), 7.63 (d, J=11.6 Hz, 1H), 7.48 (s, 1H), 7.32-7.25 (m, 2H), 6.02 (t, J=6.2 Hz, 1H), 5.75 (s, 1H), 4.94 (d, J=12.0 Hz, 1H), 4.83-4.82 (m, 1H), 4.60 (d, J=12.4 Hz, 1H), 4.49 (brs, 2H), 4.10 (t, J=9.8 Hz, 1H), 3.84 (t, J=7.8 Hz, 1H), 3.72-3.62 (m, 2H), 2.04 (s, 3H).

Example 26

(S,S)—N-{3-[2,6-Difluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide:

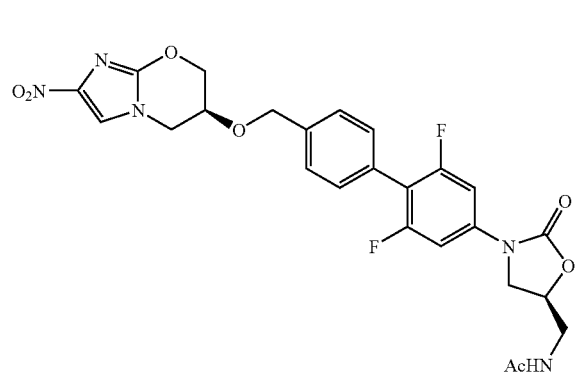

Step 1. 2-Nitro-6(S)-[4-(4,4,5,5-tetramethyl-[1,3,2]dioxaborolan-2-yl)-benzyloxy]-6,7-dihydro-5H-imidazo[2,1-b][1,3]oxazine. To a solution of 2-nitro-6,7-dihydro-5H-imidazo[2,1-b][1,3]oxazin-6-ol (420 mg, 2.28 mmol) and 2-(4-bromomethyl-phenyl)-4,4,5,5-tetramethyl-[1,3,2]dioxaborolane (339 mg, 1.14 mmol) in DMF (10.0 mL) at −60° C. under nitrogen was added NaH (137 mg, 3.42 mmol, 60% dispersion in mineral oil). The mixture was slowly warmed to room temperature and stirred at room temperature for 1 h. The reaction mixture was diluted with EtOAc, washed with brine and concentrated in vacuo to give the title compound as a yellow solid (0.460 g, 89%). ESI MS m/z 402.4 (M+H+).

Step 2. (S,S)—N-{3-[2,6-Difluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide. To a suspension of 2-nitro-6(S)-[4-(4,4,5,5-tetramethyl-[1,3,2]dioxaborolan-2-yl)-benzyloxy]-6,7-dihydro-5H-imidazo[2,1-b][1,3]oxazine (160 mg, 0.40 mmol), N-[3-(3,5-difluoro-4-iodo-phenyl)-2-oxo-oxazolidin-5(S)-ylmethyl]-acetamide (158 mg, 0.40 mmol) (prepared as described by Das et. al. WO 2006/038100 A1), Pd(Ph3P)4 (58 mg, 0.05 mmol) and K2CO3 (121 mg, 0.88 mmol) in DMF/H2O (10/1. 5.5 mL) was degassed. The mixture was heated to 80° C. for 2.5 h, diluted with EtOAc, washed with brine and concentrated in vacuo to give a crude product. The crude product was triturated with methylene chloride to afford the title product (172 mg, 79%). ESI MS m/z 544.5 (M+H+).

Example 27

N-{3-[4-(6-Nitro-imidazo[2,1-b]-2(3H)-8-aza-spiro[4.5]dec-8-yl)-3-fluorophenyl]-2-oxo-oxazolidin-5(S)-ylmethyl}-acetamide

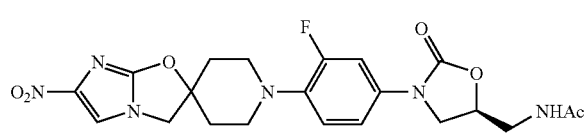

Step 1. N-{3-[3-Fluoro-4-(1-oxa-6-aza-spiro[2.5]oct-6-yl)-phenyl]-2-oxo-oxazolidin-5(S)-ylmethyl}-acetamide. To a solution of trimethylsulfoxonium iodide (0.96 g, 4.35 mmol) in DMSO (10.0 mL) was added NaH (232 mg, 5.8 mmol, 60% dispersion in mineral oil) at room temperature. The mixture was stirred at room temperature for 30 min and N-{3-[3-fluoro-4-(4-oxo-piperidin-1-yl)-phenyl]-2-oxo-oxazolidin-5-ylmethyl}-acetamide (prepared as described by WO 2005/054234) was added to the reaction mixture. The reaction mixture was stirred at room temperature for 3 h, poured into ice-water and extracted with ethyl acetate. The organic layer was washed with water, brine, dried, and concentrated by vacuum to give the title product (650 mg, 62%) as a yellow solid. ESI MS m/z 364 (M+H$^+$).

Step 2. N-(3-{4-[4-(2-Bromo-4-nitro-imidazol-1-ylmethyl)-4-hydroxy-piperidin-1-yl]-3-fluoro-phenyl}-2-oxo-oxazolidin-5(S)-ylmethyl)-acetamide. A solution of N-{3-[3-fluoro-4-(1-oxa-6-aza-spiro[2.5]oct-6-yl)-phenyl]-2-oxo-oxazolidin-5(S)-ylmethyl}-acetamide (100 mg, 0.275 mmol), 2-bromo-4-nitro-1H-imidazole (158 mg, 0.83 mmol), and triethylamine (0.40 mL) in acetonitrile (3.0 mL) was stirred at 80° C. for 36 h. The mixture was diluted with EtOAc and washed with brine to give a crude product, which was purified by flash chromatography to give the title product. This is directly used for next step. ESI MS m/z 555, 557 (bromine isotope pattern, M+H$^+$).

Step 4. N-{3-[4-(6-Nitro-imidazo[2,1-b]-2(3H)-8-aza-spiro[4.5]dec-8-yl)-3-fluorophenyl]-2-oxo-oxazolidin-5(S)-ylmethyl}-acetamide. To a solution of N-(3-{4-[4-(2-bromo-4-nitro-imidazol-1-ylmethyl)-4-hydroxy-piperidin-1-yl]-3-fluoro-phenyl}-2-oxo-oxazolidin-5(S)-ylmethyl)-acetamide in DMF (3.0 mL) at 0° C. was added NaH (80 mg, 60% dispersion in mineral oil). The reaction mixture was slowly warmed to room temperature and stirred at room temperature for 1 h. The reaction mixture was quenched by addition of MeOH, diluted with EtOAc, washed with brine, dried, and concentrated in vacuo to give a crude product. This was purified by flash chromatography to give the title product (35 mg, 27% over 2 steps) as yellow oil. ESI MS m/z 475 (M+H$^+$).

Example 28

(S,R)-3-[2-Fluoro-4'-(2-nitro-6,7-dihydro-5H-imidazo[2,1-b][1,3]oxazin-6-yloxymethyl)-biphenyl-4-yl]-5-hydroxymethyl-oxazolidin-2-one

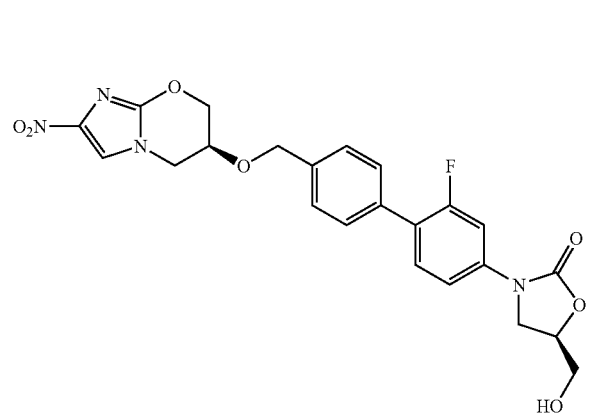

Step 1. 5-(tert-Butyl-dimethyl-silanyloxymethyl)-3-[2-fluoro-4'-(2-nitro-6,7-dihydro-5H-imidazo[2,1-b][1,3]oxazin-6-yloxymethyl)-biphenyl-4-yl]-oxazolidin-2-one. The title compound was prepared by following the same procedure as described in the preparation of Example 26, except 3-(4-bromo-3-fluoro-phenyl)-5(S)-(tert-butyl-dimethyl-silanyloxymethyl)-oxazolidin-2-one was used in place of N-[3-(3,5-difluoro-4-iodo-phenyl)-2-oxo-oxazolidin-5(R)-ylmethyl]-acetamide. ESI MS m/z 599.6 (M+H$^+$); $^1$H NMR (400 MHz, DMSO) δ 8.00 (s, 1H), 7.56 (dd, J=13.6, 2.4 Hz, 1H), 7.52-7.47 (m, 3H), 7.40-7.35 (m, 3H), 5.71 (s, 2H), 4.77-4.74 (m, 1H), 4.67-4.62 (m, 3H), 4.43 (d, J=11.6 Hz, 1H), 4.24-4.20 (m, 2H), 4.11 (t, J=9.2 Hz, 1H), 3.84 (dd, J=11.6, 2.4 Hz, 1H), 3.79 (dd, J=9.2, 5.2 Hz, 1H), 3.71 (dd, J=11.6, 2.8 Hz, 1H), 0.74 (s, 9H), 0.002 (s, 3H), 0.000 (s, 3H).

Step 2. 3-[2-Fluoro-4'-(2-nitro-6,7-dihydro-5H-imidazo[2,1-b][1,3]oxazin-6(S)-yloxymethyl)-biphenyl-4-yl]-5(R)-hydroxymethyl-oxazolidin-2-one. To a solution of 5(R)-(tert-butyl-dimethyl-silanyloxymethyl)-3-[2-fluoro-4'-(2-nitro-6,7-dihydro-5H-imidazo[2,1-b][1,3]oxazin-6(S)-yloxymethyl)-biphenyl-4-yl]-oxazolidin-2-one (70 mg, 0.117 mmol) in THF (8.0 mL) was added TBAF (1.0 mL, 1.0 mmol, 1.0 M in THF). The mixture was stirred at room temperature for 1 h. The reaction mixture was diluted with EtOAc, washed with brine, purified by flash chromatography to give the title product (36 mg, 64%) as a yellow solid. ESI MS m/z 485.3 (M+H$^+$); $^1$H NMR (400 MHz, DMSO) δ 8.03 (s, 1H), 7.60 (dd, J=13.6, 2.4 Hz, 1H), 7.56-7.50 (m, 3H), 7.44-7.38 (m, 3H), 5.23 (t, J=5.6 Hz, 1H), 4.74-4.66 (m, 4H), 4.46 (d, J=12.0 Hz, 1H), 4.26-4.20 (m, 2H), 4.10 (t, J=9.2 Hz, 1H), 3.85 (dd, J=8.8, 6.0 Hz, 1H), 3.68-3.64 (m, 1H), 3.58-3.52 (m, 1H).

Example 29

(S,R)-3-{3-Fluoro-4-[2-(2-nitro-6,7-dihydro-5H-imidazo[2,1-b][1,3]oxazin-6-yloxy)-pyrimidin-5-yl]-phenyl}-5-hydroxymethyl-oxazolidin-2-one

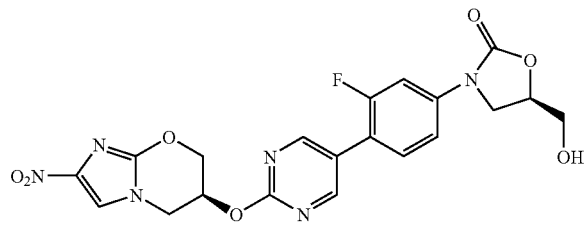

Step 1. 3-(4-Bromo-3-fluoro-phenyl)-5 (R)-hydroxymethyl-oxazolidin-2-one. Bromine (0.07 mL, 1.41 mmol) was added in a dropwise fashion to 3-(3-Fluoro-phenyl)-5(R)-hydroxymethyl-oxazolidin-2-one (0.1 g, 0.47 mmol) in 2 mL of chloroform at room temperature. The reaction mixture was stirred for 3 hours at room temperature, the solvent was removed in vacuo. The residue was washed with saturated $Na_2S_2O_3$, brine, and dried with $Na_2SO_4$. The solvent was removed and the residue was crystallized from ethyl acetate/hexanes to yield the title compound as a solid. ESI MS m/z 290 (M+H$^+$); $^1$H NMR (400 MHz, CDCl$_3$) δ 7.43 (m, 2H), 7.01 (t, J=21 Hz, 1H), 4.68 (m, 1H), 3.90 (m, 2H), 3.67 (m, 1H), 3.20 (bs, 1H).

Step 2. 3-(4-Bromo-3-fluoro-phenyl)-5(R)-(tert-butyl-dimethyl-silanyloxymethyl)-oxazolidin-2-one. A solution of 3-(4-Bromo-3-fluoro-phenyl)-5(R)-hydroxymethyl-oxazolidin-2-one (2.5 g, 8.6 mmol), TBSCl (1.7 g, 11.1 mmol) and imidazole (0.76 g, 11.1 mmol) in THF was stirred overnight. The reaction mixture was diluted with EtOAc, washed with brine and concentrated in vacuo to give the title compound as a white solid. ESI MS m/z 405 (M+H$^+$). $^1$H NMR (400 MHz, CDCl$_3$) δ 7.45 (m, 2H), 7.10 (m, 1H), 4.61 (m, 1H), 3.93 (t, J=23 Hz, 1H), 3.85 (m, 2H), 3.71 (dd, J=7, 28 Hz, 1H), 0.76 (s, 9H), 0 (s, 6H).

Step 3. 5(R)-(tert-Butyl-dimethyl-silanyloxymethyl)-3-[3-fluoro-4-(4,4,5,5-tetramethyl-[1,3,2]dioxaborolan-2-yl)-phenyl]-oxazolidin-2-one. A solution of 3-(4-bromo-3-fluoro-phenyl)-5(R)-(tert-butyl-dimethyl-silanyloxymethyl)-oxazolidin-2-one (4.45 g, 11.0 mmol), PdCl$_2$dppf (1.346 g, 1.65 mmol), bis(pinacolato)diboron (3.92 g, 15.4 mmol) and potassium acetate (3.20 g) in DMSO (100 mL) was degassed (3×) and stirred at 80° C. for 2.5 h. The reaction mixture was diluted with EtOAc, washed with brine, dried, and concentrated in vacuo to give a crude product. The crude product was purified by flash chromatography to give the title product as a white solid (5.73 g). ESI MS m/z 452.4 (M+H$^+$).

Step 4. 5 (R)-(tert-Butyl-dimethyl-silanyloxymethyl)-3-{3-fluoro-4-[2-(2-nitro-6,7-dihydro-5H-imidazo[2,1-b][1,3]oxazin-6(S)-yloxy)-pyrimidin-5-yl]-phenyl}-oxazolidin-2-one. The title compound was prepared by following the same procedure as described in the preparation of Example 8, except 5(R)-(tert-butyl-dimethyl-silanyloxymethyl)-3-[3-fluoro-4-(4,4,5,5-tetramethyl-[1,3,2]dioxaborolan-2-yl)-phenyl]-oxazolidin-2-one was used in place of N-{3-[3-fluoro-4-(4,4,5,5-tetramethyl-[1,3,2]dioxaborolan-2-yl)-phenyl]-2-oxo-oxazolidin-5(S)-ylmethyl}-acetamide. ESI MS m/z 587 (M+H$^+$).

Step 5. (S,R)-3-{3-Fluoro-4-[2-(2-nitro-6,7-dihydro-5H-imidazo[2,1-b][1,3]oxazin-6-yloxy)-pyrimidin-5-yl]-phenyl}-5-hydroxymethyl-oxazolidin-2-one. The title compound was prepared by following the same procedure as described in the preparation of Example 28, except 5(R)-(tert-butyl-dimethyl-silanyloxymethyl)-3-{3-fluoro-4-[2-(2-nitro-6,7-dihydro-5H-imidazo[2,1-b][1,3]oxazin-6(S)-yloxy)-pyrimidin-5-yl]-phenyl}-oxazolidin-2-one was used in place of 3-[2-fluoro-4'-(2-nitro-6,7-dihydro-5H-imidazo[2,1-b][1,3]oxazin-6(S)-yloxymethyl)-biphenyl-4-yl]-5(R)-hydroxymethyl-oxazolidin-2-one. ESI MS m/z 473 (M+H$^+$); $^1$H NMR (400 MHz, DMSO) δ 8.86 (s, 2H), 8.06 (s, 1H), 7.68 (d, J=8.8 Hz, 1H), 7.66 (t, J=2.8 Hz, 1H), 7.47 (dd, J=8.8, 2.4 Hz, 1H), 5.74 (s, 1H), 5.23 (t, J=5.6 Hz, 1H), 4.77-4.70 (m, 2H), 4.47 (s, 1H), 4.11 (t, J=9.0 Hz, 1H), 3.86 (dd, J=8.8, 6.0 Hz, 1H), 3.71-3.65 (m, 1H), 3.57-3.53 (m, 1H), 3.38-3.35 (m, 1H).

Example 30

(S,R)-3-{3-Fluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one

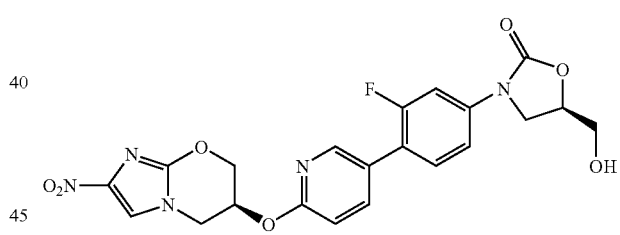

Step 1. 5(R)-(tert-Butyl-dimethyl-silanyloxymethyl)-3-{3-fluoro-4-[6-(2-nitro-6,7-dihydro-5H-imidazo[2,1-b][1,3]oxazin-6(S)-yloxy)-pyridin-3-yl]-phenyl}-oxazolidin-2-one.

The title compound was prepared by following the same procedure as described in the preparation of Example 29, except 6(S)-(5-bromo-pyridin-2-yloxy)-2-nitro-6,7-dihydro-5H-imidazo[2,1-b][1,3]oxazine was used in place of 6(S)-(5-bromo-pyrimidin-2-yloxy)-2-nitro-6,7-dihydro-5H-imidazo[2,1-b][1,3]oxazine. ESI MS m/z 586.5 (M+H$^+$).

Step 2. (S,R)-3-{3-Fluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one. The title compound was prepared by following the same procedure as described in the preparation of Example 28, except 5(R)-(tert-butyl-dimethyl-silanyloxymethyl)-3-{3-fluoro-4-[6-(2-nitro-6,7-dihydro- 5H-imidazo[2,1-b][1,3]oxazin-6(S)-yloxy)-pyridin-3-yl]-phenyl}-oxazolidin-2-one was used. ESI MS m/z 472.3 (M+H+); ¹H NMR (400 MHz, DMSO) δ 8.38 (s, 1H), 8.06 (s, 1H), 7.94-7.91 (m, 1H), 7.63 (dt, J=13.6, 2.4 Hz, 1H), 7.57 (d, J=8.8 Hz, 1H), 7.46-7.43 (m, 1H), 6.97 (d, J=9.2 Hz, 1H), 5.76 (s, 1H), 5.24 (t, J=5.6 Hz, 1H), 4.74-4.67 (m, 2H), 4.48-4.38 (m, 2H), 4.13-4.09 (m, 1H), 3.86 (dd, J=8.8, 6.0 Hz, 1H), 3.70-3.64 (m, 1H), 3.56-3.52 (m, 1H), 3.14 (d, J=5.2 Hz, 1H).

Example 31

(S,S)—N-{3-[2-Fluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide:

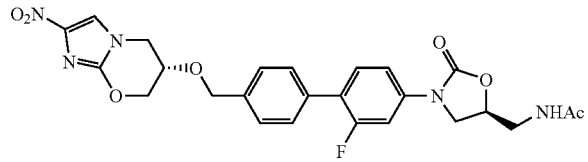

Step 1. 6(S)-(4-Bromo-benzyloxy)-2-nitro-6,7-dihydro-5H-imidazo[2,1-b][1,3]oxazine. A solution of 2-nitro-6,7-dihydro-5H-imidazo[2,1-b][1,3]oxazin-6(S)-ol (0.5 g, 2.7 mmol) and 4-bromobenzylbromide (0.81 g, 3.24 mmol) was dissolved in DMF (50 ml) and treated with NaH (0.13 g, 3.24 mmol). The mixture was stirred for 4 hours at room temperature and diluted with water (100 ml) and extracted with EtOAc. The organic layer was separated and washed with water (2x), dried over Na₂SO₄ and concentrated. The resulting gum was washed with hexanes to remove unreacted benzyl bromide. The mixture was purified by preparative TLC. ESI MS m/z 356 (M+H+); ¹H NMR (400 MHz, CDCl₃) δ 7.56-7.42 (m, 2H), 7.40 (s, 1H), 7.24-7.18 (m, 2H), 4.73-4.50 (m, 4H), 4.39-4.30 (m, 1H), 4.28-4.03 (m, 2H).

Step 2. (S,S)—N-{3-[2-Fluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide. 6(S)-(4-Bromo-benzyloxy)-2-nitro-6,7-dihydro-5H-imidazo[2,1-b][1,3]oxazine (92 mg, 0.26 mmol), N-{3-[3-fluoro-4-(4,4,5,5-tetramethyl-[1,3,2]dioxaborolan-2-yl)-phenyl]-2-oxo-oxazolidin-5(S)-ylmethyl}-acetamide (100 mg, 0.26 mmol) and K₂CO₃ (72 mg, 0.52 mmol) and Pd(PPh₃)₄ (45 mg, 0.039 mmol) were combined and suspended in DMF (5 ml) and water (0.7 ml). The mixture was heated to 75° C. for 4 h then poured into cold water (30 ml). The mixture was extracted with EtOAc then dried over Na₂SO₄ and concentrated. The oil was purified by preparative TLC to give 11 mg (1%) of the product as a tan solid. ESI MS m/z 526 (M+H+); ¹H NMR (400 MHz, CDCl₃) δ 8.28-8.22 (s, 1H), 7.61-7.25 (m, 7H), 4.80-4.62 (m, 4H), 4.50-4.40 (m, 1H), 4.30-4.08 (m, 1H), 4.31-4.08 (m, 2H), 3.80-3.71 (m, 1H), 3.40-3.25 (m, 4H), 1.80 (s, 3H).

Example 32

(S,S)—N-[3-(3-Fluoro-4-{4-[2-(2-nitro-6,7-dihydro-5H-imidazo[2,1-b][1,3]oxazin-6-yloxy)-acetyl]-piperazin-1-yl}-phenyl)-2-oxo-oxazolidin-5-ylmethyl]-acetamide

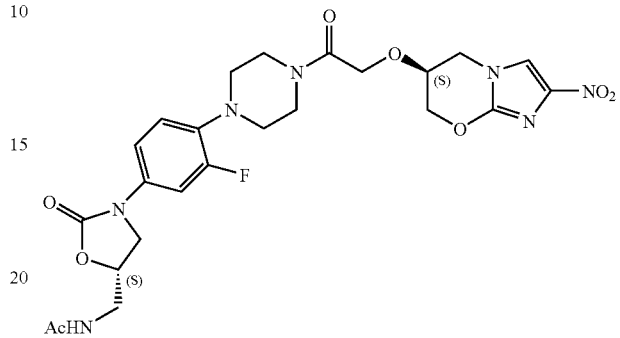

Step 1. (2-Nitro-6,7-dihydro-5H-imidazo[2,1-b][1,3]oxazin-6-yloxy)-acetic acid tert-butyl ester. A solution of the 2-nitro-6,7-dihydro-5H-imidazo[2,1-b][1,3]oxazin-6(S)-ol (0.5 g, 2.7 mmol) and bromo-acetic acid tert-butyl ester (0.48 ml, 3.2 mmol) in DMF (10 ml) was treated with NaH (0.124 g, 3.2 mmol) and stirred at room temperature for 3 hours. The reaction was quenched by addition of sat. ammonium chloride and the mixture washed with EtOAc. The organic layer was washed with water, dried over Na₂SO₄ and concentrated to give a white solid. The solid is filtered through silica gel to give the product as a white solid (1.86 g, 99%). ESI MS m/z 300 (M+H+); ¹H NMR (400 MHz, CDCl₃) δ 8.01 (s, 1H), 4.62-4.58 (m, 1H), 4.39-4.36 (m, 1H), 4.25 (s, 2H), 4.20-4.02 (m, 3H), 1.52 (s, 9H).

Step 2. (2-Nitro-6,7-dihydro-5H-imidazo[2,1-b][1,3]oxazin-6(S)-yloxy)-acetic acid. 2-Nitro-6,7-dihydro-5H-imidazo[2,1-b][1,3]oxazin-6(S)-yloxy)-acetic acid tert-butyl ester (1.2 g, 4.0 mmol) in CH₂Cl₂ (5 ml) was treated with TFA (5 ml) and stirred for 1 h at rt. The mixture was concentrated, the waxy solid (1.12 g) was used without further purification. ESI MS m/z 244 (M+H+); ¹H NMR (400 MHz, CDCl₃) δ 8.10 (s, 1H), 4.62-4.49 (m, 1H), 4.43-4.32 (m, 1H), 4.25 (s, 2H), 4.20-4.01 (m, 2H).

Step 3. N-[3-(3-Fluoro-4-{4-[2-(2-nitro-6,7-dihydro-5H-imidazo[2,1-b][1,3]oxazin-6-yloxy)-acetyl]-piperazin-1-yl}-phenyl)-2-oxo-oxazolidin-5-ylmethyl]-acetamide. A mixture of (2-nitro-6,7-dihydro-5H-imidazo[2,1-b][1,3]oxazin-6-yloxy)-acetic acid (53 mg, 0.22 mmol), N-[3-(3-fluoro-4-piperazin-1-yl-phenyl)-2-oxo-oxazolidin-5-ylmethyl]-acetamide (73 mg, 0.228 mmol) (prepared as described by Barbachyn et al, U.S. Pat. No. 5,547,950) and TBTU (114 mg, 0.35 mmol) is dissolved in DMF (5 ml) and treated with Et₃N (0.122 ml, 0.88 mmol) and stirred at room temperature for 12 hours. The mixture was diluted with EtOAc and water. The organic layer was washed with water, dried over sodium sulfate and concentrated. The residue was purified by preparative TLC to give 13 mg (10%) of the titled product as a tan solid. ESI MS m/z 562 (M+H+); ¹H NMR (400 MHz, CDCl₃) δ 7.50 (d, J=11.6 Hz, 1H), 7.44 (s, 1H), 7.21-7.02 (m, 1H), 7.00-6.85 (m, 1H), 5.99-5.92 (m, 1H), 4.76-4.67 (m, 2H), 4.44-4.22 (m, 4H), 4.05-4.01 (m, 1H), 3.79-3.44 (m, 4H), 3.49 (s, 2H), 3.10-2.62 (m, 4H), 2.02 (s, 3H), 1.24 (s, 3H).

Example 33

N-(3-{3-Fluoro-4-[4-(2-methyl-6-nitro-2,3-dihydro-imidazo[2,1-b]oxazol-2-ylmethyl)-piperazin-1-yl]-phenyl}-2-oxo-oxazolidin-5-ylmethyl)-acetamide

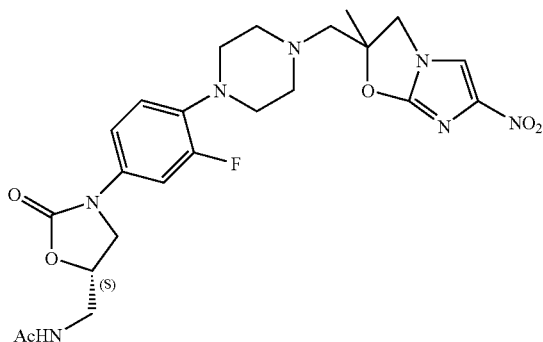

Step 1. N-[3-(4-{4-[3-(2-Bromo-4-nitro-imidazol-1-yl)-2-hydroxy-2-methyl-propyl]-piperazin-1-yl}-3-fluoro-phenyl)-2-oxo-oxazolidin-5-ylmethyl]-acetamide. A solution of N-[3-(3-fluoro-4-piperazin-1-yl-phenyl)-2-oxo-oxazolidin-5(S)-ylmethyl]-acetamide (335 mg, 0.99 mmol) (prepared as described by Barbachyn et al, U.S. Pat. No. 5,547,950) and 2-Bromo-1-(2-methyl-oxiranylmethyl)-4-nitro-1H-imidazole (261 mg, 1 mmol) was heated to reflux in IPA for 4 h. The mixture is concentrated to give a mixture of N-[3-(4-{4-[3-(2-bromo-4-nitro-imidazol-1-yl)-2-hydroxy-2-methyl-propyl]-piperazin-1-yl}-3-fluoro-phenyl)-2-oxo-oxazolidin-5-ylmethyl]-acetamide and N-(3-{3-fluoro-4-[4-(2-methyl-6-nitro-2,3-dihydro-imidazo[2,1-b]oxazol-2-ylmethyl)-piperazin-1-yl]-phenyl}-2-oxo-oxazolidin-5-ylmethyl)-acetamide (233 mg, 48%). The mixture was used in the next step without further purification. ESI MS m/z 518, 598 (M+H$^+$).

Step 2. N-(3-{3-Fluoro-4-[4-(2-methyl-6-nitro-2,3-dihydro-imidazo[2,1-b]oxazol-2-ylmethyl)-piperazin-1-yl]-phenyl}-2-oxo-oxazolidin-5-ylmethyl)-acetamide. The above mixture containing N-[3-(4-{4-[3-(2-bromo-4-nitro-imidazol-1-yl)-2-hydroxy-2-methyl-propyl]-piperazin-1-yl}-3-fluoro-phenyl)-2-oxo-oxazolidin-5-ylmethyl]-acetamide (233 mg, 0.39 mmol) in DMF (10 ml) was treated with NaH (39 mg, 0.97 mmol) and heated to 60° C. for 2 h. The reaction mixture is cooled, diluted with saturated NH$_4$Cl (aq) and extracted with EtOAc. The organic layer was dried over Na$_2$SO$_4$, concentrated and purified by preparative TLC to give N-(3-{3-fluoro-4-[4-(2-methyl-6-nitro-2,3-dihydro-imidazo[2,1-b]oxazol-2-ylmethyl)-piperazin-1-yl]-phenyl}-2-oxo-oxazolidin-5-ylmethyl)-acetamide (48 mg, 24%). ESI MS m/z 518 (M+H$^+$); $^1$H NMR (400 MHz, CD$_3$OD) δ 7.82 (s, 1H), 7.4-7.25 (m, 1H), 7.0-6.85 (m, 1H), 6.85-6.75 (m, 1H), 4.72-4.65 (m, 1H), 4.30-4.25 (m, 1H), 4.01-3.72 (m, 6H), 3.62-3.32 (m, 5H), 2.85-2.58 (m, 5H), 1.93 (s, 3H), 1.58 (s, 3H).

Example 34

(S,R)-3-[2-Fluoro-4'-(2-nitro-6,7-dihydro-5H-imidazo[2,1-b][1,3]oxazin-6-yloxymethyl)-biphen-4-yl]-5-[1,2,3]triazol-1-ylmethyl-oxazolidin-2-one

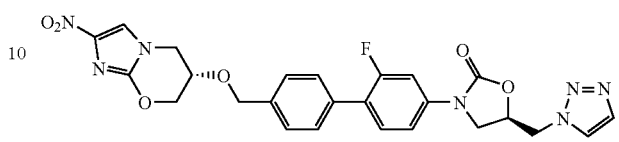

Step 1. 5(R)-Azidomethyl-3-(3-fluoro-4-iodo-phenyl)-oxazolidin-2-one. This title compound was prepared following a procedure described in WO 2006/022794.

Step 2. 3-(3-Fluoro-4-iodo-phenyl)-5(R)-[1,2,3]triazol-1-ylmethyl-oxazolidin-2-one. To a solution of 5(R)-azidomethyl-3-(3-fluoro-4-iodo-phenyl)-oxazolidin-2-one (770 mg, 2.138 mmol) in 1,4-dioxane (2 mL) was added bicyclo[2.2.1]hepta-2,5-diene (2.2 mL, 21.37 mmol), and the reaction mixture was heated at 100° C. for 27 h in a sealed tube. The reaction mixture was cooled to rt, filtered, the solid was washed with hexanes to provide 610 mg (74%) of the title product as a light brown solid. LCMS (ESI) m/z 389 (M+H$^+$).

Step 3. (S,R)-3-[2-Fluoro-4'-(2-nitro-6,7-dihydro-5H-imidazo[2,1-b][1,3]oxazin-6-yloxymethyl)-biphen-4-yl]-5-[1,2,3]triazol-1-ylmethyl-oxazolidin-2-one. 3-(3-Fluoro-4-iodo-phenyl)-5(R)-[1,2,3]triazol-1-ylmethyl-oxazolidin-2-one (50 mg, 0.129 mmol), 2-nitro-6(S)-[4-(4,4,5,5-tetramethyl-[1,3,2]dioxaborolan-2-yl)-benzyloxy]-6,7-dihydro-5H-imidazo[2,1-b][1,3]oxazine (62 mg, 0.155 mmol), K$_2$CO$_3$ (136 mg, 0.258 mmol) and Pd(PPh$_3$)$_4$ (15 mg, 0.013 mmol) were combined and suspended in DMF (1 ml) and water (0.1 ml). The mixture was heated to 60° C. for 5 hours then quenched with sat. aqueous NH$_4$Cl (1 mL) at rt. The mixture was diluted with EtOAc (10 mL) and washed with water (5 mL×5). The organic phases were dried (MgSO$_4$) and concentrated. Column chromatography (2% MeOH/CH$_2$Cl$_2$) provided 54 mg (78%) of the title product as yellow solid. LCMS (ESI) m/z 536 (M+H$^+$).

Example 35

(S,R)-3-{3-Fluoro-4-[6-(2-nitro-6,7-dihydro-5H-imidazo[2,1-b][1,3]oxazin-6-yloxymethyl)-pyridin-3-yl]-phenyl}-5-[1,2,3]triazol-1-ylmethyl-oxazolidin-2-one

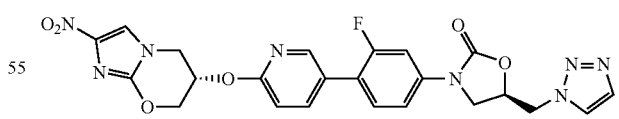

3-(3-Fluoro-4-iodo-phenyl)-5(R)-[1,2,3]triazol-1-ylmethyl-oxazolidin-2-one (90 mg, 0.232 mmol), 2-Nitro-6(S)-[5-(4,4,5,5-tetramethyl-[1,3,2]dioxaborolan-2-yl)-pyridin-2-ylmethoxy]-6,7-dihydro-5H-imidazo[2,1-b][1,3]oxazine (108 mg, 0.278 mmol), K$_2$CO$_3$ (244 mg, 0.464 mmol) and Pd(PPh$_3$)$_4$ (27 mg, 0.023 mmol) were combined and suspended in DMF (2 ml) and water (0.2 ml). The mixture was heated to 60° C. for 1½ hours then quenched with sat. aqueous NH$_4$Cl (2 mL) at rt. The mixture was diluted with EtOAc (10 mL) and washed with water (5 mL×5). The organic phases were dried (MgSO$_4$) and concentrated. Column chromatography (2% MeOH/CH$_2$Cl$_2$) provided 60 mg (50%) of the title product as yellow solid. LCMS (ESI) m/z 523 (M+H$^+$).

Example 36

N-{3-[2-Fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide

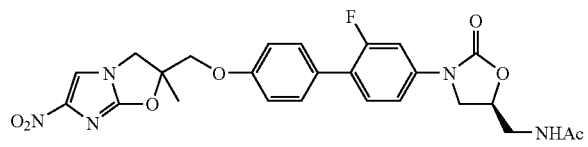

To an oven dried round bottom flask was charged N-{3-[3-Fluoro-4-(4,4,5,5-tetramethyl-[1,3,2]dioxaborolan-2-yl)-phenyl]-2-oxo-oxazolidin-5-ylmethyl}-acetamide (78 mg, 0.2 mmol), 2-(4-Bromo-phenoxymethyl)-2-methyl-6-nitro-2,3-dihydro-imidazo[2,1-b]oxazole (prepared similarly as described by Sasaki, H. et al: Journal of Medicinal Chemistry (2006), 49(26), 7854-7860; 71 mg, 0.2 mmol), Ph(PPh$_3$)$_4$ (23 mg, 0.02 mmol) and K$_2$CO$_3$ (55 mg, 0.4 mmol). The flask was flushed with nitrogen and was added 3 mL degassed DMF/H$_2$O (10/1, v/v). The resulting mixture was stirred at 80° C. for 3 hours before it was cooled down and partitioned into 50 mL EtOAc/50 mL water. The organic layer was washed with brine and dried over Na$_2$SO$_4$, concentrated, and purified by column chromatography (CH$_2$Cl$_2$/MeOH, v/v, 20:1 to 10:1) gave the titled compound (70 mg) as off-white solid. ESI MS m/z 526 (M+H). $^1$H NMR (400 MHz, CD$_3$OD) δ 7.86 (s, 1H), 7.52-7.59 (m, 1H), 7.45-7.52 (m, 3H), 7.32-7.38 (m, 1H), 6.96-7.02 (m, 2H), 4.76-4.84 (m, 1H), 4.51 (d, J=6.8 Hz, 1H), 4.38 (d, J=6.8 Hz, 1H), 4.27 (d, J=6.8 Hz, 1H), 4.18 (d, J=6.8 Hz, 1H), 3.89 (s, 1H), 3.83 (dd, J=6.8, 9.2 Hz, 1H), 3.55-3.59 (m, 2H), 1.96 (s, 3H), 1.77 (s, 3H).

Example 37

N-{3-[2-Fluoro-3'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide

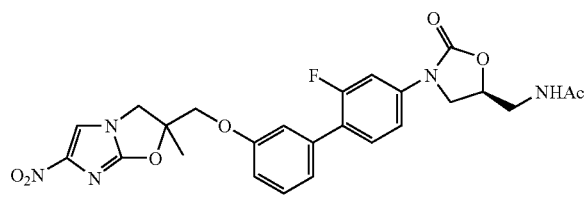

The titled compound was prepared by using the same procedure as described in Example 36, except that 2-(3-bromo-phenoxymethyl)-2-methyl-6-nitro-2,3-dihydro-imidazo[2,1-b]oxazole was used in the place of 2-(4-Bromo-phenoxymethyl)-2-methyl-6-nitro-2,3-dihydro-imidazo[2,1-b]oxazole. The titled compound was obtained as pale solid (62 mg, ~60% yield). ESI MS m/z 526 (M+H); $^1$H NMR (400 MHz, acetone-d$_6$) δ 7.84 (s, 1H), 7.63-7.70 (m, 1H), 7.56-7.62 (m, 1H), 7.40-7.52 (m, 2H), 7.25-7.31 (m, 1H), 7.14-7.19 (m, 1H), 6.98-7.04 (m, 1H), 6.85 (b, 1H), 4.81-4.90 (m, 1H), 4.56 (d, J=6.8 Hz, 1H), 4.45 (d, J=6.8 Hz, 1H), 4.35 (d, J=6.8 Hz, 1H), 4.22 (d, J=6.8 Hz, 1H), 4.20 (t, J=9.2 Hz, 1H), 3.89 (dd, J=6.8, 9.2 Hz, 1H), 3.57-3.68 (m, 2H), 1.99 (s, 3H), 1.83 (s, 3H).

Example 38

N-{3-[2'-Chloro-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide

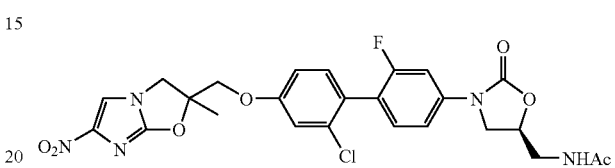

The titled compound was prepared by using the same procedure as described in Example 36, except that 2-(4-bromo-3-chloro-phenoxymethyl)-2-methyl-6-nitro-2,3-dihydro-imidazo[2,1-b]oxazole was used in the place of 2-(4-Bromo-phenoxymethyl)-2-methyl-6-nitro-2,3-dihydro-imidazo[2,1-b]oxazole. The titled compound was obtained as pale solid (64 mg, 57% yield). ESI MS m/z 560 (M+H).

Example 39

N-{3-[3'-Chloro-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide

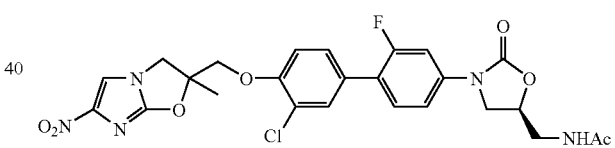

The titled compound was prepared by using the same procedure as described in Example 36, except that 2-(4-bromo-2-chloro-phenoxymethyl)-2-methyl-6-nitro-2,3-dihydro-imidazo[2,1-b]oxazole was used in the place of 2-(4-Bromo-phenoxymethyl)-2-methyl-6-nitro-2,3-dihydro-imidazo[2,1-b]oxazole. The titled compound was obtained as pale solid (64 mg, ~57% yield). ESI MS m/z 560 (M+H).

Example 40

N-{3-[3'-Cyano-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide

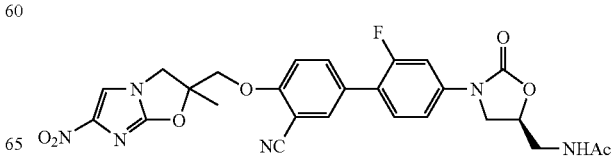

The titled compound was prepared by using the same procedure as described in Example 36, except that 5-Bromo-2-(2-methyl-6-nitro-2,3-dihydro-imidazo[2,1-b]oxazol-2-yl-methoxy)-benzonitrile was used in the place of 2-(4-Bromo-phenoxymethyl)-2-methyl-6-nitro-2,3-dihydro-imidazo[2,1-b]oxazole. The titled compound was obtained as pale solid (35 mg, ~40% yield). ESI MS m/z 551 (M+H). $^1$H NMR (400 MHz, DMSO-$d_6$) δ 7.64-7.70 (M, 1H), 7.56 (s, 1H), 7.23-7.32 (m, 2H), 6.96-7.04 (m, 2H), 6.75-6.84 (m, 2H), 4.12-4.22 (m, 1H), 3.95 (q, J=8.0 Hz, 2H), 3.87 (d, J=11.2 Hz, 1H), 3.65 (d, J=11.2 Hz, 1H), 3.57 (t, J=8.0 Hz, 1H), 3.15-3.22 (m, 1H), 2.6-3.0 (m, 2H, overlapped with water peak), 1.25 (s, 3H), 1.14 (s, 3H).

Example 41

N-(3-{2-Fluoro-4'-[(2-methyl-6-nitro-2,3-dihydro-imidazo[2,1-b]oxazol-2-ylmethyl)-amino]-biphenyl-4-yl}-2-oxo-oxazolidin-5-ylmethyl)-acetamide

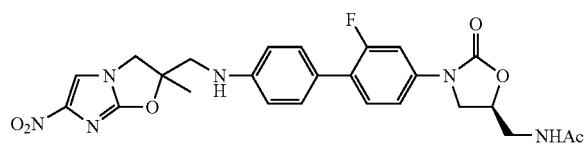

Step 1: (4-Iodo-phenyl)-(2-methyl-6-nitro-2,3-dihydro-imidazo[2,1-b]oxazol-2-ylmethyl)-amine. 2-Bromo-1-(2-methyl-oxiranylmethyl)-4-nitro-1H-imidazole (prepared as described by Goto, F.; et al: WO 2004035547; 0.54 g, 2 mmol), 4-iodoaniline (1.31 g, 6 mmol) and cobalt (II) chloride hexahydrate were suspended in 15 mL acetonitrile and stirred at 60° C. for 3 hours. The resulting mixture was filtered through a Celite pad and washed with EtOAc. Upon removing solvent, brown solid precipitated out. The precipitate (~200 mg) was dried and dissolved in 5 mL DMF. The solution was cooled to −78° C. before NaH (20 mg, 60% in mineral oil) was added quickly. The resulting mixture was warmed up to room temperature and stirred for one hour, before it was quenched with 1 mL water and partitioned in 50 mL EtOAc/50 mL water. The organic layer was washed with brine and dried over $Na_2SO_4$. The concentrated residue was purified by aolumn chromatography (EtOAc/Hexanes, v/v, 1/1 to 4/1) to give the titled product (90 mg) as yellow solid. ESI MS m/z 401 (M+H). $^1$H NMR (400 MHz, MeCN-$d_3$) δ 7.66 (s, 1H), 7.39 (d, J=5.2 Hz, 2H), 6.52 (d, J=5.2 Hz, 2H), 4.75-4.91 (m, 1H), 4.20 (d, J=10.4 Hz, 1H), 4.02 (d, J=10.4 Hz, 1H), 3.37-3.58 (m, 2H), 1.63 (s, 3H).

Step 2: N-(3-{2-Fluoro-4'-[(2-methyl-6-nitro-2,3-dihydro-imidazo[2,1-b]oxazol-2-ylmethyl)-amino]-biphenyl-4-yl}-2-oxo-oxazolidin-5-ylmethyl)-acetamide. The titled compound was prepared by using the same procedure as described in Example 36, except that (4-Iodo-phenyl)-(2-methyl-6-nitro-2,3-dihydro-imidazo[2,1-b]oxazol-2-ylmethyl)-amine was used in the place of 2-(4-Bromo-phenoxymethyl)-2-methyl-6-nitro-2,3-dihydro-imidazo[2,1-b]oxazole and the reaction was conducted at 50° C. for one hour. The titled compound was obtained as pale solid (60 mg, 80% yield). ESI MS m/z 525 (M+H).

Example 42

(S,S)—N-(3-{3-Fluoro-4-[3-(2-nitro-6,7-dihydro-5H-imidazo[2,1-b][1,3]oxazin-6-yloxy)-propenyl]-phenyl}-2-oxo-oxazolidin-5-ylmethyl)-acetamide

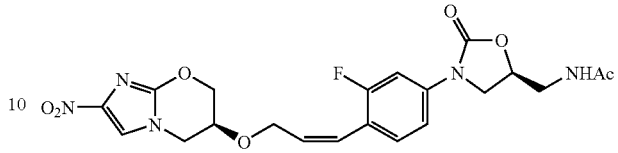

Step 1: (Z)-6(S)-(3-Bromo-allyloxy)-2-nitro-6,7-dihydro-5H-imidazo[2,1-b][1,3]oxazine and (E)-6(S)-(3-Bromo-allyloxy)-2-nitro-6,7-dihydro-5H-imidazo[2,1-b][1,3]oxazine. A solution of 2-Nitro-6,7-dihydro-5H-imidazo[2,1-b][1,3]oxazin-6(S)-ol (380 mg, 2 mmol) and 1,3-dibromopropene (trans-cis mixture, 0.3 mL, 3 mL) in 5 mL DMF was cooled down to −78° C. before NaH (120 mg, 60% in mineral oil) was added quickly. The resulting mixture was warmed up to room temperature and stirred for 3 hours, before it was quenched with 1 mL water and partitioned in 50 mL EtOAc/50 mL water. The organic layer was washed with brine and dried over $Na_2SO_4$. Column chromatography (dichlromethane/methanol, v/v, 20/11) gave the titled product (E isomer, 125 mg) as yellow solid. ESI MS m/z 306 (M+H). $^1$H NMR (400 MHz, $CDCl_3$) δ 7.31 (s, 1H), 6.33 (d, J=7.6 Hz, 1H), 6.19 (q, J=7.6 Hz, 1H), 4.49-4.56 (m, 1H), 3.96-4.32 (m, 6H). A mixture of E/Z isomer of the titled compound (260 mg) was also obtained. The Z isomer of the titled compound is obtained after prep-TLC separation.

Step 2: (Z)-N-(3-{3-Fluoro-4-[3-(2-nitro-6,7-dihydro-5H-imidazo[2,1-b][1,3]oxazin-6-yloxy)-propenyl]-phenyl}-2-oxo-oxazolidin-5-ylmethyl)-acetamide. The titled compound was prepared by using the same procedure as described in Example 36, except that 6(S)-(3-Bromo-allyloxy)-2-nitro-6,7-dihydro-5H-imidazo[2,1-b][1,3]oxazine was used in the place of 2-(4-Bromo-phenoxymethyl)-2-methyl-6-nitro-2,3-dihydro-imidazo[2,1-b]oxazole. The titled compound was obtained as off-white solid (55 mg, 62% yield). ESI MS m/z 476 (M+H).). $^1$H NMR (400 MHz, DMF-$d_4$) 8.29 (t, J=5.6 Hz, 1H), 8.07 (s, 1H), 7.68 (t, J=8.8 Hz, 1H), 7.58 (dd, J=2.0, 13.6 Hz, 1H), 7.35 (dd, J=2.0, 8.8 Hz, 1H), 6.75 (d, J=16.4 Hz, 1H), 6.47 (dt, J=16.4, 6.0 Hz, 1H), 4.86 (b, 1H), 4.77 (d, J=11.6 Hz, 1H), 4.63 (d, J=12.4 Hz, 1H), 4.36-4.50 (m, 5H), 4.25 (t, J=8.8 Hz, 1H), 3.90 (dd, J=6.4, 9.2 Hz, 1H), 3.56-3.64 (m, 2H), 1.92 (s, 3H).

Example 43

(E)-N-(3-{3-Fluoro-4-[3-(2-nitro-6,7-dihydro-5H-imidazo[2,1-b][1,3]oxazin-6(S)-yloxy)-propenyl]-phenyl}-2-oxo-oxazolidin-5(S)-ylmethyl)-acetamide

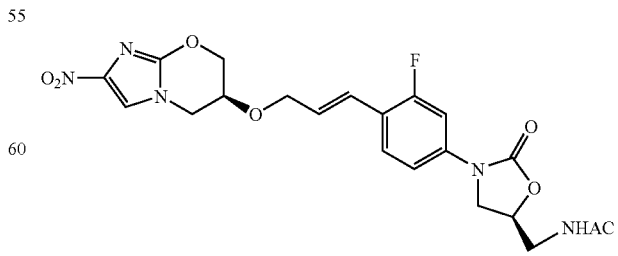

The titled compound was prepared by using the same procedure as described in Example 36, except that (E)-6-(3-

Bromo-allyloxy)-2-nitro-6,7-dihydro-5H-imidazo[2,1-b][1,3]oxazine was used in the place of 2-(4-Bromo-phenoxymethyl)-2-methyl-6-nitro-2,3-dihydro-imidazo[2,1-b]oxazole. The titled compound was obtained as off-white solid (80 mg, 88% yield). ESI MS m/z 476 (M+H); $^1$H NMR (400 MHz, MeCN-$d_3$) 7.71 (s, 1H), 7.59 (d, J=12.8 Hz, 1H), 7.32-7.42 (m, 2H), 6.87 (b, 1H), 6.72 (d, J=11.6 Hz, 1H), 6.01 (dt, J=11.6, 4.8 Hz, 1H), 4.86 (b, 1H), 4.63-4.69 (m, 1H), 4.39-4.48 (m, 2H), 4.46 (d, J=12.0 Hz, 1H), 4.20-4.28 (m, 3H), 4.18 (t, J=8.8 Hz, 1H), 3.87 (dd, J=9.2, 6.4 Hz, 1H), 3.64 (t, J=5.6 Hz, 1H), 2.00 (s, 3H).

Example 44

N-(3-{3-Fluoro-4-[1-(2-nitro-6,7-dihydro-5H-imidazo[2,1-b][1,3]oxazin-6(S)-yloxymethyl)-vinyl]-phenyl}-2-oxo-oxazolidin-5(S)-ylmethyl)-acetamide

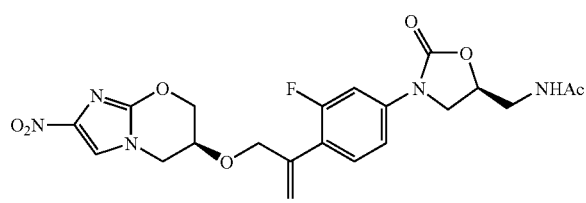

Step 1: 6(S)-(2-Bromo-allyloxy)-2-nitro-6,7-dihydro-5H-imidazo[2,1-b][1,3]oxazine. The titled compound was prepared by using the same procedure as described in Example 42, step 1, except that 2,3-dibromopropene was used instead. The titled compound was obtained as yellow solid (220 mg, 45% yield). ESI MS m/z 306 (M+H). $^1$H NMR (400 MHz, acetone-$d_6$) δ 7.78 (s, 1H), 6.03 (s, 1H), 5.65 (s, 1H), 4.69 (d, J=12.0 Hz, 1H), 4.58 (d, J=12.0 Hz, 1H), 4.34-4.46 (m, 5H).

Step 2: N-(3-{3-Fluoro-4-[1-(2-nitro-6,7-dihydro-5H-imidazo[2,1-b][1,3]oxazin-6-yloxymethyl)-vinyl]-phenyl}-2-oxo-oxazolidin-5-ylmethyl)-acetamide. The titled compound was prepared by using the same procedure as described in Example 36, except that 6-(2-Bromo-allyloxy)-2-nitro-6,7-dihydro-5H-imidazo[2,1-b][1,3]oxazine was used in the place of 2-(4-Bromo-phenoxymethyl)-2-methyl-6-nitro-2,3-dihydro-imidazo[2,1-b]oxazole. The titled compound was obtained as brown solid (252 mg, 74% yield). ESI MS m/z 476 (M+H).). $^1$H NMR (400 MHz, MeCN-$d_3$) 7.64 (s, 1H), 7.56 (dd, J=13.6, 2.0 Hz, 1H), 7.46 (t, J=8.8 Hz, 1H), 7.2 (dd, J=8.8, 2.4 Hz, 1H), 6.86 (b, 1H), 5.60 (s, 1H), 5.55 (s, 1H), 4.80-4.88 (m, 1H), 4.54-4.63 (m, 3H), 4.45 (d, J=11.2 Hz, 1H), 4.16-4.27 (m, 3H), 4.15 (t, J=9.2 Hz, 1H), 3.84 (dd, J=6.4, 9.2 Hz, 1H), 3.56-3.66 (m, 2H), 3.39 (d, J=5.6 Hz, 1H), 1.99 (s, 3H).

Example 45

N-(3-{3-Fluoro-4-[2-(2-nitro-6,7-dihydro-5H-imidazo[2,1-b][1,3]oxazin-6-yloxy)-acetyl]-phenyl}-2-oxo-oxazolidin-5-ylmethyl)-acetamide

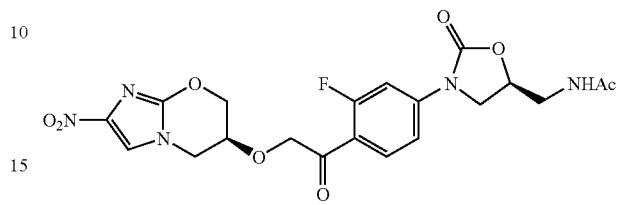

N-(3-{3-Fluoro-4-[1-(2-nitro-6,7-dihydro-5H-imidazo[2,1-b][1,3]oxazin-6-yloxymethyl)-vinyl]-phenyl}-2-oxo-oxazolidin-5-ylmethyl)-acetamide (48 mg) was dissolved in 1.5 mL methanol, followed by addition of NaIO$_4$ (54 mg) and OsO$_4$ (0.02 mL, 2.5% in water). The solution was stirred at room temperature for 4 hours and then Celite (500 mg) was added. The resulting mixture was stirred for 30 min before it was filtered and washed with EtOAc. The organic layer was dried over Na$_2$SO$_4$ and purified with preparative TLC (CH$_2$Cl$_2$/MeOH, v/v, 10/1). The titled compound was obtained as yellow solid (8 mg). ESI MS m/z 478 (M+H). $^1$H NMR (400 MHz, MeCN-$d_3$) 8.06 (t, J=8.4 Hz, 1H), 7.74 (s, 1H), 7.69 (dd, J=14.0, 2.0 Hz, 1H), 7.52 (dd, J=8.8, 2.4 Hz, 1H), 6.84 (b, 1H), 4.95-5.00 (m, 2H), 4.83-4.92 (m, 1H), 4.78 (dt, J=12.0, 2.8 Hz, 1H), 4.53 (d, J=12.8 Hz, 1H), 4.41 (dt, J=12.8, 2.0 Hz, 1H), 4.30-4.35 (m, 1H), 4.29 (dd, J=12.8, 3.2 Hz, 1H), 4.21 (t, J=9.2 Hz, 1H), 3.89 (dd, J=9.2, 6.4 Hz, 1H), 3.58-3.68 (m, 2H), 3.39 (d, J=5.2 Hz, 1H), 1.98 (s, 3H).

Example 46

N-(3-{3-Fluoro-4-[1-hydroxy-1-hydroxymethyl-2-(2-nitro-6,7-dihydro-5H-imidazo[2,1-b][1,3]oxazin-6-yloxy)-ethyl]-phenyl}-2-oxo-oxazolidin-5-ylmethyl)-acetamide

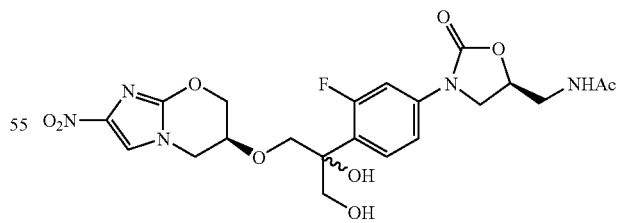

The titled compound was prepared as a side product of N-(3-{3-Fluoro-4-[2-(2-nitro-6,7-dihydro-5H-imidazo[2,1-b][1,3]oxazin-6-yloxy)-acetyl]-phenyl}-2-oxo-oxazolidin-5-ylmethyl)-acetamide, as described in Example 45. A disterosteric mixture of titled compounds was obtained as white solid (16 mg). ESI MS m/z 510 (M+H).

Example 47

(S,S)—N-(3-{3-Fluoro-4-[3-(2-nitro-6,7-dihydro-5H-imidazo[2,1-b][1,3]oxazin-6-yloxy)-prop-1-ynyl]-phenyl}-2-oxo-oxazolidin-5-ylmethyl)-acetamide

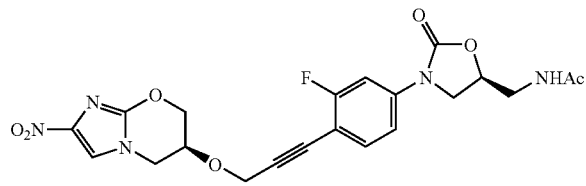

Step 1: 2-Nitro-6(S)-prop-2-ynyloxy-6,7-dihydro-5H-imidazo[2,1-b][1,3]oxazine. The titled compound was prepared by using the same procedure as described in Example 42, step 1, except 3-(trimethylsilyl)propargyl bromide was used instead. The titled compound was obtained as orange solid (155 mg, 34% yield). ESI MS m/z 224 (M+H). $^1$H NMR (400 MHz, CDCl$_3$) δ 7.42 (s, 1H), 4.62 (dq, J=12.8, 2.0 Hz, 1H), 4.30-4.42 (m, 2H), 4.33 (t, J=2.4 Hz, 2H), 4.23 (d, J=4.0 Hz, 1H), 4.22 (t, J=2.4 Hz, 1H), 2.55 (t, J=2.4 Hz, 1H).

Step 2: (S,S)—N-(3-{3-Fluoro-4-[3-(2-nitro-6,7-dihydro-5H-imidazo[2,1-b][1,3]oxazin-6-yloxy)-prop-1-ynyl]-phenyl}-2-oxo-oxazolidin-5-ylmethyl)-acetamide. To an oven dried round bottom flask was charged 2-Nitro-6(S)-prop-2-ynyloxy-6,7-dihydro-5H-imidazo[2,1-b][1,3]oxazine (75 mg, 0.34 mmol), N-[3-(3-Fluoro-4-iodo-phenyl)-2-oxo-oxazolidin-5(S)-ylmethyl]-acetamide (127 mg, 0.34 mmol), PhCl$_2$(PPh$_3$)$_2$ (23 mg, 0.02 mmol) and CuI (3.2 mg, 0.017 mmol). The flask was flushed with nitrogen before degassed DMF (4 mL) and Et$_3$N (0.15 mL, 1.05 mmol) were added. The resultant mixture was stirred at 80° C. for one hour before it was cooled down and partitioned into 50 mL EtOAc/50 mL water. The organic layer was washed with brine and dried over Na$_2$SO$_4$. Column chromatography (CH$_2$Cl$_2$/MeOH, v/v, 20:1 to 10:1) of the concentrated residue gave the titled compound (60 mg) as yellow solid. ESI MS m/z 474 (M+H). $^1$H NMR (400 MHz, MeCN-d$_3$) 7.73 (s, 1H), 7.65 (dd, J=12.4, 2.4 Hz, 1H), 7.59 (t, J=8.4 Hz, 1H), 7.39 (dd, J=8.8, 2.4 Hz, 1H), 6.84 (b, 1H), 4.20-4.99 (m, 1H), 4.76 (dt, J=12.4, 2.8 Hz, 1H), 4.67 (s, 2H), 4.53 (d, J=12.8 Hz, 1H), 4.45-4.51 (m, 1H), 4.26-4.42 (m, 2H), 4.17 (t, J=9.2 Hz, 1H), 3.85 (dd, J=9.6, 5.2 Hz, 1H), 3.56-3.68 (m, 2H), 1.98 (s, 3H).

Example 48

(S,S)—N-{3-[2,2'-Difluoro-5'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide

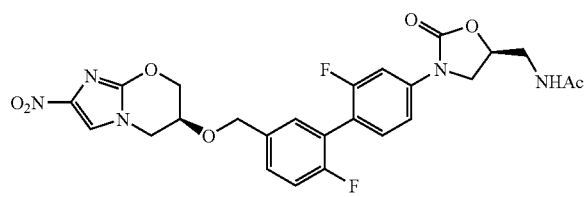

Step 1. 6(S)-(3-Bromo-4-fluoro-benzyloxy)-2-nitro-6,7-dihydro-5H-imidazo[2,1-b][1,3]oxazine. The title compound was prepared by following the same procedure as described in the preparation of Example 2, step 1. ESI MS m/z 374 (M+H$^+$); $^1$H NMR (400 MHz, CDCl$_3$) δ 7.96 (s, 1H), 7.39 (d, J=15 Hz, 1H), 7.18 (m, 1H), 7.06 (m, 1H), 4.57 (m, 3H), 4.34 (m, 1H), 4.15 (m, 3H).

Step 2. (S,S)—N-{3-[2,2'-Difluoro-5'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide. The title compound was prepared by following the same procedure as described in the preparation of Example 7, step 2, except 6(S)-(3-Bromo-4-fluoro-benzyloxy)-2-nitro-6,7-dihydro-5H-imidazo[2,1-b][1,3]oxazine was used in the place of 6(S)-(5-bromo-pyridin-2-yloxy)-2-nitro-6,7-dihydro-5H-imidazo[2,1-b][1,3]oxazine. ESI MS m/z 544 (M+H$^+$); $^1$H NMR (400 MHz, CDCl$_3$) δ7.19 (m, 7H), 4.55 (m, 3H), 4.07 (m, 4H), 4.50 (m, 4H), 2.88 (m, 2H), 1.90 (m, 3H).

Example 49

(S,S)—N-{3-[2-Fluoro-3'-(2-nitro-6,7-dihydro-5H-imidazo[2,1-b][1,3]oxazin-6-loxymethyl)-biphenyl-4-yl]-2-oxo-oxazolidin-5-ylmethyl}-acetamide

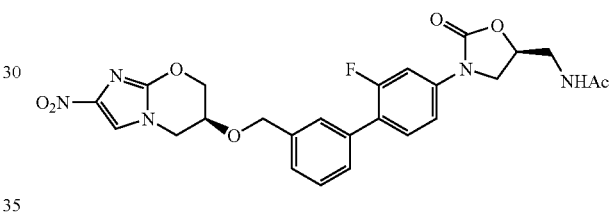

The title compound was prepared by following the same procedure as described in the preparation of Example 7, step 2, except 6(S)-(3-Bromo-benzyloxy)-2-nitro-6,7-dihydro-5H-imidazo[2,1-b][1,3]oxazine was used in the place of 6(S)-(5-bromo-pyridin-2-yloxy)-2-nitro-6,7-dihydro-5H-imidazo[2,1-b][1,3]oxazine. ESI MS m/z 526 (M+H$^+$); $^1$H NMR (400 MHz, CDCl$_3$) δ 7.33 (m, 8H), 4.60 (m, 3H), 4.28 (m, 1H), 4.04 (m, 4H), 3.73 (m, 1H), 3.56 (s, 2H), 2.51 (bs, 2H), 1.94 (d, J=15 Hz, 3H).

Example 50

N-{3-[3-Fluoro-4-(2-methyl-6-nitro-2,3-dihydro-imidazo[2,1-b]oxazol-2-ylmethoxy)-phenyl]-2-oxo-oxazolidin-5-ylmethyl}-acetamide

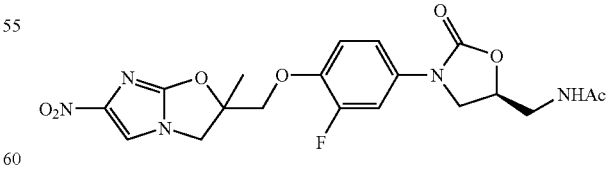

The title compound was prepared by following the same procedure as described in the preparation of Example 36, 2-(4-Bromo-phenoxymethyl)-2-methyl-6-nitro-2,3-dihydro-imidazo[2,1-b]oxazole (prepared similarly as described by Sasaki, H. et al: Journal of Medicinal Chemistry (2006), 49(26), 7854-7860), except N-[3-(3-fluoro-4-hydroxy-phenyl)-2-oxo-oxazolidin-5(S)-ylmethyl]-acetamide was used in the place of 4-bromophenol. The product isolated as a solid. ESI MS m/z 450 (M+H+).

Example 51

N-(((5S)-3-(3-Fluoro-4-(2-((2-methyl-6-nitro-2,3-dihydroimidazo[2,1-b]oxazol-2-yl)methoxy)pyrimidin-5-yl)phenyl)-2-oxooxazolidin-5-yl)methyl)acetamide

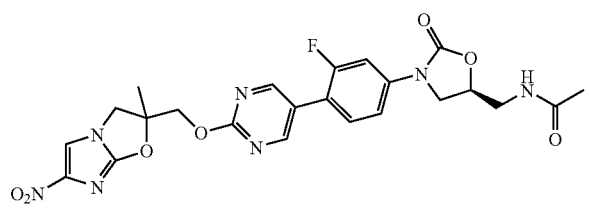

Step 1: 2-((5-Bromopyrimidin-2-yloxy)methyl)-2-methyl-6-nitro-2,3-dihydroimidazo[2,1-b]oxazole. (2-Methyl-6-nitro-2,3-dihydroimidazo[2,1-b]oxazol-2-yl)-methanol (0.10 g, 0.50 mmol), 5-bromo-2-chloropyrimidine (0.16 g, 0.82 mmol) and NaH (~30 mg, 60% in mineral oil) were suspended in 2 mL DMF and stirred at r.t. for 2 hours. The resulting mixture was diluted with 150 mL EtOAc, washed with 100 mL NaHCO₃ and 100 mL water. The aqueous layer was re-extracted with 100 mL EtOAc. The organic layer was washed with brine and dried over Na₂SO₄. The concentrated residue was purified by column chromatography (DCM/MeOH, 0 to 3%) to give the title compound (152 mg, 83%) as a white solid. APCI MS m/z 356.6, 358.6 (M+H). ¹H NMR (400 MHz, (CD₃)₂SO) δ 8.77 (s, 2H), 8.14 (s, 1H), 4.61 (s, 2H), 4.41 (d, J=11.1 Hz, 1H), 4.20 (d, J=11.1 Hz, 1H), 1.70 (s, 3H).

Step 2: N-(((5S)-3-(3-Fluoro-4-(2-((2-methyl-6-nitro-2,3-dihydroimi-dazo[2,1-b]oxazol-2-yl)methoxy)pyrimidin-5-yl)phenyl)-2-oxooxazolidin-5-yl)methyl)-acetamide. A mixture of (S)—N—((3-(3-fluoro-4-(4,4,5,5-tetramethyl-1,3,2-dioxaborolan-2-yl)phenyl)-2-oxooxazolidin-5-yl)methyl) acetamide (0.14 g, 0.37 mmol) and 2-((5-bromopyrimidin-2-yloxy)methyl)-2-methyl-6-nitro-2,3-dihydroimidazo[2,1-b] oxazole (0.105 g, 0.29 mmol) in toluene (2.5 mL), EtOH (1.5 mL), DMF (4 mL) and K₂CO₃ (2 M, 1 mL, 2 mmol) was purged with nitrogen. PdCl₂(dppf) (12 mg, 0.015 mmol) was added and the mixture was refluxed (100° C.) under nitrogen for 1 h, then partitioned between EtOAc (150 mL) and water (100 mL). The aqueous layer was re-extracted with 100 mL EtOAc. The organic layer was washed with brine, dried (Na₂SO₄) and evaporated, column chromatography using gradient elution (DCM/MeOH 0 to 5%) gave the title compound as a brown solid (60 mg, 39%). APCI MS m/z 528.3 (M+H). ¹H NMR (400 MHz, (CD₃)₂SO) δ 8.81 (d, J=1.3 Hz, 2H), 8.22 (t, J=5.8 Hz, 1H), 8.16 (s, 1H), 7.68 (t, J=8.8 Hz, 1H), 7.65 (dd, J=13.4, 2.2 Hz, 1H), 7.45 (dd, J=8.6, 2.2 Hz, 1H), 4.81-4.73 (m, 1H), 4.71 (d, J=11.9 Hz, 1H), 4.67 (d, J=11.9 Hz, 1H), 4.45 (d, J=11.0 Hz, 1H), 4.23 (d, J=11.0 Hz, 1H), 4.18 (t, J=9.1 Hz, 1H), 3.79 (dd, J=9.2, 6.4 Hz, 1H), 3.44 (t, J=5.5 Hz, 2H), 1.84 (s, 3H), 1.73 (s, 3H).

Example 52

N—(((S)-3-(3-Fluoro-4-(5-(((S)-2-nitro-6,7-dihydro-5H-imidazo[2,1-b][1,3]-oxazin-6-yloxy)methyl)pyridin-3-yl)phenyl)-2-oxooxazolidin-5-yl)methyl)acetamide

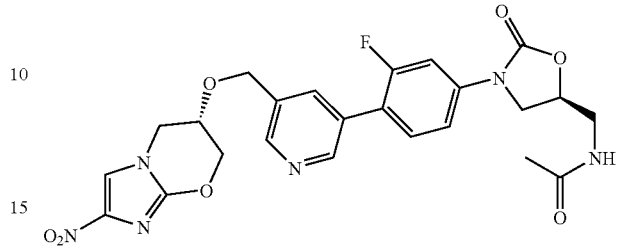

Step 1: (6S)-6-[(5-Bromopyridin-3-yl)methoxy]-2-nitro-6,7-dihydro-5H-imi-dazo[2,1-b][1,3]oxazine. A solution of (S)-2-nitro-6,7-dihydro-5H-imidazo[2,1-b][1,3]oxa-zin-6-ol (3.63 g, 19.6 mmol) and 3-bromo-5-(chloromethyl)pyridine hydrochloride (4.78 g, 19.6 mmol, 1 eq) in dry DMF (80 mL) was treated with NaH (1.88 g, 47 mmol, 2.4 eq, 60% in mineral oil) at 0-5° C., then stirred at room temperature overnight (16 h), quenched with water (150 mL), and extracted into EtOAc. Chromatography of the crude product on silica gel, eluting with MeOH/CH₂Cl₂ (1:19), gave the title product (2.10 g, 30%) as white solid. APCI MS m/z 355.7, 357.7 (M+H). ¹H NMR (400 MHz, (CD₃)₂SO) δ 8.64 (d, J=2.3 Hz, 1H), 8.52 (d, J=1.7 Hz, 1H), 8.03 (s, 1H), 7.97 (br t, J=2.1 Hz, 1H), 4.73 (d, J=12.6 Hz, 1H), 4.70-4.65 (m, 2H), 4.48 (d, J=12 Hz, 1H), 4.31-4.20 (m, 3H).

Step 2: N—(((S)-3-(3-Fluoro-4-(5-(((S)-2-nitro-6,7-dihydro-5H-imidazo-[2,1-b][1,3]oxazin-6-yloxy)methyl)pyridin-3-yl)phenyl)-2-oxooxazolidin-5-yl)methyl)acet-amide. The title compound was prepared by following the same procedure as described in the preparation of Example 51, step 2, except (6S)-6-[(5-bromopyridin-3-yl)methoxy]-2-nitro-6,7-dihydro-5H-imidazo[2,1-b][1,3]oxazine was used in the place of 2-((5-bromopyrimidin-2-yloxy)methyl)-2-methyl-6-nitro-2,3-dihydroimidazo[2,1-b]oxazole. APCI MS m/z 527.4 (M+H). ¹H NMR (400 MHz, (CD₃)₂SO) δ 8.69 (t, J=1.8 Hz, 1H), 8.54 (d, J=2.0 Hz, 1H), 8.22 (t, J=5.8 Hz, 1H), 8.01 (s, 1H), 7.88 (d, J=1.4 Hz, 1H), 7.66-7.59 (m, 2H), 7.45 (dd, J=8.6, 2.2 Hz, 1H), 4.82-4.73 (m, 3H), 4.69 (dt, J=12.0, 2.5 Hz, 1H), 4.49 (d, J=11.6 Hz, 1H), 4.34-4.28 (m, 2H), 4.25 (dd, J=13.6, 3.4 Hz, 1H), 4.18 (t, J=9.0 Hz, 1H), 3.80 (dd, J=9.2, 6.4 Hz, 1H), 3.44 (t, J=5.5 Hz, 2H), 1.84 (s, 3H).

Example 53

N—(((S)-3-(3-Fluoro-4-(2-(((S)-2-nitro-6,7-dihydro-5H-imidazo[2,1-b][1,3]-oxazin-6-yloxy)methyl)pyridin-4-yl)phenyl)-2-oxooxazolidin-5-yl)methyl)acetamide

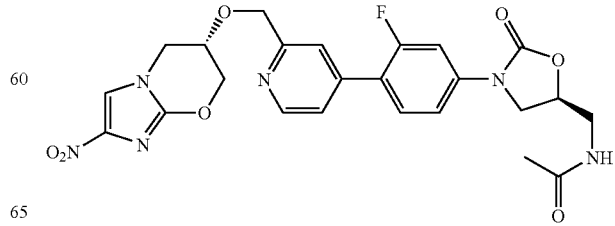

Step 1: 4-Bromo-2-(chloromethyl)pyridine. To a solution of 4-bromo-2-pyridylmethanol (3.38 g, 0.016 mol) in CH$_2$Cl$_2$ (210 mL) was slowly added SOCl$_2$ (21 mL) at 0° C. The mixture was allowed to warm to room temperature and stirred for 20 h, then satd. NaHCO$_3$ was added. The organic layer was washed with brine, dried (MgSO$_4$), and concentrated to give crude 4-bromo-2-(chloromethyl)pyridine (2.93 g, 79%) as a yellow oil. APCI MS m/z 205.7, 207.7 (M+H). $^1$H NMR (400 MHz, (CD$_3$)$_2$SO) δ 8.47 (d, J=5.3 Hz, 1H), 7.68 (d, J=1.7 Hz, 1H), 7.42 (dd, J=5.3, 1.75 Hz, 1H), 4.64 (s, 2H).

Step 2: (6S)-6-[(4-Bromopyridin-2-yl)methoxy]-2-nitro-6,7-dihydro-5H-imidazo[2,1-b][1,3]oxazine. A solution of (S)-2-nitro-6,7-dihydro-5H-imidazo[2,1-b][1,3]oxa-zin-6-ol (2.87 g, 15.5 mmol) and 4-bromo-2-(chloromethyl)pyridine (2.91 g, 14 mmol) in dry DMF (60 mL) was treated with NaH (0.68 g of a 60% dispersion in mineral oil, 16.9 mmol,) at 0-5° C., and the mixture was stirred at room temperature for 3 h, then quenched with water (150 mL) and extracted with EtOAc (6×150 mL). The organic layers were dried (MgSO$_4$), evaporated, and chromatographed on silica gel, eluting with MeOH/EtOAc (1:19), to give the title compound (2.701 g, 54%) as a light yellow solid. APCI MS m/z 355.7, 357.7 (M+H). $^1$H NMR (400 MHz, (CD$_3$)$_2$SO) 68.41 (d, J=5.3 Hz, 1H), 8.01 (s, 1H), 7.59 (dd, J=5.3, 1.9 Hz, 1H), 7.55 (d, J=1.5 Hz, 1H), 4.78-4.68 (m, 3H), 4.50 (d, J=12.0 Hz, 1H), 4.35-4.22 (m, 3H).

Step 3: N—(((S)-3-(3-Fluoro-4-(2-(((S)-2-nitro-6,7-dihydro-5H-imidazo-[2,1-b][1,3]-oxazin-6-yloxy)methyl)pyridin-4-yl)phenyl)-2-oxooxazolidin-5-yl)methyl)acet-amide. The title compound was prepared by following the same procedure as described in the preparation of Example 51, step 2, except (6S)-6-[(4-bromopyridin-2-yl)methoxy]-2-nitro-6,7-dihydro-5H-imidazo[2,1-b][1,3]oxazine was used in the place of 2-((5-bromopyrimidin-2-yloxy)methyl)-2-methyl-6-nitro-2,3-dihydroimidazo[2,1-b]oxazole. APCI MS m/z 527.4 (M+H). $^1$H NMR (400 MHz, (CD$_3$)$_2$SO) δ 8.60 (br d, J=5.9 Hz, 1H), 8.27 (t, J=5.8 Hz, 1H), 8.03 (s, 1H), 7.65 (t, J=8.8 Hz, 1H), 7.63 (dd, J=13.8, 2.2 Hz, 1H), 7.53-7.49 (m, 2H), 7.45 (dd, J=8.6, 2.2 Hz, 1H), 4.82 (d, J=13.4 Hz, 1H), 4.78 (d, J=13.4 Hz, 1H), 4.80-4.74 (m, 1H), 4.71 (dt, J=12.0, 2.5 Hz, 1H), 4.50 (d, J=11.8 Hz, 1H), 4.39-4.30 (m, 2H), 4.24 (dd, J=13.4, 3.1 Hz, 1H), 4.17 (t, J=9.1 Hz, 1H), 3.79 (dd, J=9.2, 6.5 Hz, 1H), 3.44 (t, J=5.5 Hz, 2H), 1.84 (s, 3H).

Example 54

N—(((S)-3-(3-Fluoro-4-(4-(((S)-2-nitro-6,7-dihydro-5H-imidazo[2,1-b][1,3]-oxazin-6-yloxy)methyl)pyridin-2-yl)phenyl)-2-oxooxazolidin-5-yl)methyl)acetamide

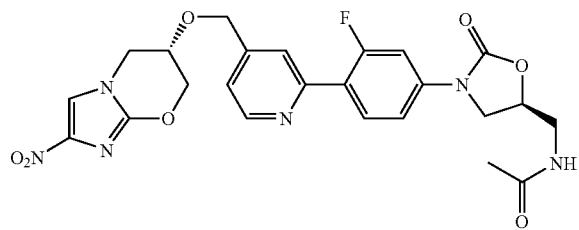

Step 1: 2-Bromo-4-(bromomethyl)pyridine hydrobromide salt. (2-Bromo-4-pyridyl)methanol (2.00 g, 10.6 mmol) was dissolved in dry CH$_2$Cl$_2$ (10 mL) and then SOBr$_2$ (0.90 mL, 11.7 mmol) was added at 0° C. The reaction mixture was stirred overnight, then the solvent was evaporated and the residue crystallised from MeOH-Et$_2$O to give the title compound (2.81 g, 79%) as a white solid. APCI MS m/z 252.2 (M+H). $^1$H-NMR (400 MHz, (CD$_3$)$_2$SO) δ 8.39 (d, J=5.0 Hz, 1H), 7.74 (d, J=0.9 Hz, 1H), 7.51 (dd, J=5.0, 1.4 Hz, 1H), 4.66 (s, 2H).

Step 2: (S)-6-((2-Bromopyridin-4-yl)methoxy)-2-nitro-6,7-dihydro-5H-imidazo[2,1-b][1,3]oxazine. The title compound was prepared by following the same procedure as described in the preparation of Example 53, step 2, except 2-bromo-4-(bromomethyl)pyridine hydrobromide was used in the place of 4-bromo-2-(chloromethyl)pyridine. APCI MS m/z 355.7, 357.7 (M+H). $^1$H-NMR (400 MHz, (CD$_3$)$_2$SO) δ 8.34 (dd, J=4.8, 0.4 Hz, 1H), 8.02 (s, 1H), 7.51 (d, J=0.4 Hz, 1H), 7.35 (dt, J=5.1, 0.6 Hz, 1H), 4.75 (d, J=14.1 Hz, 1H), 4.72-4.65 (m, 2H), 4.49 (d, J=12.0 Hz, 1H), 4.31-4.21 (m, 3H).

Step 3: N—(((S)-3-(3-Fluoro-4-(4-(((S)-2-nitro-6,7-dihy-dro-5H-imidazo-[2,1-b][1,3]-oxazin-6-yloxy)methyl)pyridin-2-yl)phenyl)-2-oxooxazolidin-5-yl)methyl)acet-amide. The title compound was prepared by following the same procedure as described in the preparation of Example 51, step 2, except (S)-6-((2-bromopyridin-4-yl)methoxy)-2-nitro-6,7-dihydro-5H-imidazo[2,1-b][1,3]oxazine was used in the place of 2-((5-bromopyrimidin-2-yloxy)methyl)-2-methyl-6-nitro-2,3-dihydroimidazo[2,1-b]oxazole. APCI MS m/z 527.4 (M+H). $^1$H NMR (400 MHz, (CD$_3$)$_2$SO) δ 8.65 (dd, J=5.0, 0.5 Hz, 1H), 8.27 (t, J=5.8 Hz, 1H), 8.04 (s, 1H), 8.00 (t, J=8.9 Hz, 1H), 7.67 (br s, 1H), 7.60 (dd, J=14.2, 2.2 Hz, 1H), 7.45 (dd, J=8.7, 2.2 Hz, 1H), 7.29 (dd, J=5.0, 1.3 Hz, 1H), 4.81 (d, J=13.9 Hz, 1H), 4.77 (d, J=13.9 Hz, 1H), 4.79-4.72 (m, 1H), 4.70 (dt, J=12.0, 2.5 Hz, 1H), 4.50 (d, J=11.9 Hz, 1H), 4.35-4.21 (m, 3H), 4.18 (t, J=9.0 Hz, 1H), 3.80 (dd, J=9.2, 6.5 Hz, 1H), 3.44 (t, J=5.5 Hz, 2H), 1.84 (s, 3H).

Example 55

N—(((S)-3-(3-Fluoro-4-(6-(((S)-2-nitro-6,7-dihydro-5H-imidazo[2,1-b][1,3]-oxazin-6-yloxy)methyl)pyridin-2-yl)phenyl)-2-oxooxazolidin-5-yl)methyl)acetamide

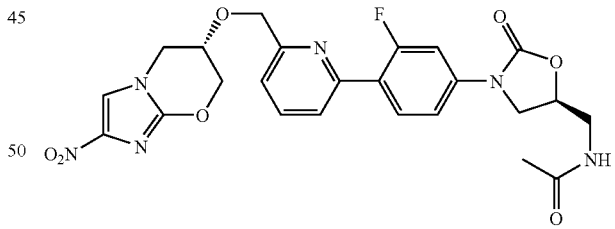

Step 1: 6-Bromo-2-(chloromethyl)pyridine. N-Butyllithium (10 mL, 25.32 mmol, 2.5 M solution in hexanes) was added dropwise over a period of 20 min at −78° C. to a degassed solution of 2,5-dibromopyridine (5.0 g, 21.1 mmol) in toluene (250 mL), and the solution was then stirred for 2 h at −78° C. DMF (2.1 mL, 27.43 mmol) was then added dropwise, and the reaction was left at −78° C. for 1 h. MeOH (20 mL) and NaBH (1.60 g, 42.2 mmol) were then added at −78° C., and the reaction mixture was allowed to slowly reach room temperature and stirring was continued for 16 h. Saturated aqueous NH$_4$Cl (100 mL) was added at −10° C. and stirring was continued for 30 min. The two layers were separated. The toluene layer was concentrated and dried in vacuo to give 6-bromo-2-pyridinyl)methanol (3.74 g, 94%) as a light yellow oil. A solution of this oil (3.74 g, 19.8 mmol) in CHCl$_3$ (250 mL) was treated with SOCl$_2$ (25 mL) at 0° C., then the reaction mixture was refluxed for 1 h, poured into ice-water, and extracted into $^i$Pr$_2$O. The combined organic layers were washed with brine, dried (MgSO$_4$) and concentrated to dryness, to give the title compound as a yellow oil (3.42 g, 83%). APCI MS m/z 205.9, 207.9 (M+H). $^1$H NMR (400 MHz, CDCl$_3$) δ 7.59 (t, J=7.7 Hz, 1H), 7.47 (d, J=7.4 Hz, 1H), 7.44 (d, J=7.9 Hz, 1H), 4.63 (s, 2H).

Step 2: (6S)-6-[(6-Bromopyridin-2-yl)methoxy]-2-nitro-6,7-dihydro-5H-imidazo[2,1-b][1,3]oxazine. The title compound was prepared by following the same procedure as described in the preparation of Example 53, step 2, except 6-bromo-2-(chloromethyl)pyridine was used in the place of 4-bromo-2-(chloromethyl)pyridine. APCI MS m/z 355.7, 357.7 (M+H). $^1$H-NMR (400 MHz, (CD$_3$)$_2$SO) δ 8.02 (s, 1H), 7.76 (t, J=7.8 Hz, 1H), 7.56 (d, J=7.6 Hz, 1H), 7.40 (d, J=7.5 Hz, 1H), 4.76-4.67 (m, 3H), 4.49 (d, J=12.0 Hz, 1H), 4.34-4.22 (m, 3H).

Step 3: N—(((S)-3-(3-Fluoro-4-(6-(((S)-2-nitro-6,7-dihydro-5H-imidazo-[2,1-b]-[1,3]-oxazin-6-yloxy)methyl)pyridin-2-yl)phenyl)-2-oxooxazolidin-5-yl)methyl)acet-amide. The title compound was prepared by following the same procedure as described in the preparation of Example 51, step 2, except (6S)-6-[(6-bromopyridin-2-yl)methoxy]-2-nitro-6,7-dihydro-5H-imidazo[2,1-b][1,3]oxazine was used in the place of 2-((5-bromopyrimidin-2-yloxy)methyl)-2-methyl-6-nitro-2,3-dihydroimidazo[2,1-b]oxazole. APCI MS m/z 527.4 (M+H). $^1$H NMR (400 MHz, (CD$_3$)$_2$SO) δ 8.27 (t, J=5.8 Hz, 1H), 8.05 (s, 1H), 7.98 (t, J=8.9 Hz, 1H), 7.89 (t, J=7.8 Hz, 1H), 7.70 (br d, J=6.8 Hz, 1H), 7.62 (dd, J=14.1, 2.2 Hz, 1H), 7.46 (dd, J=8.8, 2.2 Hz, 1H), 7.36 (d, J=7.6 Hz, 1H), 4.83 (d, J=13.6 Hz, 1H), 4.80 (d, J=13.6 Hz, 1H), 4.80-4.75 (m, 1H), 4.74 (dt, J=12.0, 2.5 Hz, 1H), 4.51 (d, J=11.9 Hz, 1H), 4.40-4.33 (m, 2H), 4.26 (dd, J=13.9, 3.6 Hz, 1H), 4.18 (t, J=9.0 Hz, 1H), 3.80 (dd, J=9.2, 6.5 Hz, 1H), 3.44 (t, J=5.5 Hz, 2H), 1.84 (s, 3H).

Example 56

N—(((S)-3-(3-Fluoro-4-(6-(((S)-2-nitro-6,7-dihydro-5H-imidazo[2,1-b][1,3]-oxazin-6-yloxy)methyl)pyridazin-3-yl)phenyl)-2-oxooxazolidin-5-yl)methyl) acetamide

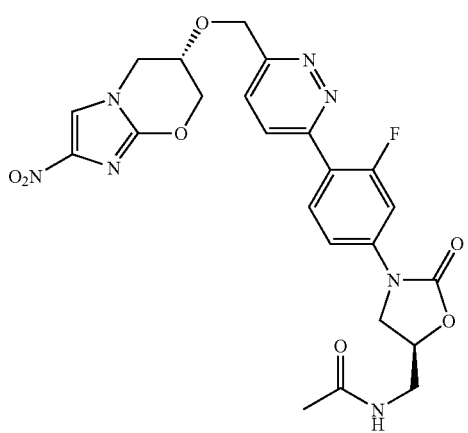

Step 1: (6S)-6-[(6-Chloro-3-pyridazinyl)methoxy]-2-nitro-6,7-dihydro-5H-imidazo[2,1-b][1,3]oxazine. Sodium hydride (60% w/w, 0.30 g, 7.6 mmol) was added to a solution of (6S)-2-nitro-6,7-dihydro-5H-imidazo[2,1-b][1,3]oxazin-6-ol (0.89 g, 4.8 mmol) in DMF (20 mL) at 0° C. The resultant solution was cooled to −42° C. and a solution of 3-(bromomethyl)-6-chloropyridazine (1.05 g, 5.1 mmol) in DMF (5 mL) was added. The mixture was stirred at −42° C. for 1 h and then quenched with ice. EtOAc (200 mL) was added, the organic layer was dried (MgSO$_4$) and concentrated under reduced pressure. The residue was chromatographed on silica gel, initially eluting with hexanes/EtOAc (1:1) to remove unreacted 3-(bromomethyl)-6-chloropyridazine and then EtOAc to give the title compound (0.84 g, 56%) as a white solid. APCI MS m/z 312.6 (M+H). $^1$H NMR (400 MHz, (CD$_3$)$_2$SO) δ 8.02 (s, 1H), 7.93 (d, J=8.8 Hz, 1H), 7.74 (d, J=8.8 Hz, 1H), 4.97 (d, J=13.2 Hz, 1H), 4.94 (d, J=13.2 Hz, 1H), 4.69 (dt, J=12.0, 2.6 Hz, 1H), 4.50 (d, J=12.1 Hz, 1H), 4.30-4.39 (m, 2H), 4.25 (dd, J=13.5, 3.3 Hz, 1H).

Step 2: N—(((S)-3-(3-Fluoro-4-(6-(((S)-2-nitro-6,7-dihydro-5H-imidazo-[2,1-b][1,3]-oxazin-6-yloxy)methyl)pyridazin-3-yl)phenyl)-2-oxooxazolidin-5-yl)methyl)-acetamide. The title compound was prepared by following the same procedure as described in the preparation of Example 51, step 2, except (6S)-6-[(6-chloro-3-pyridazinyl)methoxy]-2-nitro-6,7-dihydro-5H-imidazo[2,1-b][1,3]oxazine was used in the place of 2-((5-bromopyrimidin-2-yloxy)methyl)-2-methyl-6-nitro-2,3-dihydroimidazo[2,1-b]oxazole. APCI MS m/z 528.3 (M+H). $^1$H NMR (400 MHz, (CD$_3$)$_2$SO) δ 8.23 (t, J=5.8 Hz, 1H), 8.09-8.02 (m, 2H), 8.03 (s, 1H), 7.75 (d, J=8.8 Hz, 1H), 7.68 (dd, J=14.0, 2.2 Hz, 1H), 7.52 (dd, J=8.7, 2.2 Hz, 1H), 5.04 (d, J=13.6 Hz, 1H), 5.00 (d, J=13.6 Hz, 1H), 4.83-4.75 (m, 1H), 4.74 (dt, J=12.0, 2.5 Hz, 1H), 4.52 (d, J=11.9 Hz, 1H), 4.43-4.34 (m, 2H), 4.28 (dd, J=13.5, 3.2 Hz, 1H), 4.20 (t, J=9.0 Hz, 1H), 3.82 (dd, J=9.2, 6.4 Hz, 1H), 3.45 (t, J=5.5 Hz, 2H), 1.84 (s, 3H).

Example 57

N—(((S)-3-(3-Fluoro-4-(5-(((S)-2-nitro-6,7-dihydro-5H-imidazo[2,1-b][1,3]-oxazin-6-yloxy)methyl) pyrazin-2-yl)phenyl)-2-oxooxazolidin-5-yl)methyl) acetamide

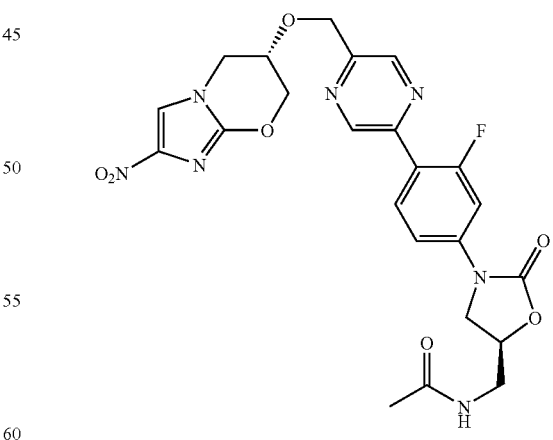

Step 1: (6S)-6-[(5-Chloro-2-pyrazinyl)methoxy]-2-nitro-6,7-dihydro-5H-imidazo[2,1-b][1,3]oxazine. Triethylamine (4.17 mL, 3.0 mmol) and mesyl chloride (1.57 mL, 2.00 mmol) were added to a solution of (5-chloro-2-pyrazinyl) methanol (1.44 g, 10.0 mmol) in anhydrous THF (20 mL) at 0° C. The mixture was stirred at 0° C. for 0.5 h then partitioned between EtOAc/water. The organic fraction was dried (MgSO$_4$) and the solvent was removed under reduced pressure to give the crude mesylate. The mesylate was dissolved in acetone (40 mL), sodium iodide (7.5 g, 50 mmol) was added and the mixture was refluxed for 1 h. The solvent was removed under reduced pressure and the residue was partitioned between EtOAc/water. The residue was chromatographed on silica gel (DCM) to give 2-chloro-5-(iodomethyl) pyrazine. Sodium hydride (60% w/w, 0.36 g, 9.0 mmol) was added to a solution of (S)-2-nitro-6,7-dihydro-5H-imidazo[2,1-b][1,3]oxa-zin-6-ol (0.93 g, 5.02 mmol) and 2-chloro-5-(iodomethyl)pyrazine (1.54 g, 6.05 mmol) in DMF (10 mL) at −78° C. The mixture was stirred at 0° C. for 1 h and then quenched with ice. EtOAc (200 mL) was added, the organic layer was dried (MgSO$_4$) and concentrated under reduced pressure. The residue was chromatographed on silica gel, eluting with a gradient (0-5%) MeOH/EtOAc to give the title compound (1.015 g, 65%) as a white solid. APCI MS m/z 312.6 (M+H). $^1$H NMR (400 MHz, (CD$_3$)$_2$SO) δ 8.76 (d, J=1.4 Hz, 1H), 8.50 (d, J=1.4 Hz, 1H), 8.02 (s, 1H), 4.85 (d, J=13.7 Hz, 1H), 4.81 (d, J=13.7 Hz, 1H), 4.70 (td, J=12.1, 2.6 Hz, 1H), 4.49 (bd, J=12.0 Hz, 1H), 4.29-4.38 (m, 2H), 4.25 (dd, J=13.5, 3.3 Hz, 1H).

Step 2: N—(((S)-3-(3-Fluoro-4-(5-(((S)-2-nitro-6,7-dihydro-5H-imidazo-[2,1-b][1,3]-oxazin-6-yloxy)methyl) pyrazin-2-yl)phenyl)-2-oxooxazolidin-5-yl)methyl)acetamide. The title compound was prepared by following the same procedure as described in the preparation of Example 51, step 2, except (6S)-6-[(5-chloro-2-pyrazinyl)methoxy]-2-nitro-6,7-dihydro-5H-imidazo[2,1-b][1,3]oxazine was used in the place of 2-((5-bromopyrimidin-2-yloxy)methyl)-2-methyl-6-nitro-2,3-dihydroimidazo[2,1-b]oxazole. APCI MS m/z 528.3 (M+H). $^1$H NMR (400 MHz, (CD$_3$)$_2$SO) δ 8.98 (dd, J=2.1, 1.7 Hz, 1H), 8.76 (d, J=1.4 Hz, 1H), 8.22 (t, J=5.8 Hz, 1H), 8.04 (s, 1H), 8.02 (t, J=8.8 Hz, 1H), 7.67 (dd, J=14.0, 2.2 Hz, 1H), 7.51 (dd, J=8.8, 2.2 Hz, 1H), 4.89 (d, J=13.4 Hz, 1H), 4.86 (d, J=13.4 Hz, 1H), 4.82-4.75 (m, 1H), 4.74 (dt, J=12.0, 2.5 Hz, 1H), 4.52 (d, J=12.0 Hz, 1H), 4.43-4.32 (m, 2H), 4.27 (dd, J=13.5, 3.2 Hz, 1H), 4.19 (t, J=9.0 Hz, 1H), 3.81 (dd, J=9.2, 6.5 Hz, 1H), 3.44 (t, J=5.5 Hz, 2H), 1.84 (s, 3H).

Example 58

N-({(5S)-3-[3-Fluoro-4-(2-{4-[(2-methyl-6-nitro-2,3-dihydroimidazo[2,1-b][1,3]oxazol-2-yl)methyl]-1-piperazinyl}-5-pyrimidinyl)phenyl]-2-oxo-1,3-oxazolidin-5-yl}methyl)acetamide

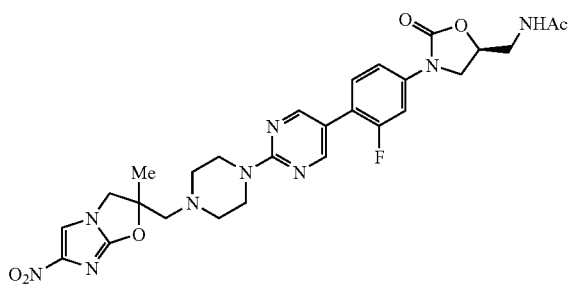

Step 1. tert-Butyl 4-[5-(4-{(5S)-5-[(acetylamino)methyl]-2-oxo-1,3-oxazolidin-3-yl}-2-fluorophenyl)-2-pyrimidinyl]-1-piperazinecarboxylate. A mixture of tert-butyl 4-(5-bromo-2-pyrimidinyl)-1-piperazinecarboxylate (57 mg, 0.165 mmol) (prepared as described in US 2007/0149561 A1), N-{3-[3-fluoro-4-(4,4,5,5-tetramethyl-[1,3,2]dioxaborolan-2-yl)-phenyl]-2-oxo-oxazolidin-5-ylmethyl}acetamide (75 mg, 1.98 mmol) (prepared as described by Chen, S. et al: U.S. Pat. No. 7,129,259 or Gravestock et. al. WO 2004/078753), PdCl$_2$(dppf) (7.0 mg, 0.08 mmol) and 2N Na$_2$CO$_3$ (1.0 mL, 2.00 mmol) in a mixture of toluene (5.0 mL) and ethanol (2.0 mL) was purged with nitrogen, then refluxed under an atmosphere of nitrogen for 5 h. The product was extracted with EtOAc and the extract was washed well with water, then worked up and chromatographed on silica. EtOAc eluted fore fractions, while MeOH/EtOAc (1:19) eluted the title product as a cream solid (69.4 mg, 81%), APCI MS m/z 515.5 (M+H$^+$); $^1$H NMR (400 MHz, DMSO) δ 8.59 (d, J=1.4 Hz, 2H), 8.22 (t, J=5.8 Hz, 1H), 7.63-7.57 (m, 2H), 7.40 (dd, J=8.6, 2.1 Hz, 1H), 4.80-4.70 (m, TH), 4.16 (t, J=9.1 Hz, 1H), 3.79-3.76 (m, 5H), 3.45-3.40 (m, 6H), 1.84 (s, 3H), 1.43 (s, 9H).

Step 2. N-[((5S)-3-{3-Fluoro-4-[2-(1-piperazinyl)-5-pyrimidinyl]phenyl}-2-oxo-1,3-oxazolidin-5-yl)methyl]acetamide. A solution of tert-butyl 4-[5-(4-{(5S)-5-[(acetylamino)methyl]-2-oxo-1,3-oxazolidin-3-yl}-2-fluorophenyl)-2-pyrimidinyl]-1-piperazinecarboxylate (0.24 g, 0.47 mmol) in CH$_2$Cl$_2$ (10 mL) and TFA (10 mL) was stirred at room temperature for 90 min, then concentrated to dryness in vacuo. The residue was partitioned between EtOAc and 1N NaOH and the organic solution was worked up to give the title compounds as a tan powder (0.18 g, 94%), APCI MS m/z 415.5 (M+H$^+$); $^1$H NMR (400 MHz, DMSO) 8.55 (d, J=1.4 Hz, 2H), 8.27 (t, J=5.8 Hz, 1H), 7.63-7.57 (m, 2H), 7.39 (dd, J=8.6, 2.1 Hz, 1H), 4.80-4.71 (m, 1H), 4.16 (t, J=9.1 Hz, 1H), 3.77 (dd, J=9.1, 6.5 Hz, 1H), 3.72-3.69 (m, 4H), 3.43 (t, J=5.5 Hz, 2H), 2.75-2.72 (m, 4H), 1.83 (s, 3H).

Step 3. N-({(5S)-3-[3-Fluoro-4-(2-{4-[(2-methyl-6-nitro-2,3-dihydroimidazo[2,1-b][1,3]oxazol-2-yl)methyl]-1-piperazinyl}-5-pyrimidinyl)phenyl]-2-oxo-1,3-oxazolidin-5-yl}methyl)acetamide. A solution of 2-bromo-1-(2-methyloxiranylmethyl)-4-nitro-1H-imidazole (42 mg, 0.16 mmol) and N-[((5S)-3-{3-Fluoro-4-[2-(1-piperazinyl)-5-pyrimidinyl]phenyl}-2-oxo-1,3-oxazolidin-5-yl)methyl]acetamide (69 mg, 0.17 mmol) in isopropanol (4 mL) was refluxed for 16 h. The solvent was removed in vacuo and the residue was dried well under high vacuum. The residue was dissolved in dry DMF (2 mL) and the solution was cooled to 5° C. NaH (16 mg of a 60% dispersion in mineral oil, 0.40 mmol) was added and the mixture was warmed to room temperature and stirred for 30 min. Water was added, the mixture was extracted with EtOAc and the extract was worked up and chromatographed on silica. EtOAc eluted fore fractions, while MeOH/EtOAc (1:19) eluted the title compound as a cream powder, following trituration with MeOH (31 mg, 32%), APCI MS m/z 596.5 (M+H$^+$); $^1$H NMR (400 MHz, DMSO) 8.5 (d, J=1.4 Hz, 2H), 8.22 (t, J=5.8 Hz, 1H), 8.12 (s, 1H), 7.61-7.56 (m, 2H), 7.39 (dd, J=8.6, 2.1 Hz, 1H), 4.79-4.72 (m, 1H), 4.28 (d, J=10.7 Hz, 1H), 4.15 (t, J=9.1 Hz, 1H), 4.10 (t, J=10.7 Hz, 1H), 3.78 (dd, J=9.3, 6.5 Hz, 1H), 3.73-3.58 (m, 4H), 3.43 (t, J=5.4 Hz, 2H), 2.82 (d, J=15.4 Hz, 1H), 2.77 (d, J=15.4 Hz, 1H), 2.64-2.59 (m, 4H), 1.84 (s, 3H), 1.58 (s, 3H).

Example 59

(S,S)—N-(3-{2,3'-Difluoro-4'-{-2-nitro-6,7-dihydro-5H-imidazo[2,1-b][1,3]oxazin-6-yloxymethyl)-biphenyl-4-yl]-2-oxo-oxazolidin-5-yl}methyl)acetamide

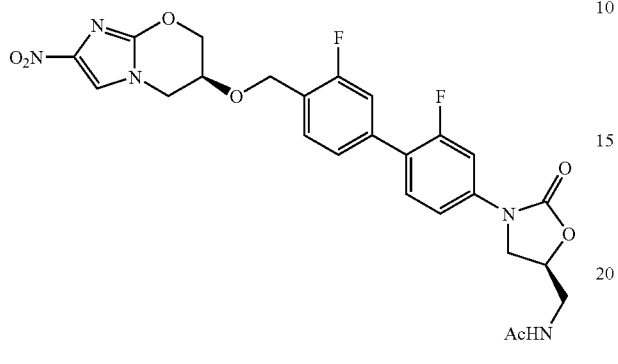

Step 1. 6(S)-(4-Bromo-2-fluorobenzyloxy)-2-nitro-6,7-dihydro-5H-imidazo[2,1-b][1,3]oxazine. To a solution of 2-nitro-6,7-dihydro-5H-imidazo[2,1-b][1,3]oxazin-6(S)-ol (1.40 g, 7.58 mmol) and 4-bromo-1-(bromomethyl)-2-fluorobenzene (2.66 g, 9.93 mmol) in anhydrous DMF (30 mL) under $N_2$ at 0° C. was added 60% NaH (427 mg, 10.70 mmol) then quickly degassed and resealed under $N_2$. The mixture was slowly warmed to room temperature and stirred at room temperature for 3 h. The reaction mixture was cooled (solid $CO_2$/acetone), quenched with ice/aqueous $NaHCO_3$ (20 mL), added to brine (150 mL) and extracted with $CH_2Cl_2$ (4×80 mL). The combined extracts were evaporated to dryness and the residue was chromatographed on silica gel. Elution with 0-2% EtOAc/$CH_2Cl_2$ firstly gave foreruns, and then elution with 3-5% EtOAc/$CH_2Cl_2$ gave the title compound as a pale yellow solid (2.63 g, 93%); APCI MS m/z 372, 374 (bromine isotope pattern, M+H$^+$); $^1$H NMR (400 MHz, $(CD_3)_2SO$) δ 8.01 (s, 1H), 7.54 (dd, J=9.7, 1.8 Hz, 1H), 7.42 (dd, J=8.2, 1.8 Hz, 1H), 7.37 (dd, J=8.1, 7.7 Hz, 1H), 4.72-4.62 (m, 3H), 4.47 (br d, J=11.9 Hz, 1H), 4.30-4.19 (m, 3H).

Step 2. (S,S)—N-(3-{2,3'-Difluoro-4'-{-2-nitro-6,7-dihydro-5H-imidazo[2,1-b][1,3]oxazin-6-yloxy)biphenyl-4-yl]-2-oxooxazolidin-5-yl}methyl)acetamide: To a degassed solution of 6(S)-(4-bromo-2-fluorobenzyloxy)-2-nitro-6,7-dihydro-5H-imidazo[2,1-b][1,3]oxazine (100 mg, 0.26 mmol), N-{3-[3-fluoro-4-(4,4,5,5-tetramethyl-[1,3,2]dioxaborolan-2-yl)-phenyl]-2-oxo-oxazolidin-5-ylmethyl}-acetamide (112 mg, 0.29 mmol), and 2M $K_2CO_3$ (1 mL, 2.00 mmol) in toluene/EtOH (5/3, 4 mL) and DMF (4 mL), $PdCl_2$(dppf) (12 mg, 0.05 mmol) was added. The mixture was heated under $N_2$ to 100° C. for 1 h, diluted with water and extracted into EtOAc (3×50 mL) and concentrated in vacuo. The crude product was purified by flash chromatography on silica (0-5% MeOH/$CH_2Cl_2$) to afford the title product (75 mg, 52%). APCI MS m/z 544.4 (M+H$^+$); $^1$H NMR (400 MHz, $(CD_3)_2SO$) δ 8.22 (t, J=5.7, 1H), 8.03 (s, 1H), 7.63-7.58 (m, 2H), 7.51 (t, J=7.8 Hz, 1H), 7.43-7.38 (m, 3H), 4.80-4.67 (m, 4H), 4.50 (d, J=11.9 Hz, 1H), 4.33-4.24 (m, 3H), 4.17 (t, J=9.1 Hz, 1H), 3.79 (dd, J=9.2, 6.5 Hz, 1H), 3.43 (t, J=5.4 Hz, 2H), 1.84 (s, 3H).

Example 60

N-[((5S)-3-{3-Fluoro-4-[5-({[(6S)-2-nitro-6,7-dihydro-5H-imidazo[2,1-b][1,3]oxazin-6-yl]oxy}methyl)-2-thienyl]phenyl}-2-oxo-1,3-oxazolidin-5-yl)methyl]acetamide

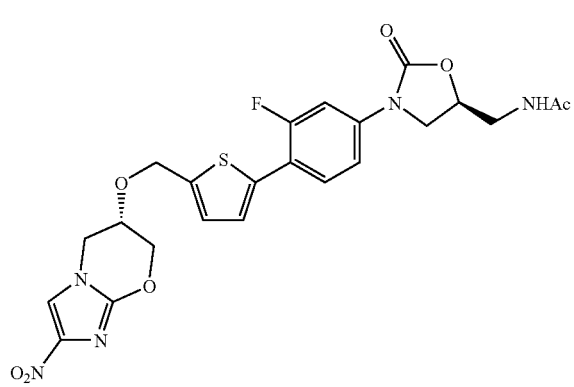

Step 1: (6S)-6-[(5-Bromo-2-thienyl)methoxy]-2-nitro-6,7-dihydro-5H-imidazo[2,1-b][1,3]oxazine. NaH (60% w/w, 0.60 g, 15 mmol) was added to a solution of (6S)-2-nitro-6,7-dihydro-5H-imidazo[2,1-b][1,3]oxazin-6-ol (2.00 g, 10.8 mmol) and 2-bromo-5-(bromomethyl)thiophene (prepared by the method of Mamane et al., Synthesis, 3; 2003; 455-467) (3.20 g, 12.5 mmol) in DMF (40 mL) at 0° C. The mixture was stirred at 0° C. for 2 h, then poured onto ice and extracted with EtOAc (2×200 mL). The organic layer was dried and evaporated. Column chromatography (hexanes/EtOAc, gradient elution) gave the titled compound (2.985 g, 77%) as a white solid. APCI MS m/z 360, 362 (M+H). $^1$H NMR (400 MHz, DMSO-$d_6$) δ 8.00 (s, 1H), 7.11 (d, J=3.7 Hz, 1H), 6.95 (d, J=3.7 Hz, 1H), 4.79 (d, J=13.2 Hz, 1H), 4.76 (d, J=13.2 Hz, 1H), 4.60 (dt, J=12.0, 1.6 Hz, 1H), 4.44 (d, J=12.0 Hz, 1H), 4.19-4.25 (m, 3H).

Step 2: N-[((5S)-3-{3-Fluoro-4-[5-({[(6S)-2-nitro-6,7-dihydro-5H-imidazo[2,1-b][1,3]oxazin-6-yl]oxy}methyl)-2-thienyl]phenyl}-2-oxo-1,3-oxazolidin-5-yl)methyl]acetamide. A mixture of (6S)-6-[(5-bromo-2-thienyl)methoxy]-2-nitro-6,7-dihydro-5H-imidazo[2,1-b][1,3]oxazine (0.200 g, 0.555 mmol) and N-({(5S)-3-[3-fluoro-4-(4,4,5,5-tetramethyl-1,3,2-dioxaborolan-2-yl)phenyl]-2-oxo-1,3-oxazolidin-5-yl}methyl)acetamide (0.252 g, 0.666 mmol) in EtOH (3 mL), toluene (5 mL), DMF (8 mL) and $K_2CO_3$ (2 mL, 2 M, 4 mmol) was purged with nitrogen. $PdCl_2$(dppf) (23 mg, 0.03 mmol) was added and the mixture was refluxed under nitrogen for 1 h then partitioned between EtOAc and water. Column chromatography (9:1 DCM/MeOH) gave a solid which was then reprecipitated from DCM/MeOH to give the titled compound (0.142 g, 48%) as a pale grey solid. APCI MS m/z 532 (M+H). $^1$H NMR (400 MHz, DMSO-$d_6$) δ 8.21 (t, J=5.7 Hz, 1H), 8.02 (s, 1H), 7.76 (t, J=8.9 Hz, 1H), 7.59 (dd, J=14.0, 2.1 Hz, 1H), 7.36-7.43 (m, 2H), 7.13 (d, J=3.3, 1H), 4.87 (d, J=13.6 Hz, 1H), 4.84 (d, J=13.6 Hz, 1H), 4.72-4.80 (m, 1H), 4.64 (bd, J=12.4 Hz, 1H), 4.47 (d, J=11.9 Hz, 1H), 4.21-4.30 (m, 3H), 4.15 (t, J=9.1 Hz, 1H), 3.74-3.81 (m, 1H), 3.43 (t, J=5.4 Hz, 2H), 1.84 (s, 3H).

Example 61

N-({(5S)-3-[3-Fluoro-4-(6-{4-[(2-methyl-6-nitro-2,3-dihydroimidazo[2,1-b][1,3]oxazol-2-yl)methyl]-1-piperazinyl}-3-pyridinyl)phenyl]-2-oxo-1,3-oxazolidin-5-yl}methyl)acetamide

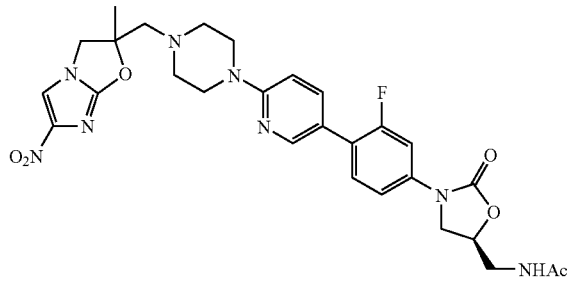

Step 1: tert-Butyl 4-[5-(4-{(5S)-5-[(acetylamino)methyl]-2-oxo-1,3-oxazolidin-3-yl}-2-fluorophenyl)-2-pyridinyl]-1-piperazinecarboxylate. A mixture of tert-Butyl 4-(5-bromo-2-pyridinyl)-1-piperazinecarboxylate (0.203 g, 0.593 mmol) and N-({(5S)-3-[3-fluoro-4-(4,4,5,5-tetramethyl-1,3,2-dioxaborolan-2-yl)phenyl]-2-oxo-1,3-oxazolidin-5-yl}methyl)acetamide (0.270 g, 0.714 mmol) in dmf (4 mL), EtOH (1.5 mL), toluene (2.5 mL) and $K_2CO_3$ (1 mL, 2 M, 2 mmol) was purged with nitrogen. $PdCl_2$(dppf) (24 mg, 0.03 mmol) was added and the mixture was heated to 90° C. under nitrogen for 1 h, then partitioned between EtOAc and water. Column chromatography (EtOAc) gave the titled compound (0.210 g, 69%) as a white solid. APCI MS m/z 514 (M+H). $^1$H NMR (400 MHz, DMSO-$d_6$) δ 8.32 (bs, 1H), 8.27 (t, J=5.9 Hz, 1H), 7.75 (ddd, J=8.9, 2.4, 1.7 Hz, 1H), 7.53-7.60 (m, 2H), 7.38 (dd, J=8.6, 2.2 Hz, 1H), 6.94 (d, J=8.9 Hz, 1H), 4.72-4.79 (m, 1H), 4.15 (t, J=9.1 Hz, 1H), 3.77 (dd, J=9.2, 6.5 Hz, 1H), 3.52-3.57 (m, 4H), 3.40-3.46 (m, 6H), 1.84 (s, 3H), 1.43 (s, 9H).

Step 2: N-[((5S)-3-{3-Fluoro-4-[6-(1-piperazinyl)-3-pyridinyl]phenyl}-2-oxo-1,3-oxazolidin-5-yl)methyl]acetamide. A solution of tert-butyl 4-[5-(4-{(5S)-5-[(acetylamino)methyl]-2-oxo-1,3-oxazolidin-3-yl}-2-fluorophenyl)-2-pyridinyl]-1-piperazinecarboxylate (0.191 g, 0.372 mmol) in DCM (10 mL) and trifluoroacetic acid (10 mL) was stirred at room temperature for 3 h. The solvent was removed in vacuo and the residue was partitioned between EtOAc and 1 M NaOH solution. The organic layer was dried and evaporated to give the titled compound (0.150 g, 98%) as a colourless foam. APCI MS m/z 414 (M+H). $^1$H NMR (400 MHz, DMSO-$d_6$) δ 8.30 (s, 1H), 8.22 (t, J=5.8 Hz, 1H), 7.72 (bdt, J=9.0, 2.1 Hz, 1H), 7.52-7.60 (m, 2H), 7.38 (dd, J=8.6, 2.1 Hz, 1H), 6.89 (d, J=9.0 Hz, 1H), 4.72-4.80 (m, 1H), 4.16 (t, J=9.0 Hz, 1H), 3.78 (dd, J=9.1, 6.7 Hz, 1H), 3.41-3.51 (m, 6H), 2.80-2.85 (m, 4H), 1.84 (s, 3H).

Step 3: N-({(5S)-3-[3-Fluoro-4-(6-{4-[(2-methyl-6-nitro-2,3-dihydroimidazo[2,1-b][1,3]oxazol-2-yl)methyl]-1-piperazinyl}-3-pyridinyl)phenyl]-2-oxo-1,3-oxazolidin-5-yl}methyl)acetamide. A solution of N-[((5S)-3-{3-fluoro-4-[6-(1-piperazinyl)-3-pyridinyl]phenyl}-2-oxo-1,3-oxazolidin-5-yl)methyl]acetamide (0.147 g, 0.355 mmol), 2-bromo-1-[(2-methyl-2-oxiranyl)methyl]-4-nitro-1H-imidazole (0.092 g, 0.35 mmol) and diisopropylethylamine (70 μL, 0.40 mmol) in ethoxyethanol (10 mL) was refluxed for 2.5 h. The solution was evaporated onto silica gel, column chromatography (0-10% MeOH/EtOAc, gradient elution) gave a solid which was reprecipitated from refluxing MeOH to give the titled compound (25 mg, 12%) as a cream solid. APCI MS m/z 595 (M+H). $^1$H NMR (400 MHz, DMSO-$d_6$) δ 8.28 (bs, 1H), 8.21 (t, J=5.8 Hz, 1H), 8.12 (s, 1H), 7.70 (bdt, J=9.0, 2.2 Hz, 1H), 7.51-7.59 (m, 2H), 7.37 (dd, J=8.6, 2.2 Hz, 1H), 6.88 (d, J=9.0 Hz, 1H), 4.71-4.79 (m, 1H), 4.29 (d, J=10.7 Hz, 1H), 4.15 (t, J=9.0 Hz, 1H), 4.09 (d, J=10.7 Hz, 1H), 3.77 (dd, J=9.2, 6.5 Hz, 1H), 3.31-3.47 (m, 6H), 2.82 (d, J=14.7 Hz, 1H), 2.78 (d, J=14.7 Hz, 1H), 2.72-2.79 (m, 4H), 1.84 (s, 3H), 1.58 (s, 3H).

Example 62

3-{3-Fluoro-4-[5-(2-nitro-6,7-dihydro-5H-imidazo[2,1-b][1,3]oxazin-6-yloxymethyl)-pyridin-2-yl]-phenyl}-5-hydroxymethyl-oxazolidin-2-one

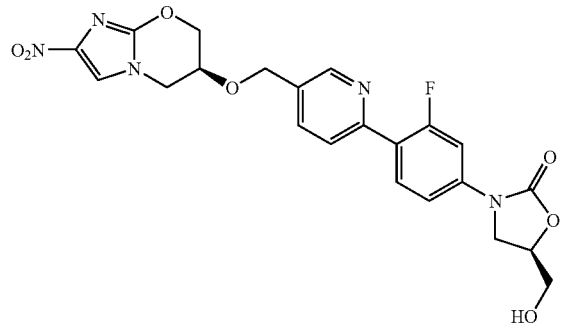

Step 1. 5-(tert-Butyl-dimethyl-silanyloxymethyl)-3-{3-fluoro-4-[5-(2-nitro-6,7-dihydro-5H-imidazo[2,1-b][1,3]oxazin-6-yloxymethyl)-pyridin-2-yl]-phenyl}-oxazolidin-2-one: To a suspension of 6-(6-bromo-pyridin-3-ylmethoxy)-2-nitro-6,7-dihydro-5H-imidazo[2,1-b][1,3]oxazine (150 mg, 0.40 mmol), 5-(tert-butyl-dimethyl-silanyloxymethyl)-3-[3-fluoro-4-(4,4,5,5-tetramethyl-[1,3,2]dioxaborolan-2-yl)-phenyl]-oxazolidin-2-one (198 mg, 0.44 mmol), Pd(Ph$_3$P)$_4$ (58 mg, 0.05 mmol) and $K_2CO_3$ (121 mg, 0.88 mmol) in DMF/H$_2$O (10/1. 5.5 mL) was degassed. The mixture was heated to 80° C. for 2.5 h, diluted with EtOAc, washed with brine and concentrated in vacuo to give a crude product. The crude product was purified by flash chromatography (5% MeOH in EtOAc) to afford the title product (170 mg). ESI MS m/z 600.5 (M+H$^+$).

Step 2. 3-{3-Fluoro-4-[5-(2-nitro-6,7-dihydro-5H-imidazo[2,1-b][1,3]oxazin-6-yloxymethyl)-pyridin-2-yl]-phenyl}-5-hydroxymethyl-oxazolidin-2-one: To a solution of 5-(tert-butyl-dimethyl-silanyloxymethyl)-3-{3-fluoro-4-[5-(2-nitro-6,7-dihydro-5H-imidazo[2,1-b][1,3]oxazin-6-yloxymethyl)-pyridin-2-yl]-phenyl}-oxazolidin-2-one (170 mg) in THF (8.0 mL) was added TBAF (1.0 mL, 1.0 mmol, 1.0 M in THF). The mixture was stirred at room temperature for 1 h. The reaction mixture was diluted with EtOAc, washed with brine, purified by flash chromatography to give the title product (89 mg) as a yellow solid. ESI MS m/z 486.4 (M+H$^+$); $^1$H NMR (400 MHz, DMSO) δ 8.63 (d, J=1.6 Hz, 1H), 8.03 (s, 1H), 7.99 (t, J=9.0 Hz, 1H), 7.81 (dd, J=8.4, 2.0 Hz, 1H), 7.75 (d, J=8.0 Hz, 1H), 7.63 (dd, J=14.8, 2.8 Hz, 1H), 7.46 (dd, J=8.8, 1.6 Hz, 1H), 5.24 (t, J=5.6 Hz, 1H), 4.74-4.66 (m, 3H), 4.46 (d, J=12.0 Hz, 1H), 4.30-4.20 (m, 2H), 4.12 (t, J=9.0 Hz, 1H), 3.86 (dd, J=9.2, 6.4 Hz, 1H), 3.79-3.64 (m, 1H), 3.58-3.52 (m, 1H), 3.16-3.12 (m, 2H).

Example 63

3-{3-Fluoro-4-[6-(2-nitro-6,7-dihydro-5H-imidazo[2,1-b][1,3]oxazin-6-yloxy)-pyridazin-3-yl]-phenyl}-5-hydroxymethyl-oxazolidin-2-one

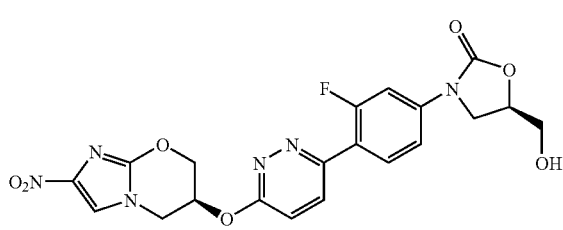

The title compound is prepared by following the same procedure as described in the preparation of Example 62, except 6-(6-chloro-pyridazin-3-yloxy)-2-nitro-6,7-dihydro-5H-imidazo[2,1-b][1,3]oxazine was used in place of 6-(6-bromo-pyridin-3-ylmethoxy)-2-nitro-6,7-dihydro-5H-imidazo[2,1-b][1,3]oxazine. ESI MS m/z 473.4 (M+H$^+$). $^1$H NMR (400 MHz, DMSO) δ 8.07 (s, 1H), 7.98 (dd, J=9.2, 1.6 Hz, 1H), 7.94 (d, J=9.2 Hz, 1H), 7.67 (dd, J=14.4, 2.4 Hz, 1H), 7.53 (dd, J=8.8, 2.0 Hz, 1H), 7.39 (d, J=9.2 Hz, 1H), 6.00 (s, 1H), 5.24 (t, J=5.4 Hz, 1H), 4.83-4.73 (m, 3H), 4.53 (s, 1H), 4.14 (t, J=9.2 Hz, 1H), 3.88 (dd, J=8.8, 6.0 Hz, 1H), 3.72-3.66 (m, 1H), 3.59-3.53 (m, 1H).

Example 64

3-{3-Fluoro-4-[6-(2-nitro-6,7-dihydro-5H-imidazo[2,1-b][1,3]oxazin-6-yloxymethyl)-pyridin-3-yl]-phenyl}-5-hydroxymethyl-oxazolidin-2-one

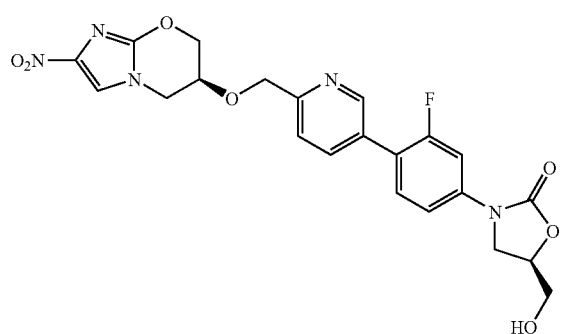

The title compound is prepared by following the same procedure as described in the preparation of Example 62, except 6-(5-bromo-pyridin-2-ylmethoxy)-2-nitro-6,7-dihydro-5H-imidazo[2,1-b][1,3]oxazine was used in place of 6-(6-bromo-pyridin-3-ylmethoxy)-2-nitro-6,7-dihydro-5H-imidazo[2,1-b][1,3]oxazine. ESI MS m/z 486.4 (M+H$^+$). $^1$H NMR (400 MHz, DMSO) δ 8.68 (s, 1H), 8.04 (s, 1H), 7.96 (dt, J=8.8, 1.6 Hz, 1H), 7.65 (dd, J=13.6, 2.4 Hz, 1H), 7.60 (d, J=8.8 Hz, 1H), 7.46 (dd, J=8.4, 2.8 Hz, 2H), 5.74 (s, 1H), 5.24 (t, J=5.6 Hz, 1H), 4.77-4.69 (m, 3H), 4.48 (d, J=12.0 Hz, 1H), 4.35-4.22 (m, 3H), 4.12 (t, J=9.2 Hz, 1H), 3.86 (dd, J=8.8, 5.6 Hz, 1H), 3.70-3.65 (m, 1H), 3.58-3.52 (m, 1H), 3.16-3.12 (m, 1H).

Example 65

N-(3-{3,5-Difluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide

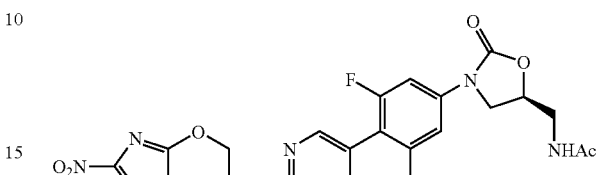

To a suspension of 6-(5-bromo-pyridin-2-yloxy)-2-nitro-6,7-dihydro-5H-imidazo[2,1-b][1,3]oxazine (200 mg, 0.515 mmol), N-{3-[3,5-difluoro-4-(4,4,5,5-tetramethyl-[1,3,2]dioxaborolan-2-yl)-phenyl]-2-oxo-oxazolidin-5-ylmethyl}-acetamide (238 mg, 0.60 mmol) (Biswajit et. al. WO 2006038100 A1 and Gravestock et. al. WO2004/078753 A1), Pd(Ph$_3$P)$_4$(70 mg) and K$_2$CO$_3$ (150 mg) in DMF/H$_2$O (10/1.5.5 mL) was degassed. The mixture was heated to 80° C. for 2 h, diluted with EtOAc, washed with brine and concentrated in vacuo to give a crude product. The crude product was purified by flash chromatography (5% MeOH in EtOAc) to afford the title product (117 mg, 43%). ESI MS m/z 531.5 (M+H$^+$). $^1$H NMR (400 MHz, DMSO) δ 8.30 (s, 1H), 8.28 (t, J=6.0 Hz, 1H), 8.07 (s, 1H), 7.93 (s, 1H), 7.85 (d, J=8.8 Hz, 1H), 7.46 (d, J=10.4 Hz, 1H), 7.00 (d, J=8.8 Hz, 1H), 5.77 (s, 1H), 4.80-4.68 (m, 3H), 4.48-4.40 (m, 2H), 4.14 (t, J=9.4 Hz, 1H), 3.75 (dd, J=9.2, 6.4 Hz, 1H), 3.41 (t, J=5.4 Hz, 2H), 1.82 (s, 3H).

Example 66

3-{3-Fluoro-4-[2-methyl-6-(2-nitro-6,7-dihydro-5H-imidazo[2,1-b][1,3]oxazin-6-yloxy)-pyridin-3-yl]-phenyl}-5-hydroxymethyl-oxazolidin-2-one

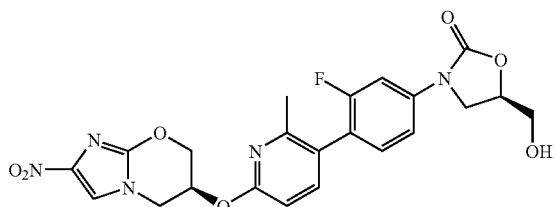

The title compound is prepared by following the same procedure as described in the preparation of Example 1, except 6-(5-bromo-6-methyl-pyridin-2-yloxy)-2-nitro-6,7-dihydro-5H-imidazo[2,1-b][1,3]oxazine was used in place of 6-(6-bromo-pyridin-3-ylmethoxy)-2-nitro-6,7-dihydro-5H-imidazo[2,1-b][1,3]oxazine. ESI MS m/z 486.4 (M+H$^+$).

Example 67

3-{3,5-Difluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one

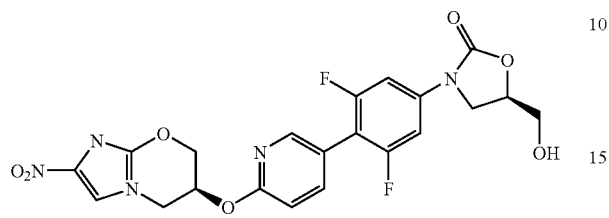

The title compound is prepared by following the same procedure as described in the preparation of Example 30, except 5 (R)-(tert-butyl-dimethyl-silanyloxymethyl)-3-[3,5-difluoro-4-(4,4,5,5-tetramethyl-[1,3,2]dioxaborolan-2-yl)-phenyl]-oxazolidin-2-one (Biswajit et. al. WO 2006038100 A1 and Gravestock et. al. WO 2004/078753 A1) was used in place of 5(R)-(tert-butyl-dimethyl-silanyloxymethyl)-3-[3-fluoro-4-(4,4,5,5-tetramethyl-[1,3,2]dioxaborolan-2-yl)-phenyl]-oxazolidin-2-one. ESI MS m/z 490.3 (M+H$^+$).

Example 68

5-Hydroxymethyl-3-{4-[6-(2-nitro-6,7-dihydro-5H-imidazo[2,1-b][1,3]oxazin-6-yloxy)-pyridin-3-yl]-3-trifluoromethoxy-phenyl}-oxazolidin-2-one

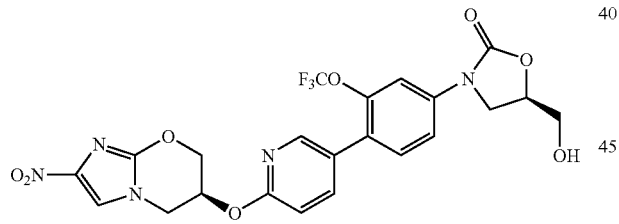

The title compound is prepared by following the same procedure as described in the preparation of Example 30, except 5 (R)-(tert-butyl-dimethyl-silanyloxymethyl)-3-[4-(4,4,5,5-tetramethyl-[1,3,2]dioxaborolan-2-yl)-3-trifluoromethoxy-phenyl]-oxazolidin-2-one (Biswajit et. al. WO 2006038100 A1 and Gravestock et. al. WO 2004/078753 A1) was used in place of 5(R)-(tert-butyl-dimethyl-silanyloxymethyl)-3-[3-fluoro-4-(4,4,5,5-tetramethyl-[1,3,2]dioxaborolan-2-yl)-phenyl]-oxazolidin-2-one. ESI MS m/z 538.4 (M+H$^+$).$^+$. $^1$H NMR (400 MHz, CDCl$_3$) δ 8.20 (d, J=2.4 Hz, 1H), 7.75 (dd, J=8.8, 2.4 Hz, 1H), 7.69 (s, 1H), 7.58 (dd, J=8.0, 2.0 Hz, 1H), 7.47 (s, 1H), 7.39 (d, J=8.8 Hz, 1H), 6.84 (dd, J=8.8, 1.2 Hz, 1H), 5.81-5.79 (m, 1H), 4.86-4.78 (m, 2H), 4.55 (dd, J=12.0, 0.8 Hz, 1H), 4.42 (d, J=2.8 Hz, 2H), 4.11-4.03 (m, 2H), 3.82-3.78 (m, 1H).

Example 69

5-Hydroxymethyl-3-[6'-(2-nitro-6,7-dihydro-5H-imidazo[2,1-b][1,3]oxazin-6-yloxy)-[2,3']bipyridinyl-5-yl]-oxazolidin-2-one

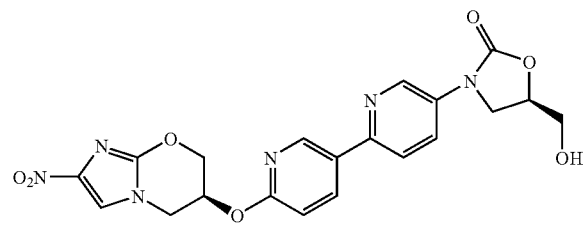

The title compound is prepared by following the same procedure as described in the preparation of Example 30, except 5(R)-(tert-butyl-dimethyl-silanyloxymethyl)-3-[6-(4,4,5,5-tetramethyl-[1,3,2]dioxaborolan-2-yl)-pyridin-3-yl]-oxazolidin-2-one (Biswajit et. al. WO 2006038100 A1 and Gravestock et. al. WO 2004/078753 A1) was used in place of 5(R)-(tert-butyl-dimethyl-silanyloxymethyl)-3-[3-fluoro-4-(4,4,5,5-tetramethyl-[1,3,2]dioxaborolan-2-yl)-phenyl]-oxazolidin-2-one. ESI MS m/z 455.3 (M+H$^+$). $^1$H NMR (400 MHz, DMSO) δ 8.88 (d, J=2.4 Hz, 1H), 8.81 (d, J=2.4 Hz, 1H), 8.38 (dd, J=8.8, 2.8 Hz, 1H), 8.12 (dd, J=8.8, 2.8 Hz, 1H), 8.06 (s, 1H), 8.02 (d, J=8.8 Hz, 1H), 6.97 (d, J=8.0 Hz, 1H), 5.78 (brs, 1H), 5.25 (t, J=5.8 Hz, 1H), 4.78-4.68 (m, 1H), 4.47 (dd, J=14.4, 3.6 Hz, 2H), 4.40 (d, J=13.6 Hz, 1H), 4.16 (t, J=9.0 Hz, 1H), 3.90 (dd, J=8.8, 6.4 Hz, 1H), 3.71-3.66 (m, 1H), 3.60-3.54 (m, 1H).

Example 70

3-{4-[4-Dimethylamino-2-(2-nitro-6,7-dihydro-5H-imidazo[2,1-b][1,3]oxazin-6-yloxy)-pyrimidin-5-yl]-3-fluoro-phenyl}-5-hydroxymethyl-oxazolidin-2-one

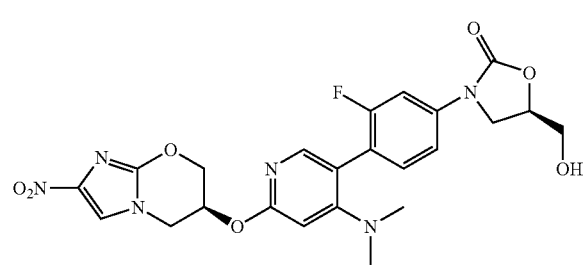

The title compound is prepared by following the same procedure as described in the preparation of Example 62, except [5-bromo-2-(2-nitro-6,7-dihydro-5H-imidazo[2,1-b][1,3]oxazin-6-yloxy)-pyrimidin-4-yl]-dimethyl-amine was used in place of 6-(6-bromo-pyridin-3-ylmethoxy)-2-nitro-6,7-dihydro-5H-imidazo[2,1-b][1,3]oxazine. ESI MS m/z 516.3 (M+H$^+$).

Example 71

N-[3-(3-Fluoro-4-{5-[(2-nitro-6,7-dihydro-5H-imidazo[2,1-b][1,3]oxazin-6-ylamino)-methyl]-pyridin-2-yl}-phenyl)-2-oxo-oxazolidin-5-ylmethyl]-acetamide

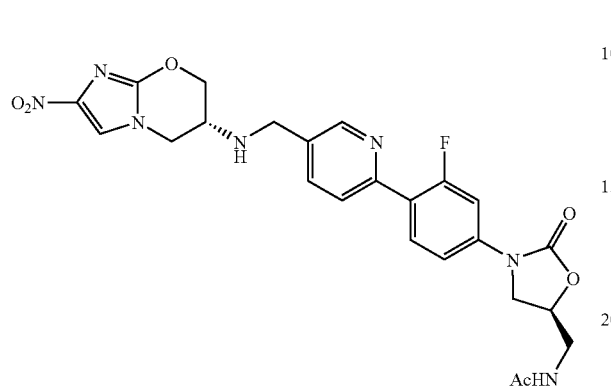

Step 1. (6-Bromo-pyridin-3-ylmethyl)-(2-nitro-6,7-dihydro-5H-imidazo[2,1-b][1,3]oxazin-6-yl)-amine: To a stirred solution of 2-nitro-6,7-dihydro-5H-imidazo[2,1-b][1,3]oxazin-6-ylamine (92 mg, 0.5 mmol) in CH$_2$Cl$_2$ and MeOH are added 6-bromo-pyridine-3-carbaldehyde (93 mg, 0.5 mmol) and acetic acid (0.01 mL) and allowed to stir for 1 h at room temperature. NaBH(OAc)$_3$ (1.0 g) was added to the reaction mixture and allowed to stir overnight at room temperature. The mixture was quenched by saturated NaHCO$_3$ and extracted with CH$_2$Cl$_2$. The combined organic layer is dried over anhydrous Na$_2$SO$_4$, filtered and evaporated. The residue is purified by silica gel column chromatography (10% MeOH in CH$_2$Cl$_2$) to give the title product (76 mg). ESI MS m/z 354.3 (M+H$^+$).

Step 2. N-[3-(3-Fluoro-4-{5-[(2-nitro-6,7-dihydro-5H-imidazo[2,1-b][1,3]oxazin-6-ylamino)-methyl]-pyridin-2-yl}-phenyl)-2-oxo-oxazolidin-5-ylmethyl]-acetamide: To a suspension of (6-bromo-pyridin-3-ylmethyl)-(2-nitro-6,7-dihydro-5H-imidazo[2,1-b][1,3]oxazin-6-yl)-amine (65 mg), N-{3-[3-fluoro-4-(4,4,5,5-tetramethyl-[1,3,2]dioxaborolan-2-yl)-phenyl]-2-oxo-oxazolidin-5-ylmethyl}-acetamide (70 mg) (Gravestock et. al. WO 2004/078753 A1), Pd(Ph$_3$P)$_4$ (30 mg) and K$_2$CO$_3$ (60 mg) in DMF/H$_2$O (10/1. 5.5 mL) was degassed. The mixture was heated to 80° C. for 2.5 h, diluted with EtOAc, washed with brine and concentrated in vacuo to give a crude product. The crude product was purified by flash chromatography (5% MeOH in EtOAc) to afford the title product (30 mg). ESI MS m/z 526.3 (M+H$^+$); $^1$H NMR (400 MHz, DMSO) δ 8.62 (d, J=2.0 Hz, 1H), 8.27 (t, J=5.8 Hz, 1H), 7.99 (t, J=8.8 Hz, 1H), 7.81 (dd, J=7.6, 2.0 Hz, 1H), 7.72 (d, J=6.8 Hz, 1H), 7.59 (dd, J=14.4, 2.0 Hz, 1H), 7.43 (dd, J=8.8, 2.4 Hz, 1H), 4.77-4.72 (m, 1H), 4.45-4.40 (m, 1H), 4.18-4.11 (m, 2H), 3.99 (dd, J=15.2, 3.2 Hz, 1H), 3.84 (d, J=6.8 Hz, 1H), 3.77 (dd, J=9.2, 6.0 Hz, 1H), 3.41 (t, J=5.4 Hz, 2H), 3.28-3.24 (m, 1H), 2.92-2.89 (m, 1H), 1.81 (s, 3H).

Example 72

N-[3-(3-Fluoro-4-{6-[(2-nitro-6,7-dihydro-5H-imidazo[2,1-b][1,3]oxazin-6-ylamino)-methyl]-pyridin-3-yl}-phenyl)-2-oxo-oxazolidin-5-ylmethyl]-acetamide

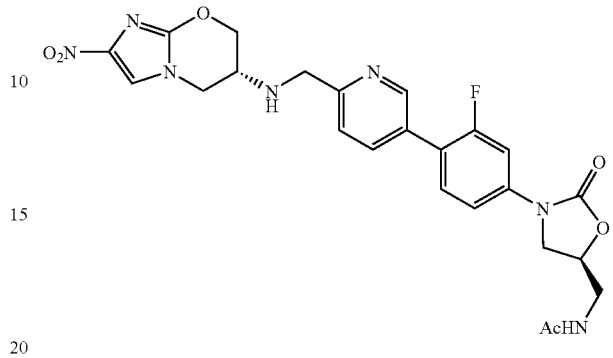

Step 1. (5-Bromo-pyridin-2-ylmethyl)-(2-nitro-6,7-dihydro-5H-imidazo[2,1-b][1,3]oxazin-6-yl)-amine: The title compound is prepared by following the same procedure as described in the preparation of Example 71, except 5-bromo-pyridine-2-carbaldehyde was used in place of (6-bromo-pyridin-3-ylmethyl)-(2-nitro-6,7-dihydro-5H-imidazo[2,1-b][1,3]oxazin-6-yl)-amine. ESI MS m/z 354.1 (M+H$^+$).

Step 2. N-[3-(3-Fluoro-4-{6-[(2-nitro-6,7-dihydro-5H-imidazo[2,1-b][1,3]oxazin-6-ylamino)-methyl]-pyridin-3-yl}-phenyl)-2-oxo-oxazolidin-5-ylmethyl]-acetamide: The title compound is prepared by following the same procedure as described in the preparation of Example 71, except 5-bromo-pyridin-2-ylmethyl)-(2-nitro-6,7-dihydro-5H-imidazo[2,1-b][1,3]oxazin-6-yl)-amine was used in place of 6-bromo-pyridine-3-carbaldehyde. ESI MS m/z 526.3 (M+H$^+$). $^1$H NMR (400 MHz, DMSO) δ 8.66 (brs, 1H), 8.27 (t, J=5.8 Hz, 1H), 7.94-7.89 (m, 1H), 7.64-7.60 (m, 1H), 7.49 (d, J=8.0 Hz, 1H), 7.59 (dd, J=8.8, 2.4 Hz, 1H), 4.77-4.73 (m, 1H), 4.44 (d, J=2.8 Hz, 1H), 4.19-4.11 (m, 2H), 4.04 (dd, J=12.0, 4.0 Hz, 1H), 3.93 (d, J=6.8 Hz, 1H), 3.77 (dd, J=9.2, 6.4 Hz, 1H), 3.41 (t, J=5.6 Hz, 2H), 2.92-2.89 (m, 1H), 1.81 (s, 3H).

Example 73

5-Hydroxymethyl-3-{4-[6-(2-nitro-6,7-dihydro-5H-imidazo[2,1-b][1,3]oxazin-6-yloxymethyl)-pyridin-3-yl]-3-trifluoromethoxy-phenyl}-oxazolidin-2-one

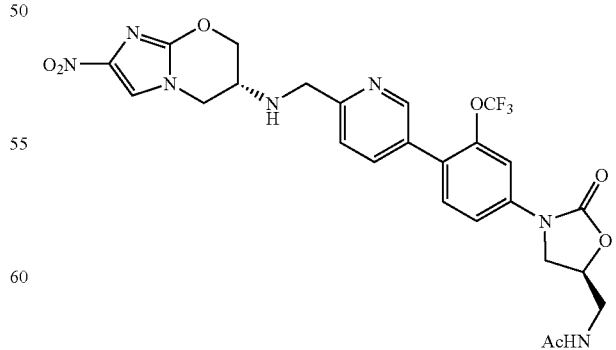

The title compound is prepared by following the same procedure as described in the preparation of Example 68, except 6-(5-Bromo-pyridin-2-ylmethoxy)-2-nitro-6,7-dihydro-5H-imidazo[2,1-b][1,3]oxazine was used in place of 6-(5-bromo-pyridin-2-yloxy)-2-nitro-6,7-dihydro-5H-imidazo[2,1-b][1,3]oxazine. ESI MS m/z 552.3 (M+H+). $^1$H NMR (400 MHz, DMSO) δ 8.60 (d, J=2.0 Hz, 1H), 8.04 (s, 1H), 7.94 (brs, 1H), 7.89 (dd, J=8.4, 2.4 Hz, 1H), 7.61 (d, J=8.4 Hz, 1H), 7.53 (dd, J=8.8, 2.4 Hz, 1H), 7.46 (d, J=8.0 Hz, 1H), 5.74 (s, 2H), 5.24 (t, J=5.6 Hz, 1H), 4.79-4.70 (m, 2H), 4.50 (d, J=12.0 Hz, 1H), 4.36-4.33 (m, 1H), 4.27-4.22 (dd, J=14.0, 3.6 Hz, 1H), 4.14 (t, J=8.8 Hz, 1H), 3.88 (dd, J=9.6, 6.4 Hz, 1H), 3.71-3.67 9m, 1H), 3.59-3.54 (m, 1H).

Example 74

3-[2-Fluoro-4'-(2-methyl-6-nitro-2,3-dihydro-imidazo[2,1-b]oxazol-2-yl)-biphenyl-4-yl]-5-hydroxymethyl-oxazolidin-2-one

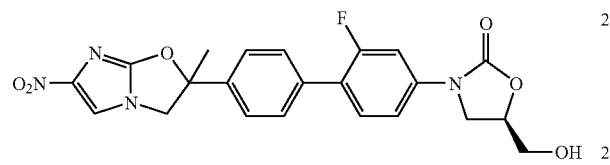

Figure 5:
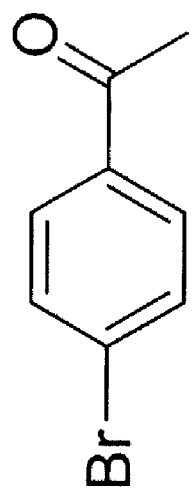
FIG. 5 shows a scheme for synthesizing 2-(4-Bromo-phenyl)-2-methyl-oxirane.
Figure 5:
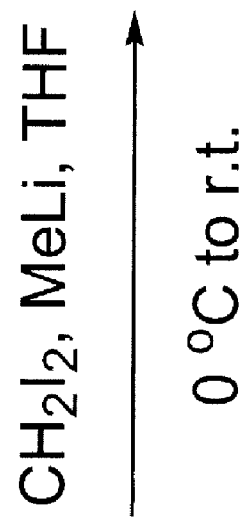
Figure 5:
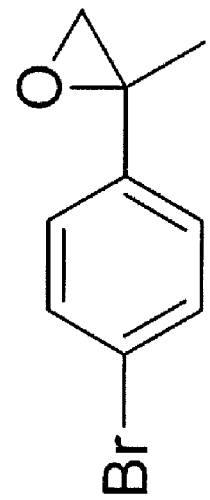

Step 1: 2-(4-Bromo-phenyl)-2-methyl-oxirane was synthesized according to the scheme shown in FIG. 5. 4'-Bromoacetophenone (0.60 g, 3 mmol) and diiodomethane (1.6 g, 6 mmol) were dissolved in 12 mL dry THF. Methyllithium (5.6 mL, 1.6M in ether) was added via syringe in 10 min at 0° C. The resulting clear yellow solution was stirred at 0° C. for 30 min and was then warmed up to room temperature. After stirring at room temperature for 1 hour, the reaction mixture was quenched with ice. The resulting mixture was extracted with EtOAc, washed with brine and dried over Na$_2$SO$_4$. After removing the solvent, fairly pure product (0.62 g) was obtained as yellow solid, which was directly used for next step without further purification. ESI MS m/z 213, 215 (M+H).

Figure 6:
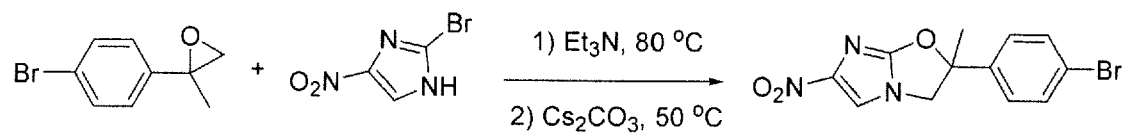
FIG. 6 shows a scheme for synthesizing 2-(4-Bromo-phenyl)-2-methyl-6-nitro-2,3-dihydro-imidazo[2,1-b]oxazole.

Step 2: 2-(4-Bromo-phenyl)-2-methyl-6-nitro-2,3-dihydro-imidazo[2,1-b]oxazole was synthesized according to the scheme shown in FIG. 6. 2-(4-Bromo-phenyl)-2-methyl-oxirane (213 mg, 1 mmol), 2-bromo-5-nitroimidazole (191 mg, 1 mmol) and triethylamine (0.4 mL) were stirred in a sealed tube at 80° C. for 6 hours Column chromatography (EtOAc/Hexanes, v/v, 1/1 to 3/1) gave 330 mg yellow solid. The solid was dissolved in 5 mL DMF with Cs$_2$CO$_3$ (780 mg, 2.4 mmol). The resulting mixture was stirred at 50° C. for 24 hours and then partitioned in EtOAc/water (200 mL, 1/1, v/v). The organic layer was washed with brine and dried over Na$_2$SO$_4$ Column chromatography (EtOAc/Hexanes, v/v, 1/1 to 3/1) gave the titled compound (178 mg, 55% yield in two steps) as yellow solid. ESI MS m/z 324, 326 (M+H). $^1$H NMR (400 MHz, Acetone-d$_6$) δ 7.66 (s, 1H), 7.76 (s, 1H), 7.52 (d, J=8.2 Hz, 2H), 7.41 (d, J=8.2 Hz, 2H), 4.58 (d, J=10.8 Hz, 1H), 4.47 (d, J=10.8 Hz, 1H), 1.89 (s, 3H).

Figure 7:
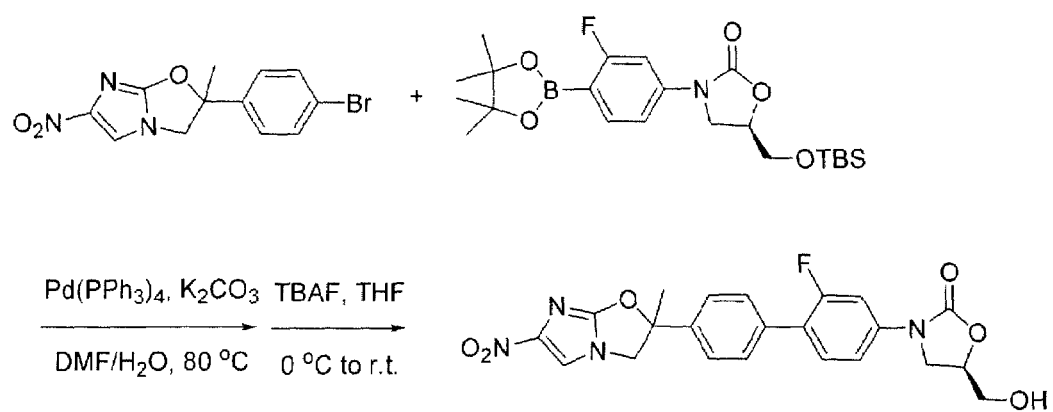
FIG. 7 shows a scheme for synthesizing 3-[2-Fluoro-4'-(2-methyl-6-nitro-2,3-dihydro-imidazo[2,1-b]oxazol-2-yl)-biphenyl-4-yl]-5-hydroxymethyl-oxazolidin-2-one.

Step 3: 3-[2-Fluoro-4'-(2-methyl-6-nitro-2,3-dihydro-imidazo[2,1-b]oxazol-2-yl)-biphenyl-4-yl]-5-hydroxymethyl-oxazolidin-2-one was synthesized according to the scheme shown in FIG. 7. To a dry round bottom flask was added 5-(tert-Butyl-dimethyl-silanyloxymethyl)-3-[3-fluoro-4-(4,4,5,5-tetramethyl-[1,3,2]dioxaborolan-2-yl)-phenyl]-oxazolidin-2-one (148 mg, 0.33 mmol), 2-(4-Bromo-phenyl)-2-methyl-6-nitro-2,3-dihydro-imidazo[2,1-b]oxazole (~97 mg, 0.3 mmol, impure), Ph(PPh$_3$)$_4$ (60 mg, 0.06 mmol) and K$_2$CO$_3$ (85 mg, 0.6 mmol). The flask was flushed with nitrogen and was added 4 mL degassed DMF/H$_2$O (10/1, v/v). The resulting mixture was stirred at 80° C. for 2 hours before it was cooled down and partitioned in 60 mL EtOAc/60 mL water. The organic layer was washed with brine and dried over Na$_2$SO$_4$. Column chromatography (CH$_2$Cl$_2$/MeOH, v/v, 20:1 to 10:1) gave impure TBS-protected titled compound (~22 mg) as yellow solid. This intermediate was dissolved in 2 mL THF and cooled to 0° C. TBAF (0.15 mL, 1M in THF) was added dropwise via syringe. The resulting mixture was warmed up and stirred for 2 hours at root temperature. It was then quenched with 0.4 mL saturated aqueous NH$_4$Cl. After removing all the solvents in vacuo, the product (4 mg) was obtained as yellow solid through preparative TLC(CH$_2$Cl$_2$/MeOH, v/v, 10:1). ESI MS m/z 455 (M+H). $^1$H NMR (400 MHz, CD$_3$OD) δ7.61 (s, 1H), 7.48-7.52 (m, 3H), 7.41-7.46 (m, 2H), 7.34-7.40 (m, 1H), 7.24-7.27 (m, 1H), 4.66-4.74 (m, 1H), 4.40 (s, 2H), 4.03 (t, J=8.8 Hz, 1H), 3.96 (dd, J=8.8, 6.8 Hz, 1H), 3.83 (dd, J=12.8, 3.6 Hz, 1H), 3.65 (dd, J=12.8, 3.6 Hz, 1H), 1.96 (s, 3H).

Example 75

N-{3-[2-Fluoro-4'-(2-methyl-6-nitro-2,3-dihydro-imidazo[2,1-b]oxazol-2-yl)-biphenyl-4-yl]-2-oxo-oxazolidin-5-ylmethyl}-acetamide

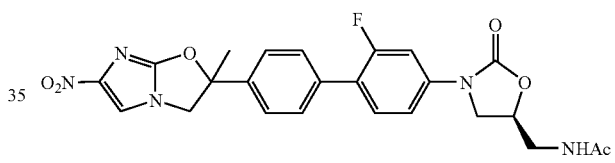

Figure 8:
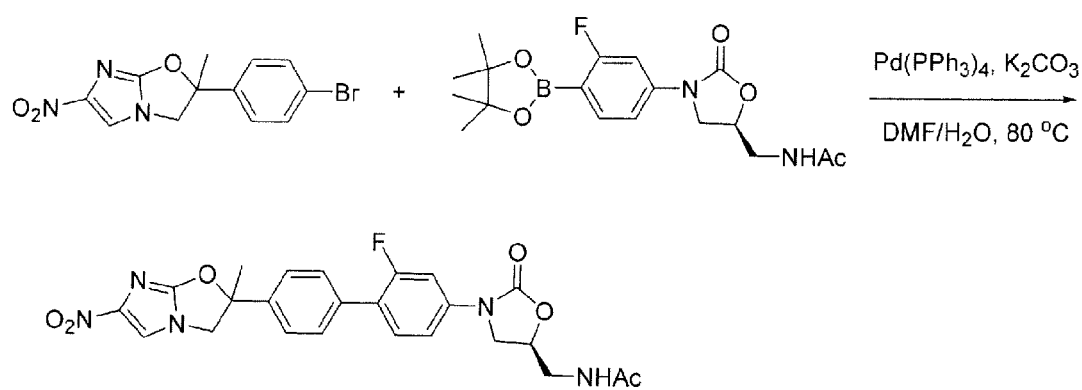
FIG. 8 shows a scheme for synthesizing N-{3-[2-Fluoro-4'-(2-methyl-6-nitro-2,3-dihydro-imidazo[2,1-b]oxazol-2-yl)-biphenyl-4-yl]-2-oxo-oxazolidin-5-ylmethyl}-acetamide.

The titled compound was prepared by using the same procedure as described in Example 74, except that 2-(4-Bromo-phenyl)-2-methyl-6-nitro-2,3-dihydro-imidazo[2,1-b]oxazole was used instead. The titled compound was prepared according to the scheme shown in FIG. 8. The titled compound was obtained as pale solid (12 mg). ESI MS m/z 496 (M+H). $^1$H NMR (400 MHz, CD$_3$OD) δ 7.71 (s, 1H), 7.50-7.58 (m, 3H), 7.44-7.50 (m, 2H), 7.36-7.44 (m, 1H), 7.22-7.30 (m, 1H), 4.68-4.80 (m, 1H), 4.40-4.50 (m, 2H), 4.09 (t, J=8.8 Hz, 1H), 3.78 (dd, J=9.6, 6.8 Hz, 1H), 3.44-3.58 (m, 2H), 1.95 (s, 3H), 1.92 (s, 3H).

Example 76

N-(3-{3-Fluoro-4-[6-(2-methyl-6-nitro-2,3-dihydro-imidazo[2,1-b]oxazol-2-yl)-pyridin-3-yl]-phenyl}-2-oxo-oxazolidin-5-ylmethyl)-acetamide

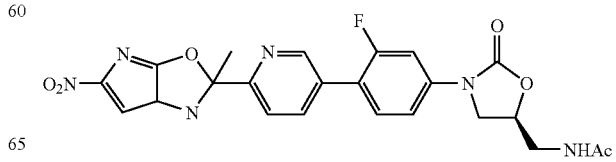

Figure 9:
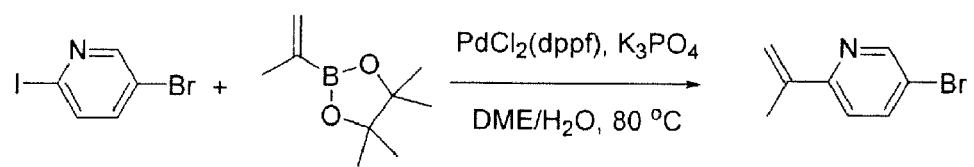
FIG. 9 shows a scheme for synthesizing 5-Bromo-2-isopropenyl-pyridine.

Step 1: 5-Bromo-2-isopropenyl-pyridine was prepared according to the scheme shown in FIG. 9. In the sealed round bottom flask, 2-Iodo-5-bromopyridine (4.34 g, 15.3 mmol), isopropenylboronic acid pinacol ester (2.57 g, 15.3 mmol), PdCl$_2$(dppf) (1.87 g, 2.3 mmol) and potassium phosphate (8.2 g, 38 mmol) were dissolved in 25 mL DME and 8 mL water. The resulting solution was stirred at 80° C. for 3 hours and was then cooled down to room temperature. After separation, the aqueous phase was extracted with EtOAc. The combined organic layers were washed with brine and dried over Na$_2$SO$_4$. After removing the solvent, fairly pure product (about 3.0 g) was obtained as yellow solid, which was directly used for next step without further purification. ESI MS m/z 198, 200 (M+H).

Figure 10:
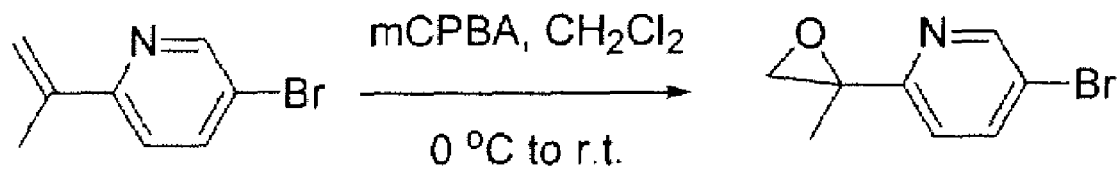
FIG. 10 shows a scheme for synthesizing 5-Bromo-2-(2-methyl-oxiranyl)-pyridine.

Step 2: 5-Bromo-2-(2-methyl-oxiranyl)-pyridine was prepared according to the scheme shown in FIG. 10. To the solution of 5-Bromo-2-isopropenyl-pyridine (850 mg, 4.3 mmol) in 20 mL CH$_2$Cl$_2$ was added mCPBA (1.43 g, 6.4 mmol, 77% max. purity) at 0° C. The resulting mixture was warmed up to room temperature slowly and kept stirring at room temperature for 1 hour, before it was quenched with saturated aqueous NaHCO$_3$. The phases were separated and the organic layer was washed with saturated aqueous NaHCO$_3$, water and brine. Column chromatography (EtOAc/Hexanes, v/v, 1/2) gave fairly pure titled compound (280 mg, 34% yield in two steps) as slightly yellow oil. ESI MS m/z 214, 216 (M+H).

Figure 11:
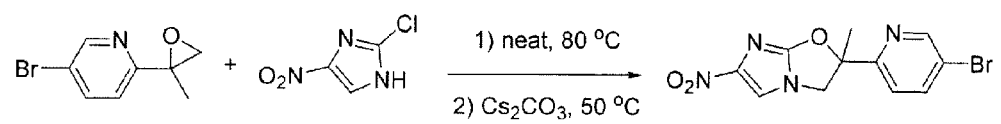
FIG. 11 shows a scheme for synthesizing 2-(5-Bromo-pyridin-2-yl)-2-methyl-6-nitro-2,3-dihydro-imidazo[2,1-b] oxazole

Step 3: 2-(5-Bromo-pyridin-2-yl)-2-methyl-6-nitro-2,3-dihydro-imidazo[2,1-b]oxazole was prepared according to the scheme shown in FIG. 11. The titled compound was prepared by using the same procedure as described in Example 74, Step 2, except that 5-Bromo-2-(2-methyl-oxiranyl)-pyridine and 2-chloro-5-nitroimidazole were used as the starting materials. The titled compound was obtained as off-white solid (323 mg, 26% yield in two steps). ESI MS m/z 325, 327 (M+H). $^1$H NMR (400 MHz, CDCl$_3$) δ 8.57 (d, J=2.4 Hz, 1H), 7.84 (dd, J=8.4, 2.4 Hz, 1H), 7.51 (d, J=8.4 Hz, 1H), 7.46 (s, 1H), 4.84 (d, J=10.8 Hz, 1H), 4.24 (d, J=10.8 Hz, 1H), 1.90 (s, 3H).

Figure 12:
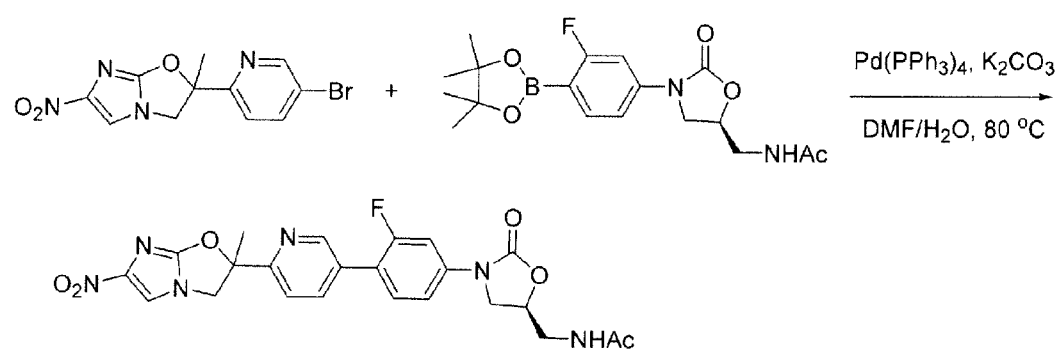
FIG. 12 shows a scheme for synthesizing N-(3-{3-Fluoro-4-[6-(2-methyl-6-nitro-2,3-dihydro-imidazo[2,1-b]oxazol-2-yl)-pyridin-3-yl]-phenyl}-2-oxo-oxazolidin-5-ylmethyl)-acetamide.

Step 4: N-(3-{3-Fluoro-4-[6-(2-methyl-6-nitro-2,3-dihydro-imidazo[2,1-b]oxazol-2-yl)-pyridin-3-yl]-phenyl}-2-oxo-oxazolidin-5-ylmethyl)-acetamide was prepare according to the scheme shown in FIG. 12. The titled compound was prepared by using the same procedure as described previously, except that 2-(5-Bromo-pyridin-2-yl)-2-methyl-6-nitro-2,3-dihydro-imidazo[2,1-b]oxazole was used instead. The titled compound was obtained as brown solid (103 mg, 59% yield). ESI MS m/z 497 (M+H). $^1$H NMR (400 MHz, Acetone-d$_6$) δ 8.82 (s, 1H), 8.06-8.14 (m, 1H), 7.91 (s, 1H), 7.81 (d, J=8.4 Hz, 1H), 7.72 (dd, J=14.0, 2.0 Hz, 1H), 7.59-7.69 (m, 1H), 7.50-7.58 (m, 1H), 7.47 (dd, J=8.4, 2.0 Hz, 1H), 5.07 (d, J=11.2 Hz, 1H), 4.81-4.92 (m, 1H), 4.61 (d, J=11.2 Hz, 1H), 4.27 (t, J=9.2 Hz, 1H), 3.94 (dd, J=9.2, 6.4 Hz, 1H), 3.52-3.69 (m, 2H), 1.92 (s, 3H), 1.16 (s, 3H).

Example 77

N-[3-(3-Fluoro-4-{2-[4-(2-methyl-6-nitro-2,3-dihydro-imidazo[2,1-b]oxazol-2-ylmethyl)-piperazin-1-yl]-pyrimidin-5-yl}-phenyl)-2-oxo-oxazolidin-5-ylmethyl]-acetamide

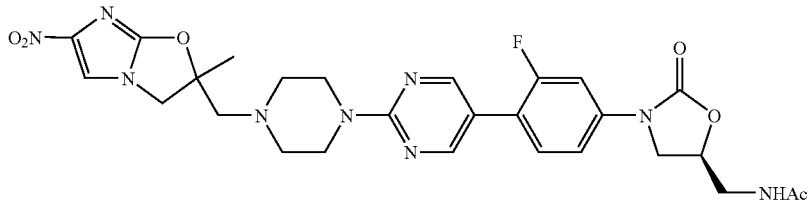

Figure 13:
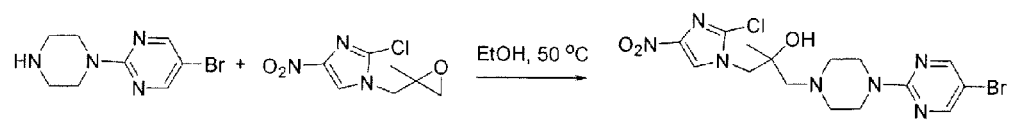
FIG. 13 shows a scheme for synthesizing 1-[4-(5-Bromo-pyrimidin-2-yl)-piperazin-1-yl]-3-(2-chloro-4-nitro-imidazol-1-yl)-2-methyl-propan-2-ol.

Step 1: 1-[4-(5-Bromo-pyrimidin-2-yl)-piperazin-1-yl]-3-(2-chloro-4-nitro-imidazol-1-yl)-2-methyl-propan-2-ol was prepare according to the scheme shown in FIG. 13. In a round bottom flask was added 5-Bromo-2-piperazin-1-yl-pyrimidine (1.07 g, 4.4 mmol), 2-Chloro-1-(2-methyl-oxiranylmethyl)-4-nitro-1H-imidazole (0.87 g, 4.0 mmol) and 24 mL EtOH. The resulting reaction mixture was stirred at 50° C. for 24 hours. After cooled to room temperature, the solid was filtered and washed with EtOAc to give the titled compound. The mother liquor was triturated for more product. The titled compound (1.38 g, 75% yield) was obtained as off-white solid without further purification. ESI MS m/z 462 (M+H). $^1$H NMR (400 MHz, CDCl$_3$) δ 8.29 (s, 2H), 8.06 (s, 1H), 4.01 (s, 2H), 3.79 (b, 4H), 3.35 (s, 1H), 2.57-2.80 (m, 4H), 2.53 (d, J=14.0 Hz, 1H), 2.37 (d, J=14.0 Hz, 1H), 1.16 (s, 3H).

Figure 14:
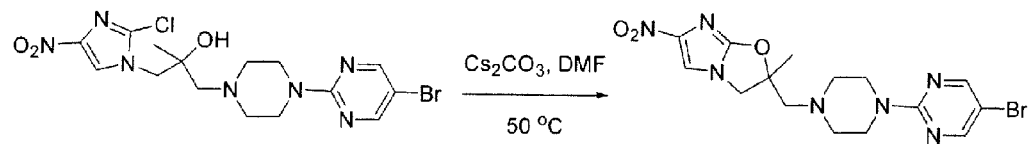
FIG. 14 shows a scheme for synthesizing 2-[4-(5-Bromo-pyrimidin-2-yl)-piperazin-1-ylmethyl]-2-methyl-6-nitro-2,3-dihydro-imidazo[2,1-b]oxazole.

Step 2: 2-[4-(5-Bromo-pyrimidin-2-yl)-piperazin-1-ylmethyl]-2-methyl-6-nitro-2,3-dihydro-imidazo[2,1-b]oxazole was prepared according to the scheme shown in FIG. 14. The product from step 1 (1.38 g, 3.02 mmol) was dissolved in 20 mL DMF with Cs$_2$CO$_3$ (1.96 g, 6.04 mmol). The resulting mixture was stirred at 50° C. for 28 hours and then partitioned in EtOAc/water (200 mL, 1/1, v/v). The organic layer was washed with brine and dried over Na$_2$SO$_4$. Column chromatography (MeOH/Dichloromethane, v/v, 1/10) gave the titled compound (1.05 g, 93% recovered yield) as pale solid. ESI MS m/z 424, 426 (M+H). $^1$H NMR (400 MHz, CDCl$_3$) δ 8.25 (s, 2H), 7.55 (s, 1H), 4.35 (d, J=9.6 Hz, 1H), 3.95 (d, J=9.6 Hz, 1H), 3.54-3.73 (m, 4H), 2.88 (d, J=14.8 Hz, 1H), 2.53-2.77 (m, 4H), 2.60 (d, J=14.8 Hz, 1H), 1.63 (s, 3H).

Figure 15:
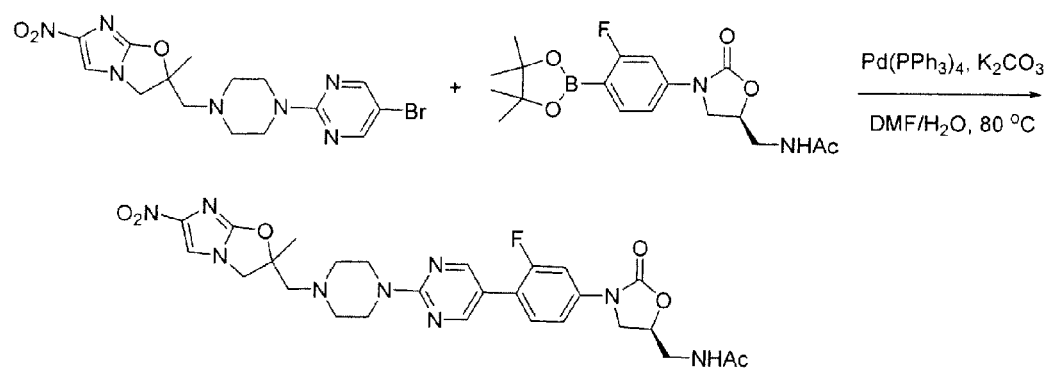
FIG. 15 shows a scheme for synthesizing N-[3-(3-Fluoro-4-{2-[4-(2-methyl-6-nitro-2,3-dihydro-imidazo[2,1-b]oxazol-2-ylmethyl)-piperazin-1-yl]-pyrimidin-5-yl}-phenyl)-2-oxo-oxazolidin-5-ylmethyl]-acetamide.

Step 3: N-[3-(3-Fluoro-4-{2-[4-(2-methyl-6-nitro-2,3-dihydro-imidazo[2,1-b]oxazol-2-ylmethyl)-piperazin-1-yl]-pyrimidin-5-yl}-phenyl)-2-oxo-oxazolidin-5-ylmethyl]-acetamide was prepared according to the scheme shown in FIG. 15. The titled compound was prepared using the same procedure as described previously, except that 2-[4-(5-Bromo-pyrimidin-2-yl)-piperazin-1-ylmethyl]-2-methyl-6-nitro-2,3-dihydro-imidazo[2,1-b]oxazole was used as the starting material. The titled compound was obtained as brown solid (680 mg, 66% yield). ESI MS m/z 596 (M+H). $^1$H NMR (400 MHz, CD$_3$OD) δ 8.40 (s, 2H), 7.83-7.92 (m, 1H), 7.59 (s, 1H), 7.40-7.52 (m, 1H), 7.25-7.36 (m, 1H), 7.17-7.25 (m, 1H), 4.68-4.80 (m, 1H), 4.31 (d, J=10.0 Hz, 1H), 3.42-3.80 (m, 8H), 2.78-2.95 (m, 2H), 2.45-2.76 (m, 5H), 1.93 (s, 3H), 1.58 (s, 3H).

Example 78

3-(3-Fluoro-4-{2-[4-(2-methyl-6-nitro-2,3-dihydro-imidazo[2,1-b]oxazol-2-ylmethyl)-piperazin-1-yl]-pyrimidin-5-yl}-phenyl)-5-hydroxymethyl-oxazolidin-2-one

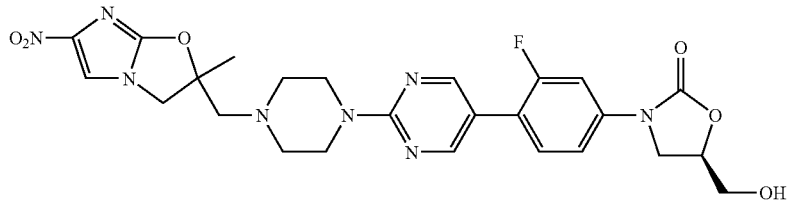

The titled compound was prepared using the same procedure as described previously (see Example 77), except that 5-(tert-Butyl-dimethyl-silanyloxymethyl)-3-[3-fluoro-4-(4,4,5,5-tetramethyl-[1,3,2]dioxaborolan-2-yl)-phenyl]-oxazolidin-2-one was used as the Suzuki coupling reactant, and TBAF deprotection required (see example 2-1). The titled compound was obtained as yellow solid (103 mg, 52% yield). ESI MS m/z 555 (M+H). $^1$H NMR (DMSO-$d_6$) δ 8.53 (s, 2H), 8.13 (s, 1H), 7.50-7.66 (m, 2H), 7.30-7.50 (m, 2H), 5.24 (t, J=5.2 Hz, 1H), 4.66-4.77 (m, 1H), 4.26 (d, J=10.8 Hz, 1H), 4.00-4.16 (m, 2H), 3.84 (dd, J=8.0, 6.8 Hz, 1H), 3.48-3.74 (m, 5H), 2.77 (s, 2H), 2.59 (s, 4H), 1.55 (s, 3H).

Example 79

3-{3-Fluoro-4-[6-(2-methyl-6-nitro-2,3-dihydro-imidazo[2,1-b]oxazol-2-yl)-pyridin-3-yl]-phenyl}-5-hydroxymethyl-oxazolidin-2-one The titled compound was prepared using the same procedure as described previously (see Example 2-1, Step 3), except that 5-(tert-Butyl-dimethyl-silanyloxymethyl)-3-[3-fluoro-4-(4,4,5,5-tetramethyl-[1,3,2]dioxaborolan-2-yl)-phenyl]-oxazolidin-2-one, and 2-(5-Bromo-pyridin-2-yl)-2-methyl-6-nitro-2,3-dihydro-imidazo[2,1-b]oxazole were used as the starting materials, and TBAF deprotection required. The titled compound was obtained as slightly yellow solid (60 mg). ESI MS m/z 456 (M+H). $^1$H NMR (DMSO-$d_6$) δ 8.79 (s, 1H), 8.14 (s, 1H), 8.05-8.12 (m, 1H), 7.75 (d, J=8.8 Hz, 1H), 7.63 (dd, J=5.2, 2.8 Hz, 1H), 7.48 (dd, J=8.8, 2.0 Hz, 1H), 5.24 (t, J=5.6 Hz, 1H), 4.85 (d, J=10.8 Hz, 1H), 4.69-4.77 (m, 1H), 4.49 (d, J=10.8 Hz, 1H), 4.12 (t, J=8.8 Hz, 1H), 3.86 (dd, J=8.8, 5.6 Hz, 1H), 3.64-3.72 (m, 1H), 3.50-3.59 (m, 1H), 1.97 (s, 3H).

Example 80

N-(3-{2-Fluoro-4'-[4-(2-methyl-6-nitro-2,3-dihydro-imidazo[2,1-b]oxazol-2-ylmethyl)-piperazin-1-yl]-biphenyl-4-yl}-2-oxo-oxazolidin-5-ylmethyl)-acetamide

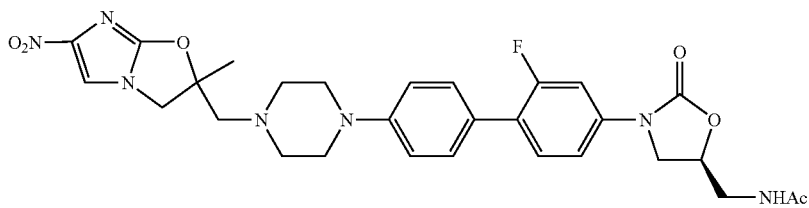

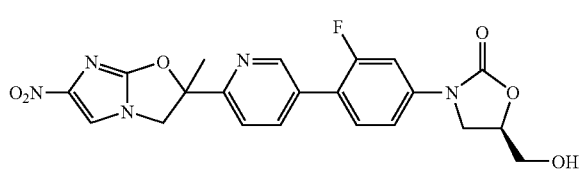

The titled compound was prepared using the same procedure as described previously (see Example 77), except that 1-(4-Bromo-phenyl)-piperazine was used as the starting material in Step 1. The titled compound was obtained as slightly yellow solid (130 mg, 60% yield in the last step). ESI MS m/z 594 (M+H). $^1$H NMR (DMSO-$d_6$) δ 8.25 (t, J=4.4 Hz, 1H), 8.12 (s, 1H), 7.44-7.56 (m, 3H), 7.29-7.39 (m, 3H), 6.94 (d, J=8.4 Hz, 1H), 4.68-4.77 (m, 1H), 4.25 (d, J=10.8 Hz, 1H), 4.11 (t, J=8.8 Hz, 1H), 4.06 (d, J=10.8 Hz, 1H), 3.74 (dd, J=8.8, 6.8 Hz, 1H), 3.36-3.43 (m, 2H), 2.94-3.12 (m, 4H), 2.61-2.70 (m, 4H), 1.81 (s, 3H), 1.55 (s, 3H).

Example 81

N-[3-(3-Fluoro-4-{6-[4-(2-methyl-6-nitro-2,3-dihydro-imidazo[2,1-b]oxazol-2-ylmethyl)-piperazin-1-yl]-pyridin-3-yl}-phenyl)-2-oxo-oxazolidin-5-ylmethyl]-acetamide

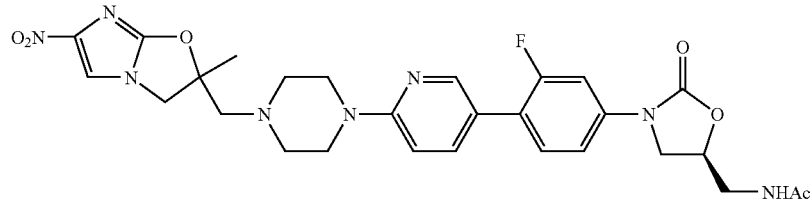

The titled compound was prepared using the same procedure as described previously (see Example 77), except that 1-(5-Bromo-pyridin-2-yl)-piperazine was used as the starting material in Step 1. The titled compound was obtained as brown solid (196 mg, 75% yield in the last step). ESI MS m/z 595 (M+H). $^1$H NMR (DMSO-d$_6$) δ 8.25 (s, 1H), 8.12 (s, 1H), 7.68 (d, J=8.8 Hz, 1H), 7.44-7.58 (m, 3H), 7.34 (d, J=8.8 Hz, 1H), 6.86 (d, J=8.8 Hz, 1H), 4.68-4.77 (m, 1H), 4.26 (d, J=10.8 Hz, 1H), 4.04-4.17 (m, 3H), 3.74 (dd, J=8.4, 6.4 Hz, 1H), 3.36-3.45 (m, 3H), 3.14 (dd, J=5.6, 1.6 Hz, 1H), 2.61 (s, 2H), 2.48 (m, 4H), 1.81 (s, 3H), 1.55 (s, 3H).

Example 82

Phosphoric acid mono-(3-{3-fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl) ester

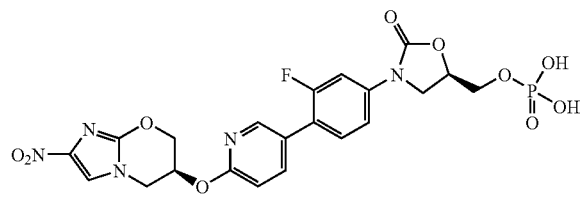

Figure 16:
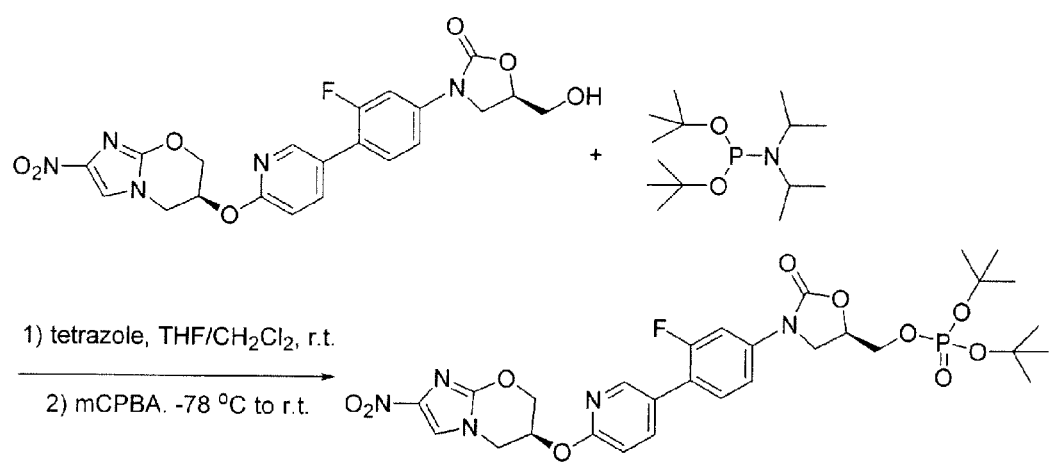
FIG. 16 shows a scheme for synthesizing Phosphoric acid di-tert-butyl ester 3-{3-fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl ester.

Step 1: Phosphoric acid di-tert-butyl ester 3-{3-fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl ester was prepared according to the scheme shown in FIG. 16. In a round bottom flask was added 3-{3-Fluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one (53 mg, 0.1 mmol), Diisopropyl-phosphoramidous acid di-tert-butyl ester (0.078 mL, 0.3 mmol), tetrazole (0.68 mL, ~0.31 mmol, 0.45 M in MeCN), 15 mL dry THF and 2 mL dry dichloromethane. The resulting reaction mixture was stirred at room temperature for 16 hours before it was then cooled to −78° C. mCPBA (34 mg, 0.15 mmol) was added and the resulting solution was stirred at −78° C. for 2 hours. It was then warmed up to room temperature and diluted with 100 mL EtOAc, washed with saturated aqueous NaHCO$_3$ (2×100 mL), brine, and dried over Na$_2$SO$_4$. Preparative TLC (CH$_2$Cl$_2$/MeOH, v/v, 10:1) gave the titled compound (46 mg, 70% yield) as white solid. ESI MS m/z 664 (M+H). $^1$H NMR (CDCl$_3$) δ 8.29 (s, 1H), 7.79-7.84 (m, 1H), 7.58 (dd, J=12.8, 2.0 Hz, 1H), 7.45 (s, 1H), 7.39 (t, J=8.8 Hz, 1H), 7.33 (dd, J=8.8, 2.4 Hz, 1H), 6.86 (d, J=8.8 Hz, 1H), 5.77-5.82 (m, 1H), 4.84-4.92 (m, 1H), 4.84 (dd, J=12.4, 2.8 Hz, 1H), 4.55 (dd, J=12.4, 1.6 Hz, 1H), 4.41 (d, J=2.8 Hz, 2H), 4.04-4.27 (m, 4H), 1.49 (s, 9H), 1.45 (s, 9H).

Figure 17:
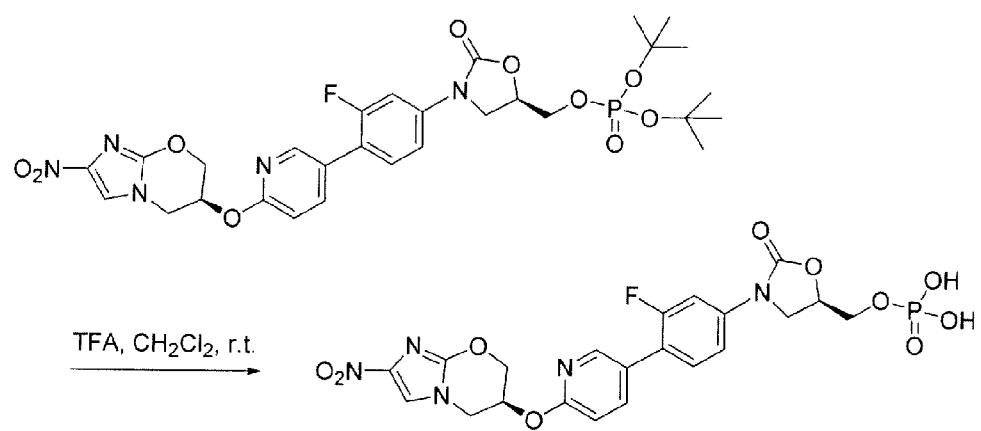
FIG. 17 shows a scheme for synthesizing Phosphoric acid mono-(3-{3-fluoro-4-[6-(2-nitro-6,7-dihydro-5H-imidazo [2,1-b][1,3]oxazin-6-yloxy)-pyridin-3-yl]-phenyl}-2-oxo-oxazolidin-5-ylmethyl)ester.

Step 2: Phosphoric acid mono-(3-{3-fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl) ester was prepared according to the scheme shown in FIG. 17. Phosphoric acid di-tert-butyl ester 3-{3-fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl ester (13 mg) was dissolved with 1 mL TFA/CH$_2$Cl$_2$ (v/v, ½). The resulting solution was stirred at room temperature for 1 hour before all the solvent was removed. The residue was washed with 3 mL CH$_2$Cl$_2$, 3 mL EtOAc and 3 mL MeOH consequently. The residue was dried in vacuo to give the titled compound (8 mg) as white solid. ESI MS m/z 552 (M+H).

Example 83

3-[3-Fluoro-4-(2-nitro-6,7-dihydro-5H-imidazo[2,1-b][1,3]oxazin-6-yl)-phenyl]-5-hydroxymethyl-oxazolidin-2-one

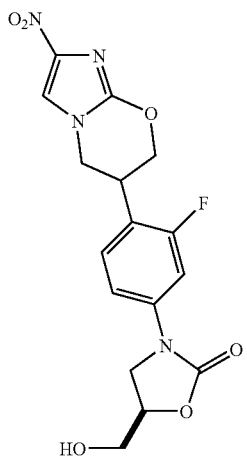

Figure 18:
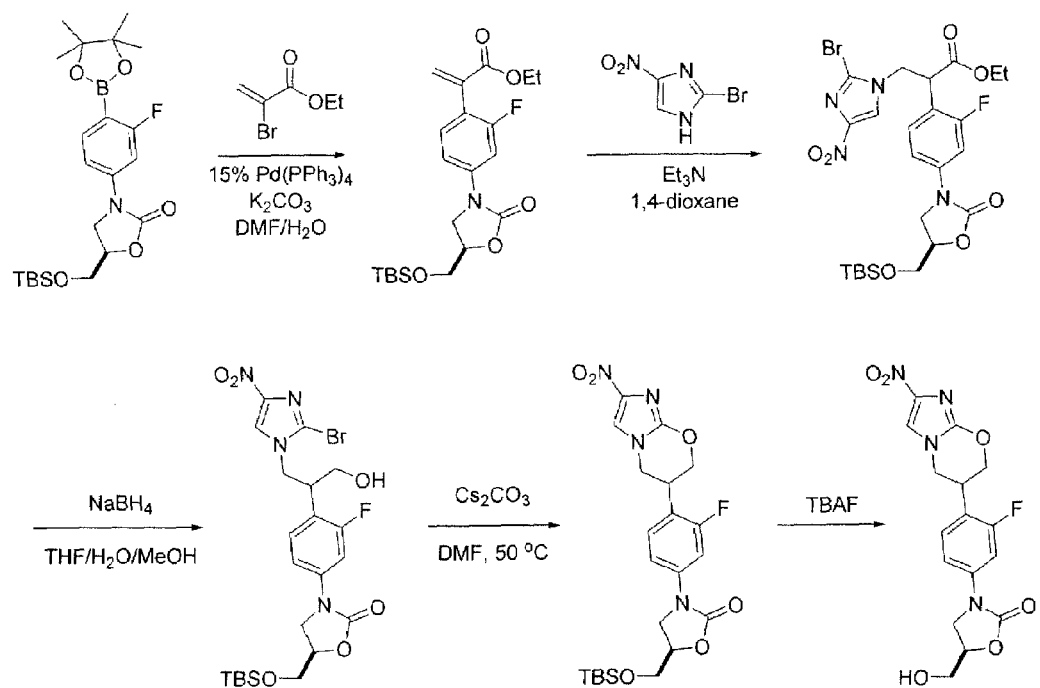
FIG. 18 shows a scheme for synthesizing 3-[3-Fluoro-4-(2-nitro-6,7-dihydro-5H-imidazo[2,1-b][1,3]oxazin-6-yl)-phenyl]-5-hydroxymethyl-oxazolidin-2-one.

The title compound was synthesized according to the scheme shown in FIG. 18. Step 1. 2-{4-[5-(tert-Butyl-dimethyl-silanyloxymethyl)-2-oxo-oxazolidin-3-yl]-2-fluoro-phenyl}-acrylic acid ethyl ester:

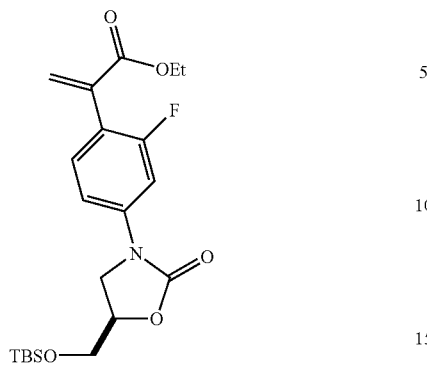

To a mixture of 5-(tert-butyl-dimethyl-silanyloxymethyl)-3-[3-fluoro-4-(4,4,5,5-tetramethyl-[1,3,2]dioxaborolan-2-yl)-phenyl]-oxazolidin-2-one (3.553 g, 7.879 mmol), 2-bromo-acrylic acid ethyl ester (1 g, 6.06 mmol), Pd(PPh$_3$)$_4$ (1 g, 0.909 mmol) and K$_2$CO$_3$ (6.4 g, 12.12 mmol) was added anhydrous DMF/H$_2$O (10:1, 66 mL total). The mixture was degassed under N$_2$ atmosphere by repeating evaporation under vacuum at −78° C. and warming up to rt under N$_2$ three times. The degassed mixture was stirred for 2 h at 60° C., cooled to rt, quenched with water, diluted with EtOAc, washed with brine and water. The organic layers were separated, dried (MgSO$_4$), and concentrated. Column chromatography provided 810 mg (56%) of product as an yellow oil. ESI MS m/z 410 (M+H$^+$).

Step 2. 3-(2-Bromo-4-nitro-imidazol-1-yl)-2-{4-[5-(tert-butyl-dimethyl-silanyloxymethyl)-2-oxo-oxazolidin-3-yl]-2-fluoro-phenyl}-propionic acid ethyl ester:

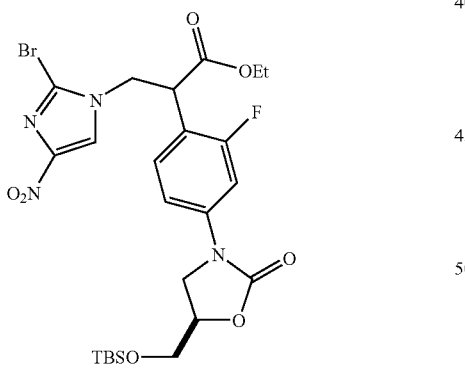

A solution of 2-bromo-4-nitro-1H-imidazole (1.9 g, 9.9 mmol) and Et$_3$N (483 μl, 3.465 mmol) in 1,4-dioxane (10 mL) was stirred for 1 h at rt (solution became a clear solution from a turbid solution), then was added a solution of 2-{4-[5-(tert-Butyl-dimethyl-silanyloxymethyl)-2-oxo-oxazolidin-3-yl]-2-fluoro-phenyl}-acrylic acid ethyl ester (810 mg, 1.98 mmol) in 1,4-dioxane (10 mL). The mixture stirred for overnight (19 h) at 80° C., cooled to rt and concentrated. The concentrated material was directly applied to column (25% EtOAc/hexanes→2% MeOH/CH$_2$Cl$_2$) to provide 996 mg (84%) of product as an yellow oil. ESI MS m/z 602 (M+H$^+$).

Step 3. 3-{4-[2-(2-Bromo-4-nitro-imidazol-1-yl)-1-hydroxymethyl-ethyl]-3-fluoro-phenyl}-5-(tert-butyl-dimethyl-silanyloxymethyl)-oxazolidin-2-one:

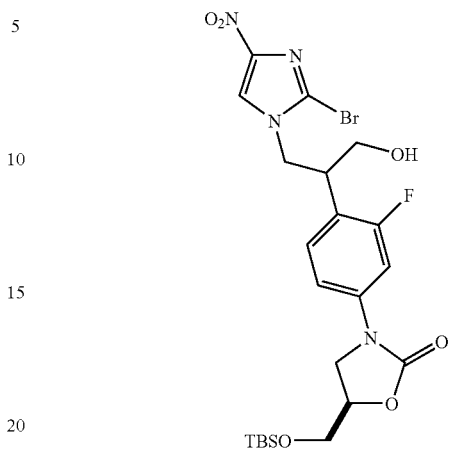

To a solution of 3-(2-Bromo-4-nitro-imidazol-1-yl)-2-{4-[5-(tert-butyl-dimethyl-silanyloxymethyl)-2-oxo-oxazolidin-3-yl]-2-fluoro-phenyl}-propionic acid ethyl ester (100 mg, 0.166 mmol) in THF/H$_2$O/MeOH (3:0.1, 3.1 mL total, 0.05M) was added NaBH$_4$ (19 mg, 0.498 mmol) in H$_2$O (1 mL) at rt. The reaction mixture was stirred for 40 min at rt, diluted with EtOAc and quenched with sat. aqueous NH$_4$Cl at 0° C. The organic layer was separated and the aqueous layer was extracted with EtOAc, washed with brine & water. The organic layers were combined, dried (MgSO$_4$) and concentrated. Column (50% EtOAc/hexanes) provided 41 mg of product as a colorless oil. ESI MS m/z 574 (M+H$^+$).

Step 4. 5-(tert-Butyl-dimethyl-silanyloxymethyl)-3-[3-fluoro-4-(2-nitro-6,7-dihydro-5H-imidazo[2,1-b][1,3]oxazin-6-yl)-phenyl]-oxazolidin-2-one:

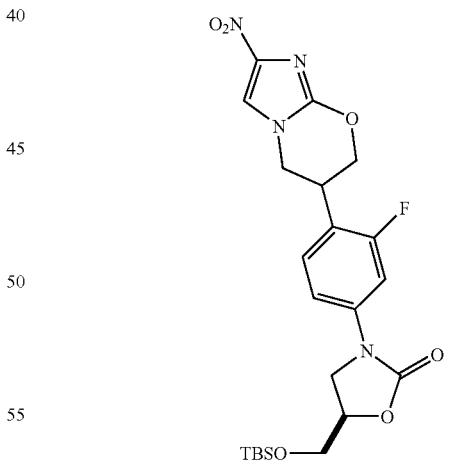

To a solution of 3-{4-[2-(2-Bromo-4-nitro-imidazol-1-yl)-1-hydroxymethyl-ethyl]-3-fluoro-phenyl}-5-(tert-butyl-dimethyl-silanyloxymethyl)-oxazolidin-2-one (210 mg, 0.366 mmol) in DMF (7 mL) was added Cs$_2$CO$_3$ (358 mg, 1.099 mmol) and stirred for 7 h at 50° C. The reaction mixture was cooled to rt, diluted with EtOAc, washed with brine & water. The organic layers were separated, dried (MgSO$_4$) and concentrated. Column (60% EtOAc/hexanes) provided 130 mg of pale yellow solid. ESI MS m/z 493 (M+H$^+$).

Step 5, 3-[3-Fluoro-4-(2-nitro-6,7-dihydro-5H-imidazo[2,1-b][1,3]oxazin-6-yl)-phenyl]-5-hydroxymethyl-oxazolidin-2-one:

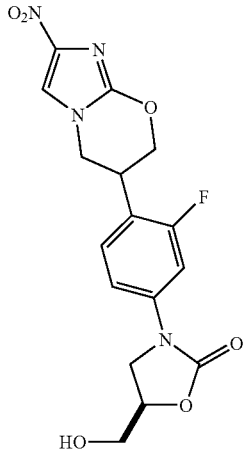

To a solution of 5-(tert-Butyl-dimethyl-silanyloxymethyl)-3-[3-fluoro-4-(2-nitro-6,7-dihydro-5H-imidazo[2,1-b][1,3]oxazin-6-yl)-phenyl]-oxazolidin-2-one (130 mg, 0.264 mmol) in THF (4 mL) was added TBAF (270 μl, 0.269 mmol) at 0° C., and stirred for 20 min at the same temperature. The reaction mixture was quenched with sat. aqueous NH$_4$Cl, diluted with EtOAc, washed with brine & water. The organic layers were separated, dried (MgSO$_4$) and concentrated. Column (5% MeOH/CH$_2$Cl$_2$→MeOH) provided 35 mg of product as a light yellow solid. $^1$H NMR (400 MHz, DMSO-d) δ 8.11 (s, 1H), 7.35 (m, 2H), 5.22 (t, J=5.6 Hz, 1H), 4.69 (m, 1H), 4.02 (m, 2H), 4.31 (m, 2H), 4.06 (t, J=9.0 Hz, 1H), 3.83 (m, 2H), 3.65 (m, 1H), 3.53 (m, 1H). ESI MS m/z 379 (M+H$^+$).

Example 84

N-{3-[3-Fluoro-4-(2-nitro-6,7-dihydro-5H-imidazo[2,1-b][1,3]oxazin-6-yl)-phenyl]-2-oxo-oxazolidin-5-ylmethyl}-acetamide

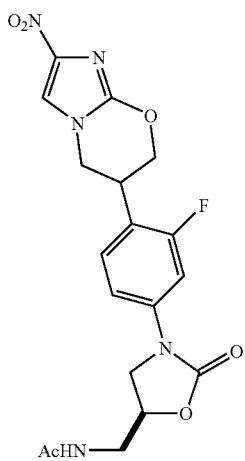

Figure 19:
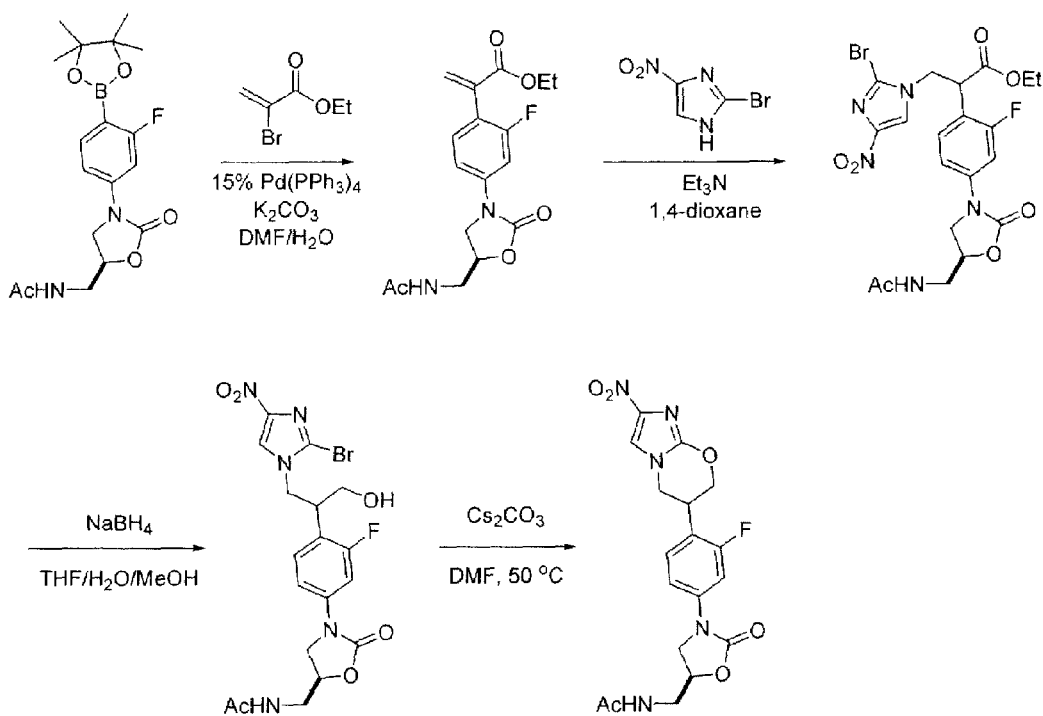
FIG. 19 shows a scheme for synthesizing N-{3-[3-Fluoro-4-(2-nitro-6,7-dihydro-5H-imidazo[2,1-b][1,3]oxazin-6-yl)-phenyl]-2-oxo-oxazolidin-5-ylmethyl}-acetamide.

The title compound was synthesized according to the scheme shown in FIG. 19. Step 1. 2-{4-[5-(Acetylamino-methyl)-2-oxo-oxazolidin-3-yl]-2-fluoro-phenyl}-acrylic acid ethyl ester:

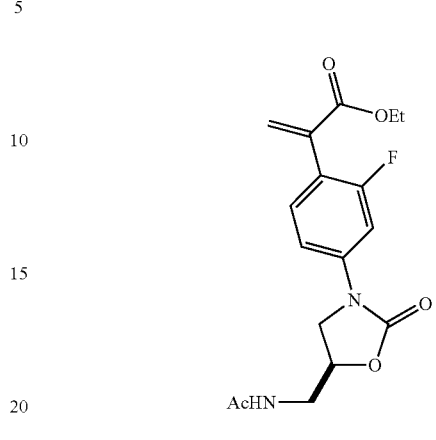

To a mixture of N-{3-[3-luoro-4-(4,4,5,5-tetramethyl-[1,3,2]dioxaborolan-2-yl)-phenyl]-2-oxo-oxazolidin-5-ylmethyl}-acetamide (1.0 g, 2.646 mmol), 2-bromo-acrylic acid ethyl ester (260 μl, 2.405 mmol), Pd(PPh$_3$)$_4$ (556 mg, 0.481 mmol) and K$_2$CO$_3$ (2.53 g, 4.81 mmol) was added anhydrous DMF/H$_2$O (10:1, 26.4 mL total). The mixture was degassed under N$_2$ atmosphere by repeating three times of evaporation under vacuum at −78° C. and warming up to rt under N$_2$. The degassed mixture was stirred for 4.5 h at 80° C., cooled to rt, quenched with water, diluted with EtOAc, washed with brine and water. The organic layers were separated, dried (MgSO$_4$), and concentrated. Column chromatography provided 2.3 mg (96%) of product as an yellow oil. ESI MS m/z 337 (M+H$^+$).

Step 2. 2-{4-[5-(Acetylamino-methyl)-2-oxo-oxazolidin-3-yl]-2-fluoro-phenyl}-3-(2-bromo-4-nitro-imidazol-1-yl)-propionic acid ethyl ester:

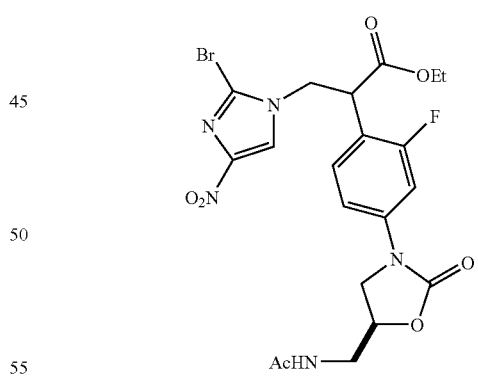

A solution of 2-bromo-4-nitro-1H-imidazole (2.54 g, 13.2 mmol) and Et$_3$N (645 μl, 4.62 mmol) in 1,4-dioxane (15 mL) was stirred for 1 h at rt (solution became a clear solution from a turbid solution), then was added a solution of 2-{4-[5-(Acetylamino-methyl)-2-oxo-oxazolidin-3-yl]-2-fluoro-phenyl}-acrylic acid ethyl ester (2.6 mmol) in 1,4-dioxane (11 mL). The mixture stirred for three days (71 h) at 80° C., cooled to rt and concentrated. The concentrated material was directly applied the next step. ESI MS m/z 530 (M+H$^+$) with bromine pattern.

Step 3. N-(3-{4-[2-(2-Bromo-4-nitro-imidazol-1-yl)1-hydroxymethyl-ethyl]-3-fluoro-phenyl}-2-oxo-oxazolidin-5-ylmethyl)-acetamide:

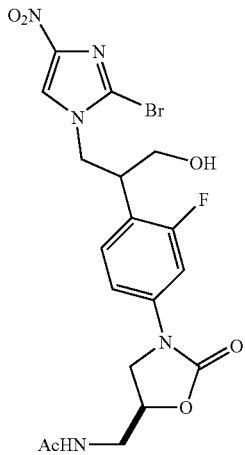

To a solution of 2-{4-[5-(Acetylamino-methyl)-2-oxo-oxazolidin-3-yl]-2-fluoro-phenyl}-3-(2-bromo-4-nitro-imidazol-1-yl)-propionic acid ethyl ester (42 mg, 0.08 mmol) in EtOH (2 mL total, 0.04M) was added NaBH (15 mg, 0.398 mmol) at 0 to −5° C. The reaction mixture was stirred for 2 h 30 min at 0 to −5° C., quenched with sat. aqueous NaHCO$_3$, diluted with EtOAc and H$_2$O and concentrated. The crude material was directly subjected to the next step. Product was confirmed by LCMS. ESI MS m/z 501 (M+H$^+$).

Step 4. N-{3-[3-Fluoro-4-(2-nitro-6,7-dihydro-5H-imidazo[2,1-b][1,3]oxazin-6-yl)-phenyl]-2-oxo-oxazolidin-5-ylmethyl}-acetamide:

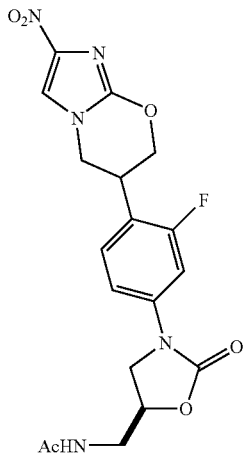

To a solution of crude N-(3-{4-[2-(2-Bromo-4-nitro-imidazol-1-yl)-1-hydroxymethyl-ethyl]-3-fluoro-phenyl}-2-oxo-oxazolidin-5-ylmethyl)-acetamide (9 mg, 0.018 mmol) in DMF (1 mL) was added Cs$_2$CO$_3$ (18 mg, 0.054 mmol) at rt, and stirred for 4 h at 50° C. The reaction mixture was cooled to rt, diluted with EtOAc, washed with brine & water. The organic layers were separated, dried (MgSO$_4$) and concentrated. Prep TLC (5% MeOH/CH$_2$Cl$_2$) provided 690 μg of pale yellow solid. ESI MS m/z 420 (M+H$^+$).

Example 85

2-Allyl-2-(4-bromo-phenyl)-6-nitro-2,3-dihydro-imidazo[2,1-b]oxazole

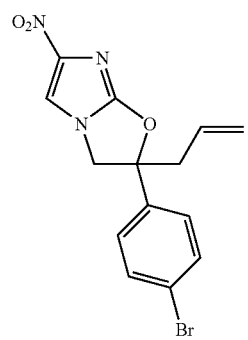

Figure 20:
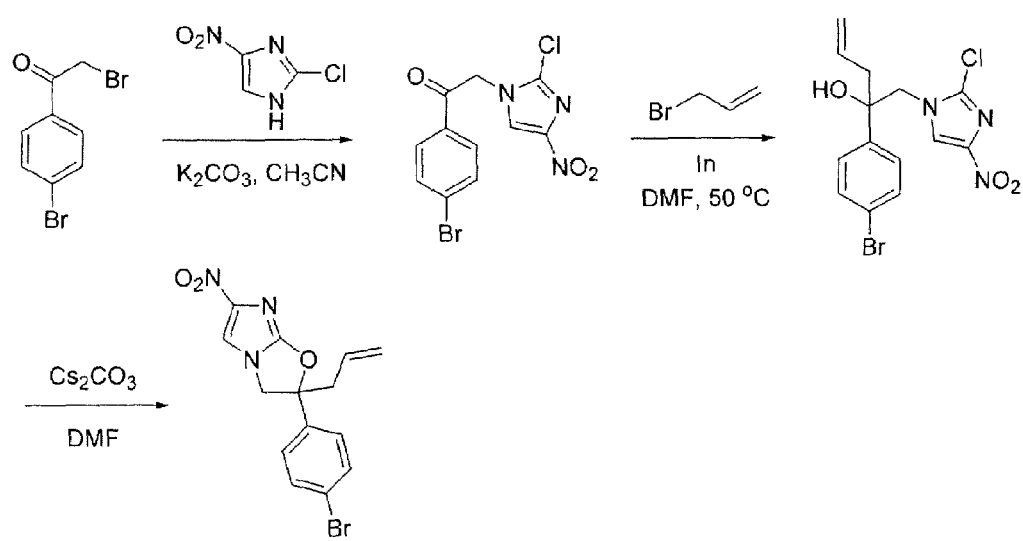
FIG. 20 shows a scheme for synthesizing 2-Allyl-2-(4-bromo-phenyl)-6-nitro-2,3-dihydro-imidazo[2,1-b]oxazole.

The title compound was synthesized according to the scheme shown in FIG. 20. Step 1. 1-(4-Bromo-phenyl)-2-(2-chloro-4-nitro-imidazol-1-yl)-ethanone:

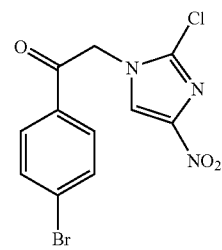

A solution of 2,4'-dibromoacetophenone (5 g, 18 mmol), 2-chloro-4-nitro-1H-imidazole (4 g, 27 mmol, 1.5 equiv.) and K$_2$CO$_3$ (3.73 g, 27 mmol, 1.5 equiv) in CH$_3$CN (180 mL) was stirred at 60° C. for 2 h. The reaction mixture was cooled to rt, and the solids precipitates were filtered. The precipitates were washed with water and the filtered mixture of organic solvents and water were separated. The organic layers were concentrated and recrystallized with acetone to provide 5.5 g (15.99 mmol, 89%) of brown solid. ESI MS m/z 346 (M+H$^+$) with bromine doublet pattern.

Step 2. 2-(4-Bromo-phenyl)-1-(2-chloro-4-nitro-imidazol-1-yl)-pent-4-en-2-ol:

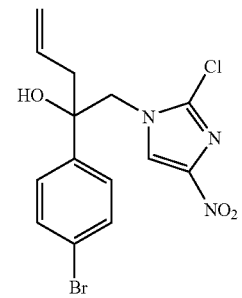

To a solution of In (669 mg, 5.814 mmol, 2.0 equiv) in anhydrous DMF (15 mL) was added allyl bromide (0.984 mL, 11.628 mmol, 4.0 equiv) and stirred for 1 h at 50° C. to become a green solution. To this mixture was added a solution of 1-(4-bromo-phenyl)-2-(2-chloro-4-nitro-imidazol-1-yl)-ethanone in anhydrous DMF (14 mL) under N2 atmosphere and stirred for 1 h at 50° C. The reaction mixture was cooled to rt, diluted with EtOAc, and was washed with brine and water. The organic layers were separated, dried (MgSO$_4$) and concentrated to provide crude product in quantitative yield. ESI MS m/z 388 (M+H$^+$) with bromine doublet pattern.

Step 3. 2-Allyl-2-(4-bromo-phenyl)-6-nitro-2,3-dihydro-imidazo[2,1-b]oxazole:

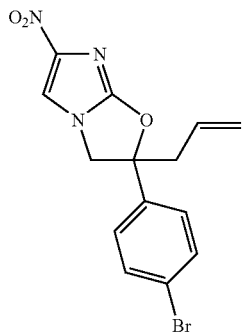

To a solution of crude 2-(4-Bromo-phenyl)-1-(2-chloro-4-nitro-imidazol-1-yl)-pent-4-en-2-ol in DMF (48 mL) was added Cs$_2$CO$_3$ (2.84 g, 8.7 mmol) and stirred for 2 h at 50° C. The reaction mixture was cooled to rt, quenched with water, diluted with EtOAC and washed with brine and water. The organic layers were separated, dried (MgSO$_4$) and concentrated. The concentrates were recrystallized with EuOAc to provide 270 mg of white solid. $^1$H NMR (400 MHz, DMSO-d) 68.11 (s, 1H), 7.64 (m, 2H), 7.38 (m, 2H), 5.80 (m, 2H), 5.12 (m, 2H), 4.62 (d, J=11.2 Hz, 1H), 4.01 (d, J=11.2 Hz, 1H), 2.96 (m, 2H); ESI MS m/z 352 (M+H$^+$).

Example 86

N-{3-[4'-(2-Allyl-6-nitro-2,3-dihydro-imidazo[2,1-b]oxazol-2-yl)-2-fluoro-biphenyl-4-yl]-2-oxo-oxazolidin-5-ylmethyl}-acetamide

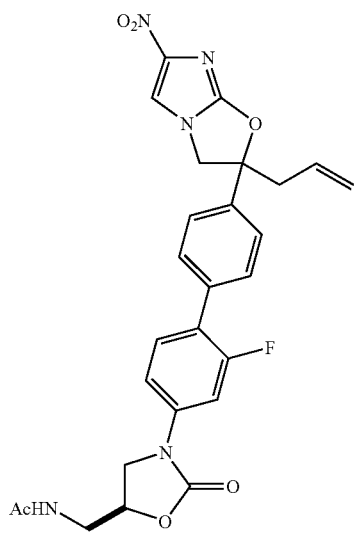

Figure 21:
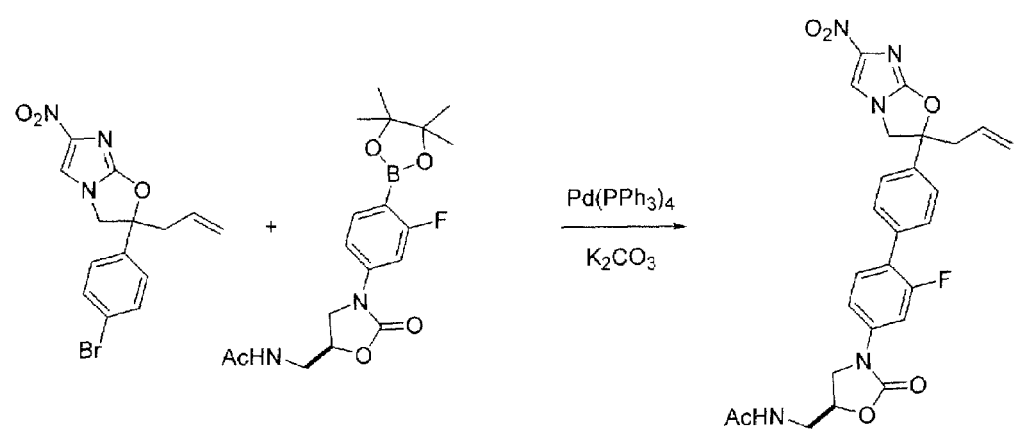
FIG. 21 shows a scheme for synthesizing N-{3-[4'-(2-Allyl-6-nitro-2,3-dihydro-imidazo[2,1-b]oxazol-2-yl)-2-fluoro-biphenyl-4-yl]-2-oxo-oxazolidin-5-ylmethyl}-acetamide.

The title compound was synthesized according to the reaction scheme shown in FIG. 21. To a mixture of 2-Allyl-2-(4-bromo-phenyl)-6-nitro-2,3-dihydro-imidazo[2,1-b]oxazole (80 mg, 0.229 mmol), N-{3-[3-Fluoro-4-(4,4,5,5-tetramethyl-[1,3,2]dioxaborolan-2-yl)-phenyl]-2-oxo-oxazolidin-5-ylmethyl}-acetamide (104 mg, 0.274 mmol), Pd(PPh$_3$)$_4$ (53 mg, 0.046 mmol) and K$_2$CO$_3$ (240 mg, 0.458 mmol) was added anhydrous DMF/H$_2$O (4 mL/0.4 mL, 4.4 mL total) under N2. The reaction mixture was stirred for 2 h at 80° C., cooled to rt, quenched with water, diluted with EtOAc, washed with brine and water. The organic layers were separated, dried (MgSO$_4$) and concentrated. Column chromatography provided 63 mg of yellow solid. $^1$H NMR (400 MHz, DMSO-d) δ 8.26 (t, J=5.8 Hz, 1H), 7.60 (m, 2H), 7.41 (m, 2H), 5.61 (m, 1H), 5.16 (m, 2H), 4.74 (m, 1H), 4.65 (d, J=11.2 Hz, 1H), 4.48 (d, J=11.2 Hz, 1H), 4.15 (d, J=9.0 Hz, 1H), 3.76 (m, 1H), 3.41 (d, J=1.3 Hz, 2H), 3.02 (m, 2H); ESI MS m/z 522 (M+H$^+$)

Example 87

3-[4-(2-Allyl-6-nitro-2,3-dihydro-imidazo[2,1-b]oxazol-2-yl)-phenyl]-5-hydroxymethyl-oxazolidin-2-one

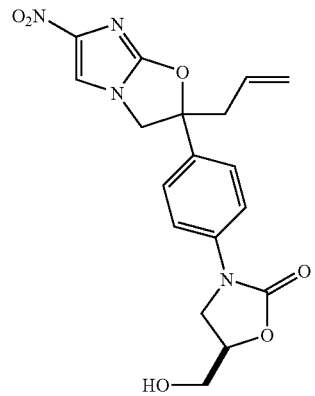

Figure 22:
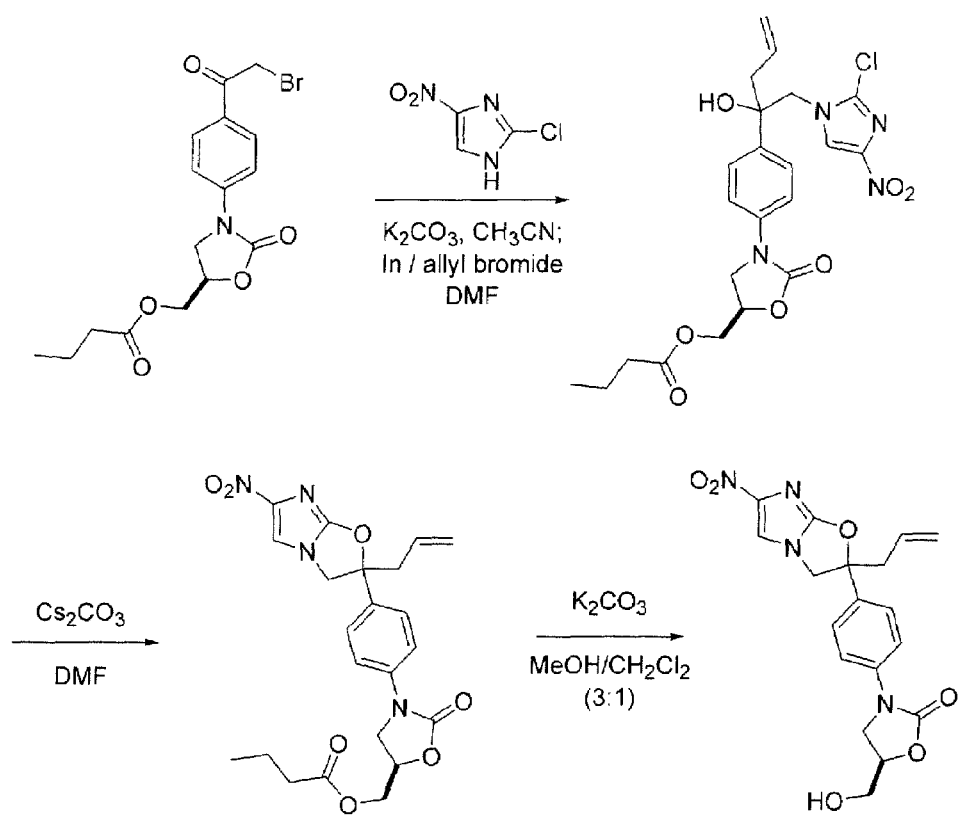
FIG. 22 shows a scheme for synthesizing 3-[4-(2-Allyl-6-nitro-2,3-dihydro-imidazo[2,1-b]oxazol-2-yl)-phenyl]-5-hydroxymethyl-oxazolidin-2-one.

The title compound was synthesized according to the scheme shown in FIG. 22. Step 1. Butyric acid 3-{4-[1-(2-chloro-4-nitro-imidazol-1-ylmethyl)-1-hydroxy-but-3-enyl]-phenyl}-2-oxo-oxazolidin-5-ylmethyl ester:

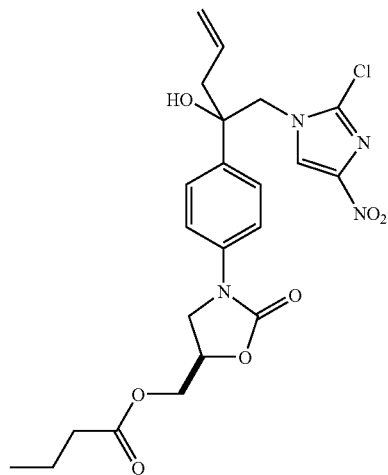

Butyric acid 3-[4-(2-bromo-acetyl)-phenyl]-2-oxo-oxazolidin-5-ylmethyl ester was prepared based on literature procedure (Ref. Tetrahedron 1989, 1323). A solution of Butyric acid 3-[4-(2-bromo-acetyl)-phenyl]-2-oxo-oxazolidin-5-ylmethyl ester (1.2 g, 3.125 mmol), 2-chloro-4-nitro-1H-imidazole (694 mg, 4.688 mmol, 1.5 equiv.) and $K_2CO_3$ (650 mg, 4.688 mmol, 1.5 equiv) in $CH_3CN$ (30 mL) was stirred at 60° C. for 2 h. The reaction mixture was cooled to rt, quenched with sat. aq. $NH_4Cl$, diluted with EtOAc, and washed with brine and water. The organic layers were separated, dried ($MgSO_4$) and concentrated. Crude material was directly used for the next step to prepare the title compound. To a solution of In (719 mg, 6.25 mmol, 2.0 equiv) in anhydrous DMF (20 mL) was added allyl bromide (1.06 mL, 12.5 mmol, 4.0 equiv) and stirred for 1 h at 50° C. to become a green solution. To this mixture was added a solution of crude butyric acid 3-{4-[2-(2-chloro-4-nitro-imidazol-1-yl)-acetyl]-phenyl}-2-oxo-oxazolidin-5-ylmethyl ester in DMF (10 mL) and stirred for 3½ h at 50° C. The reaction mixture was cooled to rt, diluted with EtOAc, and was washed with brine and water. The organic layers were separated, dried ($MgSO_4$) and concentrated. Column chromatography (50% EtOAc/hexanes 4 EtOAc) provided 693 mg (45% for two steps) of yellow oil. ESI MS m/z 493 (M+H$^+$).

Step 2. Butyric acid 3-[4-(2-allyl-6-nitro-2,3-dihydro-imidazo[2,1-b]oxazol-2-yl)-phenyl]-2-oxo-oxazolidin-5-ylmethyl ester:

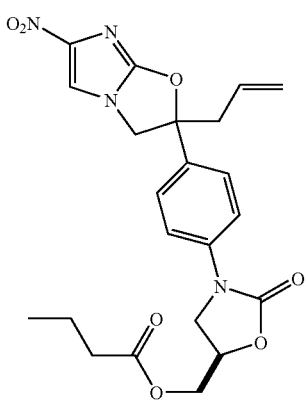

To a solution of butyric acid 3-{4-[1-(2-chloro-4-nitro-imidazol-1-ylmethyl)-1-hydroxy-but-3-enyl]-phenyl}-2-oxo-oxazolidin-5-ylmethyl ester (693 mg, 1.409 mmol) in DMF (24 mL) was added $Cs_2CO_3$ (1.38 g, 4.226 mmol) and stirred for 18 h at 50° C. The reaction mixture was cooled to rt, quenched with water, diluted with EtOAC and washed with brine and water. The organic layers were separated, dried ($MgSO_4$) and concentrated. ESI MS m/z 457 (M+H$^+$).

Step 3. 3-[4-(2-Allyl-6-nitro-2,3-dihydro-imidazo[2,1-b]oxazol-2-yl)-phenyl]-5-hydroxymethyl-oxazolidin-2-one:

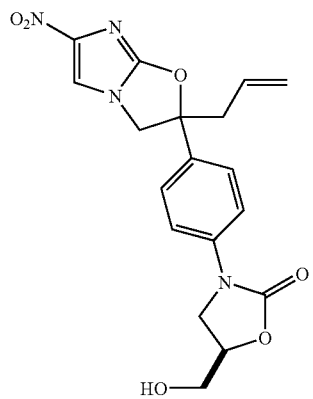

To a solution of Butyric acid 3-[4-(2-allyl-6-nitro-2,3-dihydro-imidazo[2,1-b]oxazol-2-yl)-phenyl]-2-oxo-oxazolidin-5-ylmethyl ester (32 mg, 0.07 mmol) in MeOH/$CH_2Cl_2$ (3:1, 2.7 mL total) was added $K_2CO_3$ (15 mg, 0.105 mmol) and stirred for 1 h 30 min at rt, quenched with 10% aq. AcOH, diluted with water and EtOAc, concentrated and extracted with EtOAc. The concentrate was applied on prep-TLC to provide 2.2 mg of product.

Example 88

3-(3-Fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-5-hydroxymethyl-oxazolidin-2-one

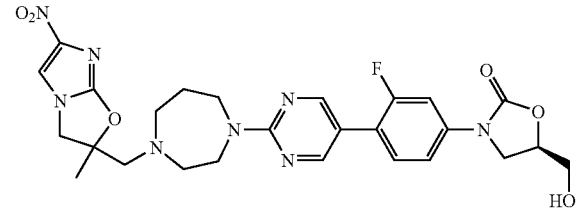

Step 1: 1-(5-Bromo-pyrimidin-2-yl)-[1,4]diazepane. A solution of 5-Bromo-2-chloro-pyrimidine (1.0 g, 5.1 mmol), [1,4]Diazepane (1.0 g, 10.2 mmol) in $CH_3CN$ (5.0 mL) was stirred at 50° C. for 3 hrs. Filter of the solid and the solution was washed with brine, and concentrated in vacuo to give the title product (1.1 g, 85%) as a brown solid. ESI MS m/z 258 (M+H$^+$); $^1$H NMR (400 MHz, CDCl$_3$) δ 8.22 (s, 2H), 3.77 (m, 4H), 2.97 (q, J=10 Hz, 2H), 2.81 (q, J=15 Hz, 2H), 2.02 (s, 1H) 1.83 (qt, J=15 Hz, 2H).

Step 2: 1-(2-Bromo-4-nitro-imidazol-1-yl)-3-[4-(5-bromo-pyrimidin-2-yl)-[1,4]diazepan-1-yl]-2-methyl-propan-2-ol. The solution of 1-(5-Bromo-pyrimidin-2-yl)-[1,4] diazepane (0.5 g, 1.9 mol) and 2-Bromo-1-(2-methyl-oxiranylmethyl)-4-nitro-1H-imidazolemethane (0.5 g, 1.9 mmol) in ETOH (5 mL) was stirred at 50° C. for 12 hours.

Remove the solvent and purification by column chromatography gave the titled compound (604 mg, 61% yield) as brown solid. ESI MS m/z 394, 519 (M+H). ¹H NMR (400 MHz, CDCl₃) δ 8.29 (s, 2H), 8.05 (s, 1H) 3.92 (q, J=36 Hz, 2H), 3.79 (m, 4H), 2.96 (q, J=12 Hz, 2H), 2.81 (q, J=15 Hz, 2H), 2.63 (d, J=35 Hz, 2H), 2.45 (d, J=35 Hz, 2H) 1.85 (qt, J=15 Hz, 2H), 1.63 (bs, 1H), 1.07 (s, 1H).

Step 3: 2-[4-(5-Bromo-pyrimidin-2-yl)-[1,4]diazepan-1-ylmethyl]-2-methyl-6-nitro-2,3-dihydro-imidazo[2,1-b]oxazole. The 1-(2-Bromo-4-nitro-imidazol-1-yl)-3-[4-(5-bromo-pyrimidin-2-yl)-[1,4]diazepan-1-yl]-2-methyl-propan-2-ol (600 mg, 1.15 mmol) in DMF (4 ml) was treated with NaH (33 mg, 1.4 mmol) at 0° C. and heated to 60° C. for 2 h. The reaction mixture is cooled, diluted with saturated NH₄Cl (aq) and extracted with EtOAc. The organic layer was dried over Na₂SO₄, concentrated and purified by column chromatography to titled compound (384 mg, 75%). ESI MS m/z 439 (M+H⁺); ¹H NMR (400 MHz, CDCl₃) δ 8.24 (s, 2H), 7.4 (s, 1H) 4.15 (d, J=23 Hz, 1H), 3.81 (m, 5H), 3.06 (d, J=38 Hz, 1H), 2.95 (m, 2H), 2.85 (m, 1H), 2.75 (m, 1H), 2.62 (d, J=29 Hz, 1H), 1.63 (m, 2H), 1.54 (s, 3H).

Step 4: 5-(tert-Butyl-dimethyl-silanyloxymethyl)-3-(3-fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-oxazolidin-2-one. To a suspension of 2-nitro-6(S)-[4-(4,4,5,5-tetramethyl-[1,3,2]dioxaborolan-2-yl)-benzyloxy]-6,7-dihydro-5H-imidazo[2,1-b][1,3]oxazine (160 mg, 0.40 mmol), N-[3-(3,5-difluoro-4-iodo-phenyl)-2-oxo-oxazolidin-5(S)-ylmethyl]-acetamide (158 mg, 0.40 mmol) (prepared as described by Das et. al. WO 2006/038100 A1), Pd(Ph₃P)₄ (58 mg, 0.05 mmol) and K₂CO₃ (121 mg, 0.88 mmol) in DMF/H₂O (10/1.5.5 mL) was degassed. The mixture was heated to 80° C. for 2.5 h, diluted with EtOAc, washed with brine and concentrated in vacuo to give a crude product. (172 mg, 79%). ESI MS m/z 683 (M+H⁺).

Step 5: 3-(3-Fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-5-hydroxymethyl-oxazolidin-2-one. To a solution of 5-(tert-Butyl-dimethyl-silanyloxymethyl)-3-(3-fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-oxazolidin-2-one (580 mg, 0.84 mmol) in THF (8.0 mL) was added TBAF (3.3 mL, 3.3 mmol, 1.0 M in THF). The mixture was stirred at room temperature for 1 h. The reaction mixture was diluted with EtOAc, washed with brine, dried with Na₂SO₄, purified by flash chromatography to give the title product (100 mg, 21%) as a yellow solid. ESI MS m/z 569 (M+H⁺); ¹H NMR (400 MHz, CDCl₃) δ 8.34 (s, 1H), 7.60 (dd, J=30, 3.0 Hz, 1H), 7.36 (t, J=20 Hz, 1H), 7.29 (d, J=3.0 Hz, 1H), 7.25 (s, 2H), 4.70 (m, 1H), 4.10 (d, J=25.0 Hz, 1H), 3.95-4.06 (m, 2H), 3.82-3.88 (m, 2H), 3.76 (d, J=23.0 Hz, 1H), 3.64 (dd, J=33, 10.0 Hz, 1H), 3.41-3.58 (m, 2H), 3.31 (bs, 3H), 3.02 (d, J=38.0, 1H), 2.94 (q, J=16.0 Hz, 1H), 2.82-2.84 (m, 1H), 2.70-2.78 (m, 1H), 2.60 (d, J=38.0, 1H), 1.64-1.72 (m, 1H), 1.50-1.58 (m, 1H), 1.48 (s, 3H).

Example 89

3-(3-Fluoro-4-{6-[4-(2-methyl-6-nitro-2,3-dihydro-imidazo[2,1-b]oxazol-2-ylmethyl)-[1,4]diazepan-1-yl]-pyridin-3-yl}-phenyl)-5-hydroxymethyl-oxazolidin-2-one

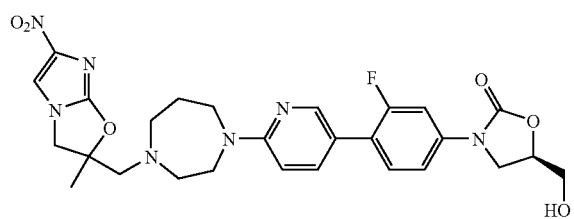

Step 1: 1-(5-Bromo-pyridin-2-yl)-[1,4]diazepane. A solution of 5-Bromo-2-fluoro-pyridine (2.0 g, 11.4 mmol), [1,4]Diazepane (2.2 g, 22.8 mmol) in CH₃CN (5.0 mL) was stirred at 50° C. for 3 hrs. Filter of the solid and the mother solution was brine, and concentrated in vacuo to give the title product (1.47 g, 51%) as a brown solid. ESI MS m/z 256 (M+H⁺); ¹H NMR (400 MHz, CDCl₃) δ 8.12 (d, J=7.0 Hz, 1H), 7.45 (dd, J=22.0, 6 Hz, 1H), 6.38 (d, J=22.0 Hz, 1H), 3.66 (m, 4H), 2.81 (t, J=15.0 Hz, 2H), 1.86 (m, 2H).

Step 2: 1-(2-Bromo-4-nitro-imidazol-1-yl)-3-[4-(5-bromo-pyridin-2-yl)-[1,4]diazepan-1-yl]-2-methyl-propan-2-ol. The title compound was prepared by following the same procedure as described in the preparation of Example 1, step 2,1-(5-Bromo-pyridin-2-yl)-[1,4]diazepane was used in place of 1-(5-Bromo-pyrimidin-2-yl)-[1,4]diazepane ESI MS m/z 518 (M+H⁺); ¹H NMR (400 MHz, CDCl₃) δ 8.13 (d, J=7.0 Hz, 1H), 8.01 (s, 1H), 7.48 (dd, J=25.0, 5.0 Hz, 1H), 6.41 (d, J=22.0 Hz, 1H), 3.89 (q, J=35.0 Hz, 2H), 3.68-3.74 (m, 2H), 3.60 (t, J=16.0 Hz, 2H), 2.95 (m, 2H), 2.78 (m, 2H), 2.61 (d, J=35.0 Hz, 2H), 2.45 (d, J=35.0 Hz, 2H), 2.20 (s, 1H), 1.89 (m, 2H), 1.03 (s, 3H).

Step 3: 2-[4-(5-Bromo-pyrimidin-2-yl)-[1,4]diazepan-1-ylmethyl]-2-methyl-6-nitro-2,3-dihydro-imidazo[2,1-b]oxazole. The title compound was prepared by following the same procedure as described in the preparation of Example 88, Step 3,1-(2-Bromo-4-nitro-imidazol-1-yl)-3-[4-(5-bromo-pyrimidin-2-yl)-[1,4]diazepan-1-yl]-2-methyl-propan-2-ol was used in place of 1-(2-Bromo-4-nitro-imidazol-1-yl)-3-[4-(5-bromo-pyrimidin-2-yl)-[1,4]diazepan-1-yl]-2-methyl-propan-2-ol. ESI MS m/z 518 (M+H⁺); ¹H NMR (400 MHz, CDCl₃) δ 8.08 (d, J=7.0 Hz, 1H), 7.99 (s, 1H), 7.41 (dd, J=16.0, 6.0 Hz, 1H), 6.41 (d, J=23.0 Hz, 1H), 4.05 (d, J=25.0 Hz, 1H), 3.3.74-3.79 (m, 2H), 3.52-3.57 (m, 1H), 3.33-3.39 (m, 2H), 3.02 (d, J=39.0 Hz, 1H), 2.90-2.95 (m, 4H), 2.81-2.87 (m, 2H), 2.72-2.75 (m, 1H), 2.59 (d, J=38.0 Hz, 1H), 1.57 (m, 1H), 1.50 (s, 3H).

Step 4: 5-(tert-Butyl-dimethyl-silanyloxymethyl)-3-(3-fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-oxazolidin-2-one. The title compound was prepared by following the same procedure as described in the preparation of Example 88, Step 4,3-(3-Fluoro-4-{6-[4-(2-methyl-6-nitro-2,3-dihydro-imidazo[2,1-b]oxazol-2-ylmethyl)-[1,4]diazepan-1-yl]-pyridin-3-yl}-phenyl)-5-hydroxymethyl-oxazolidin-2-one was used in place of 2-[4-(5-Bromo-pyrimidin-2-yl)-[1,4]diazepan-1-ylmethyl]-2-methyl-6-nitro-2,3-dihydro-imidazo[2,1-b]ESI MS m/z 682 (M+H$^+$).

Step 5: 3-(3-Fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-5-hydroxymethyl-oxazolidin-2-one. The title compound was prepared by following the same procedure as described in the preparation of Example 88, Step 4,5-(tert-Butyl-dimethyl-silanyloxymethyl)-3-(3-fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-oxazolidin-2-one. ESI MS m/z 569 (M+H$^+$); $^1$H NMR (400 MHz, CDCl$_3$) δ 8.21 (s, 1H), 7.60 (dd, J=30, 3.0 Hz, 1H), 7.47 (m, 1H), 7.41 (d, J=18.0 Hz, 1H), 7.33 (d, J=16.0 Hz, 2H), 7.15 (s, 1H), 4.70 (m, 1H), 6.35 (d, J=21.0 Hz, 1H), 5.23 (d, J=2.0 Hz, 2H), 4.7 (bs, 2H), 3.84-3.97 (m, 6H), 3.58-3.97 (m, 6H), 3.33 (m, 2H), 2.97-3.01 (m, 2H), 2.81-2.91 (m, 2H), 2.69 (t, J=27.0, 1H), 2.53 (d, J=38.0, 1H), 1.60 (m, 2H), 1.43-1.48 (m, 4H), 1.18 (m, 4H), 0.76-0.82 (m, 1H).

Example 90

N-[3-(3-Fluoro-4-{6-[4-(2-methyl-6-nitro-2,3-dihydro-imidazo[2,1-b]oxazol-2-ylmethyl)-[1,4]diazepan-1-yl]-pyridin-3-yl}-phenyl)-2-oxo-oxazolidin-5-ylmethyl]-acetamide

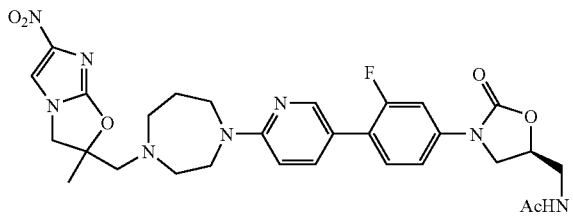

The title compound was prepared by following the same procedure as described in the preparation of Example 88, Step 5,5-(tert-Butyl-dimethyl-silanyloxymethyl)-3-(3-fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl) oxazolidin-2-one was in place of N-{3-[3-Fluoro-4-(4,4,5,5-tetramethyl-[1,3,2]dioxaborolan-2-yl)-phenyl]-2-oxo-oxazolidin-5-ylmethyl}Acetamide. ESI MS m/z 609 (M+H$^+$); $^1$H NMR (400 MHz, CDCl$_3$) δ 8.29 (s, 1H), 7.56 (m, 2H), 7.47 (m, 2H), 7.22 (m, 2H), 6.42 (d, J=23.0 Hz, 1H), 4.81 (m, 1H), 4.08 (t, J=25.0 Hz, 1H), 4.02 (d, J=24.0 Hz, 1H), 3.91-3.96 (m, 1H), 3.81 (m, 1H), 3.62-3.74 (m, 2H), 3.36-3.45 (m, 2H), 3.06 (d, J=38.0 Hz, 1H), 2.87-2.98 (m, 2H), 2.73-2.79 (m, 1H), 2.60 (d, J=38.0, 1H), 2.03 (s, 3H), 1.67 (s, 3H), 1.50 (s, 3H), 0.82-0.89 (m, 2H).

Example 91

3-{3-Fluoro-4-[4-(2-methyl-6-nitro-2,3-dihydro-imidazo[2,1-b]oxazol-2-ylmethyl)-piperazin-1-yl]-phenyl}-5-hydroxymethyl-oxazolidin-2-one

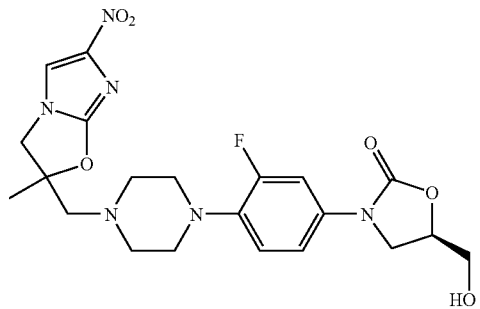

Step 1. 3-(4-{4-[3-(2-Bromo-4-nitro-imidazol-1-yl)-2-hydroxy-2-methyl-propyl]-piperazin-1-yl}-3-fluoro-phenyl)-5-hydroxymethyl-oxazolidin-2-one. The title compound was prepared by following the same procedure as described in the preparation of Example 88, Step 2,3-(3-Fluoro-4-piperazin-1-yl-phenyl)-5-hydroxymethyl-oxazolidin-2-one was used in place of 1-(5-Bromo-pyrimidin-2-yl)-[1,4]diazepane. ESI MS m/z 558 (M+H$^+$). $^1$H NMR (400 MHz, CD$_3$OD) δ 8.24 (s, 1H), 7.45 (dd, J=37.0, 6 Hz, 1H), 7.12 (dd, J=22.0, 6 Hz, 1H), 6.98 (t, J=24.0 Hz, 1H), 4.73 (m, 1H), 4.24 (d, J=36.0 Hz, 1H), 4.08 (m, 4H), 3.86 (m, 2H), 3.69 (dd, J=31.0, 9.0 Hz, 2H), 3.39 (bs, 2H), 3.34 (s, 2H), 3.01 (bs, 2H), 2.83 (m, 2H), 2.69 (m, 2H), 1.13 (s, 3H).

Step 2: 3-{3-Fluoro-4-[4-(2-methyl-6-nitro-2,3-dihydro-imidazo[2,1-b]oxazol-2-ylmethyl)-piperazin-1-yl]-phenyl}-5-hydroxymethyl-oxazolidin-2-one. The title compound was prepared by following the same procedure as described in the preparation of Example 1, step 3,3-(4-{4-[3-(2-Bromo-4-nitro-imidazol-1-yl)-2-hydroxy-2-methyl-propyl]-piperazin-1-yl}-3-fluoro-phenyl)-5-hydroxymethyl-oxazolidin-2-one was used in place of 1-(2-Bromo-4-nitro-imidazol-1-yl)-3-[4-(5-bromo-pyrimidin-2-yl)-[1,4]diazepan-1-yl]-2-methyl-propan-2-ol. ESI MS m/z 477 (M+H$^+$); $^1$H NMR (400 MHz, CD$_3$OD) δ 7.90 (s, 1H), 7.36 (m, 1 H), 7.00 (m, 1H), 6.85 (m, 1H), 4.64 (m, 1H), 3.77-3.94 (m, 3H), 3.63 (m, 2H), 2.87-3.01 (m, 3H), 2.78-2.86 (m, 4H), 2.83 (m, 2H), 2.69 (m, 2H), 1.6 (s, 1H), 1.18 (s, 3H).

Example 92

N-[3-(3-Fluoro-4-{2-[4-(2-methyl-6-nitro-2,3-dihydro-imidazo[2,1-b]oxazol-2-ylmethyl)-piperazin-1-yl]-thiazol-5-yl}-phenyl)-2-oxo-oxazolidin-5-ylmethyl]-acetamide

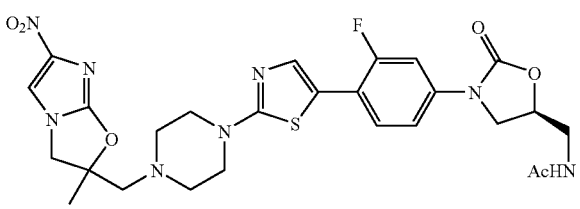

Step 1. 1-(5-Bromo-thiazol-2-yl)-piperazine. A solution of 2,5-Dibromo-thiazole (1.0 g, 4.1 mmol), piperazine (0.71 g, 8.2 mmol) in BuOH (5.0 mL) was stirred at 117° C. for 3 hrs. Remove solvent and extracted with 30% IPA in DCM, dry with sodium sulfate, and concentrated in vacuo to give the title product (1.1 g, 85%) as a brown solid. ESI MS m/z 247 (M+H$^+$).

Step 2: 1-(2-Bromo-4-nitro-imidazol-1-yl)-3-[4-(5-bromo-thiazol-2-yl)-piperazin-1-yl]-2-methyl-propan-2-ol. The title compound was prepared by following the same procedure as described in the preparation of Example 88, Step 2,1-(5-Bromo-pyridin-2-yl)-[1,4]diazepane was used in place of 1-(5-Bromo-thiazol-2-yl)-piperazine. ESI MS m/z 510 (M+H$^+$).

Step 3: 2-[4-(5-Bromo-thiazol-2-yl)-piperazin-1-ylmethyl]-2-methyl-6-nitro-2,3-dihydro-imidazo[2,1-b]oxazole. The title compound was prepared by following the same procedure as described in the preparation of Example 88, Step 3,: 1-(2-Bromo-4-nitro-imidazol-1-yl)-3-[4-(5-bromo-thiazol-2-yl)-piperazin-1-yl]-2-methyl-propan-2-ol was used in place of 1-(2-Bromo-4-nitro-imidazol-1-yl)-3-[4-(5-bromo-pyrimidin-2-yl)-[1,4]diazepan-1-yl]-2-methyl-propan-2-ol. ESI MS m/z 430 (M+H$^+$). $^1$H NMR (400 MHz, CDCl$_3$) δ 7.74 (s, 1H), 6.97 (s, 1H), 4.31 (d, J=25 Hz, 2H), 4.02 (d, J=25 Hz, 2H), 3.30 (m, 2H), 3.24 (m, 2H), 2.78 (m, 2H), 2.67 (m, 2H), 1.60 (s, 3H).

Step 4. N-[3-(3-Fluoro-4-{2-[4-(2-methyl-6-nitro-2,3-dihydro-imidazo[2,1-b]oxazol-2-ylmethyl)-piperazin-1-yl]-thiazol-5-yl}-phenyl)-2-oxo-oxazolidin-5-ylmethyl]-acetamide. The title compound was prepared by following the same procedure as described in the preparation of Example 88, Step 5, 2-[4-(5-Bromo-thiazol-2-yl)-piperazin-1-ylmethyl]-2-methyl-6-nitro-2,3-dihydro-imidazo[2,1-b]oxazole was in place of 2-[4-(5-Bromo-pyrimidin-2-yl)-[1,4]diazepan-1-ylmethyl]-2-methyl-6-nitro-2,3-dihydro-imidazo[2,1-b]oxazole ESI MS m/z (M+H$^+$). $^1$H NMR (400 MHz, CDCl$_3$) δ 7.66 (s, 1H), 7.46 (dd, J=33.0, 5.0 Hz, 1H), 7.36 (t, J=21.0 Hz, 1H), 7.16 (dd, J=21.0, 5.0 Hz, 1H), 4.73 (m, 1H), 4.06 (t, J=26 Hz, 1H), 3.99 (d, J=26 Hz, 1H), 3.93 (bs, 2H), 3.76 (m, 1H), 3.54 (m, 2H), 3.34 (t, J=11.0 Hz, 2H), 3.30 (bs, 2H), 2.90 (d, J=38.0 Hz, 1H), 2.78 (m, 2H), 2.68 (m, 4H), 1.95 (s, 3H), 1.60 (s, 3H).

Example 93

Biological Activity

Representative examples of this invention compounds and their reference standards (linezolid, and PA-824) were assayed for antimicrobial activity as follows: Minimum Inhibtory Concentrations (MICs) against *Staphylococcus aureus* ATCC 29213, and its isogenic strain exhibits linezolid-resistance were determined by the microbroth dilution method, as per NCCLS guidelines (National Committee for Clinical Laboratory Standards). Minimum Inhibitory Concentrations (MICs) against *Mycobacterium tuberculosis* H37Rv, and its resistant strain exhibits PA-824-resistance were determined by a method reported by Gruppo (Gruppo V. 2006). Anaerobic activity of the compounds against *Mycobacterium tuberculosis* H37Rv was determined under Wayne conditions by a method reported by Lenaerts (Lenaerts 2005). The results are reported as % survival at 10 micg/mL concentration. The antimicrobial activity of the exemplary compounds of the current invention and reference compounds are shown in Table 1.

The inventive compounds display excellent activity against Gram-positive species, for example, *Staphylococcus aureus* ATCC 29213. For examples, a diverse set of examples with different linker "L", such as Example 8 and Example 31 are more potent than linezolid, especially against a strain that is resistant to linezolid, where linezolid exhibits MIC of 64 micg/mL, the two hybrids show MICs of 8 and 4 micg/mL respectively. All examples exhibit excellent activity against *Mycobacterium tuberculosis* H37Rv. Unlike PA-824, however, the activity of the hybrids is not affected by a strain that is resistant to PA-824. Example 8 and Example 31 show MICs of 0.5 and 1 micg/mL respectively against PA-824 resistant strain of *Mycobacterium tuberculosis* H37Rv, while PA-824 loses its activity. The unique characteristics of the inventive compounds exhibiting activity against resistant strains are not expected from either class of oxazolidinone or bicyclic nitroimidazoles. It is also to be noted that Example 50 is 2-fold less potent than linezolid, and 8-fold less potent than PA-824 in term of in vitro MIC against aerobically grown *Mycobacterium tuberculosis* H37Rv, but Example 50 (1.8% bacterial survival at end of the treatment) is more active than either linezolid (28.2% survival) or PA-824 (3.6% survival) against anaerobically grown *Mycobacterium tuberculosis* H37Rv. This is again not anticipated from either oxazolidinone or bicyclic nitroimidazole class of compounds.

The present compounds are active against both aerobic and anaerobic bacteria, and accordingly are useful as broad spectrum antibacterial agents. The present compounds are surprisingly effective when compared to either parent class of compounds against a number of human and veterinary aerobic and anaerobic Gram positive, Gram negative pathogens, including the Staphylococci, for example *S. aureus*; Enterococci, for example *E. faecalis*; Streptococci, for example *S. pneumoniae*; *Mycobacteria*, for example *M. tuberculosis*; *Helicobacter*, for example *H. pylori*; *Clostridium*, for example *C. difficile*. The inventive bicyclic nitroimidazole-substituted

TABLE 1

Antibacterial Activity of Selected Examples

| Compound | MIC (ug/mL) | | | | M. tuberculosis |
|---|---|---|---|---|---|
| | S. aureus ATCC# 29213 | S. aureus ATCC# 29213 (Lzd-resistant) | M. tuberculosis H37rv | M. tuberculosis (PA-resistant) | H37Rv % survival at 10 ug/mL (Low O$_2$) |
| Linezolid | 2 | 64 | 2 | 0.5 | 28.2% |
| PA-824 | >64 | >64 | 0.5 | >32 | 3.6% |
| Example 50 | 64 | NT | 4 | NT | 1.8% |
| Example 8 | 1 | 8 | 1 | 0.5 | NT |
| Example 31 | 1 | 4 | 0.5 | 1 | NT | oxazolidinones may be used as agents effective against Tuberculosis including drug resistant variant or MDRTB, *C. difficile* associated diarrhea or Pseudomembranous colitis (PMC). The present compounds also are envisioned as cytotoxic anticancer agents, antifungal agents, and antiprotozoal agents (against, for example, *entamoeba histolyica*, and *Neglaria* sps).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES CITED

The following U.S. Patent documents and publications are hereby incorporated by reference.

U.S. PATENT DOCUMENTS

U.S. Pat. No. 4,801,600
U.S. Pat. No. 4,921,869
U.S. Pat. No. 5,547,950
U.S. Pat. No. 5,736,545
U.S. Pat. No. 5,880,118
U.S. Pat. No. 5,981,528
U.S. Pat. No. 6,087,358
U.S. Pat. No. 6,968,962
U.S. Pat. No. 7,129,259
U.S. Patent Publication No. US2007/0155714

OTHER PATENT DOCUMENTS

EPA 0316594
EPA 0352781
WO 2004/078753
WO 2005/042542 A1
WO 2005/054234
WO 2006/022794
WO 2006/038100
WO 2006/043121

PUBLICATIONS

Ashtekar, D. et al., "In Vitro and In Vivo Activities of the Nitroimidazole CGI 17341 against *Mycobacterium tuberculosis*," *Antimicrobial Agents and Chemotherapy*, 37(2): 183-186 1993.
Brickner et al, *J. Med. Chem.* 1996, 39, 673-679.
Gruppo, V. et al: *Antimicrob. Agents Chemother.* 2006, vol 50, 1245.
Lenaerts A. et al: *Antimicrob. Agents Chemother.* 2005, vol 49, 2294
Nagarajan, K. et al., "Nitroimidazoles XXI. 2,3-dihydro-6-nitroimidazo[2.1-b]oxazoles with antitubercular activity," *Eur. J. Med. Chem.* 24:631-633 (1989).
National Committee for Clinical Laboratory Standards. 2000. Methods for dilution antimicrobial susceptibility tests for bacteria that grow aerobically, 5th ed. M7-A5. National Committee for Clinical Laboratory Standards, Wayne, Pa.
Ondi et. al. *Eur. J. Org. Chem.* 2004, 3714-3718.

Sasaki, H. et al: *Journal of Medicinal Chemistry* (2006), 49(26), 7854-7860.
*Tetrahedron* 1989, 1323.

What is claimed is:

1. A compound of structural formula (I):

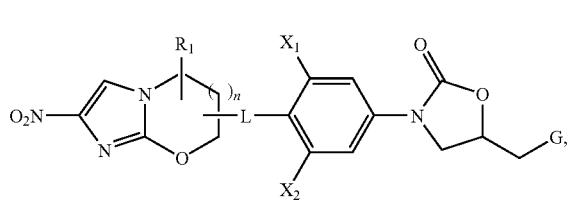

having a nitroimidazole ring,
or a pharmaceutically acceptable salt thereof;
wherein
$R_1$ is hydrogen, $(C_1-C_6)$alkyl, aryl, heteroaryl, or heterocycloalkyl;
n is 0, 1, or 2;
$X_1$ and $X_2$ are independently H, $CF_3$, Cl, $OCF_3$ or F;
G is —OH, -substituted or unsubstituted triazole, heteroaryl or —NHCOR$_2$;
$R_2$ is $(C_1-C_6)$alkyl, cycloalkyl, aryl, or heteroaryl; and
L is a bond, or a linker group selected from one or any combination of two to five of the following groups:
  1) $(C_1-C_6)$alkylene,
  2) $(C_3-C_8)$cycloalkylene,
  3) arylene,
  4) heteroarylene,
  5) heterocycloalkylene containing one to three heteroatoms,
  6) —C(=O)—,
  7) —O—,
  8) —S(O)$_n$—, wherein n is number 0, 1, or 2,
  9) —N(R$_3$)—,
  10) —C(R$_4$)=C(R$_5$)—,
  wherein the carbon or nitrogen atoms of the linker group are unsubstituted or substituted by one to three substituents,
  $R_3$ is hydrogen, $(C_1-C_6)$alkyl, aryl, heteroaryl, or heterocycloalkyl, and
  $R_4$ and $R_5$ are hydrogen, $(C_1-C_6)$alkyl, aryl, heteroaryl, or heterocycloalkyl, or $R_4$ and $R_5$ can join together to form a bond.

2. The compound of claim 1, wherein L is a bond or a group selected from one or a combination of two to three structural elements selected from the group consisting of:

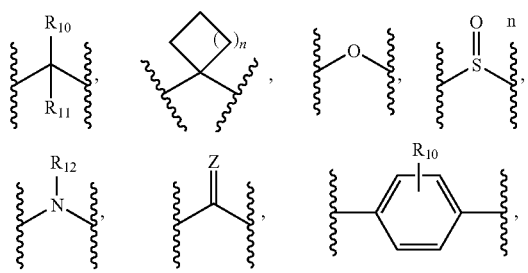

-continued

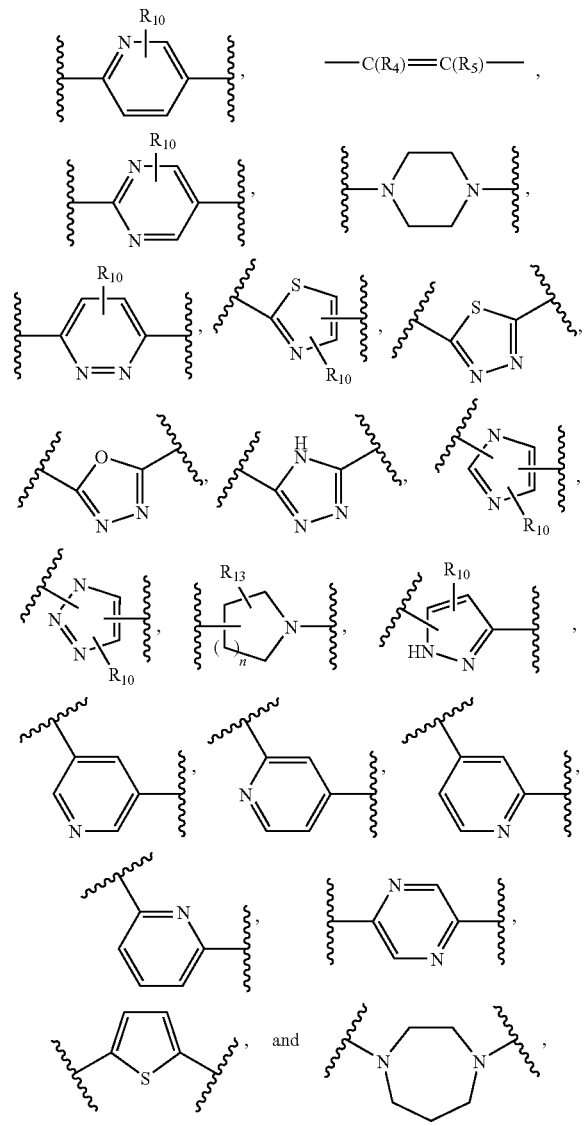

wherein $R_{10}$, $R_{11}$, $R_{12}$ is H, hydroxyl, amino, alkyl, alkylamino, alkoxy, aryl, or heteroaryl that are unsubstituted or substituted, $R_{13}$ is H, hydroxyl, amino, alkyl, alkylamino, alkoxy, aryl, or heteroaryl that are unsubstituted or substituted, or $R_{13}$ in conjunction with the nitroimidazole ring can form a spiro cyclic structure, m and n are independently 0, 1 or 2, Z is O, S, or $CR_{14}R_{15}$, wherein $R_{14}$ and $R_{15}$ are independently H, alkyl, aryl or heteroaryl group, and G is —OH, -substituted or unsubstituted triazole, heteroaryl, -heteroaryl, or —$NHCOR_2$.

3. The compound of claim 2, wherein the spiro cyclic structure is

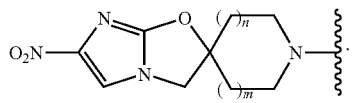

4. A compound of structural formula (II):

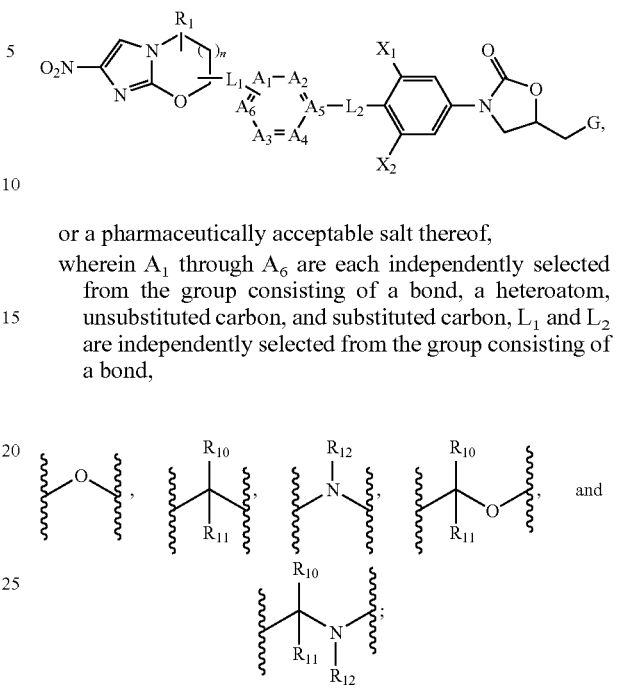

or a pharmaceutically acceptable salt thereof,
wherein $A_1$ through $A_6$ are each independently selected from the group consisting of a bond, a heteroatom, unsubstituted carbon, and substituted carbon, $L_1$ and $L_2$ are independently selected from the group consisting of a bond, G is —OH, -substituted or unsubstituted triazole, or —NHCOCH$_3$.

5. The compound of claim 4, wherein $L_2$ is a bond.

6. A pharmaceutical composition comprising a pharmaceutically effective amount of a compound of claim 1 in combination with a pharmaceutically acceptable carrier.

7. A pharmaceutical composition comprising a pharmaceutically effective amount of a compound of claim 2 in combination with a pharmaceutically acceptable carrier.

8. A pharmaceutical composition comprising a pharmaceutically effective amount of a compound of claim 4 in combination with a pharmaceutically acceptable carrier.

9. A pharmaceutical composition comprising a pharmaceutically effective amount of a compound of claim 6 in combination with a pharmaceutically acceptable carrier.

10. A method of treating a bacterial infection in a subject in need of such treatment comprising administering a pharmaceutical composition of claim 7 to the subject.

11. A method of treating a bacterial infection in a subject in need of such treatment comprising administering a pharmaceutical composition of claim 8 to the subject.

12. A method of treating a bacterial infection in a subject in need of such treatment comprising administering a pharmaceutical composition of claim 9 to the subject.

13. A method of treating a bacterial infection in a subject in need of such treatment comprising administering a pharmaceutical composition of claim 10 to the subject.

14. A compound selected from the group consisting of:
(a) (S,S)—N-{3-[3-Fluoro-4-(4-{2-[4-(2-nitro-6,7-dihydro-5H-imidazo[2,1-b][1,3]oxazin-6-yloxymethyl)-phenoxy]-acetyl}-piperazin-1-yl)-phenyl]-2-oxo-oxazolidin-5-ylmethyl}-acetamide;
(b) (S,S)—N-(3-{3-Fluoro-4-[4-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide;

(c) (S,S)—N-(3-{3-Fluoro-4-[3-(2-nitro-6,7-dihydro-5H-imidazo[2,1-b][1,3]oxazin-6-yloxymethyl)-benzyloxy]-phenyl}-2-oxo-oxazolidin-5-ylmethyl)-acetamide;

(d) (S,S)—N-(3-{3-Fluoro-4-[5-(2-nitro-6,7-dihydro-5H-imidazo[2,1-b][1,3]oxazin-6-yloxymethyl)-pyridin-2-yloxy]-phenyl}-2-oxo-oxazolidin-5-ylmethyl)-acetamide;

(e) (S,S)—N-(3-{3-Fluoro-4-[4-(2-nitro-6,7-dihydro-5H-imidazo[2,1-b][1,3]oxazin-6-yloxymethyl)-phenoxy]-phenyl}-2-oxo-oxazolidin-5-ylmethyl)-acetamide;

(f) (S,S)—N-[3-(3-Fluoro-4-{1-[4-(2-nitro-6,7-dihydro-5H-imidazo[2,1-b][1,3]oxazin-6-yloxymethyl)-benzyl]-1H-[1,2,3]triazol-4-ylmethoxy}-phenyl)-2-oxo-oxazolidin-5-ylmethyl]-acetamide;

(g) (S,S)—N-(3-{3-Fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide;

(h) (S,S)—N-(3-{3-Fluoro-4-[2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide;

(i) (S,S)—N-(3-{3-Fluoro-4-[2-(2-nitro-6,7-dihydro-5H-imidazo[2,1-b][1,3]oxazin-6-yloxy)-pyridin-4-yl]-phenyl}-2-oxo-oxazolidin-5-ylmethyl)-acetamide;

(j) N-(3-{3-Fluoro-4-[5-(2-methyl-6-nitro-2,3-dihydro-imidazo[2,1-b]oxazol-2-ylmethoxy)-pyridin-3-yl]-phenyl}-2-oxo-oxazolidin-5-ylmethyl)-acetamide;

(k) (S,S)—N-(3-{3-Fluoro-4-[5-(2-nitro-6,7-dihydro-5H-imidazo[2,1-b][1,3]oxazin-6-yloxymethyl)-pyridin-2-yl]-phenyl}-2-oxo-oxazolidin-5-ylmethyl)-acetamide;

(l) (S,S)—N-(3-{3-Fluoro-4-[6-(2-nitro-6,7-dihydro-5H-imidazo[2,1-b][1,3]oxazin-6-yloxymethyl)-pyridin-3-yl]-phenyl}-2-oxo-oxazolidin-5-ylmethyl)-acetamide;

(m) (S,S)—N-(3-{3-Fluoro-4-[6-(2-nitro-6,7-dihydro-5H-imidazo[2,1-b][1,3]oxazin-6-yloxy)-pyridazin-3-yl]-phenyl}-2-oxo-oxazolidin-5-ylmethyl)-acetamide;

(n) (S,S)—N-(3-{3-Fluoro-4-[4-morpholin-4-yl-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide;

(o) (S,S)—N-(3-{3-Fluoro-4-[4-methoxy-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide;

(p) (S,S)—N-(3-{4-[4-Dimethylamino-2-(2-nitro-6,7-dihydro-5H-imidazo[2,1-b][1,3]oxazin-6-yloxy)-pyrimidin-5-yl]-3-fluoro-phenyl}-2-oxo-oxazolidin-5-ylmethyl)-acetamide;

(q) (S,S)-5-{4-[5-(Acetylamino-methyl)-2-oxo-oxazolidin-3-yl]-2-fluoro-phenyl}-2-(2-nitro-6,7-dihydro-5H-imidazo[2,1-b][1,3]oxazin-6-yloxy)-nicotinic acid methyl ester;

(r) (S,S)-5-{4-[5-(Acetylamino-methyl)-2-oxo-oxazolidin-3-yl]-2-fluoro-phenyl}-2-(2-nitro-6,7-dihydro-5H-imidazo[2,1-b][1,3]oxazin-6-yloxy)-nicotinic acid;

(s) (S,S)—N-(3-{3-Fluoro-4-[4-(2-nitro-6,7-dihydro-5H-imidazo[2,1-b][1,3]oxazin-6-yloxy)-pyrimidin-2-yl]-phenyl}-2-oxo-oxazolidin-5-ylmethyl)-acetamide;

(t) (S,S)—N-(3-{3-Fluoro-4-[2-(2-nitro-6,7-dihydro-5H-imidazo[2,1-b][1,3]oxazin-6-yloxy)-pyrimidin-4-yl]-phenyl}-2-oxo-oxazolidin-5-ylmethyl)-acetamide;

(u) (S,S)—N-(3-{3-Fluoro-4-[5-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide;

(v) (S,S)—N-(3-{3-Fluoro-4-[2-methyl-6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide;

(w) N-(3-{3-Fluoro-4-[5-(2-methyl-6-nitro-2,3-dihydro-imidazo[2,1-b]oxazol-2-ylmethoxy)-pyridin-2-yl]-phenyl}-2-oxo-oxazolidin-5-ylmethyl)-acetamide;

(x) (S,S)—N-(3-{3-Fluoro-4-[4-(4-methoxy-benzyloxy)-2-(2-nitro-6,7-dihydro-5H-imidazo[2,1-b][1,3]oxazin-6-yloxy)-pyrimidin-5-yl]-phenyl}-2-oxo-oxazolidin-5-ylmethyl)-acetamide;

(y) (S,S)—N-(3-{3-Fluoro-4-[2-(2-nitro-6,7-dihydro-5H-imidazo[2,1-b][1,3]oxazin-6-yloxy)-6-oxo-1,6-dihydro-pyrimidin-5-yl]-phenyl}-2-oxo-oxazolidin-5-ylmethyl)-acetamide;

(z) (S,S)—N-(3-{3-Fluoro-4-[2-(2-nitro-6,7-dihydro-5H-imidazo[2,1-b][1,3]oxazin-6-yloxy)-4-trifluoromethyl-pyrimidin-5-yl]-phenyl}-2-oxo-oxazolidin-5-ylmethyl)-acetamide;

(aa) (S,S)—N-{3-[2,6-Difluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide;

(bb) N-{3-[4-(6-Nitro-imidazo[2,1-b]-2(3H)-8-aza-spiro[4,5]dec-8-yl)-3-fluorophenyl]-2-oxo-oxazolidin-5 (S)-ylmethyl}-acetamide;

(cc) (S,R)-3-[2-Fluoro-4'-(2-nitro-6,7-dihydro-5H-imidazo[2,1-b][1,3]oxazin-6-yloxymethyl)-biphenyl-4-yl]-5-hydroxymethyl-oxazolidin-2-one;

(dd) (S,S)-3-{3-Fluoro-4-[2-(2-nitro-6,7-dihydro-5H-imidazo[2,1-b][1,3]oxazin-6-yloxy)-pyrimidin-5-yl]-phenyl}-5-hydroxymethyl-oxazolidin-2-one;

(ee) (S,R)-3-{3-Fluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one;

(ff) (S,S)—N-{3-[2-Fluoro-4'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide;

(gg) (S,S)—N-[3-(3-Fluoro-4-{4-[2-(2-nitro-6,7-dihydro-5H-imidazo[2,1-b][1,3]oxazin-6-yloxy)-acetyl]-piperazin-1-yl}-phenyl)-2-oxo-oxazolidin-5-ylmethyl]-acetamide;

(hh) N-(3-{3-Fluoro-4-[4-(2-methyl-6-nitro-2,3-dihydro-imidazo[2,1-b]oxazol-2-ylmethyl)-piperazin-1-yl]-phenyl}-2-oxo-oxazolidin-5-ylmethyl)-acetamide;

(ii) (S,R)-3-[2-Fluoro-4'-(2-nitro-6,7-dihydro-5H-imidazo[2,1-b][1,3]oxazin-6-yloxymethyl)-biphen-4-yl]-5-[1,2,3]triazol-1-ylmethyl-oxazolidin-2-one;

(jj) (S,R)-3-{3-Fluoro-4-[6-(2-nitro-6,7-dihydro-5H-imidazo[2,1-b][1,3]oxazin-6-yloxymethyl)-pyridin-3-yl]-phenyl}-5-[1,2,3]triazol-1-ylmethyl-oxazolidin-2-one;

(kk) N-{3-[2-Fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide;

(ll) N-{3-[2-Fluoro-3'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide;

(mm) N-{3-[2'-Chloro-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide;

(nn) N-{3-[3'-Chloro-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide;

(oo) N-{3-[3'-Cyano-2-fluoro-4'-(2-methyl-6-nitro-2,3-dihydro-imidazo[2,1-b]oxazol-2-ylmethoxy)-biphenyl-4-yl]-2-oxo-oxazolidin-5-ylmethyl}-acetamide;

(pp) N-(3-{2-Fluoro-4'-[(2-methyl-6-nitro-2,3-dihydro-imidazo[2,1-b]oxazol-2-ylmethyl)-amino]-biphenyl-4-yl}-2-oxo-oxazolidin-5-ylmethyl)-acetamide;

(qq) (S,S)—N-(3-{3-Fluoro-4-[3-(2-nitro-6,7-dihydro-5H-imidazo[2,1-b][1,3]oxazin-6-yloxy)-propenyl]-phenyl}-2-oxo-oxazolidin-5-ylmethyl)-acetamide;

(rr) (E)-N-(3-{3-Fluoro-4-[2-(2-nitro-6,7-dihydro-5H-imidazo[2,1-b][1,3]oxazin-6(S)-yloxy)-vinyl]-phenyl}-2-oxo-oxazolidin-5(S)-ylmethyl)-acetamide;

(ss) N-(3-{3-Fluoro-4-[1-(2-nitro-6,7-dihydro-5H-imidazo[2,1-b][1,3]oxazin-6(S)-yloxymethyl)-vinyl]-phenyl}-2-oxo-oxazolidin-5(S)-ylmethyl)-acetamide;

(tt) N-(3-{3-Fluoro-4-[2-(2-nitro-6,7-dihydro-5H-imidazo[2,1-b][1,3]oxazin-6-yloxy)-acetyl]-phenyl}-2-oxo-oxazolidin-5-ylmethyl)-acetamide;

(uu) N-(3-{3-Fluoro-4-[1-hydroxy-1-hydroxymethyl-2-(2-nitro-6,7-dihydro-5H-imidazo[2,1-b][1,3]oxazin-6-yloxy)-ethyl]-phenyl}-2-oxo-oxazolidin-5-ylmethyl)-acetamide;

(vv) (S,S)—N-(3-{3-Fluoro-4-[3-(2-nitro-6,7-dihydro-5H-imidazo[2,1-b][1,3]oxazin-6-yloxy)-prop-1-ynyl]-phenyl}-2-oxo-oxazolidin-5-ylmethyl)-acetamide;

(ww) (S,S)—N-{3-[2,2'-Difluoro-5'-(2-nitro-6,7-dihydro-5H-imidazo[2,1-b][1,3]oxazin-6-yloxymethyl)-biphenyl-4-yl]-2-oxo-oxazolidin-5-ylmethyl}-acetamide;

(xx) (S,S)—N-{3-[2-Fluoro-3'-(2-nitro-6,7-dihydro-5H-imidazo[2,1-b][1,3]oxazin-6-loxymethyl)-biphenyl-4-yl]-2-oxo-oxazolidin-5-ylmethyl}-acetamide;

(yy) N-{3-[3-Fluoro-4-(2-methyl-6-nitro-2,3-dihydro-imidazo[2,1-b]oxazol-2-ylmethoxy)-phenyl]-2-oxo-oxazolidin-5-ylmethyl}-acetamide; and (zz) N-(((5S)-3-(3-Fluoro-4-(2-((2-methyl-6-nitro-2,3-dihydroimidazo[2,1-b]oxazol-2-yl)methoxy)pyrimidin-5-yl)phenyl)-2-oxooxazolidin-5-yl)methyl)acetamide, and their pharmaceutically acceptable salts.

15. A compound selected from the group consisting of:

(a) N—(((S)-3-(3-Fluoro-4-(5-(((S)-2-nitro-6,7-dihydro-5H-imidazo[2,1-b][1,3]-oxazin-6-yloxy)methyl)pyridin-3-yl)phenyl)-2-oxooxazolidin-5-yl)methyl)acetamide;

(b) N—(((S)-3-(3-Fluoro-4-(2-(((S)-2-nitro-6,7-dihydro-5H-imidazo[2,1-b][1,3]-oxazin-6-yloxy)methyl)pyridin-4-yl)phenyl)-2-oxooxazolidin-5-yl)methyl)acetamide;

(c) N—(((S)-3-(3-Fluoro-4-(4-(((S)-2-nitro-6,7-dihydro-5H-imidazo[2,1-b][1,3]-oxazin-6-yloxy)methyl)pyridin-2-yl)phenyl)-2-oxooxazolidin-5-yl)methyl)acetamide;

(d) N—(((S)-3-(3-Fluoro-4-(6-(((S)-2-nitro-6,7-dihydro-5H-imidazo[2,1-b][1,3]-oxazin-6-yloxy)methyl)pyridin-2-yl)phenyl)-2-oxooxazolidin-5-yl)methyl)acetamide;

(e) N—(((S)-3-(3-Fluoro-4-(6-(((S)-2-nitro-6,7-dihydro-5H-imidazo[2,1-b][1,3]-oxazin-6-yloxy)methyl)pyridazin-3-yl)phenyl)-2-oxooxazolidin-5-yl)methyl)acetamide;

(f) N—(((S)-3-(3-Fluoro-4-(5-(((S)-2-nitro-6,7-dihydro-5H-imidazo[2,1-b][1,3]-oxazin-6-yloxy)methyl)pyrazin-2-yl)phenyl)-2-oxooxazolidin-5-yl)methyl)acetamide;

(g) N-({(5S)-3-[3-Fluoro-4-(2-{4-[(2-methyl-6-nitro-2,3-dihydroimidazo[2,1-b][1,3]oxazol-2-yl)methyl]-1-piperazinyl}-5-pyrimidinyl)phenyl]-2-oxo-1,3-oxazolidin-5-yl}methyl)acetamide;

(h) (S,S)—N-(3-{2,3'-Difluoro-4'-{-2-nitro-6,7-dihydro-5H-imidazo[2,1-b][1,3]oxazin-6-yloxymethyl)-biphenyl-4-yl]-2-oxo-oxazolidin-5-yl}methyl)acetamide;

(i) N-[((5S)-3-{3-Fluoro-4-[5-({[(6S)-2-nitro-6,7-dihydro-5H-imidazo[2,1-b][1,3]oxazin-6-yl]oxy}methyl)-2-thienyl]phenyl}-2-oxo-1,3-oxazolidin-5-yl)methyl]acetamide;

(j) N-({(5S)-3-[3-Fluoro-4-(6-{4-[(2-methyl-6-nitro-2,3-dihydroimidazo[2,1-b][1,3]oxazol-2-yl)methyl]-1-piperazinyl}-3-pyridinyl)phenyl]-2-oxo-1,3-oxazolidin-5-yl}methyl)acetamide;

(k) 3-{3-Fluoro-4-[5-(2-nitro-6,7-dihydro-5H-imidazo[2,1-b][1,3]oxazin-6-yloxymethyl)-pyridin-2-yl]-phenyl}-5-hydroxymethyl-oxazolidin-2-one;

(l) 3-{3-Fluoro-4-[6-(2-nitro-6,7-dihydro-5H-imidazo[2,1-b][1,3]oxazin-6-yloxy)-pyridazin-3-yl]-phenyl}-5-hydroxymethyl-oxazolidin-2-one;

(m) 3-{3-Fluoro-4-[6-(2-nitro-6,7-dihydro-5H-imidazo[2,1-b][1,3]oxazin-6-yloxymethyl)-pyridin-3-yl]-phenyl}-5-hydroxymethyl-oxazolidin-2-one;

(n) N-(3-{3,5-Difluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)-acetamide;

(o) 3-{3-Fluoro-4-[2-methyl-6-(2-nitro-6,7-dihydro-5H-imidazo[2,1-b][1,3]oxazin-6-yloxy)-pyridin-3-yl]-phenyl}-5-hydroxymethyl-oxazolidin-2-one;

(p) 3-{3,5-Difluoro-4-[6-(2-nitro-6,7-dihydro-5H-imidazo[2,1-b][1,3]oxazin-6-yloxy)-pyridin-3-yl]-phenyl}-5-hydroxymethyl-oxazolidin-2-one;

(q) 5-Hydroxymethyl-3-{4-[6-(2-nitro-6,7-dihydro-5H-imidazo[2,1-b][1,3]oxazin-6-yloxy)-pyridin-3-yl]-3-trifluoromethoxy-phenyl}-oxazolidin-2-one;

(r) 5-Hydroxymethyl-3-[6'-(2-nitro-6,7-dihydro-5H-imidazo[2,1-b][1,3]oxazin-6-yloxy)-[2,3']bipyridinyl-5-yl]-oxazolidin-2-one;

(s) 3-{4-[4-Dimethylamino-2-(2-nitro-6,7-dihydro-5H-imidazo[2,1-b][1,3]oxazin-6-yloxy)-pyrimidin-5-yl]-3-fluoro-phenyl}-5-hydroxymethyl-oxazolidin-2-one;

(t) N-[3-(3-Fluoro-4-{5-[(2-nitro-6,7-dihydro-5H-imidazo[2,1-b][1,3]oxazin-6-ylamino)-methyl]-pyridin-2-yl}-phenyl)-2-oxo-oxazolidin-5-ylmethyl]-acetamide;

(u) N-[3-(3-Fluoro-4-{6-[(2-nitro-6,7-dihydro-5H-imidazo[2,1-b][1,3]oxazin-6-ylamino)-methyl]-pyridin-3-yl}-phenyl)-2-oxo-oxazolidin-5-ylmethyl]-acetamide;

(v) 5-Hydroxymethyl-3-{4-[6-(2-nitro-6,7-dihydro-5H-imidazo[2,1-b][1,3]oxazin-6-yloxymethyl)-pyridin-3-yl]-3-trifluoromethoxy-phenyl}-oxazolidin-2-one;

(w) 3-[2-Fluoro-4'-(2-methyl-6-nitro-2,3-dihydro-imidazo[2,1-b]oxazol-2-yl)-biphenyl-4-yl]-5-hydroxymethyl-oxazolidin-2-one;

(x) N-{3-[2-Fluoro-4'-(2-methyl-6-nitro-2,3-dihydro-imidazo[2,1-b]oxazol-2-yl)-biphenyl-4-yl]-2-oxo-oxazolidin-5-ylmethyl}-acetamide;

(y) N-(3-{3-Fluoro-4-[6-(2-methyl-6-nitro-2,3-dihydro-imidazo[2,1-b]oxazol-2-yl)-pyridin-3-yl]-phenyl}-2-oxo-oxazolidin-5-ylmethyl)-acetamide;

(z) N-[3-(3-Fluoro-4-{2-[4-(2-methyl-6-nitro-2,3-dihydro-imidazo[2,1-b]oxazol-2-ylmethyl)-piperazin-1-yl]-pyrimidin-5-yl}-phenyl)-2-oxo-oxazolidin-5-ylmethyl]-acetamide;

(aa) 3-(3-Fluoro-4-{2-[4-(2-methyl-6-nitro-2,3-dihydro-imidazo[2,1-b]oxazol-2-ylmethyl)-piperazin-1-yl]-pyrimidin-5-yl}-phenyl)-5-hydroxymethyl-oxazolidin-2-one;

(bb) 3-{3-Fluoro-4-[6-(2-methyl-6-nitro-2,3-dihydro-imidazo[2,1-b]oxazol-2-yl)-pyridin-3-yl]-phenyl}-5-hydroxymethyl-oxazolidin-2-one;

(cc) N-(3-{2-Fluoro-4'-[4-(2-methyl-6-nitro-2,3-dihydro-imidazo[2,1-b]oxazol-2-ylmethyl)-piperazin-1-yl]-biphenyl-4-yl}-2-oxo-oxazolidin-5-ylmethyl)-acetamide;

(dd) N-[3-(3-Fluoro-4-{6-[4-(2-methyl-6-nitro-2,3-dihydro-imidazo[2,1-b]oxazol-2-ylmethyl)-piperazin-1-yl]-pyridin-3-yl}-phenyl)-2-oxo-oxazolidin-5-ylmethyl]-acetamide;

(ee) Phosphoric acid mono-(3-{3-fluoro-4-[6-(2-nitro-6,7-dihydro-5H-imidazo[2,1-b][1,3]oxazin-6-yloxy)-pyridin-3-yl]-phenyl}-2-oxo-oxazolidin-5-ylmethyl)ester;

(ff) 3-[3-Fluoro-4-(2-nitro-6,7-dihydro-5H-imidazo[2,1-b][1,3]oxazin-6-yl)-phenyl]-5-hydroxymethyl-oxazolidin-2-one;

(gg) N-{3-[3-Fluoro-4-(2-nitro-6,7-dihydro-5H-imidazo[2,1-b][1,3]oxazin-6-yl)-phenyl]-2-oxo-oxazolidin-5-ylmethyl}-acetamide;

(hh) 2-Allyl-2-(4-bromo-phenyl)-6-nitro-2,3-dihydro-imidazo[2,1-b]oxazole;

(ii) N-{3-[4'-(2-Allyl-6-nitro-2,3-dihydro-imidazo[2,1-b]oxazol-2-yl)-2-fluoro-biphenyl-4-yl]-2-oxo-oxazolidin-5-ylmethyl}-acetamide;

(jj) 3-[4-(2-Allyl-6-nitro-2,3-dihydro-imidazo[2,1-b]oxazol-2-yl)-phenyl]-5-hydroxymethyl-oxazolidin-2-one;

(kk) 3-(3-Fluoro-4-{2-[4-(2-methyl-6-nitro-2,3-dihydro-imidazo[2,1-b]oxazol-2-ylmethyl)-[1,4]diazepan-1-yl]-pyrimidin-5-yl}-phenyl)-5-hydroxymethyl-oxazolidin-2-one;

(ll) 3-(3-Fluoro-4-{6-[4-(2-methyl-6-nitro-2,3-dihydro-imidazo[2,1-b]oxazol-2-ylmethyl)-[1,4]diazepan-1-yl]-pyridin-3-yl}-phenyl)-5-hydroxymethyl-oxazolidin-2-one;

(mm) N-[3-(3-Fluoro-4-{6-[4-(2-methyl-6-nitro-2,3-dihydro-imidazo[2,1-b]oxazol-2-ylmethyl)-[1,4]diazepan-1-yl]-pyridin-3-yl}-phenyl)-2-oxo-oxazolidin-5-ylmethyl]-acetamide;

(nn) 3-{3-Fluoro-4-[4-(2-methyl-6-nitro-2,3-dihydro-imidazo[2,1-b]oxazol-2-ylmethyl)-piperazin-1-yl]-phenyl}-5-hydroxymethyl-oxazolidin-2-one; and (oo) N-[3-(3-Fluoro-4-{2-[4-(2-methyl-6-nitro-2,3-dihydro-imidazo[2,1-b]oxazol-2-ylmethyl)-piperazin-1-yl]-thiazol-5-yl}-phenyl)-2-oxo-oxazolidin-5-ylmethyl]-acetamide, and their pharmaceutically acceptable salts.

* * * * *

UNITED STATES PATENT AND TRADEMARK OFFICE
CERTIFICATE OF CORRECTION

Page 1 of 1

PATENT NO. : 7,666,864 B2
APPLICATION NO. : 12/411220
DATED : February 23, 2010
INVENTOR(S) : Charles Z. Ding et al.

It is certified that error appears in the above-identified patent and that said Letters Patent is hereby corrected as shown below:

In Claim 2, column 101, line 56, replace "heteroaryl, -heteroaryl" with "heteroaryl, -O-heteroaryl".

In Claim 4, column 102, line 10, add "II," beneath the structural formula.

Signed and Sealed this
Fourth Day of September, 2012

David J. Kappos
*Director of the United States Patent and Trademark Office*